(12) United States Patent
Tyc et al.

(10) Patent No.: US 8,979,871 B2
(45) Date of Patent: Mar. 17, 2015

(54) IMAGE-GUIDED THERAPY OF A TISSUE

(71) Applicant: Monteris Medical Inc., Winnipeg (CA)

(72) Inventors: Richard Tyc, Winnipeg (CA); Salman Qureshi, Winnipeg (CA); Mark Andrew Grant, Winnipeg (CA); Luis Filipe Silva Fernandes, Winnipeg (CA); Daniel Prazeres Carreira, Winnipeg (CA); John Schellhorn, Edina, MN (US)

(73) Assignee: Monteris Medical Corporation, Plymouth, MN (US)

( * ) Notice: Subject to any disclaimer, the term of this patent is extended or adjusted under 35 U.S.C. 154(b) by 0 days.

(21) Appl. No.: 13/838,310

(22) Filed: Mar. 15, 2013

(65) Prior Publication Data

US 2014/0128881 A1    May 8, 2014

Related U.S. Application Data

(60) Provisional application No. 61/759,197, filed on Jan. 31, 2013, provisional application No. 61/664,791, filed on Jun. 27, 2012, provisional application No. 61/728,068, filed on Nov. 19, 2012.

(51) Int. Cl.
*A61B 19/00* (2006.01)
*A61B 5/055* (2006.01)
(Continued)

(52) U.S. Cl.
CPC .............. *A61B 19/20* (2013.01); *A61B 19/201* (2013.01); *A61B 5/055* (2013.01); *A61B 18/20* (2013.01);
(Continued)

(58) Field of Classification Search
CPC ................. A61B 19/5244; A61B 2019/507; A61B 19/50; A61B 2019/2242; A61B 19/2203; A61B 18/20; A61B 18/22; A61B 18/245

USPC .......... 606/1, 2, 2.5, 7, 13–16, 32, 39, 40, 45; 607/88, 89; 600/407, 410–412, 417
See application file for complete search history.

(56) References Cited

U.S. PATENT DOCUMENTS 3,021,842 A    2/1962  Flood
3,139,990 A    7/1964  Jelatis et al.
(Continued)

FOREIGN PATENT DOCUMENTS

CA    2348867 A1    5/2000
CA    2370222 A1    10/2000
(Continued)

OTHER PUBLICATIONS

Office Action mailed Oct. 8, 2012, in Chinese Patent Application No. 200980131600.9 (with English-language translation).
(Continued)

*Primary Examiner* — Ashley Fishback
*Assistant Examiner* — Katherine M Shi
(74) *Attorney, Agent, or Firm* — Oblon, Spivak, McClelland, Maier & Neustadt, L.L.P.

(57) ABSTRACT

Image-guided therapy of a tissue can utilize magnetic resonance imaging (MRI) or another medical imaging device to guide an instrument within the tissue. A workstation can actuate movement of the instrument, and can actuate energy emission and/or cooling of the instrument to effect treatment to the tissue. The workstation and/or an operator of the workstation can be located outside a vicinity of an MRI device or other medical imaging device, and drive means for positioning the instrument can be located within the vicinity of the MRI device or the other medical imaging device. The instrument can be an MRI compatible laser probe that provides thermal therapy to, e.g., a tissue in a brain of a patient.

18 Claims, 61 Drawing Sheets
(15 of 61 Drawing Sheet(s) Filed in Color)

(51) Int. Cl.
*A61B 18/20* (2006.01)
*A61B 18/22* (2006.01)
*A61B 17/34* (2006.01)
*A61B 18/00* (2006.01)

(52) U.S. Cl.
CPC ............... *A61B 18/22* (2013.01); *A61B 19/203* (2013.01); *A61B 2017/3407* (2013.01); *A61B 2018/00023* (2013.01); *A61B 2019/2211* (2013.01); *A61B 2019/5236* (2013.01); *A61B 19/56* (2013.01); *A61B 2019/5268* (2013.01)
USPC ..................................................... 606/130

(56) References Cited

U.S. PATENT DOCUMENTS

| | | |
|---|---|---|
| 4,111,209 A | 9/1978 | Wolvek et al. |
| 4,360,028 A | 11/1982 | Barbier et al. |
| 4,378,016 A | 3/1983 | Loeb |
| 4,402,694 A | 9/1983 | Ash et al. |
| 4,568,559 A | 2/1986 | Nuwayser et al. |
| 4,609,174 A | 9/1986 | Nakatani |
| 4,622,953 A | 11/1986 | Gordon |
| 4,623,588 A | 11/1986 | Nuwayser et al. |
| 4,671,254 A | 6/1987 | Fair |
| 4,733,660 A | 3/1988 | Itzkan |
| 4,733,929 A | 3/1988 | Brown |
| 4,832,024 A | 5/1989 | Boussignac et al. |
| 4,914,608 A | 4/1990 | LeBihan et al. |
| 4,986,628 A | 1/1991 | Lozhenko et al. |
| 5,059,415 A | 10/1991 | Neuwelt |
| 5,078,140 A | 1/1992 | Kwoh |
| 5,085,219 A | 2/1992 | Ortendahl et al. |
| 5,102,410 A | 4/1992 | Dressel |
| 5,116,344 A | 5/1992 | Sundqvist |
| 5,154,723 A | 10/1992 | Kubota et al. |
| 5,192,278 A * | 3/1993 | Hayes et al. .................... 606/15 |
| 5,196,005 A | 3/1993 | Doiron et al. |
| 5,201,742 A | 4/1993 | Hasson |
| 5,207,669 A | 5/1993 | Baker et al. |
| 5,207,681 A | 5/1993 | Ghadjar et al. |
| 5,222,953 A | 6/1993 | Dowlatshahi |
| 5,230,338 A | 7/1993 | Allen et al. |
| 5,242,438 A | 9/1993 | Saadatmanesh et al. |
| 5,246,436 A | 9/1993 | Rowe |
| 5,247,935 A | 9/1993 | Cline et al. |
| 5,263,956 A | 11/1993 | Nobles |
| 5,269,777 A | 12/1993 | Doiron et al. |
| 5,275,165 A | 1/1994 | Ettinger et al. |
| 5,281,213 A | 1/1994 | Milder et al. |
| 5,284,144 A | 2/1994 | Delannoy |
| 5,291,890 A | 3/1994 | Cline et al. |
| 5,292,320 A | 3/1994 | Brown et al. |
| 5,307,144 A | 4/1994 | Hiroshi et al. |
| 5,307,812 A | 5/1994 | Hardy et al. |
| 5,320,617 A | 6/1994 | Leach |
| 5,323,779 A | 6/1994 | Hardy et al. |
| 5,327,884 A | 7/1994 | Hardy et al. |
| 5,343,543 A | 8/1994 | Noval, Jr. et al. |
| 5,344,419 A | 9/1994 | Spears |
| 5,354,293 A | 10/1994 | Beyer et al. |
| 5,354,294 A | 10/1994 | Chou |
| 5,366,456 A | 11/1994 | Rink et al. |
| 5,368,031 A | 11/1994 | Cline et al. |
| 5,368,032 A | 11/1994 | Cline et al. |
| 5,370,649 A | 12/1994 | Gardetto et al. |
| 5,374,266 A | 12/1994 | Kataoka et al. |
| 5,387,220 A | 2/1995 | Pisharodi |
| 5,388,580 A | 2/1995 | Sullivan et al. |
| 5,433,717 A | 7/1995 | Rubinsky et al. |
| 5,443,068 A | 8/1995 | Cline et al. |
| 5,445,166 A | 8/1995 | Taylor |
| 5,454,794 A | 10/1995 | Narciso et al. |
| 5,454,807 A | 10/1995 | Lennox |
| 5,454,897 A | 10/1995 | Vaniglia |
| 5,469,353 A | 11/1995 | Pinsky et al. |
| 5,474,564 A | 12/1995 | Clayman et al. |
| 5,476,461 A | 12/1995 | Cho et al. |
| 5,490,840 A | 2/1996 | Uzgiris et al. |
| 5,492,122 A | 2/1996 | Button et al. |
| 5,496,308 A | 3/1996 | Brown et al. |
| 5,499,313 A | 3/1996 | Kleinerman |
| 5,509,917 A | 4/1996 | Cecchetti et al. |
| 5,526,814 A | 6/1996 | Cline et al. |
| 5,530,780 A | 6/1996 | Ohsawa |
| 5,534,000 A | 7/1996 | Bruce |
| 5,537,499 A | 7/1996 | Brekke |
| 5,553,618 A | 9/1996 | Suzuki et al. |
| 5,568,503 A | 10/1996 | Omori |
| 5,571,099 A | 11/1996 | Purcell, Jr. et al. |
| 5,590,653 A | 1/1997 | Aida et al. |
| 5,620,479 A | 4/1997 | Diederich |
| 5,632,767 A | 5/1997 | Sinofsky |
| 5,636,259 A | 6/1997 | Khutoryansky et al. |
| 5,638,819 A | 6/1997 | Manwaring et al. |
| 5,643,179 A | 7/1997 | Fujimoto |
| 5,647,361 A | 7/1997 | Damadian |
| 5,655,084 A | 8/1997 | Pinsky et al. |
| 5,657,760 A | 8/1997 | Ying et al. |
| 5,663,646 A | 9/1997 | Kuth et al. |
| 5,671,353 A | 9/1997 | Tian et al. |
| 5,672,171 A | 9/1997 | Andrus et al. |
| 5,672,172 A | 9/1997 | Zupkas |
| 5,695,501 A | 12/1997 | Carol et al. |
| 5,711,300 A | 1/1998 | Schneider et al. |
| 5,715,823 A | 2/1998 | Wood et al. |
| 5,719,975 A | 2/1998 | Wolfson et al. |
| 5,733,277 A | 3/1998 | Pallarito |
| 5,735,846 A | 4/1998 | Panescu |
| 5,749,362 A | 5/1998 | Funda et al. |
| 5,749,549 A | 5/1998 | Ashjaee |
| 5,752,962 A | 5/1998 | D'Urso |
| 5,762,066 A | 6/1998 | Law et al. |
| 5,769,790 A | 6/1998 | Watkins et al. |
| 5,772,657 A | 6/1998 | Hmelar et al. |
| 5,785,704 A | 7/1998 | Bille |
| 5,792,110 A | 8/1998 | Cunningham |
| 5,807,383 A | 9/1998 | Kolesa et al. |
| 5,814,008 A | 9/1998 | Chen et al. |
| 5,817,036 A | 10/1998 | Anthony et al. |
| 5,823,941 A | 10/1998 | Shaunnessey |
| 5,824,005 A | 10/1998 | Motamedi et al. |
| 5,830,209 A | 11/1998 | Savage et al. |
| 5,848,967 A | 12/1998 | Cosman |
| 5,855,582 A | 1/1999 | Gildenberg |
| 5,855,583 A | 1/1999 | Wang et al. |
| 5,861,020 A | 1/1999 | Schwarzmaier |
| 5,873,845 A | 2/1999 | Cline et al. |
| 5,874,955 A | 2/1999 | Rogowitz et al. |
| 5,876,342 A | 3/1999 | Chen et al. |
| 5,891,157 A | 4/1999 | Day et al. |
| 5,897,495 A | 4/1999 | Aida et al. |
| 5,916,161 A | 6/1999 | Ishihara et al. |
| 5,928,145 A | 7/1999 | Ocali et al. |
| 5,944,663 A | 8/1999 | Kuth et al. |
| 5,945,827 A | 8/1999 | Gronauer et al. |
| 5,947,958 A | 9/1999 | Woodard et al. |
| 5,949,929 A | 9/1999 | Hamm |
| 5,959,246 A | 9/1999 | Gretz |
| 5,961,466 A | 10/1999 | Anbar |
| 5,978,541 A | 11/1999 | Doiron et al. |
| 5,989,246 A | 11/1999 | Kaufmann et al. |
| 5,993,463 A | 11/1999 | Truwit |
| 6,004,315 A | 12/1999 | Dumont |
| 6,006,126 A | 12/1999 | Cosman |
| 6,019,724 A | 2/2000 | Gronningsaeter et al. |
| 6,022,309 A | 2/2000 | Celliers et al. |
| 6,039,728 A | 3/2000 | Berlien et al. |
| 6,047,216 A | 4/2000 | Carl |
| 6,050,943 A | 4/2000 | Slayton et al. |
| 6,053,912 A | 4/2000 | Panescu |
| 6,058,323 A | 5/2000 | Lemelson |
| 6,067,371 A | 5/2000 | Gouge et al. |
| 6,071,288 A | 6/2000 | Carol et al. |

(56) References Cited

U.S. PATENT DOCUMENTS

| | | |
|---|---|---|
| 6,081,533 A | 6/2000 | Laubach et al. |
| 6,086,532 A | 7/2000 | Panescu et al. |
| 6,106,516 A | 8/2000 | Massengill |
| 6,117,143 A | 9/2000 | Hynes et al. |
| 6,123,719 A | 9/2000 | Masychev |
| 6,128,522 A | 10/2000 | Acker et al. |
| 6,131,480 A | 10/2000 | Yoneyama |
| 6,132,437 A | 10/2000 | Omurtag et al. |
| 6,133,306 A | 10/2000 | Beal |
| 6,143,018 A | 11/2000 | Beuthan et al. |
| 6,148,225 A | 11/2000 | Kestler et al. |
| 6,151,404 A | 11/2000 | Pieper |
| 6,159,150 A | 12/2000 | Yale et al. |
| 6,162,052 A | 12/2000 | Kokubu |
| 6,164,843 A | 12/2000 | Battocchio |
| 6,167,295 A | 12/2000 | Cosman |
| 6,179,831 B1 | 1/2001 | Bliweis |
| 6,195,579 B1 | 2/2001 | Carroll et al. |
| 6,206,873 B1 | 3/2001 | Paolini et al. |
| 6,206,885 B1 | 3/2001 | Ghahremani et al. |
| 6,206,890 B1 | 3/2001 | Truwit |
| 6,226,680 B1 | 5/2001 | Boucher et al. |
| 6,241,725 B1 | 6/2001 | Cosman |
| 6,246,200 B1 | 6/2001 | Blumenkranz et al. |
| 6,246,896 B1 | 6/2001 | Dumoulin et al. |
| 6,246,912 B1 | 6/2001 | Sluijter |
| 6,254,043 B1 | 7/2001 | Schwärzler |
| 6,263,229 B1 | 7/2001 | Atalar et al. |
| 6,267,769 B1 | 7/2001 | Truwit |
| 6,267,770 B1 | 7/2001 | Truwit |
| 6,280,384 B1 | 8/2001 | Loeffler |
| 6,283,958 B1 | 9/2001 | Vogl et al. |
| 6,283,988 B1 | 9/2001 | Laufer |
| 6,286,795 B1 | 9/2001 | Johnson |
| 6,293,282 B1 | 9/2001 | Lemelson |
| 6,320,928 B1 | 11/2001 | Vaillant et al. |
| 6,321,266 B1 | 11/2001 | Yokomizo et al. |
| 6,332,891 B1 | 12/2001 | Himes |
| 6,334,847 B1 | 1/2002 | Fenster et al. |
| 6,353,445 B1 | 3/2002 | Babula et al. |
| 6,355,028 B2 | 3/2002 | Castaneda et al. |
| 6,368,329 B1 | 4/2002 | Truwit |
| 6,368,330 B1 | 4/2002 | Hynes et al. |
| 6,397,098 B1 | 5/2002 | Uber, III et al. |
| 6,398,778 B1 | 6/2002 | Gu et al. |
| 6,409,722 B1 | 6/2002 | Hoey |
| 6,413,253 B1 | 7/2002 | Koop |
| 6,413,263 B1 | 7/2002 | Lobdill et al. |
| 6,416,520 B1 | 7/2002 | Kynast et al. |
| 6,418,337 B1 | 7/2002 | Torchia et al. |
| 6,419,648 B1 | 7/2002 | Vitek et al. |
| 6,423,057 B1 | 7/2002 | He |
| 6,423,077 B2 | 7/2002 | Carol et al. |
| 6,425,867 B1 | 7/2002 | Vaezy et al. |
| 6,440,127 B2 | 8/2002 | McGovern |
| 6,447,505 B2 | 9/2002 | McGovern |
| 6,451,015 B1 | 9/2002 | Rittman, III et al. |
| 6,461,314 B1 | 10/2002 | Pant et al. |
| 6,464,690 B1 | 10/2002 | Castaneda et al. |
| 6,464,691 B1 | 10/2002 | Castaneda et al. |
| 6,464,694 B1 | 10/2002 | Massengill |
| 6,468,238 B1 | 10/2002 | Hawkins et al. |
| 6,488,697 B1 | 12/2002 | Ariura et al. |
| 6,491,699 B1 | 12/2002 | Henderson et al. |
| 6,501,978 B2 | 12/2002 | Wagshul et al. |
| 6,506,154 B1 | 1/2003 | Ezion et al. |
| 6,506,171 B1 | 1/2003 | Vitek et al. |
| 6,507,747 B1 | 1/2003 | Gowda et al. |
| 6,510,241 B1 | 1/2003 | Vaillant et al. |
| 6,522,142 B1 | 2/2003 | Freundlich |
| 6,522,913 B2 | 2/2003 | Swanson |
| 6,529,765 B1 | 3/2003 | Franck et al. |
| 6,542,767 B1 | 4/2003 | McNichols et al. |
| 6,543,272 B1 | 4/2003 | Vitek |
| 6,544,248 B1 | 4/2003 | Bass |
| 6,544,257 B2 | 4/2003 | Nagase et al. |
| 6,549,800 B1 | 4/2003 | Atalar et al. |
| 6,551,274 B2 | 4/2003 | Heiner |
| 6,554,826 B1 | 4/2003 | Deardorff |
| 6,558,375 B1 | 5/2003 | Sinofsky et al. |
| 6,559,644 B2 | 5/2003 | Froundlich et al. |
| 6,577,888 B1 | 6/2003 | Chan et al. |
| 6,579,281 B2 | 6/2003 | Palmer et al. |
| 6,582,381 B1 | 6/2003 | Yehezkeli et al. |
| 6,582,420 B2 | 6/2003 | Castaneda et al. |
| 6,589,174 B1 | 7/2003 | Chopra |
| 6,589,233 B1 | 7/2003 | Maki |
| 6,591,128 B1 | 7/2003 | Wu et al. |
| 6,603,988 B2 | 8/2003 | Dowlatshahi |
| 6,606,091 B2 | 8/2003 | Liang et al. |
| 6,606,513 B2 | 8/2003 | Lardo et al. |
| 6,612,988 B2 | 9/2003 | Maor et al. |
| 6,613,004 B1 | 9/2003 | Vitek et al. |
| 6,613,005 B1 | 9/2003 | Friedman et al. |
| 6,618,608 B1 | 9/2003 | Watkins et al. |
| 6,618,620 B1 | 9/2003 | Freundlich et al. |
| 6,626,854 B2 | 9/2003 | Friedman et al. |
| 6,628,980 B2 | 9/2003 | Atalar et al. |
| 6,631,499 B1 | 10/2003 | Tsujii |
| 6,645,162 B2 | 11/2003 | Friedman et al. |
| 6,666,833 B1 | 12/2003 | Friedman et al. |
| 6,671,535 B1 | 12/2003 | McNichols et al. |
| 6,675,033 B1 | 1/2004 | Lardo et al. |
| 6,675,037 B1 | 1/2004 | Tsekos |
| 6,684,097 B1 | 1/2004 | Parel et al. |
| 6,695,871 B1 | 2/2004 | Maki |
| 6,701,176 B1 | 3/2004 | Halperin |
| 6,701,181 B2 | 3/2004 | Tang et al. |
| 6,705,994 B2 | 3/2004 | Vortman et al. |
| 6,716,215 B1 | 4/2004 | David et al. |
| 6,731,966 B1 | 5/2004 | Spigelman |
| 6,735,461 B2 | 5/2004 | Vitek et al. |
| 6,741,883 B2 | 5/2004 | Gildenberg |
| 6,752,812 B1 | 6/2004 | Truwit |
| 6,755,849 B1 | 6/2004 | Gowda et al. |
| 6,770,031 B2 | 8/2004 | Hynynen et al. |
| 6,773,408 B1 | 8/2004 | Acker |
| 6,782,288 B2 | 8/2004 | Truwit et al. |
| 6,790,180 B2 | 9/2004 | Vitek |
| 6,801,643 B2 | 10/2004 | Pieper |
| 6,823,216 B1 | 11/2004 | Salomir et al. |
| 6,825,838 B2 | 11/2004 | Smith et al. |
| 6,843,793 B2 | 1/2005 | Brock et al. |
| 6,845,193 B2 | 1/2005 | Loeb et al. |
| 6,893,447 B2 | 5/2005 | Dominguez et al. |
| 6,898,454 B2 | 5/2005 | Atalar et al. |
| 6,902,569 B2 | 6/2005 | Parmer et al. |
| 6,904,307 B2 | 6/2005 | Karmarkar et al. |
| 6,986,764 B2 | 1/2006 | Davenport et al. |
| 7,033,367 B2 | 4/2006 | Ghahremani et al. |
| 7,072,704 B2 | 7/2006 | Bucholz |
| 7,074,233 B1 | 7/2006 | Gowda et al. |
| 7,097,641 B1 | 8/2006 | Arless |
| 7,123,255 B2 | 10/2006 | Trousett et al. |
| 7,128,711 B2 | 10/2006 | Medan et al. |
| 7,133,714 B2 | 11/2006 | Karmarkar et al. |
| 7,164,940 B2 | 1/2007 | Hareyama et al. |
| 7,166,458 B2 | 1/2007 | Ballerstadt et al. |
| 7,167,741 B2 | 1/2007 | Torchia et al. |
| 7,167,760 B2 | 1/2007 | Dawant et al. |
| 7,175,596 B2 | 2/2007 | Vitek et al. |
| 7,226,414 B2 | 6/2007 | Ballerstadt et al. |
| 7,228,165 B1 | 6/2007 | Sullivan |
| 7,229,451 B2 | 6/2007 | Day et al. |
| 7,235,084 B2 | 6/2007 | Skakoon et al. |
| 7,235,089 B1 | 6/2007 | McGuckin, Jr. |
| 7,236,812 B1 | 6/2007 | Ballerstadt et al. |
| 7,236,816 B2 | 6/2007 | Kumar et al. |
| 7,270,656 B2 | 9/2007 | Gowda et al. |
| 7,274,847 B2 | 9/2007 | Gowda et al. |
| 7,280,686 B2 | 10/2007 | Hornegger et al. |
| 7,292,719 B2 | 11/2007 | Arnon |
| 7,315,167 B2 | 1/2008 | Bottcher et al. |
| 7,321,374 B2 | 1/2008 | Naske |

(56) References Cited

U.S. PATENT DOCUMENTS

| | | | |
|---|---|---|---|
| 7,344,529 B2 | 3/2008 | Torchia et al. | |
| RE40,279 E | 4/2008 | Sluijter | |
| 7,366,561 B2 | 4/2008 | Mills et al. | |
| 7,371,210 B2 | 5/2008 | Brock et al. | |
| 7,377,900 B2 | 5/2008 | Vitek et al. | |
| 7,412,141 B2 | 8/2008 | Gowda et al. | |
| 7,450,985 B2 | 11/2008 | Meloy et al. | |
| 7,463,801 B2 | 12/2008 | Brekke et al. | |
| 7,479,139 B2 | 1/2009 | Cytron et al. | |
| 7,489,133 B1 | 2/2009 | Keidl et al. | |
| 7,507,244 B2 | 3/2009 | Dinkler et al. | |
| 7,519,210 B2 | 4/2009 | Hirsch et al. | |
| 7,521,930 B2 | 4/2009 | Li et al. | |
| 7,535,794 B2 | 5/2009 | Prus et al. | |
| 7,551,953 B2 | 6/2009 | Lardo et al. | |
| 7,561,906 B2 | 7/2009 | Atalar et al. | |
| 7,599,729 B2 | 10/2009 | Atalar et al. | |
| 7,602,190 B2 | 10/2009 | Piferi et al. | |
| 7,609,927 B2 | 10/2009 | Gowda et al. | |
| 7,611,462 B2 | 11/2009 | Vortman et al. | |
| 7,631,233 B2 | 12/2009 | Parris et al. | |
| 7,634,119 B2 | 12/2009 | Tsougarakis et al. | |
| 7,652,410 B2 | 1/2010 | Prus | |
| 7,659,719 B2 | 2/2010 | Vaughan et al. | |
| 7,661,162 B2 | 2/2010 | Soerensen et al. | |
| 7,699,780 B2 | 4/2010 | Vitek et al. | |
| 7,702,140 B2 | 4/2010 | Hirsch et al. | |
| 7,706,858 B1 | 4/2010 | Green et al. | |
| 7,717,853 B2 | 5/2010 | Nita et al. | |
| 7,736,371 B2 | 6/2010 | Schoepp | |
| 7,778,682 B2 | 8/2010 | Kumar et al. | |
| 7,792,566 B2 | 9/2010 | Roland et al. | |
| 7,794,469 B2 | 9/2010 | Kao et al. | |
| 7,801,587 B2 | 9/2010 | Webber et al. | |
| 7,848,788 B2 | 12/2010 | Tulley et al. | |
| 7,876,939 B2 | 1/2011 | Yankelevitz | |
| 7,925,328 B2 | 4/2011 | Urquhart et al. | |
| 7,957,783 B2 | 6/2011 | Atalar et al. | |
| 8,002,706 B2 | 8/2011 | Vortman et al. | |
| 8,022,705 B2 | 9/2011 | Bogdanov et al. | |
| RE42,856 E | 10/2011 | Karmarkar et al. | |
| 8,034,569 B2 | 10/2011 | Jackson et al. | |
| 8,055,351 B2 | 11/2011 | Atalar et al. | |
| 8,060,182 B2 | 11/2011 | He et al. | |
| 8,068,893 B2 | 11/2011 | Guttman et al. | |
| 8,088,067 B2 | 1/2012 | Vortman et al. | |
| 8,094,900 B2 | 1/2012 | Steines et al. | |
| 8,099,150 B2 | 1/2012 | Piferi et al. | |
| 8,100,132 B2 | 1/2012 | Markstroem et al. | |
| 8,108,028 B2 | 1/2012 | Karmarkar | |
| 8,114,068 B2 | 2/2012 | Rheinwald et al. | |
| 8,116,843 B2 | 2/2012 | Dai et al. | |
| 8,157,828 B2 | 4/2012 | Piferi | |
| 8,165,658 B2 | 4/2012 | Waynik et al. | |
| 8,175,677 B2 | 5/2012 | Sayler et al. | |
| 8,190,237 B2 | 5/2012 | Driemel et al. | |
| 8,195,272 B2 | 6/2012 | Piferi et al. | |
| 8,208,993 B2 | 6/2012 | Piferi et al. | |
| 8,211,095 B2 | 7/2012 | Gowda et al. | |
| 8,216,854 B2 | 7/2012 | Ballerstadt et al. | |
| 8,224,420 B2 | 7/2012 | Mu et al. | |
| 8,233,701 B2 | 7/2012 | Frakes et al. | |
| 8,235,901 B2 | 8/2012 | Schmidt et al. | |
| 8,251,908 B2 | 8/2012 | Vortman et al. | |
| 8,267,938 B2 | 9/2012 | Murphy | |
| 8,270,698 B2 | 9/2012 | Geiger | |
| 8,285,097 B2 | 10/2012 | Griffin | |
| 8,287,537 B2 | 10/2012 | Dinkler | |
| 8,298,245 B2 | 10/2012 | Li et al. | |
| 8,314,052 B2 | 11/2012 | Jackson | |
| 8,315,689 B2 | 11/2012 | Jenkins et al. | |
| 8,320,990 B2 | 11/2012 | Vij | |
| 8,340,743 B2 | 12/2012 | Jenkins et al. | |
| RE43,901 E | 1/2013 | Freundlich et al. | |
| 8,364,217 B2 | 1/2013 | Ballerstadt et al. | |
| 8,368,401 B2 | 2/2013 | Levy et al. | |
| 8,369,930 B2 | 2/2013 | Jenkins et al. | |
| 8,374,677 B2 | 2/2013 | Piferi et al. | |
| 8,380,277 B2 | 2/2013 | Atalar et al. | |
| 8,396,532 B2 | 3/2013 | Jenkins et al. | |
| 8,404,495 B2 | 3/2013 | Ballerstadt et al. | |
| 8,409,099 B2 | 4/2013 | Vitek et al. | |
| 8,414,597 B2 | 4/2013 | Kao et al. | |
| 8,425,424 B2 | 4/2013 | Zadicario et al. | |
| 8,433,421 B2 | 4/2013 | Atalar et al. | |
| 8,482,285 B2 | 7/2013 | Grissom et al. | |
| 8,520,932 B2 | 8/2013 | Cool et al. | |
| 8,548,561 B2 | 10/2013 | Vortman et al. | |
| 8,548,569 B2 | 10/2013 | Piferi et al. | |
| 8,608,672 B2 | 12/2013 | Vortman et al. | |
| 8,617,073 B2 | 12/2013 | Prus et al. | |
| RE44,726 E | 1/2014 | Parris et al. | |
| RE44,736 E | 1/2014 | Karmarkar et al. | |
| 8,644,906 B2 | 2/2014 | Piferi et al. | |
| 8,649,842 B2 | 2/2014 | Atalar et al. | |
| 8,661,873 B2 | 3/2014 | Medan et al. | |
| 8,688,226 B2 | 4/2014 | Atalar et al. | |
| 8,737,712 B2 | 5/2014 | Geiger | |
| 2001/0003798 A1 | 6/2001 | McGovern | |
| 2002/0019641 A1 | 2/2002 | Truwit | |
| 2002/0042605 A1 | 4/2002 | Castaneda et al. | |
| 2002/0052610 A1 | 5/2002 | Skakoon et al. | |
| 2002/0087148 A1* | 7/2002 | Brock et al. | 606/1 |
| 2002/0169460 A1 | 11/2002 | Foster et al. | |
| 2002/0177843 A1 | 11/2002 | Anderson et al. | |
| 2003/0023236 A1 | 1/2003 | Gowda et al. | |
| 2003/0060813 A1 | 3/2003 | Loeb et al. | |
| 2003/0171741 A1 | 9/2003 | Ziebol et al. | |
| 2003/0187371 A1 | 10/2003 | Vortman et al. | |
| 2004/0073100 A1 | 4/2004 | Ballerstadt et al. | |
| 2004/0075031 A1 | 4/2004 | Crain et al. | |
| 2004/0122446 A1 | 6/2004 | Solar | |
| 2004/0123870 A1 | 7/2004 | Stamper et al. | |
| 2004/0133190 A1* | 7/2004 | Hobart et al. | 606/4 |
| 2004/0134884 A1 | 7/2004 | Wei et al. | |
| 2004/0167542 A1 | 8/2004 | Solar et al. | |
| 2004/0167543 A1 | 8/2004 | Mazzocchi et al. | |
| 2004/0267284 A1 | 12/2004 | Parmer et al. | |
| 2005/0070920 A1 | 3/2005 | Solar et al. | |
| 2005/0154237 A1 | 7/2005 | Nakahara et al. | |
| 2006/0009749 A1 | 1/2006 | Weckwerth et al. | |
| 2006/0089626 A1 | 4/2006 | Vlegele et al. | |
| 2006/0122590 A1 | 6/2006 | Bliweis et al. | |
| 2006/0122629 A1 | 6/2006 | Skakoon | |
| 2006/0175484 A1 | 8/2006 | Wood, III et al. | |
| 2006/0192319 A1 | 8/2006 | Solar et al. | |
| 2006/0195119 A1 | 8/2006 | Mazzocchi et al. | |
| 2006/0206105 A1 | 9/2006 | Chopra et al. | |
| 2006/0212044 A1 | 9/2006 | Bova et al. | |
| 2006/0229641 A1 | 10/2006 | Gupta et al. | |
| 2006/0241393 A1 | 10/2006 | Liu et al. | |
| 2006/0287647 A1 | 12/2006 | Torchia et al. | |
| 2007/0016039 A1 | 1/2007 | Vortman et al. | |
| 2007/0043342 A1 | 2/2007 | Kleinberger | |
| 2007/0088416 A1 | 4/2007 | Atalar et al. | |
| 2007/0100346 A1 | 5/2007 | Wyss et al. | |
| 2007/0106305 A1 | 5/2007 | Kao et al. | |
| 2007/0149977 A1 | 6/2007 | Heavener | |
| 2007/0191867 A1 | 8/2007 | Mazzocchi et al. | |
| 2007/0197918 A1 | 8/2007 | Vitek et al. | |
| 2007/0208352 A1 | 9/2007 | Henderson et al. | |
| 2007/0225562 A1 | 9/2007 | Spivey et al. | |
| 2007/0238978 A1 | 10/2007 | Kumar et al. | |
| 2007/0239062 A1 | 10/2007 | Chopra et al. | |
| 2007/0250077 A1 | 10/2007 | Skakoon et al. | |
| 2007/0270717 A1 | 11/2007 | Tang et al. | |
| 2008/0002927 A1 | 1/2008 | Furnish | |
| 2008/0027463 A1 | 1/2008 | Labadie et al. | |
| 2008/0033278 A1 | 2/2008 | Assif | |
| 2008/0033292 A1 | 2/2008 | Shafran | |
| 2008/0046122 A1 | 2/2008 | Manzo | |
| 2008/0077159 A1 | 3/2008 | Madhani et al. | |
| 2008/0097187 A1 | 4/2008 | Gielen et al. | |
| 2008/0114340 A1 | 5/2008 | Fox et al. | |

(56) References Cited

U.S. PATENT DOCUMENTS

| | | |
|---|---|---|
| 2008/0123921 A1 | 5/2008 | Gielen et al. |
| 2008/0123922 A1 | 5/2008 | Gielen et al. |
| 2008/0195085 A1 | 8/2008 | Loeb |
| 2008/0242978 A1 | 10/2008 | Simon et al. |
| 2008/0243142 A1 | 10/2008 | Gildenberg |
| 2008/0243218 A1 | 10/2008 | Bottomley et al. |
| 2008/0255583 A1 | 10/2008 | Gielen et al. |
| 2008/0262584 A1 | 10/2008 | Bottomley et al. |
| 2008/0269588 A1 | 10/2008 | Csavoy et al. |
| 2008/0269602 A1 | 10/2008 | Csavoy et al. |
| 2008/0287917 A1 | 11/2008 | Cunningham |
| 2008/0306375 A1 | 12/2008 | Sayler et al. |
| 2009/0012509 A1 | 1/2009 | Csavoy et al. |
| 2009/0018446 A1 | 1/2009 | Medan et al. |
| 2009/0048588 A1 | 2/2009 | Peng et al. |
| 2009/0082783 A1 | 3/2009 | Piferi |
| 2009/0099045 A1 | 4/2009 | Jackson et al. |
| 2009/0112082 A1 | 4/2009 | Piferi et al. |
| 2009/0118610 A1 | 5/2009 | Karmarkar et al. |
| 2009/0124398 A1 | 5/2009 | Thompson |
| 2009/0131783 A1 | 5/2009 | Jenkins et al. |
| 2009/0148493 A1 | 6/2009 | Ballerstadt et al. |
| 2009/0192487 A1 | 7/2009 | Broaddus et al. |
| 2009/0198309 A1 | 8/2009 | Gowda et al. |
| 2009/0204111 A1 | 8/2009 | Bissig et al. |
| 2009/0234368 A1 | 9/2009 | Gore |
| 2009/0240242 A1 | 9/2009 | Neuberger |
| 2009/0266760 A1 | 10/2009 | Jackson et al. |
| 2009/0275130 A1 | 11/2009 | Navran et al. |
| 2009/0287199 A1 | 11/2009 | Hanley et al. |
| 2009/0308400 A1 | 12/2009 | Wilson et al. |
| 2009/0326525 A1 | 12/2009 | Hixon et al. |
| 2010/0016930 A1 | 1/2010 | Gowda et al. |
| 2010/0030076 A1 | 2/2010 | Vortman et al. |
| 2010/0041938 A1 | 2/2010 | Stoianovici et al. |
| 2010/0042112 A1* | 2/2010 | Qureshi et al. ............... 606/130 |
| 2010/0082035 A1 | 4/2010 | Keefer |
| 2010/0087336 A1 | 4/2010 | Jackson et al. |
| 2010/0795580 | 4/2010 | Waring, IV |
| 2010/0146713 A1 | 6/2010 | Medan et al. |
| 2010/0179425 A1 | 7/2010 | Zadicario |
| 2010/0198052 A1 | 8/2010 | Jenkins et al. |
| 2010/0241036 A1 | 9/2010 | Vortman et al. |
| 2010/0312094 A1 | 12/2010 | Guttman et al. |
| 2010/0312095 A1 | 12/2010 | Jenkins et al. |
| 2010/0312096 A1 | 12/2010 | Guttman et al. |
| 2010/0318002 A1 | 12/2010 | Prus et al. |
| 2011/0034800 A1 | 2/2011 | Vitek et al. |
| 2011/0040172 A1 | 2/2011 | Carpentier et al. |
| 2011/0046472 A1 | 2/2011 | Schmidt et al. |
| 2011/0046475 A1 | 2/2011 | Assif et al. |
| 2011/0066032 A1 | 3/2011 | Vitek et al. |
| 2011/0118715 A1 | 5/2011 | Zerfas |
| 2011/0137147 A1 | 6/2011 | Skliar et al. |
| 2011/0141759 A1 | 6/2011 | Smith |
| 2011/0166447 A1 | 7/2011 | Windolf et al. |
| 2011/0175615 A1 | 7/2011 | Grissom et al. |
| 2011/0190787 A1 | 8/2011 | Sahni et al. |
| 2011/0217665 A1 | 9/2011 | Walsh et al. |
| 2011/0224576 A1 | 9/2011 | Jackson et al. |
| 2011/0226260 A1 | 9/2011 | Eder et al. |
| 2011/0230753 A1 | 9/2011 | Mahon et al. |
| 2011/0237930 A1 | 9/2011 | Donaldson et al. |
| 2011/0238139 A1 | 9/2011 | Gowda et al. |
| 2011/0251528 A1 | 10/2011 | Canney et al. |
| 2011/0260728 A1 | 10/2011 | Biber et al. |
| 2011/0267059 A1 | 11/2011 | Shvartsberg et al. |
| 2011/0270075 A1 | 11/2011 | Vitek et al. |
| 2011/0270136 A1 | 11/2011 | Vitek et al. |
| 2011/0270366 A1 | 11/2011 | Mahon et al. |
| 2011/0295161 A1 | 12/2011 | Chopra et al. |
| 2011/0301450 A1 | 12/2011 | Hue et al. |
| 2011/0306054 A1 | 12/2011 | Jackson et al. |
| 2011/0319747 A1 | 12/2011 | Schmidt et al. |
| 2011/0319748 A1 | 12/2011 | Bronskill et al. |
| 2011/0319910 A1 | 12/2011 | Roelle et al. |
| 2012/0015359 A1 | 1/2012 | Jackson et al. |
| 2012/0029396 A1 | 2/2012 | Vortman et al. |
| 2012/0053573 A1 | 3/2012 | Alksnis |
| 2012/0059243 A1 | 3/2012 | Vortman et al. |
| 2012/0070058 A1 | 3/2012 | Raju et al. |
| 2012/0071746 A1 | 3/2012 | Vortman et al. |
| 2012/0101412 A1 | 4/2012 | Vortman et al. |
| 2012/0108459 A1 | 5/2012 | Jackson et al. |
| 2012/0121533 A1 | 5/2012 | Jackson |
| 2012/0165225 A1 | 6/2012 | Stepanov et al. |
| 2012/0191020 A1 | 7/2012 | Vitek et al. |
| 2012/0197112 A1 | 8/2012 | McNichols |
| 2012/0245573 A1 | 9/2012 | Gowda et al. |
| 2013/0006095 A1 | 1/2013 | Jenkins et al. |
| 2013/0018430 A1 | 1/2013 | Murphy |
| 2013/0030408 A1 | 1/2013 | Piferi et al. |
| 2013/0034915 A1 | 2/2013 | Ballerstadt et al. |
| 2013/0035582 A1 | 2/2013 | Radulescu et al. |
| 2013/0041356 A1 | 2/2013 | Smith et al. |
| 2013/0053678 A1 | 2/2013 | Vitek et al. |
| 2013/0053867 A1 | 2/2013 | Gowda et al. |
| 2013/0060253 A1 | 3/2013 | Couture et al. |
| 2013/0085342 A1 | 4/2013 | Stefanchik et al. |
| 2013/0102883 A1 | 4/2013 | Piferi et al. |
| 2013/0116543 A1 | 5/2013 | Jenkins et al. |
| 2013/0119984 A1 | 5/2013 | Levy et al. |
| 2013/0123598 A1 | 5/2013 | Jenkins et al. |
| 2013/0131496 A1 | 5/2013 | Jenkins et al. |
| 2013/0150704 A1 | 6/2013 | Vitek et al. |
| 2013/0150756 A1 | 6/2013 | Vitek et al. |
| 2013/0157871 A1 | 6/2013 | Jackson |
| 2013/0158577 A1 | 6/2013 | Mahon et al. |
| 2013/0163841 A1 | 6/2013 | Geiger |
| 2013/0184563 A1 | 7/2013 | Driemel et al. |
| 2013/0190607 A1 | 7/2013 | Biber et al. |
| 2013/0217950 A1 | 8/2013 | Partanen et al. |
| 2013/0245243 A1 | 9/2013 | Jackson |
| 2013/0245741 A1 | 9/2013 | Atalar et al. |
| 2013/0325012 A1 | 12/2013 | Piferi et al. |
| 2014/0024909 A1 | 1/2014 | Vij et al. |
| 2014/0024925 A1 | 1/2014 | Piferi |
| 2014/0024927 A1 | 1/2014 | Piferi |
| 2014/0034377 A1 | 2/2014 | Vij |
| 2014/0046167 A1 | 2/2014 | Vij et al. |
| 2014/0066750 A1 | 3/2014 | Piferi et al. |
| 2014/0112095 A1 | 4/2014 | Medan et al. |

FOREIGN PATENT DOCUMENTS

| | | |
|---|---|---|
| CA | 2398967 A1 | 8/2001 |
| CA | 2403822 A1 | 10/2001 |
| CA | 2404352 A1 | 10/2001 |
| CA | 2482291 A1 | 10/2002 |
| CA | 2587691 A1 | 5/2006 |
| CA | 2606824 A1 | 11/2006 |
| CA | 2681367 A1 | 9/2008 |
| CA | 2695494 A1 | 12/2008 |
| CA | 2700523 A1 | 4/2009 |
| CA | 2700529 A1 | 4/2009 |
| CA | 2700531 A1 | 4/2009 |
| CA | 2700577 A1 | 4/2009 |
| CA | 2700607 A1 | 4/2009 |
| CA | 2704739 A1 | 4/2009 |
| CA | 2252431 C | 7/2009 |
| CA | 2648973 C | 7/2009 |
| CA | 2715015 A1 | 9/2009 |
| CA | 2748053 A1 | 4/2010 |
| CA | 2753397 A1 | 9/2010 |
| CA | 2372001 C | 10/2010 |
| CA | 2764677 A1 | 12/2010 |
| CA | 1317641 | 5/2011 |
| CA | 2487140 C | 9/2011 |
| CA | 2800238 A1 | 9/2011 |
| CA | 2482202 C | 7/2012 |
| CA | 2849106 A1 | 4/2013 |
| CA | 2575313 C | 7/2013 |
| CA | 2548226 C | 1/2014 |
| CN | 2620289 Y | 6/2004 |

(56) References Cited

FOREIGN PATENT DOCUMENTS

| | | |
|---|---|---|
| CN | 2748071 Y | 12/2005 |
| CN | 101040772 A | 9/2007 |
| CN | 101194853 A | 6/2008 |
| EP | 0 610 991 A2 | 8/1994 |
| EP | 0 614 651 A1 | 9/1994 |
| EP | 0 755 697 A2 | 1/1997 |
| EP | 0 844 581 B1 | 7/2007 |
| EP | 1 829 764 | 9/2007 |
| EP | 1 985 330 A1 | 10/2008 |
| JP | 54-88120 | 7/1979 |
| JP | 59-042165 | 3/1984 |
| JP | 60-154698 | 10/1985 |
| JP | 7-308393 | 11/1995 |
| JP | 9-038220 | 2/1997 |
| JP | 10-155805 | 6/1998 |
| JP | 10-258066 | 9/1998 |
| JP | 11-253562 | 9/1999 |
| JP | 2000-000319 | 1/2000 |
| JP | 2000-126316 | 5/2000 |
| JP | 2002-543865 | 12/2002 |
| WO | WO 90/05494 | 5/1990 |
| WO | WO 92/10142 | 6/1992 |
| WO | WO 93/20769 | 10/1993 |
| WO | WO 94/04220 | 3/1994 |
| WO | WO 94/23308 | 10/1994 |
| WO | WO 95/29737 | 11/1995 |
| WO | WO 97/40396 | 10/1997 |
| WO | WO 98/23214 | 6/1998 |
| WO | WO 98/51229 | 11/1998 |
| WO | WO 98/52465 | 11/1998 |
| WO | WO 99/51156 | 10/1999 |
| WO | WO 00/23000 | 4/2000 |
| WO | WO 00/28895 | 5/2000 |
| WO | WO 00/32102 | 6/2000 |
| WO | WO 00/62672 | 10/2000 |
| WO | WO 00/64003 | 10/2000 |
| WO | WO 00/67640 | 11/2000 |
| WO | WO 01/06925 | 2/2001 |
| WO | WO 01/25810 | 4/2001 |
| WO | WO 01/35825 | 5/2001 |
| WO | WO 01/40819 | 6/2001 |
| WO | WO 01/56469 | 8/2001 |
| WO | WO 01/65490 | 9/2001 |
| WO | WO 01/73461 | 10/2001 |
| WO | WO 01/74241 | 10/2001 |
| WO | WO 01/76498 A3 | 10/2001 |
| WO | WO 01/80708 | 11/2001 |
| WO | WO 01/80709 | 11/2001 |
| WO | WO 01/82806 | 11/2001 |
| WO | WO 02/00093 | 1/2002 |
| WO | WO 02/09812 | 2/2002 |
| WO | WO 02/24075 | 3/2002 |
| WO | WO 02/24094 | 3/2002 |
| WO | WO 02/43804 | 6/2002 |
| WO | WO 02/43805 | 6/2002 |
| WO | WO 02/44753 | 6/2002 |
| WO | WO 02/45073 | 6/2002 |
| WO | WO 02/051501 | 7/2002 |
| WO | WO 02/058791 | 8/2002 |
| WO | WO 02/083016 | 10/2002 |
| WO | WO 02/084316 | 10/2002 |
| WO | WO 02/097466 | 12/2002 |
| WO | WO 02/103380 | 12/2002 |
| WO | WO 03/011160 | 2/2003 |
| WO | WO 03/017843 | 3/2003 |
| WO | WO 03/042707 | 5/2003 |
| WO | WO 03/048702 | 6/2003 |
| WO | WO 03/052444 | 6/2003 |
| WO | WO 03/094759 A1 | 11/2003 |
| WO | WO 03/097162 | 11/2003 |
| WO | WO 03/102614 | 12/2003 |
| WO | WO 2004/056421 | 7/2004 |
| WO | WO 2004/075722 A2 | 9/2004 |
| WO | WO 2004/103472 | 12/2004 |
| WO | WO 2004/105624 | 12/2004 |
| WO | WO 2005/046451 A2 | 5/2005 |
| WO | WO 2005/046753 | 5/2005 |
| WO | WO 2006/014966 | 2/2006 |
| WO | WO 2006/018686 | 2/2006 |
| WO | WO 2006/021851 | 3/2006 |
| WO | WO 2006/055554 | 5/2006 |
| WO | WO 2006/119492 | 11/2006 |
| WO | WO 2006/136912 | 12/2006 |
| WO | WO 2007/047966 | 4/2007 |
| WO | WO 2007/056458 A2 | 5/2007 |
| WO | WO 2007/060474 A1 | 5/2007 |
| WO | WO 2007/064937 | 6/2007 |
| WO | WO 2007/085892 | 8/2007 |
| WO | WO 2007/129166 | 11/2007 |
| WO | WO 2008/015520 | 2/2008 |
| WO | WO 2008/015521 | 2/2008 |
| WO | WO 2008/015522 | 2/2008 |
| WO | WO 2008/015523 | 2/2008 |
| WO | WO 2008/070685 | 6/2008 |
| WO | WO 2008/109864 | 9/2008 |
| WO | WO 2008/115383 | 9/2008 |
| WO | WO 2008/115426 | 9/2008 |
| WO | WO 2008/153975 | 12/2008 |
| WO | WO 2009/007847 | 1/2009 |
| WO | WO 2009/042130 | 4/2009 |
| WO | WO 2009/042131 | 4/2009 |
| WO | WO 2009/042135 | 4/2009 |
| WO | WO 2009/042136 | 4/2009 |
| WO | WO 2009/042152 | 4/2009 |
| WO | WO 2009/042155 | 4/2009 |
| WO | WO 2009/042160 | 4/2009 |
| WO | WO 2009/044276 | 4/2009 |
| WO | WO 2009/067205 | 5/2009 |
| WO | WO 2009/117069 | 9/2009 |
| WO | WO 2009/124301 | 10/2009 |
| WO | WO 2009/135198 | 11/2009 |
| WO | WO 2010/030373 | 3/2010 |
| WO | WO 2010/034099 | 4/2010 |
| WO | WO 2010/058292 | 5/2010 |
| WO | WO 2010/058293 | 5/2010 |
| WO | WO 2010/082135 | 7/2010 |
| WO | WO 2010/087961 | 8/2010 |
| WO | WO 2010/110929 | 9/2010 |
| WO | WO 2010/119340 | 10/2010 |
| WO | WO 2010/141102 | 12/2010 |
| WO | WO 2010/143072 | 12/2010 |
| WO | WO 2010/144402 | 12/2010 |
| WO | WO 2010/144405 | 12/2010 |
| WO | WO 2010/144419 | 12/2010 |
| WO | WO 2010/148083 | 12/2010 |
| WO | WO 2010/148088 | 12/2010 |
| WO | WO 2011/013001 | 2/2011 |
| WO | WO 2011/015949 | 2/2011 |
| WO | WO 2011/021106 | 2/2011 |
| WO | WO 2011/024074 | 3/2011 |
| WO | WO 2011/028505 | 3/2011 |
| WO | WO 2011/045669 | 4/2011 |
| WO | WO 2011/058437 | 5/2011 |
| WO | WO 2011/087495 | 7/2011 |
| WO | WO 2011/090990 | 7/2011 |
| WO | WO 2011/112249 | 9/2011 |
| WO | WO 2011/112251 | 9/2011 |
| WO | WO 2011/115664 | 9/2011 |
| WO | WO 2011/130107 | 10/2011 |
| WO | WO 2011/135455 | 11/2011 |
| WO | WO 2011/135458 | 11/2011 |
| WO | WO 2012/014074 | 2/2012 |
| WO | WO 2012/038826 | 3/2012 |
| WO | WO 2012/052847 | 4/2012 |
| WO | WO 2012/112829 | 8/2012 |
| WO | WO 2012/116265 | 8/2012 |
| WO | WO 2012/154961 | 11/2012 |
| WO | WO 2013/028811 | 2/2013 |
| WO | WO 2013/030671 | 3/2013 |
| WO | WO 2013/049108 | 4/2013 |
| WO | WO 2013/117991 | 8/2013 |
| WO | WO 2013/117992 | 8/2013 |

(56) References Cited

FOREIGN PATENT DOCUMENTS

| WO | WO 2013/181008 | 12/2013 |
|---|---|---|
| WO | WO 2014/014585 | 1/2014 |
| WO | WO 2014/039481 | 3/2014 |

OTHER PUBLICATIONS

Office Action mailed Jul. 17, 2013, in Japanese Patent Application No. 2011-522361 (with English-language translation).
Office Action mailed Jul. 29, 2013, in Japanese Patent Application No. 2011-522360 (with English-language translation).
International Search Report and Written Opinion mailed Jun. 10, 2013, in PCT/US13/32273.
Office Action mailed Dec. 27, 2013, in Israeli Patent Application No. 210878.
International Preliminary Report on Patentability mailed Feb. 15, 2011, in PCT/CA2009/01137, 8 pages.
International Preliminary Report on Patentability mailed Feb. 15, 2011, in PCT/CA2009/001138, 5 pages.
Office Action mailed Oct. 25, 2011, in Brazilian Patent Application No. PI-0214951-6 (English translation).
Office Action mailed May 28, 2013, in Brazilian Patent Application No. PI-0214951-6 (English translation).
Office Action mailed Nov. 1, 2012, in Japanese Patent Application No. 2011-522361 (with English-language translation).
Combined Chinese OA and Search Report mailed Mar. 13, 2013, in Chinese Patent Application No. 200980131609.X.
Kahn et al., "MRI-Guided Laser-Induced Interstitial Thermotherapy of Cerebral Neoplasms," Journal of Computer Assisted Tomography, vol. 18, No. 4, pp. 519-532, Jul./Aug. 1994, Raven Press, Ltd., New York, NY.
Kahn et al., "In Vivo MRI Thermometry Using a Phase-Sensitive Sequence: Preliminary Experience During MRI-Guided Laser-Induced Interstitial Thermotherapy of Brain Tumors," Journal of Magnetic Resonance Imaging, vol. 8, No. 1, pp. 160-164, Williams & Wilkins, 1998, Baltimore, MD.
Vogl et al., "Internally Cooled Power Laser for MR-guided Interstitial Laser-induced Thermotherapy of Liver Lesions: Initial Clinical Results", in Radiology, 1998, 209: pp. 381-385.
McNichols et al., "MR Thermometry-Based Feedback Control of Laser Interstitial Thermal Therapy at 980 nm," Lasers in Surgery and Medicine, 2004, 34: 48-55, Wiley -Liss, Inc.
Schwarzmaier et al., "MR-guided laser-induced interstitial thermotherapy of recurrent glioblastoma multiforme: Preliminary results in 16 patients," European Journal of Radiology, vol. 59, Issue 2, pp. 208-215, Aug. 2006.
Carpentier, et al. "Real-Time Magnetic Resonance-Guided Laser Thermal Therapy for Focal Metastatic Brain Tumors", Operative Neurogurgery 1, vol. 63, pp. 21-39.
Canney, et al. "A Multi-element Interstitial Ultrasound Applicator for the Thermal Therapy of Brain Tumors", Acoustical Society of America, Pt. 2, Aug. 2013, pp. 1647-1655.
Japanese Office Action mailed Nov. 6, 2012, in Japanese Application No. 2011-522360. (with English translation).
European Search Report and Search Opinion, dated Oct. 10, 2013, in European Patent Application No. 09806277.1.
Nabavi, et al. "Neurosurgical procedures in a 0.5 tesla, open-configuration intraoperative MRI: planning, visualization, and navigation" ,Automedica, vol. 00, pp. 1-35, 2001.
Castro, et al. "Interstitial laaser phototherapy assisted by magnetic resonance imaging: A new technique for monitoring laser-tissue interaction", The Laryngoscope, vol. 100, Issue , pp. 541-547, May 1990 (abstract only).
Carpentier, et al. "MR-Guided Laser Induced Thermal Therapy (LITT) for Recurrent Glioblastomas", Lasers in Surgery and Medicine, vol. 44, pp. 361-368, 2012.
Carpentier, et al. "Laser Thermal Therapy: Real-time MRI-guided and Computer-controlled Procedures for Metastatic Brain Tumors", Lasers in Surgery and Medicine, vol. 43, pp. 943-950, 2011.

Gewiese, et al. "Magenetic Resonance Imaging-Controlled Laser-Induced Interstitial Thermotherapy", Investigative Radiology, vol. 29, No. 3, pp. 345-351, 1994.
Japanese Office Action mailed Jul. 29, 2013, Japanese Application No. 2011-522360 (with English translation).
Jerome Shaunnessey, Petition for General Supervisory Review by the Director under 37 CFR 1.181, Jul. 2014, 6 pages.
T. Menovsky, et al., "Interstitial Laser Thermotherapy in Neurosurgery: A Review", Acta Neurochir (Wien) (1996) 138:1019-1026, 8 pages.
Ferenc A. Jolesz M.D., et al., "MRI-Guided Laser-Induced Interstitial Thermotherapy: Basic Principles", Harvard Medical School and Brigham and Women's Hospital, Department of Radiology, appears in: SPIE Institute on Laser-Induced Interstitial Thermotherapy (LITT), Jun. 22-23, 1995, 17 pages.
Thorsten Harth, et al., "Determination of Laser-Induced Temperature Distributions Using Echo-Shifted TurboFLASH", MRM 38:238-245 (1997), 8 pages.
Lawrence P. Panych, et al., "Effects Related to Temperature Changes during MR Imaging", JMRI, vol. 2, No. 1, Jan./Feb. 1992, pp. 69-74.
John De Poorter, "Noninvasive MRI Thermometry with the Proton Resonance Frequency Method: Study of Susceptibility Effects", MRM 34:359-367 (1995), 9 pages.
Ron Corbett, et al., "Noninvasive Measurements of Human Brain Temperature Using Volume-Localized Proton Magnetic Resonance Spectroscopy", Journal of Cerebral Blood Flow and Metabolism, vol. 17, No. 4, 1997, pp. 363-369.
Waldemar Wlodarczyk, et al., "Comparison of four magnetic resonance methods for mapping small temperature changes", Phys. Med. Biol. 44, 1999, pp. 607-624.
Ferenc A. Jolesz, MD, et al., "MR Imaging of Laser-Tissue Interactions", Magnetic Resonance Imaging, Radiology 1988; 168, pp. 249-253.
Yoshimi Anzai, MD, et al., "Nd:YAG Interstitial Laser Phototherapy Guided by Magnetic Resonance Imaging in an Ex Vivo Model: Dosimetry of Laser-MR-Tissue Interaction", Laryngoscope 101: Jul. 1991, pp. 755-760.
Harvey E. Cline, et al., "MR-Guided Focused Ultrasound Surgery", Journal of Computer Assisted Tomography, Nov./Dec. 1992, vol. 16, No. 6, pp. 956-965.
Harvey E. Cline, PhD, et al., "Focused US System for MR Imaging-guided Tumor Ablation" Magnetic Resonance Imaging, Radiology 1995; Mar. 1995, vol. 194, No. 3, pp. 731-737.
Kullervo Hynynen, PhD, et al, " A Clinical, Noninvasive, MR Imaging-monitored Ultrasound Surgery Method", Imaging & Therapeutic Technology, RadioGraphics 1996; Jan. 1996, vol. 16, No. 1, pp. 185-195.
Nobuhiko Hata, et al., "Computer-Assisted Intra-Operative Magnetic Resonance Imaging Monitoring of Interstitial Laser Therapy in the Brain: A Case Report", Journal of Biomedical Optics, Jul. 1998, vol. 3, No. 3, pp. 304-311.
Joachim Kettenbach, Md, et al., "Monitoring and Visualization Techniques for MR-Guided Laser Ablations in an Open MR System" Journal of Magnetic Resonance Imaging, Jul./Aug. 1998, vol. 8, No. 4, pp. 933-943.
Ferenc A. Jolesz, MD, et al., "Integration of Interventional MRI with Computer-Assisted Surgery", Journal of Magnetic Resonance Imaging, Jan. 2001;13(1), pp. 69-77.
Frederic C. Vimeux, et al., "Real-Time Control of Focused Ultrasound Heating Based on Rapid MR Thermometry", Investigative Radiology, Mar. 1999, vol. 34(3), pp. 190-193.
J. Delannoy, et al., "Hyperthermia system combined with a magnetic resonance imaging unit", Medical Physics, vol. 17, No. 5, Sep./Oct. 1990, pp. 855-860.
Gary P. Zientara Ph.D., et al. "MRI-Monitoring of Laser Ablation Using Optical Flow", http://www.spl.harvard.edu/archive/spl-pre2007/pages/papers/zientara/of/optical-flow.html, 24 pages.
Alan R. Bleier, et al., "Real-Time Magnetic Resonance Imaging of Laser Heat Deposition in Tissue", Magnetic Resonance in Medicine 21, 1991, pp. 132-137.

(56) References Cited

OTHER PUBLICATIONS

Kullervo Hynynen, et al., "Focused Ultrasound Thermal Surgery Guided and Monitored by Magnetic Resonance Imaging", Interventional Radiology, 1997, vol. 2, Third Edition, pp. 1811-1816 (with cover pages).

Ferenc A. Jolesz, "MR-guided thermal ablation of brain tumors", Interventional MR: Techniques and Clinical Experience, 1998, pp. 123-129 (with cover pages).

F.A. Jolesz, et al., "Image-Guided Neurosurgery with Intraoperative MRI", Interventional Magnetic Resonance Imaging, 1998, pp. 253-260 (with cover pages).

Kullervo Hynynen, et al., "Principles of MR-Guided Focused Ultrasound", Chapter 25, Interventional MRI, 1999, pp. 237-243 (with cover pages).

Masoud Panjehpour, PhD et al., "Nd:YAG Laser-Induced Interstitial Hyperthermia Using a Long Frosted Contact Probe", Lasers in Surgery and Medicine 10, 1990, pp. 16-24.

S. Bosman, et al., "Effect of percutaneous interstitial thermal laser on normal liver of pigs: sonographic and histopathological correlations", Br. J. Surg., May 1991, vol. 78, No. 5, pp. 572-575.

M. Fan, M.D., et al., "Interstitial 1.06 Nd:YAG Laser Thermotherapy for Brain Tumors Under Real-Time Monitoring of MRI: Experimental Study and Phase I Clinical Trial", Journal of Clinical Laser Medicine & Surgery, vol. 10, No. 5, 1992, pp. 355-361.

\* cited by examiner

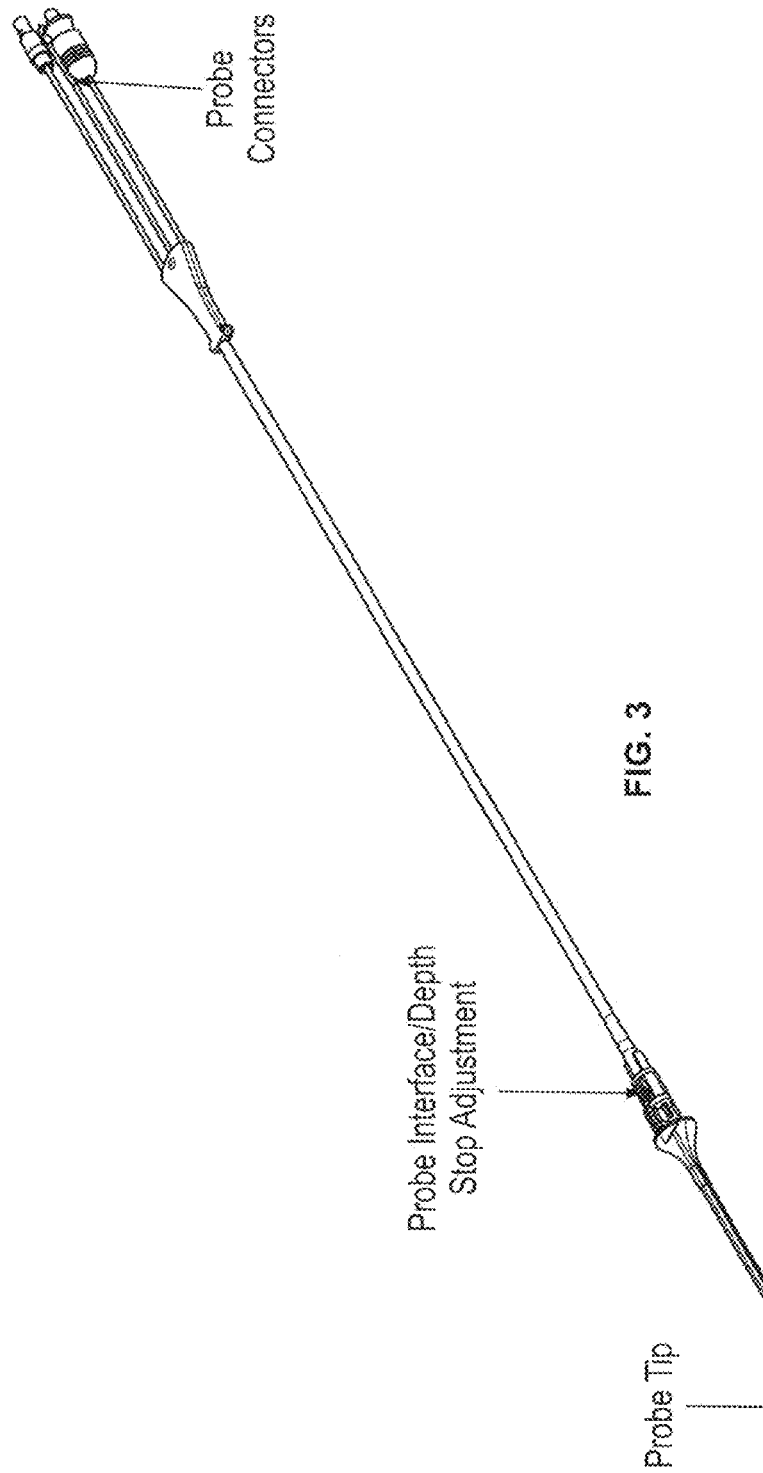
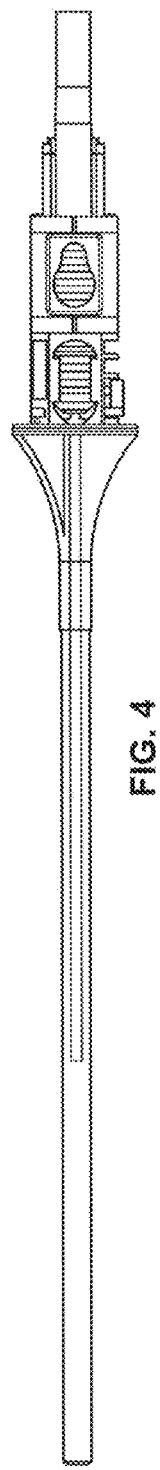
FIG. 3
FIG. 4

Unlocked

Unlocked

Locked

Locked

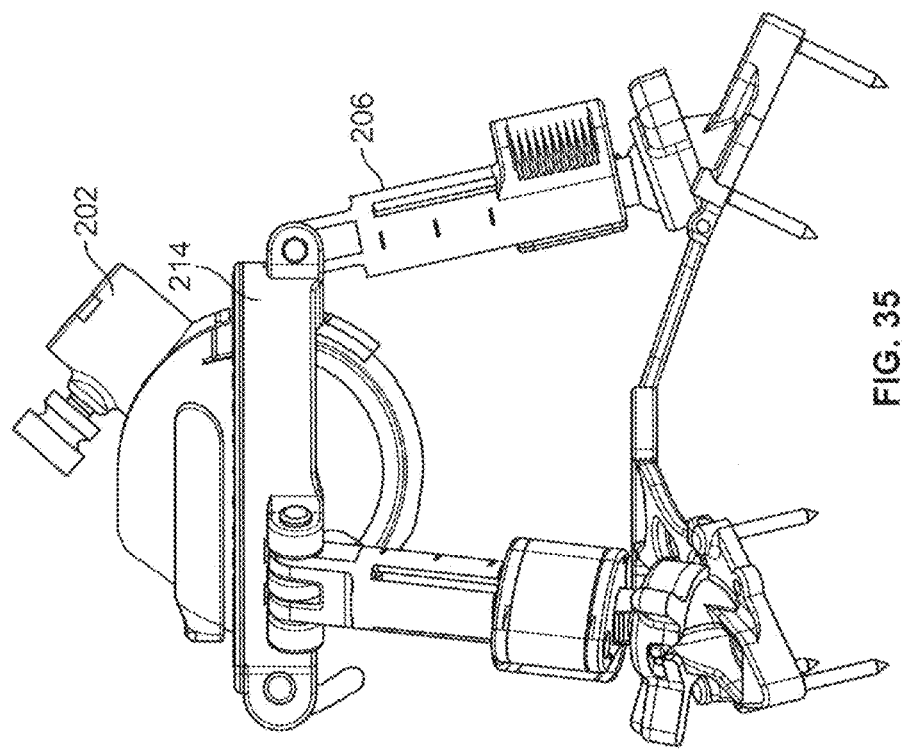
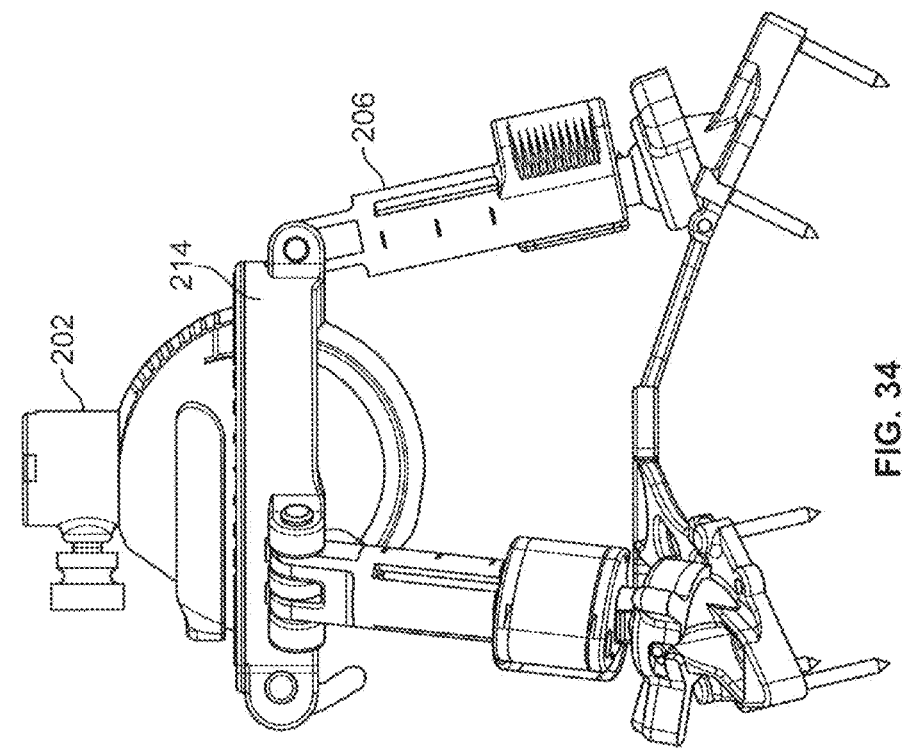

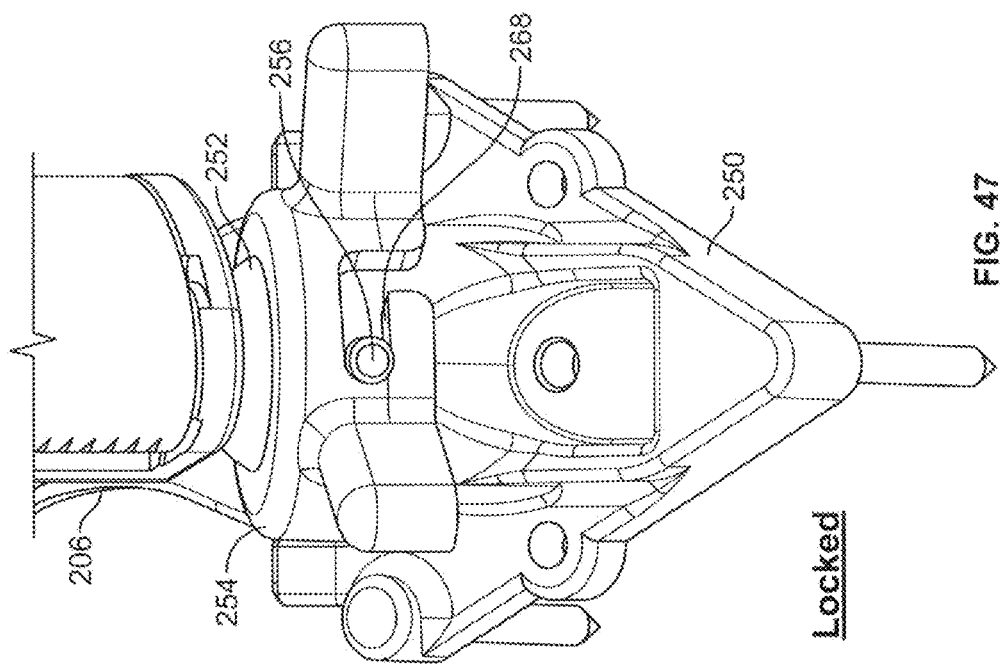
FIG. 46 Unlocked
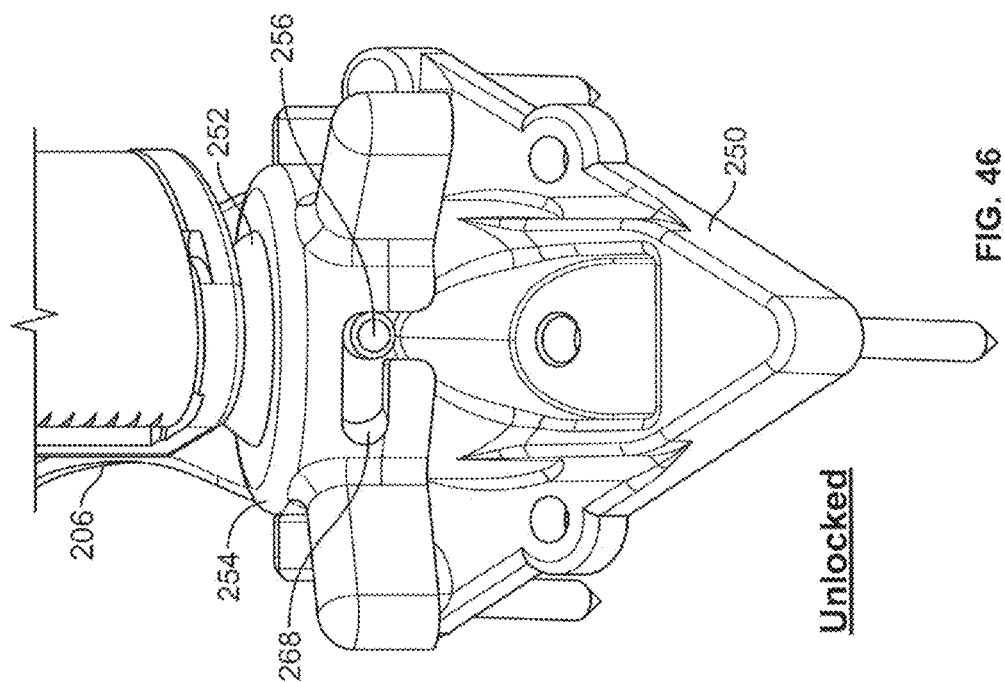
FIG. 47 Locked

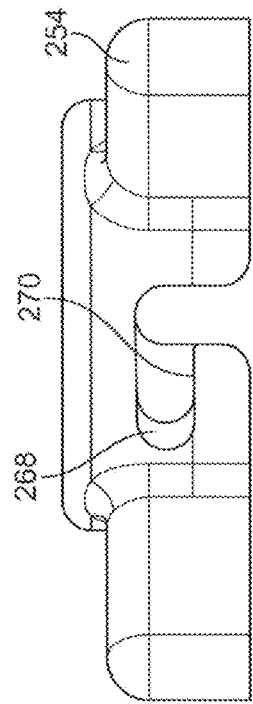
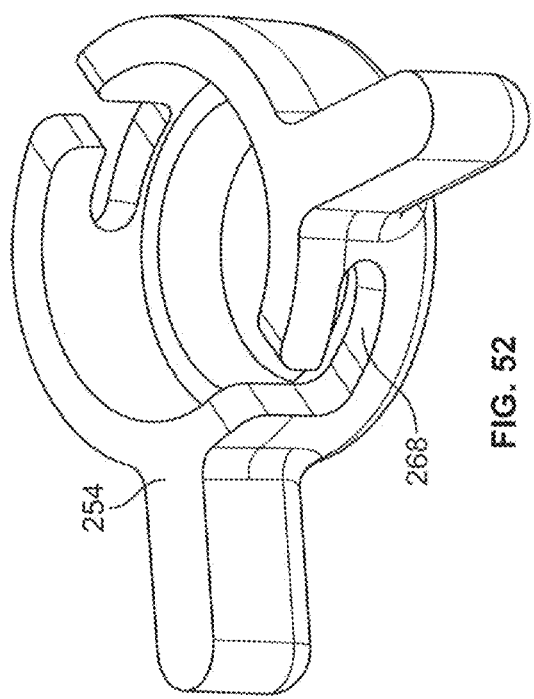
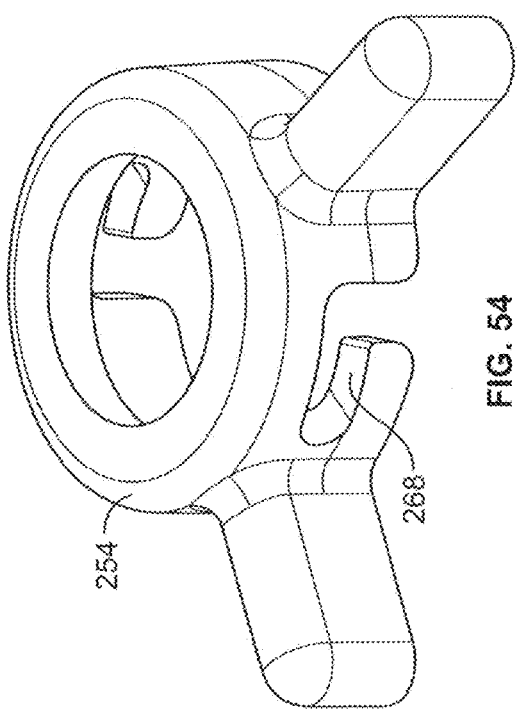

IMAGE-GUIDED THERAPY OF A TISSUE

CROSS-REFERENCE TO RELATED APPLICATIONS

This application relates to and incorporates by reference the disclosures of: U.S. Ser. No. 12/540,500, filed Aug. 13, 2009, published as US 2010/0042111; U.S. Ser. No. 12/540,558, filed Aug. 13, 2009, published as US 2010/0042112; PCT/IB2012/051716, filed Apr. 5, 2012, published as WO 2012/137179; U.S. Pat. No. 8,256,430, filed Dec. 17, 2007, issued Sep. 4, 2012; U.S. Pat. No. 7,691,100, filed Aug. 25, 2006, issued Apr. 6, 2010; U.S. Pat. No. 7,344,529, filed Nov. 5, 2003, issued Mar. 18, 2008; U.S. Pat. No. 7,167,741, filed Dec. 14, 2001, issued Jan. 23, 2007; and PCT/CA01/00905, filed Jun. 15, 2001, published as WO/2001/095821.

This application claims priority to and incorporates by reference U.S. 61/728,068, filed Nov. 19, 2012, U.S. 61/664,791, filed Jun. 27, 2012, and U.S. 61/759,197, filed Jan. 31, 2013.

BACKGROUND

Approximately 10% of cancerous brain tumors are "primary" tumors, meaning that the tumors originate in the brain. The primary tumors typically consist of brain tissue with mutated DNA that aggressively grows and displaces or replaces normal brain tissue. The most common of the primary tumors are known as gliomas, which indicate cancer of the glial cells of the brain. In most instances, primary tumors appear as single masses. However, these single masses can often be quite large, irregularly-shaped, multi-lobed and/or infiltrated into surrounding brain tissue.

Primary tumors are generally not diagnosed until the patient experiences symptoms, such as headaches, altered behavior, sensory impairment, or the like. However, by the time the symptoms develop the tumor may already be large and aggressive.

One well known treatment for cancerous brain tumors is surgery. Surgery involves a craniotomy (i.e., removal of a portion of the skull), dissection, and total or partial tumor resection. The objectives of surgery include removal or lessening of the number of active malignant cells within the brain, and a reduction in the pain or functional impairment due to the effect of the tumor on adjacent brain structures. However, by its very nature, surgery is highly invasive and risky. Furthermore, for some tumors surgery is often only partially effective. In other tumors, surgery itself may not be feasible. Surgery may risk impairment to the patient, it may not be tolerable by the patient, and/or it may involve significant costs and recovery.

Another well known treatment for cancerous brain tumors is stereotactic radiosurgery (SRS). In particular, SRS is a treatment method by which multiple intersecting beams of radiation are directed at the tumor such that the point of intersection of the beams receives a lethal dose of radiation, while tissue in the path of any single beam remains unharmed. SRS is non-invasive and is typically performed as a single outpatient procedure. However, confirmation that the tumor has been killed or neutralized is often not possible for several months post-treatment. Furthermore, in situations where high doses of radiation may be required to kill a tumor, such as in the case of multiple or recurring tumors, it is common for the patient to reach the toxic threshold prior to killing all of the tumors, where further radiation is inadvisable.

More recently, the treatment of tumors by heat (also referred to as hyperthermia or thermal therapy) has been developed. In particular, it is known that above 57° C. all living tissue is almost immediately and irreparably damaged and killed through a process called coagulation necrosis or ablation. Malignant tumors, because of their high vascularization and altered DNA, are more susceptible to heat-induced damage than normal tissue. Various types of energy sources may be used, such as laser, microwave, radiofrequency, electric, and ultrasound sources. Depending upon the application and the technology, the heat source may be extracorporeal (i.e., outside the body), extrastitial (i.e., outside the tumor), or interstitial (i.e., inside the tumor).

SUMMARY

One exemplary treatment of a tissue includes interstitial thermal therapy (ITT), which is a process designed to heat and destroy a tumor from within the tumor itself. In this type of therapy, energy may be applied directly to the tumor rather than passing through surrounding normal tissue, and energy deposition can be more likely to be extended throughout the entire tumor.

One exemplary ITT process begins by inserting an optical fiber into the tumor, wherein the tumor has an element at its "inserted" end that may redirect laser light from an exterior source in a direction generally at right angles to the length of the fiber. The energy from the laser may therefore extend into the tissue surrounding the end or tip and effects heating. The energy may be directed in a beam confined to a relatively shallow angle so that, as the fiber is rotated, the beam may also rotate around the axis of the fiber to effect heating of different parts of the tumor at positions around the fiber. The fiber may be moved longitudinally and rotated to effect heating of the tumor over a full volume of the tumor with the intention of heating the tumor to the required temperature. This may be done, in some aspects, without significantly affecting the surrounding tissue. An exemplary fiber used in the ITT process may be controlled and manipulated by a surgeon, in one implementation, with little or no guidance apart from the surgeon's knowledge of the anatomy of the patient and the location of the tumor. In another implementation, medical images may be used to provide guidance when applying the controlled heating. For example, a location of tumors and other lesions to be excised can be determined using a magnetic resonance imaging system (herein MRI). Utilizing MRI imaging in real time guidance may provide controlled accuracy, while contemporaneous thermography may provide accurate temperature information in determining whether a tissue has been ablated or necrotized.

A system or method for effecting treatment to a tissue can include an automated drive mechanism including a holder to hold a treatment device. The drive mechanism can be coupled to one or more wires or umbilicals such that a translation of the one or more wires or umbilicals effects one or more of a longitudinal displacement of the holder and a rotation of the holder.

The system or method may include a controller that may include an input interface to process position control signals for setting a position of the treatment device, and may further include an output interface to translate the one or more wires based on the position control signals.

The system or method may include a guide mechanism that may be attachable to a surface of a patient. The guide mechanism may include a base structure that may be configured to remain stationary relative to the patient when the guide mechanism is attached to the surface of the patient in a locked state. The guide mechanism may include a tilt portion that is coupled to the base structure. The tilt portion may be structured so as to hold the drive mechanism at a position that is separated from the surface of the patient. The tilt portion may provide an adjustable tilt between a trajectory of the drive mechanism and the base structure.

The guide mechanism may include a rotation portion that provides an adjustable rotation of the tilt portion relative to the base structure. The drive mechanism may be motorless and consist of thermal imaging compatible components. The drive mechanism may not include an electric motor, and may be included in an MRI or MRI head coil.

The controller may be configured to process a sequence of the position control signals to: move the holder to a first position for effecting the treatment to the tissue at a first portion of the tissue that coincides with the first position; and move the holder to a second position for effecting the treatment to the tissue at a second portion of the tissue that coincides with the second position.

A workstation may be included to transmit the position control signals to the controller and to display thermometry images of the tissue.

The workstation may continuously display the thermometry images of the tissue during the treatment to the tissue at the first and second portions of the tissue, and while the holder moves between the first and second positions.

An energy emission probe may be the treatment device, wherein the probe generates a plurality of different output patterns.

The probe may include a first laser fiber for outputting a symmetrical output pattern with respect to a longitudinal axis of the first laser fiber, and the probe may include a second laser fiber for outputting an asymmetrical output pattern with respect to a longitudinal axis of the second laser fiber.

A energy source may be included to generate energy for the probe. A workstation may be included to transmit the position control signals to the controller, and to transmit energy control signals to the energy source. The workstation may be configured to process a sequence of the energy control signals to: effect a symmetrical treatment to the tissue with the probe; and effect an asymmetrical treatment to the tissue with the probe after the symmetrical treatment.

The system or method may include a laser source to generate laser energy for the laser probe. The workstation may transmit the position control signals to the controller, and may transmit laser control signals to the laser source. The workstation may be configured to process a sequence of the position and laser control signals to: move the holder to a first position for effecting the treatment to the tissue at a first portion of the tissue that coincides with the first position; effect a symmetrical treatment to the first portion of the tissue with the first laser fiber; move the holder to a second position for effecting the treatment to the tissue at a second portion of the tissue that coincides with the second position; and effect an asymmetrical treatment to the second portion of the tissue with the second laser fiber.

The workstation may be configured to display thermometry images of the tissue continuously throughout processing of the sequence of the position and laser control signals and throughout moving the holder and effecting the symmetrical and asymmetrical treatments.

The system or method may include an imaging system to output images of the tissue and the treatment device, including thermometry images of the tissue, in real time, continuously throughout one or more steps of effecting the treatment to the tissue. The workstation may transmit the position control signals to the controller based on one or more of the images, as the images are received by the workstation in real time, and may display, in real time, one or more of the images throughout the one or more steps of effecting the treatment to the tissue.

The workstation may display, in real time, the thermometry images of the tissue with the images of the tissue and the treatment device continuously throughout a processing of the position control signals and throughout moving the holder and effecting the treatment to the tissue.

The workstation may process, in real time, the images of the tissue and the treatment device and the thermometry images of the tissue to forecast errors or interruptions in the treatment to the tissue and display a corresponding warning.

The system or method may include an energy emission probe as the treatment device. The energy emission probe may include one or more emitters selected from: a laser fiber, a radiofrequency emitter, a high-intensity focused ultrasound emitter, a microwave emitter, a cryogenic cooling device, and a photodynamic therapy light emitter.

The energy emission probe may include a plurality of the emitters, where the plurality of the emitters may be longitudinally spaced with respect to a longitudinal axis of the energy emission probe.

The system or method may include a guide sheath including a plurality of probes of different modalities as the treatment device. The modalities may include one or more of: laser, radiofrequency, high-intensity focused ultrasound, microwave, cryogenic, photodynamic therapy, chemical release and drug release.

The guide sheath may include one or more off-axis holes for positioning an emitting point of one or more of the plurality of probes at an off-axis angle.

The system or method may include one or more processors and circuits that embody portions of aspects of various functions by executing corresponding code, instructions and/or software stored on tangible memories or other storage products. A display may include various flat-panel displays, including liquid crystal displays.

The foregoing general description of the illustrative implementations and the following detailed description thereof are merely exemplary aspects of the teachings of this disclosure, and are not restrictive.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

A more complete appreciation of this disclosure and many of the attendant features thereof will be readily obtained as the same becomes better understood by reference to the following detailed description when considered in connection with the accompanying drawings, wherein:

FIGS. 3-4 illustrate components of an exemplary probe;

FIG. 34 is a side profile view of a tilt portion of a miniframe in a first tilt position;

FIG. 35 is a side profile view of a tilt portion of a miniframe in a second tilt position;

FIG. 46 is perspective view of a foot attached to a leg in an unlocked configuration;

FIG. 47 is perspective view of a foot attached to a leg in a locked configuration;

FIGS. 52-54 are, respectively, a bottom perspective view, a top perspective view, and a side view of a foot cap;

DETAILED DESCRIPTION OF THE ILLUSTRATIVE EMBODIMENTS

Figure 1:
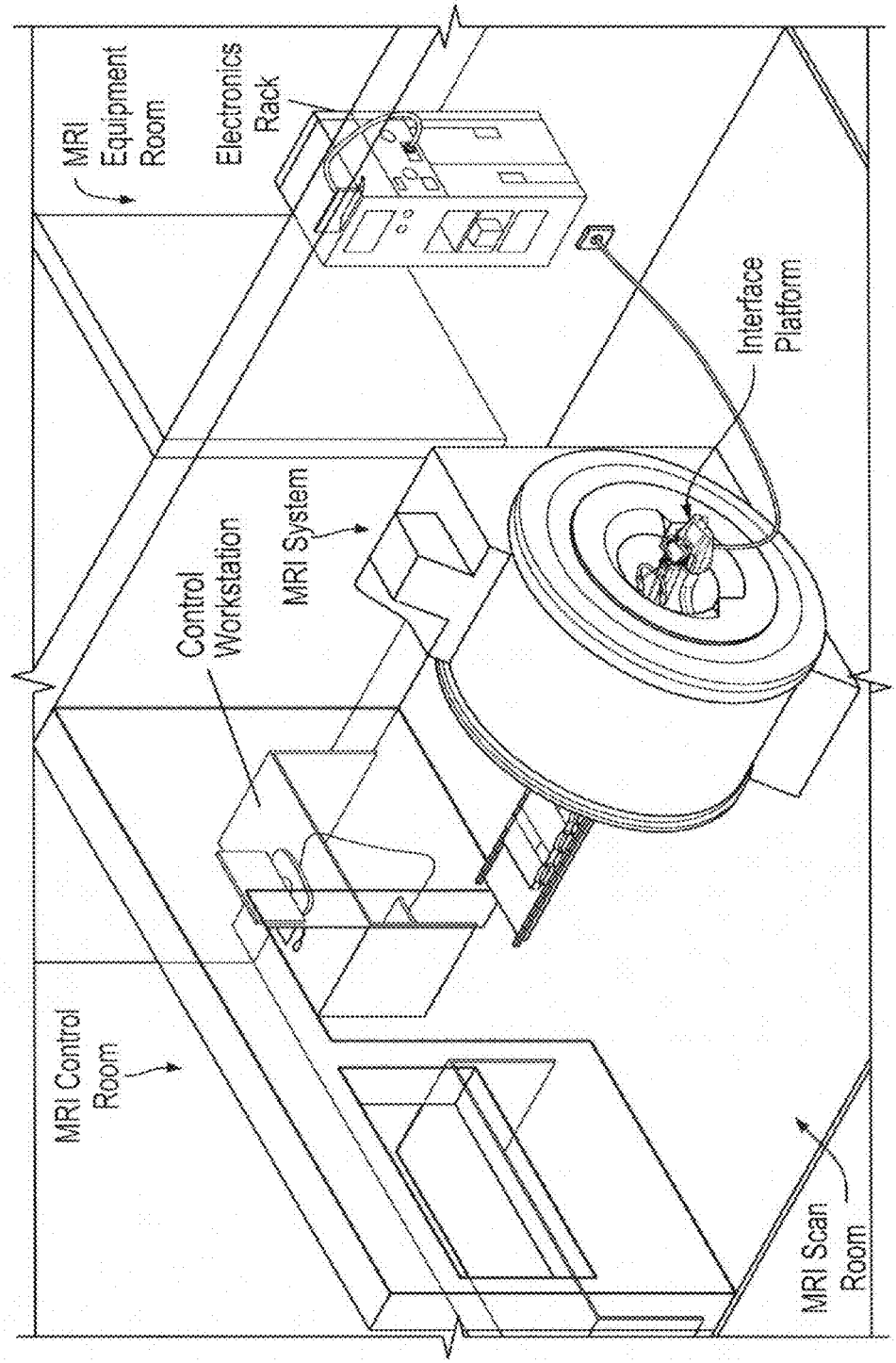
FIG. 1 is an illustration of exemplary relative locations of an MRI Control Room, an MRI Scan Room, and an MRI Equipment Room.

In the drawings, like reference numerals designate identical or corresponding parts throughout the several views. Further, as used herein, the words "a," "an" and the like generally carry a meaning of "one or more," unless stated otherwise.

Further, in individual drawings figures, the components/features shown are drawn to scale to exemplify a particular implementation. For some drawings, components/features are drawn to scale across separate drawing figures. However, for other drawings, components/features are shown magnified with respect to one or more other drawings. Measurements and ranges described herein relate to exemplary implementations and can identify a value or values within a range of 1%, 2%, 3%, 4%, 5%, or, preferably, 1.5% of the specified value(s) in some implementations.

I. SYSTEM AND WORKFLOW

System

A system in accordance with this disclosure incorporates magnetic resonance imaging (MRI) compatible laser devices and accessories for effective and controlled delivery of thermal therapy to a wide range of locations and tumor sizes within a brain. The system, however, is not limited to MRI-guided thermal therapy, as other therapies such as computer tomography (CT) can also be utilized. Further, this disclosure refers to an MRI scanner as an exemplary medical imaging machine, which may be referred to simply as an MRI.

The system includes an interface platform (herein an interface platform or interface console), a system electronics rack and components (herein rack), a control workstation (herein workstation), a probe driver, and a probe. The system can also include a stereotactic miniframe, a head coil and stabilization system (herein stabilization system), an instrument adaptor, and an MRI trajectory wand. All of the above components are MRI compatible, which refers to a capability or limited capability of a component to be used in an MRI environment. For example, an MRI compatible component operates and does not create significant interference with MRI in exemplary magnetic flux densities of 1.5 T or 3.0 T, where no hazards are known for a specified environment (e.g., 1.5 T or 3.0 T). Compatibility can also be defined with respect to other magnetic flux densities, including 0.5 T, 0.75 T, 1.0 T, 2 T or 5 T. "MRI Safe" refers to an item that poses no known hazards in all MR environments. "MRI Unsafe" refers to an item that is not MRI compatible and is known to pose a hazard in MR environments. This equipment should not be taken into the MRI room within a 5 Gauss perimeter line.

The interface platform attaches to an MRI patient table and provides supporting electronics for the probe driver and interconnections for the probe. The system electronics rack includes necessary cables, penetration panels and small hardware for system mechanical, electrical, and electronic operation. The workstation includes a user interface, e.g., a graphical user interface (GUI), for procedure planning, interactive monitoring of procedures, and interfaces to the MRI and hardware subsystems. The probe driver allows for precise positioning, stabilization and manipulation of a probe. The probe can be a gas-cooled probe for delivering controlled energy to a tissue. As discussed in Section IV, the length and diameter of the probe can be pre-selected and varied.

The stereotactic miniframe includes at least a portion that is MRI visible and used for trajectory determination, alignment, and guidance of the probe. The stabilization system is a head fixation device to immobilize a patient's head. The instrument adaptor can include a set of three reducing tubes of, e.g., 1.9±0.2 mm, 2.2±0.2 mm and 2.6±0.2 mm, that guide neurosurgical devices such as a biopsy needle through the stereotactic miniframe. The MRI trajectory wand is an MRI visible, fluid-filled tube which is placed into the stereotactic miniframe to allow trajectory confirmation of intended alignment to the target via MRI.

Exemplary MRI systems that can be utilized together with the features discussed herein include those manufactured by Siemens AG, Munich, Germany (including the MAGNETOM AVANTO, TRIO, ESPREE, VERIO MRI Systems, which are trademarks and/or trade names of Siemens AG). Further, exemplary MRI systems include those manufactured by General Electric Company, Fairfield, Conn. (including the SIGNA, OPTIMA and DISCOVERY MRI systems, which are trademarks and/or trade names of General Electric Company).

FIG. 1 illustrates an exemplary layout of various MRI components, including the MRI system in an MRI scan room, a control workstation in an MRI control room, and an electronics rack in an MRI equipment room. Also shown in FIG. 1 is an interface platform secured to a patient table of the MRI system.

Figure 2:
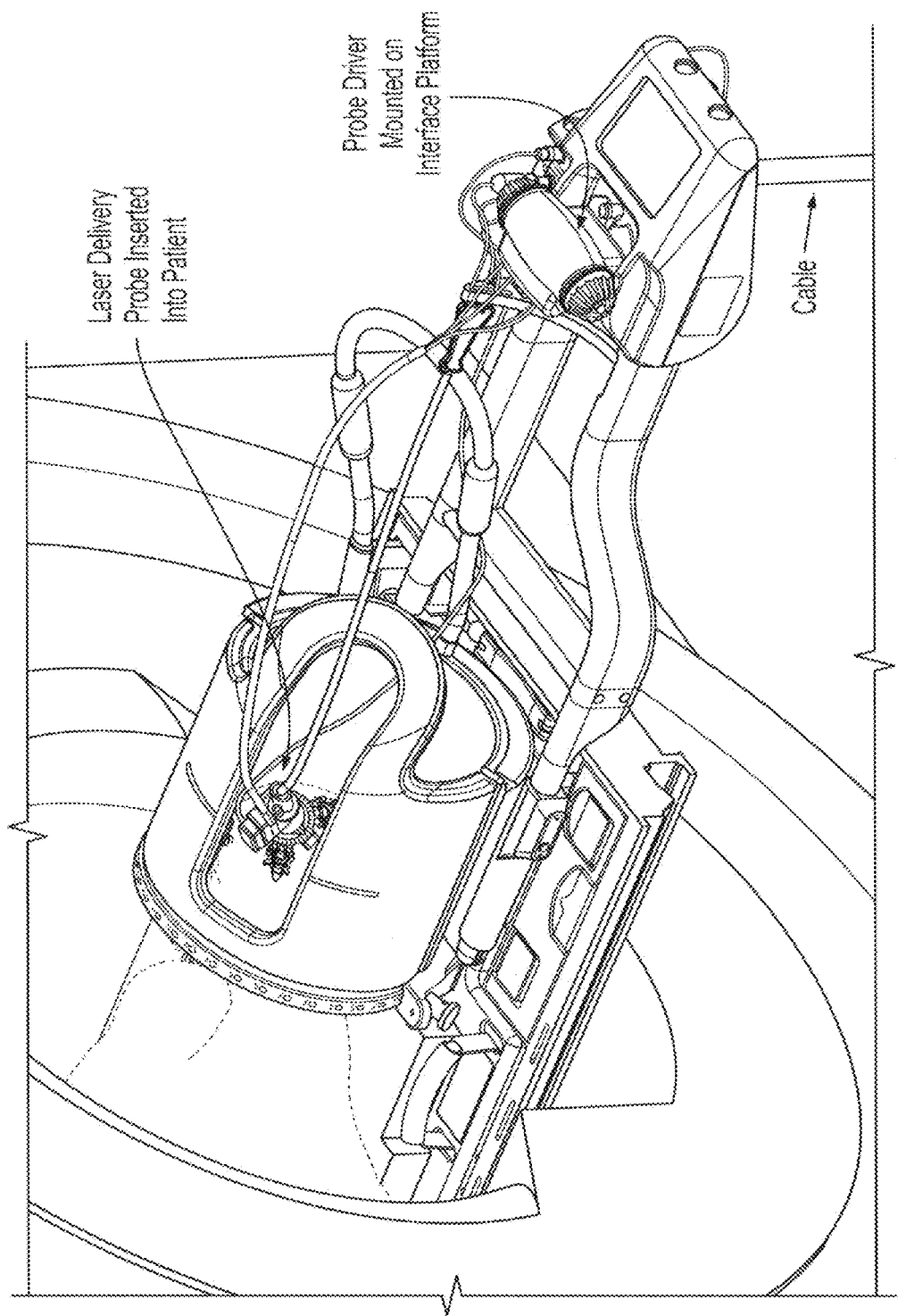
FIG. 2 is an illustration of a patient inserted into an MRI system.

FIG. 2 illustrates an exemplary layout of a patient on a patient table of an MRI system. An interface platform is secured to the patient table together with a head coil and stabilization system. A probe and probe driver are coupled to a stereotactic miniframe, and to the interface platform via umbilicals. A cable provides data, laser, fluid, etc. connections between these components and the electronics rack in the MRI equipment room.

The probe can be a laser delivery probe that is used to deliver laser interstitial thermal therapy. The probe is preferably composed of MR compatible materials allowing for simultaneous laser application and thermal imaging, and can be provided in multiple lengths and dimensions. FIGS. 3 and 4 illustrate exemplary aspects of a laser probe. Other types of probes that can be utilized with the components and procedures discussed herein include radiofrequency (RF), high-intensity focused ultrasound (HiFu), microwave, cryogenic, chemical release, which may include photodynamic therapy (PDT), and drug releasing probes. For example, modalities of probes other than a laser energy modality can be utilized. Treatments in accordance with the descriptions provided in this disclosure include treatments that ablate (i.e., "treat") a tissue to destroy, inhibit and/or stop one or more or all biological functions of the tissue. Ablation agents include, but are not limited to, laser, RF, HiFu, microwave, cryogenic, PDT and drug or chemical release. A corresponding probe and/or an other instrument, such as a needle, fiber or intravenous line can be utilized to effect treatment by one or more of these ablation agents.

A probe tip is shown in FIG. 3, which indicates an insertion end. A probe interface/depth stop adjustment provides an interface for cabling, as well as for alignment with the probe driver and/or the stereotactic miniframe. An end opposite the insertion end includes probe connectors for energy delivery, cooling, etc. FIG. 4 is an enlarged view of the probe interface to probe tip portion of the probe shown in FIG. 3.

Figure 5:
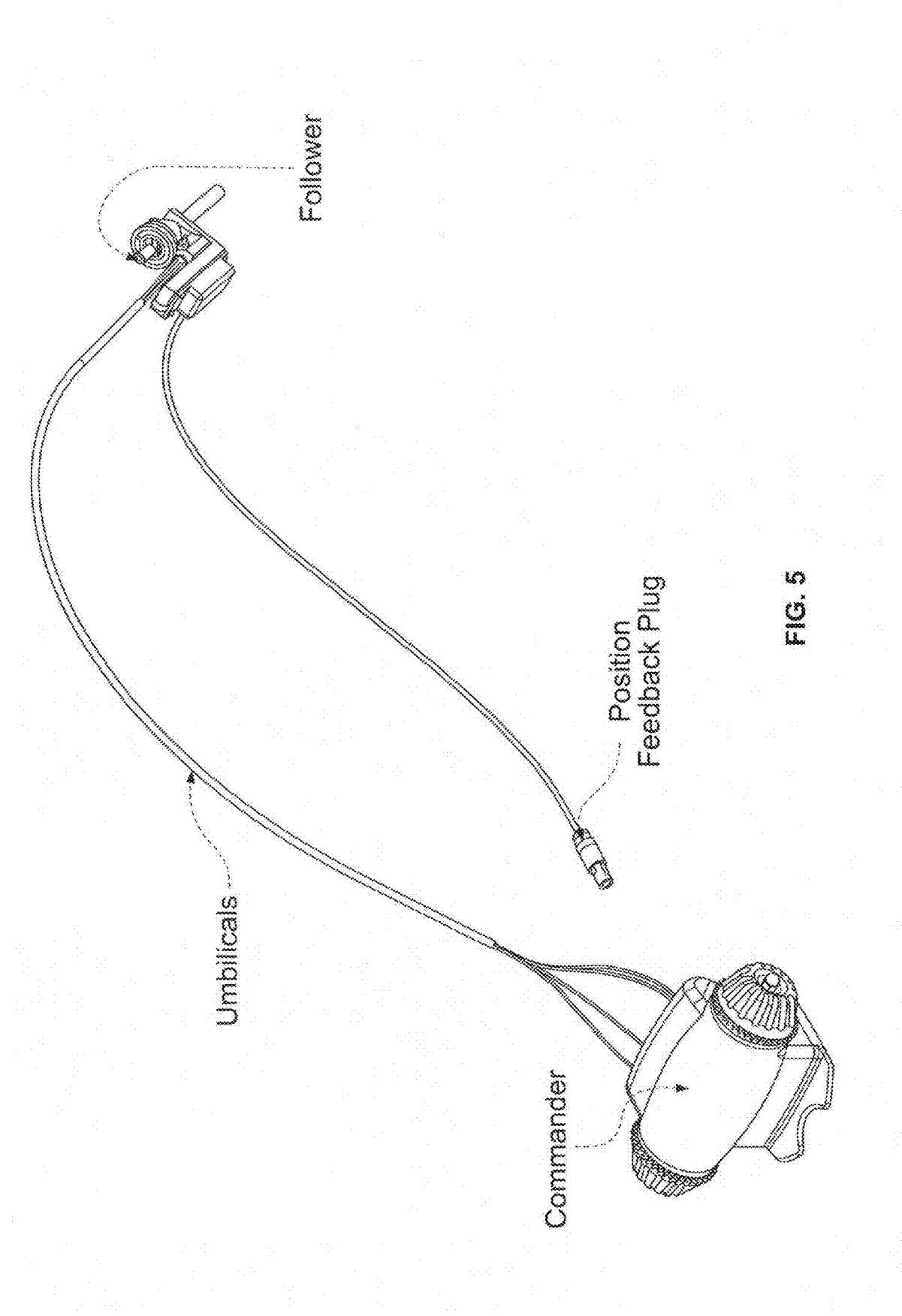
FIG. 5 illustrates a probe driver.

FIG. 5 illustrates a probe driver, which generally includes a commander, umbilicals, a follower, and a position feedback plug that receives position feedback signals from potentiometers within the follower. A probe can be inserted into the follower, and the follower can control a rotational and longitudinal alignment of the probe.

The probe driver is mounted to the interface platform, as shown for example in FIG. 2. A position feedback plug connects to the interface platform in order to communicate the probe's position to the system. The probe driver is used to rotate or translate (extended or retract) the probe. The probe driver in this illustrated implementation can provide, at a minimum, a translation of 20-80 mm, 30-70 mm, 40-60 mm or 40 mm, with a maximum translation of 60 mm, 80 mm, 100 mm, 120 mm or 60-150 mm. The probe driver in this illustrated implementation can also provide, at a minimum, a rotation of 300°-340°, with a maximum rotation of 350°, 359°, 360°, 540°, 720° or angles therebetween. The probe driver is comprised of the commander and the follower connected by an umbilical cable (umbilicals). Included with the probe driver can be a rotary test tool that can be used during a self-test procedure to simulate an attachment of a probe to the follower.

Figure 6:
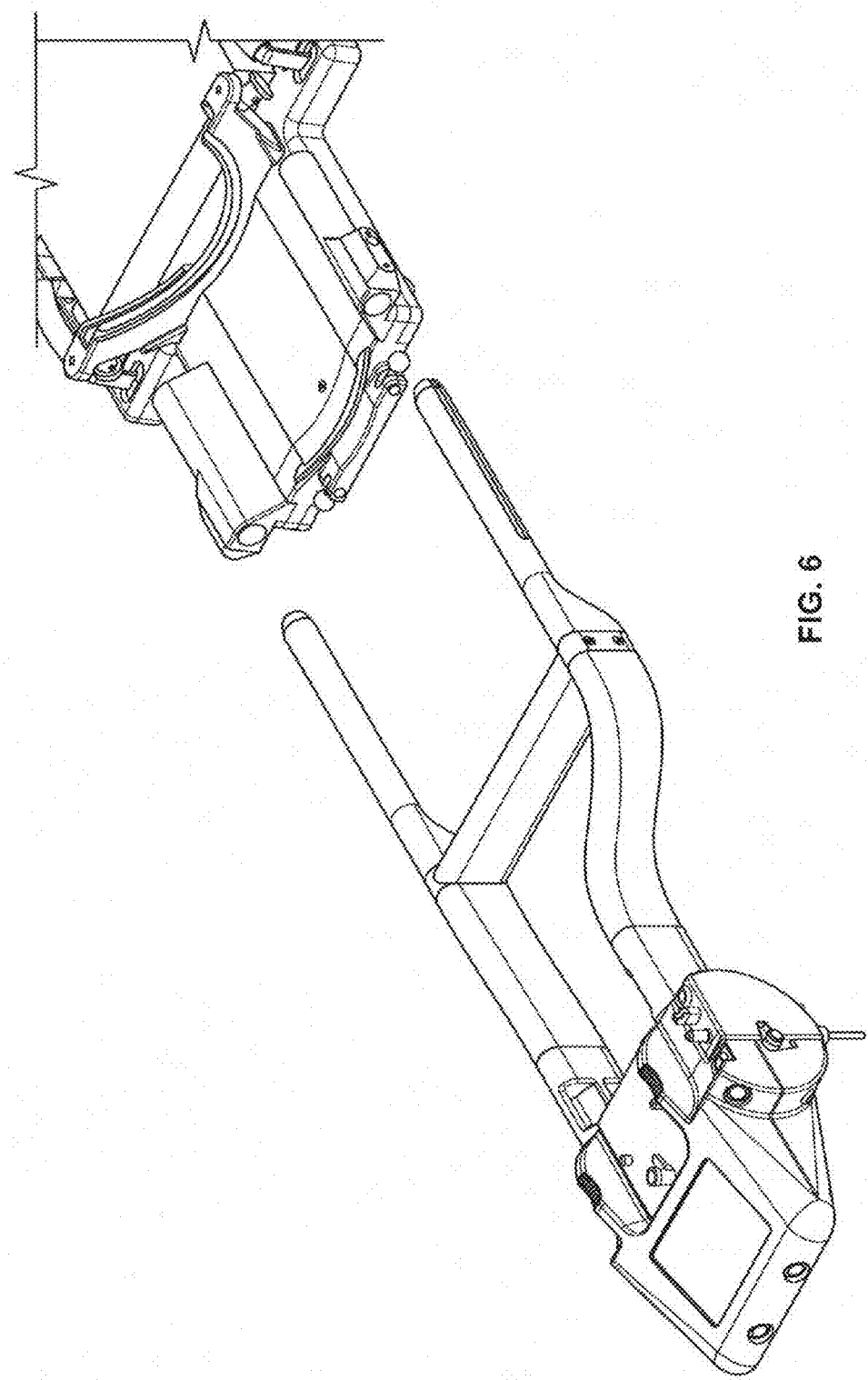
FIG. 6 illustrates an interface platform disconnected from a patient platform of a stabilization system.

FIG. 6 illustrates a coupling between an interface platform and a head end of a stabilization system. An attachment of the interface platform to the head end of the stabilization system can be performed by sliding two interface platform arms into two corresponding receptacles of the stabilization system.

Figure 7A:
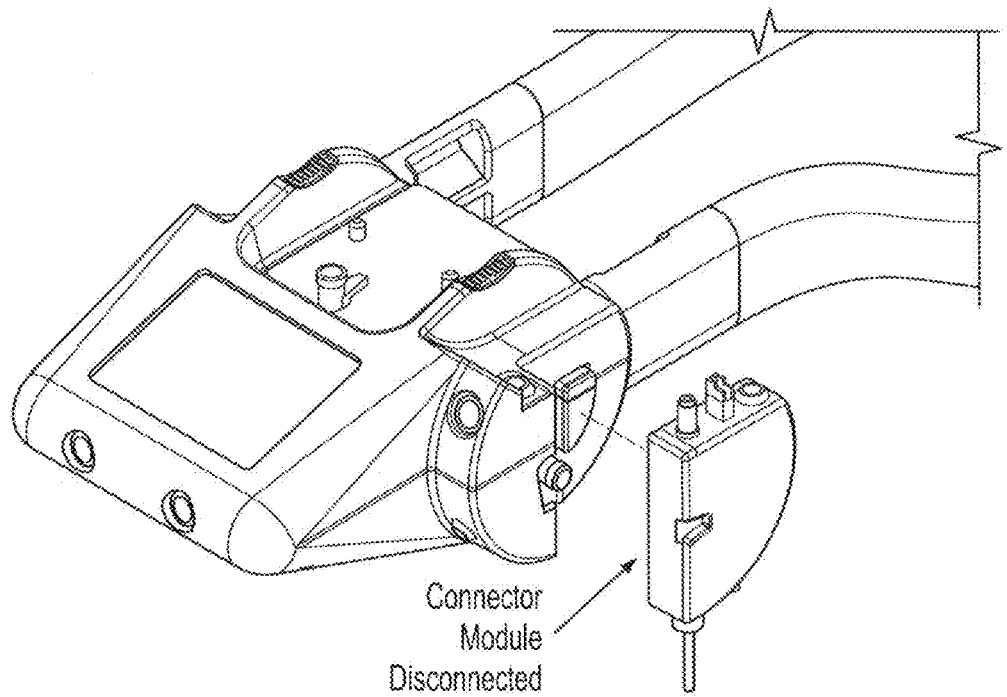
FIGS. 7A-7B illustrate a connector module being connected/disconnected to an interface platform.
Figure 7B:
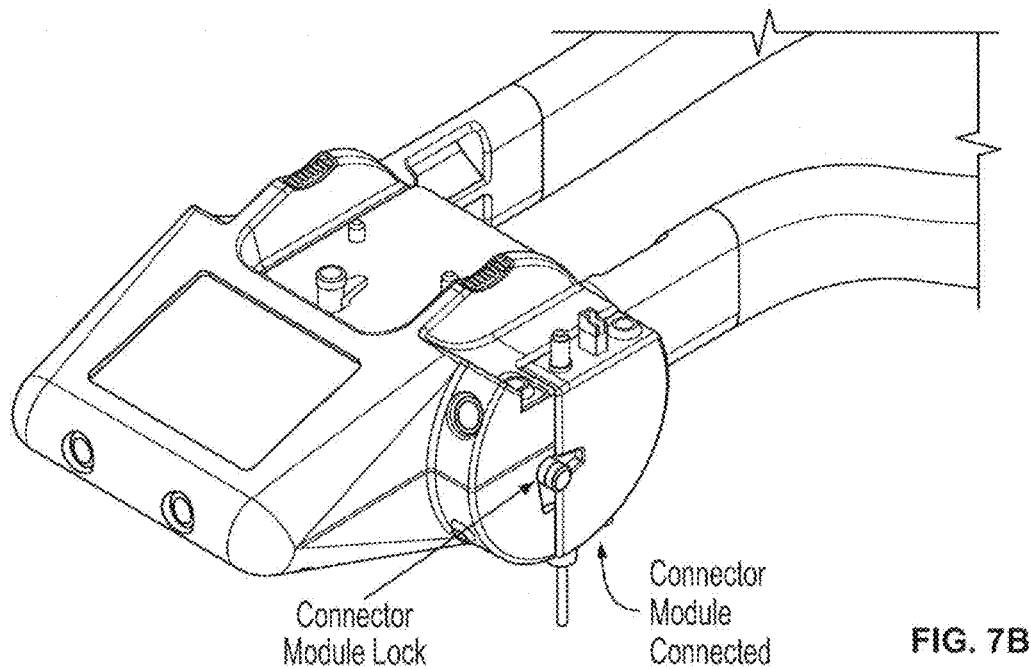

FIGS. 7a-7b illustrate an interface platform connector module of interface platform, which is detachably connected to the interface platform by a locking mechanism. This module is capable of accepting probe extension lines/cables. The connector module can be locked in place by twisting the connector module lock 80-100° or 90° counterclockwise.

Figure 8:
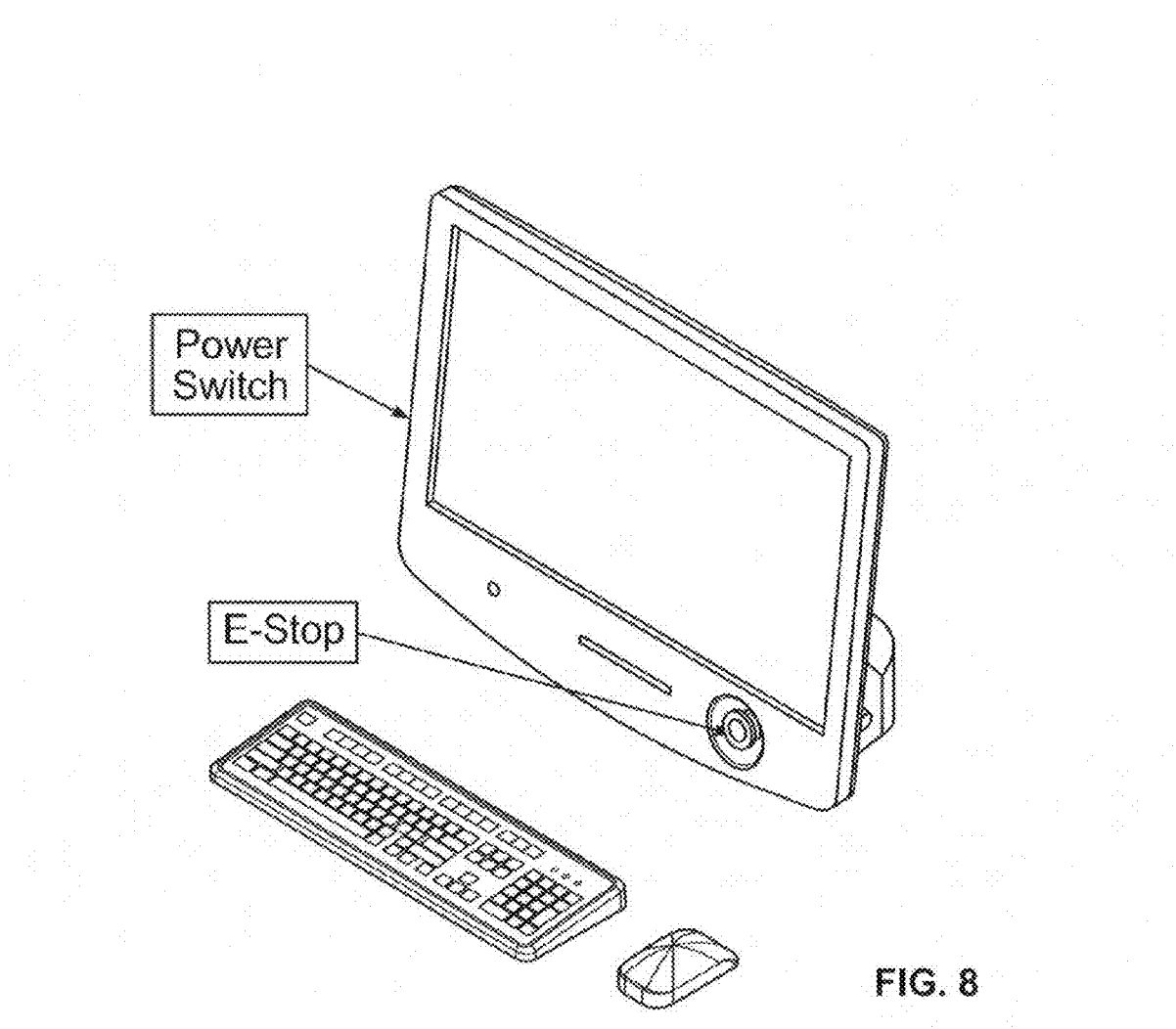
FIG. 8 illustrates a workstation.

FIG. 8 illustrates an exemplary workstation situated in the MRI control room. The workstation can include an emergency stop (E-Stop) switch, which includes a red light to indicate that it is on (i.e., the presence of the red light indicates the system and/or the MRI system has been stopped via the emergency stop switch). To release the switch, the emergency stop switch can be twisted clockwise. The workstation can also include a power switch at the side of a monitor.

Figure 9:
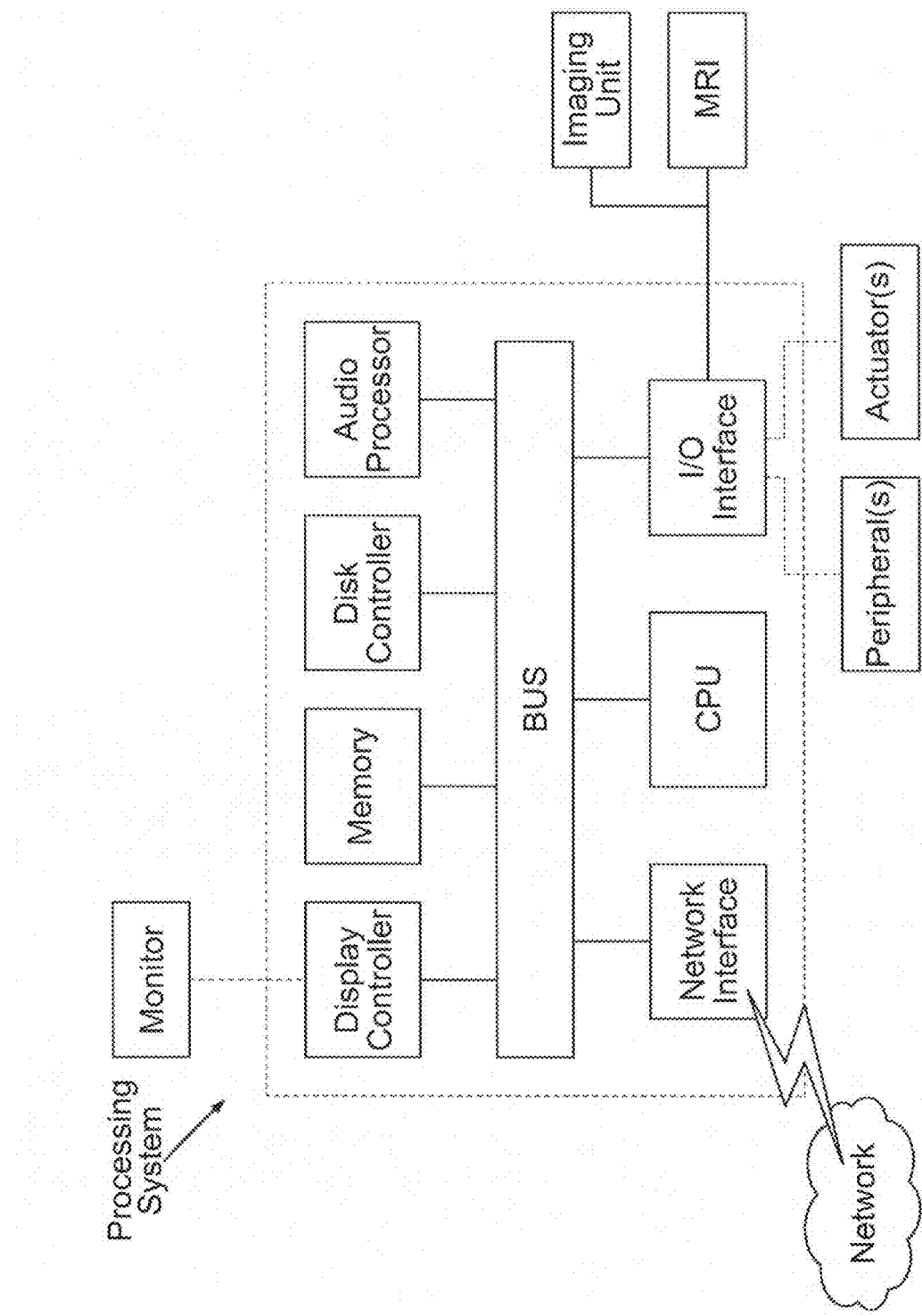
FIG. 9 illustrates exemplary hardware of a workstation.

FIG. 9 illustrates an exemplary processing system, and illustrates exemplary hardware found in a controller or computing system (such as a personal computer, i.e., a laptop or desktop computer, which can embody a workstation according to this disclosure) for implementing and/or executing the processes, algorithms and/or methods described in this disclosure. A processing system in accordance with this disclosure can be implemented in one or more the components shown in FIG. 1. One or more processing systems can be provided to collectively and/or cooperatively implement the processes and algorithms discussed herein.

As shown in FIG. 9, a processing system in accordance with this disclosure can be implemented using a microprocessor or its equivalent, such as a central processing unit (CPU) and/or at least one application specific processor ASP (not shown). The microprocessor is a circuit that utilizes a computer readable storage medium, such as a memory circuit (e.g., ROM, EPROM, EEPROM, flash memory, static memory, DRAM, SDRAM, and their equivalents), configured to control the microprocessor to perform and/or control the processes and systems of this disclosure. Other storage mediums can be controlled via a controller, such as a disk controller, which can controls a hard disk drive or optical disk drive.

The microprocessor or aspects thereof, in an alternate implementations, can include or exclusively include a logic device for augmenting or fully implementing this disclosure. Such a logic device includes, but is not limited to, an application-specific integrated circuit (ASIC), a field programmable gate array (FPGA), a generic-array of logic (GAL), and their equivalents. The microprocessor can be a separate device or a single processing mechanism. Further, this disclosure can benefit from parallel processing capabilities of a multi-cored CPU.

In another aspect, results of processing in accordance with this disclosure can be displayed via a display controller to a monitor. The display controller preferably includes at least one graphic processing unit, which can be provided by a plurality of graphics processing cores, for improved computational efficiency. Additionally, an I/O (input/output) interface is provided for inputting signals and/or data from microphones, speakers, cameras, a mouse, a keyboard, a touch-based display or pad interface, etc., which can be connected to the I/O interface as a peripheral. For example, a keyboard or a pointing device for controlling parameters of the various processes and algorithms of this disclosure can be connected to the I/O interface to provide additional functionality and configuration options, or control display characteristics. Moreover, the monitor can be provided with a touch-sensitive interface for providing a command/instruction interface.

The above-noted components can be coupled to a network, such as the Internet or a local intranet, via a network interface for the transmission or reception of data, including controllable parameters. A central BUS is provided to connect the above hardware components together and provides at least one path for digital communication there between.

The workstation shown in FIG. 8 can be implemented using one or more processing systems in accordance with that shown in FIG. 9. Further, one or more processors can be utilized to implement any functions and/or algorithms described herein, unless explicitly stated otherwise. Also, the equipment rack and the interface platform each include hardware similar to that shown in FIG. 9, with appropriate changes to control specific hardware thereof.

In some aspects, the workstation outputs signals to the MRI system to actuate particular imaging tasks or to an intermediary system that causes the MRI system to actuate particular imaging tasks. Further, in some aspects, the workstation outputs signals to the electronics rack. The electronics rack includes various actuators and controllers for controlling, e.g., a cooling fluid pressure and a flow rate of the cooling fluid, and a power source that outputs ablative energy. In utilizing a laser probe, the power source is a laser source that outputs light via an optical fiber. As illustrated in FIG. 1, the electronics rack is located in the MRI Equipment Room and includes storage tanks to hold the cooling fluid, one or more inputs to receive signals from the control workstation and/or a separate MRI workstation, a laser generating device, and an output section. The output section includes data and laser output cables that are routed to corresponding components in the MRI Scan Room through an appropriate portal to minimize interface with or by the MRI system. As discussed in other portions of this disclosure, the cables are connected at or by the interface platform to corresponding components to effect and actuate control of the components.

Figure 10:
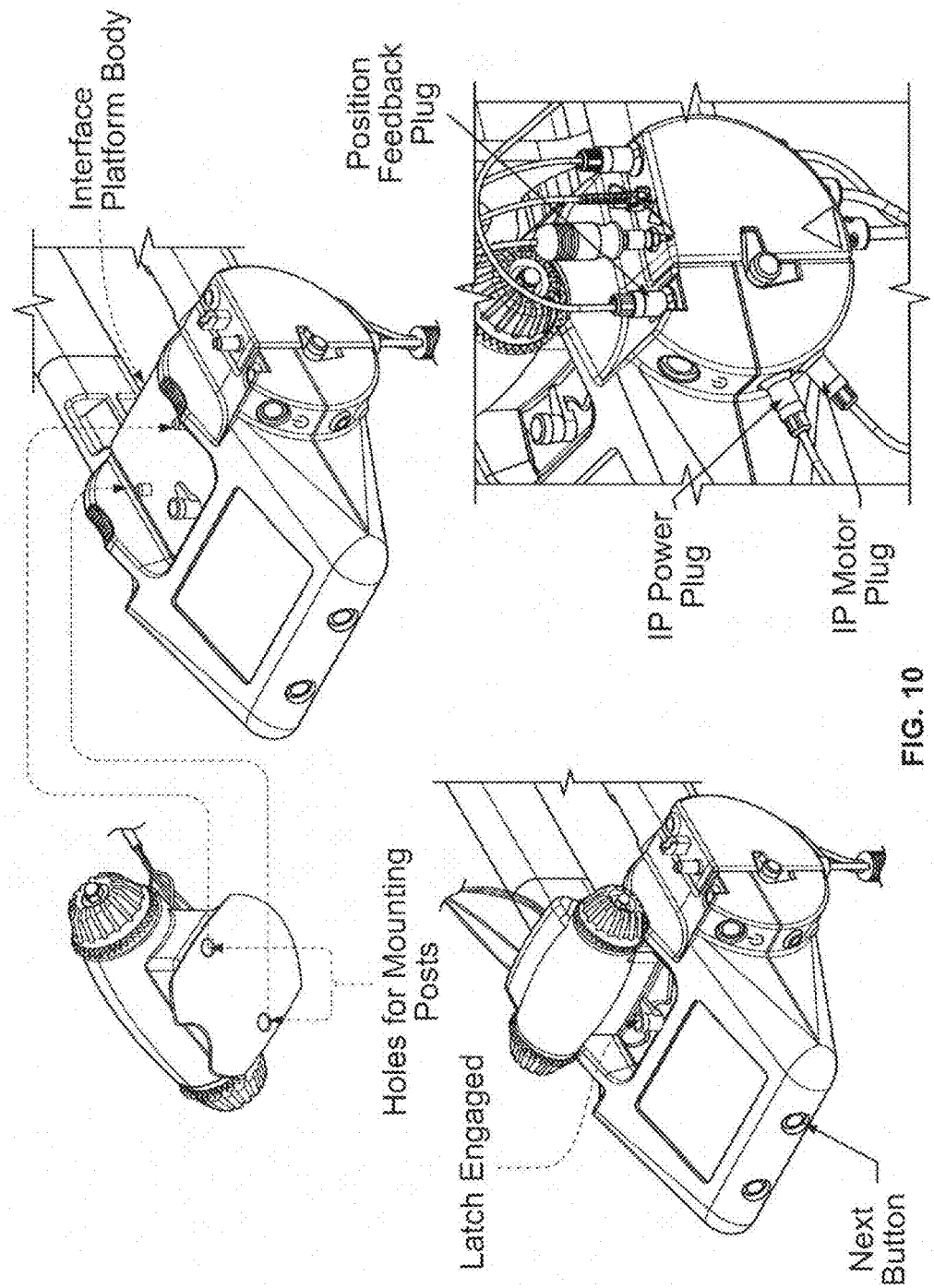
FIG. 10 illustrates a commander/interface platform engagement.

FIG. 10 illustrates the connecting of a commander to an interface platform, and the attachment of a position feedback line and probe lines to the interface platform and/or the connector module thereof. In these drawings "IP" refers to the interface platform. The commander includes holes for mounting posts of the interface platform body, and a latch of the interface platform engages the commander when the commander is properly inserted. Consistent with the descriptions provided in Section III, the commander includes knobs or dials that are coupled to a drive system of the IP. Command signals to actuate the drive system from, e.g., the workstation, are transmitted or routed to the IP, causing the drive system to operate one or both of the knobs or dials to effect movement of a probe or other member attached to the probe driver follower in accordance with the disclosures provided herein.

Figure 11A:
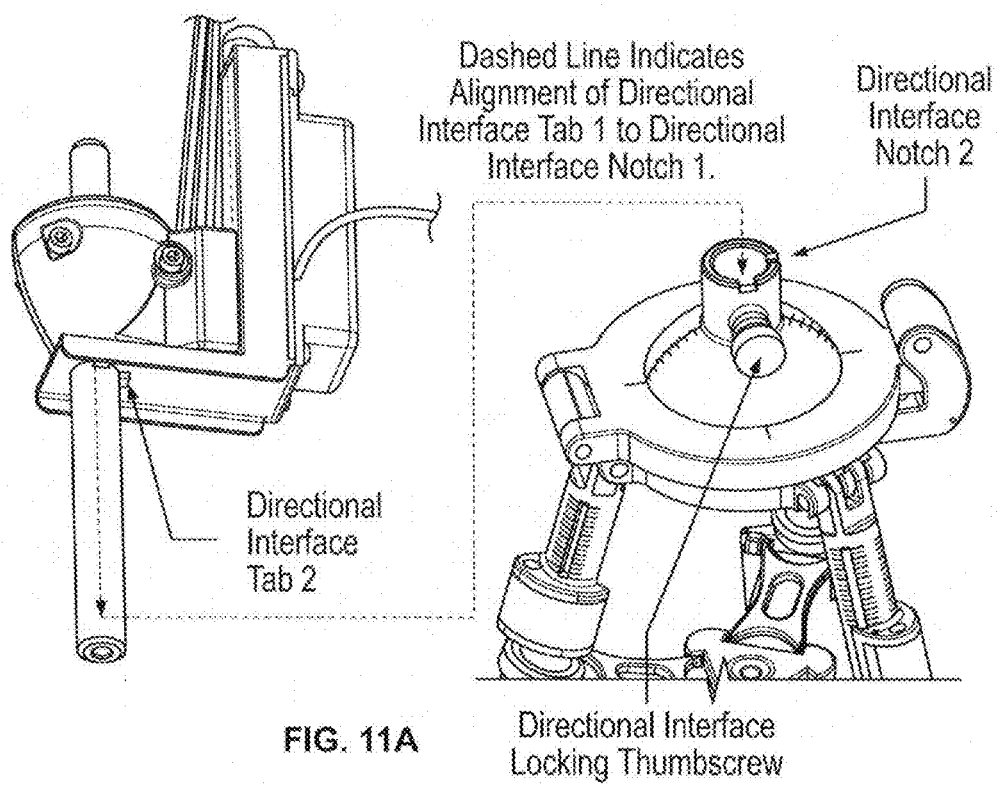
FIG. 11A illustrates a probe follower being aligned with a miniframe.
Figure 11B:
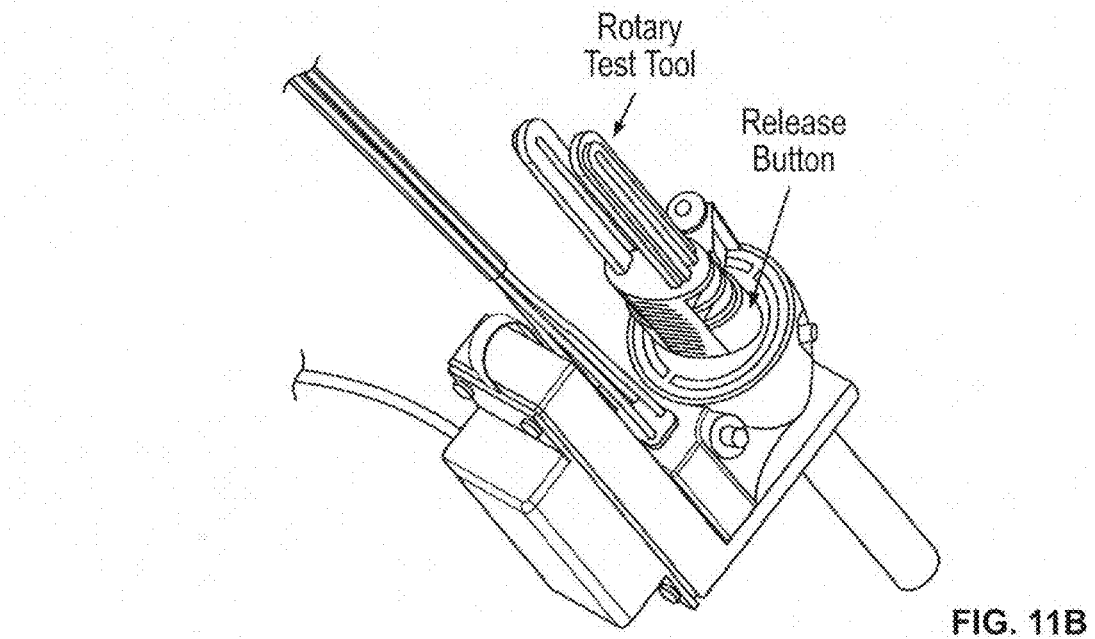
FIG. 11B illustrates a rotary test tool for a probe follower.

FIGS. 11*a* and 11*b* illustrate a coupling between the follower, which includes directional interface tabs 1 and 2, and a stereotactic miniframe, which includes directional interface notches 1 and 2, to ensure a proper registered alignment between the follower and the stereotactic miniframe. The miniframe also includes a directional interface locking thumbscrew to secure the follower to the miniframe. FIG. 11*b* illustrates the attachment of a rotary test tool to the follower to provide position feedback for a probe driver self-test procedure.

This self-test procedure can be executed via software that is displayed/illustrated to a user via the workstation and/or via the interface platform. After attaching the commander of the probe driver to the interface platform and the stereotactic miniframe, directional control and commands from the commander, the interface platform, and/or the workstation can be verified with the rotary test tool.

For installation of the above components, the follower should be kept sterile and manipulated by a sterile person, while the commander can be passed to a non-sterile person. The non-sterile person attaches the commander to the interface platform and engages the latch to lock the commander in place by twisting the latch to the centered position, as shown in FIG. 10. FIG. 10 further illustrates the attachment of a position feedback line and probe lines to the interface platform and/or the connector module thereof. In these drawings "IP" refers to the interface platform. The commander includes holes for mounting posts of the interface platform body, and a latch of the interface platform engages the commander when the commander is properly inserted.

As illustrated in FIG. 11a, the sterile person slides the sterile follower into the directional interface of the miniframe until the directional interface tabs are oriented and fully seated. The follower is then locked in place with the directional interface thumbscrew. Care should be exercised when attaching the follower to the miniframe to prevent unintended trajectory deviation. This could lead to severe injury or death of the patient. Additionally, the position feedback plug (cable) should be connected as shown in FIG. 10, and care should be taken to ensure that the cable for the plug does not rest on the patient during imaging.

The following are warnings, cautions and/or issues that apply to the system described herein.

The system is indicated for use to ablate, necrotize, and/or coagulate soft tissue through interstitial irradiation or thermal therapy in medicine and surgery in the discipline of neurosurgery with 1064 nm lasers, when a thermal probe is utilized in the system. Lasers of other outputs can be utilized, including lasers having wavelengths of 0.1 nm to 1 mm, and lasers in one or more of the ultraviolet, visible, near-infrared, mid-infrared, and far-infrared spectrums. Types of exemplary lasers include gas lasers, chemical lasers, dye lasers, metal-vapor lasers, solid-state lasers, semiconductor lasers, and free electron lasers. In one implementation, one or more wavelengths of the laser is within the visible spectrum, and one or more wavelengths of the laser is within the near-infrared spectrum. The system can be utilized for planning and monitoring thermal therapies under MRI visualization, and can provide MRI-based trajectory planning assistance for the stereotactic placement of an MRI compatible (conditional) probe. It also provides real-time thermographic analysis of selected MRI images.

When interpreted by a trained physician, this system provides information that may be useful in the determination or assessment of thermal therapy. Patient management decisions should not be made solely on the basis of an image analysis.

Probe or laser delivery in highly vascular regions can result in hemorrhage and/or post treatment aneurysm. Probe trajectories which transect or overdosing with thermal energy in regions containing cortical-spinal pathways can result in patient injury and permanent neurological deficits. Protracted surgical sessions with the patient immobilized can result in deep vein thrombosis.

The system should be operated by trained personnel under the direct supervision of a trained physician. Laser eye protection should be worn in the MRI scanner room during operation of a laser. The color perception abilities of an operator should be considered during temperature monitoring in implementations that utilize color maps, where the monitoring is manually performed by the operator. Operators who are color blind or have impaired color perception may not be able to monitor temperature during the procedure which could result in patient injury or death. Only approved accessories should be used. Failure to do so may result in improper performance and/or damage to the equipment with potential to cause harm. Only approved and verified MRI sequences for thermal imaging should be used in conjunction with this equipment. Failure to do so may result in improper thermal monitoring which could lead to patient injury.

All loaded image data should contain correct patient identification and image orientation markers prior to the commencement of a procedure to ensure an unintended area of the brain is not targeted for thermal delivery which can lead to patient injury.

Extreme care should be taken when determining patient baseline core body temperature by using an MRI compatible patient monitoring system using an internally placed temperature monitoring probe. Failure to determine an accurate value will result in improper performance of temperature monitoring software with the potential to cause patient injury. During a procedure, the treated tissue should be allowed to return to ambient temperature levels before acquiring subsequent MR thermal imaging.

The system may be contraindicated for patients with certain metallic, electronic or mechanical implants, devices or objects that should not enter the MRI scan room or serious injury may result.

Further, the user should beware of the strong magnetic field in the MRI room. Extreme caution should be used before bringing in any equipment into the MR environment. Only items identified as MR Safe or Compatible/Conditional for the particular environment should be brought into the MR room. No items identified as MR Unsafe should be brought into the MR suite within the 5 Gauss line. Serious injury can result if any equipment which is MR unsafe is brought into the MRI suite.

The following are specific warnings that apply to the probe driver and the probe.

These components are intended for single use, and should not be reused, reprocessed or re-sterilized. Reuse, reprocessing or re-sterilization can compromise the structural integrity of the device and/or lead to device failure which in turn may result in patient injury, illness or death. Reuse, reprocessing or re-sterilization may also create a risk of contamination of the device and/or cause patient infection or cross-infection, including, but not limited to, the transmission of infectious disease(s) from one patient to another. Further, contamination of the device may lead to injury, illness or death of the patient.

When aligning and connecting the probe driver follower, the user should confirm that the position displayed on the interface platform is correct. Failure to do so may cause the laser energy delivery direction to be determined incorrectly, potentially resulting in patient harm.

All cables and umbilical in the vicinity of the MRI bore should not form loops as this may result in heating (with the potential to cause burns to the patient) and RF interference (which would affect equipment performance). The probe should be fully engaged to the probe driver prior to manipulating the probe in tissue. The laser in the probe should not be fired if the probe is not inserted in tissue or before the probe connections are made. A desired probe trajectory should be ensured to not interfere with the MR bore or other required equipment prior to the insertion of the probe into tissue.

The probe can classified as a class 4 laser product in accordance with EN60825-1:2003. Irreversible injury can occur. Laser radiation should not be directed to the retina of the eye. Skin or the eye should not be subjected to direct or reflected laser radiation. Each person inside the laser area should wear protective eyewear.

Laser fiber connections should be made correctly as improper connections can lead to fire danger or operator injury. Laser connections should be fully seated. Failure to do so can cause the receptacle to heat, reduce thermal energy deposition, cause equipment damage or operator or patient injury.

The laser area can be defined by the Nominal Ocular Hazard Distance (NOHD) as 2.8 m from the laser output at the probe tip (when connected) or the extension fiber output on the interface platform. Outside of this region, laser safety eyewear is not required.

An exemplary probe and probe driver can be used under the following conditions: static magnetic field of 1.0, 1.5, 2.0, 2.5, 3.0 or 3.5 Tesla; and spatial Gradient field of 500, 360, 300 or 240 Gauss/cm or less. The whole-body-averaged specific absorption rate (SAR) should not exceed 4, 3, 2, 1.5 or 1 W/kg. Whole body transmitting coils can be used. Local transmitting coils should not be used, but local receiving coils can be used.

MRI image quality may not be affected while the interface platform display is OFF. However, image quality can be affected if the interface platform display is powered ON during acquisition, potentially causing image artifacts.

The probe and probe driver should be inspected carefully prior to use for any breach of the sterile barrier or damage to the contents, and should not be used if the sterile barrier integrity is compromised or the contents damaged.

General preferred operating conditions of the system include: temperature: 15° C. (59° F.) to 30° C. (86° F.) or around 23-26° C.; and relative humidity: <50, 60 or 70%. General preferred storage conditions of the system include: temperature: 10° C. (50° F.) to 40° C. (104° F.); relative humidity: <60%; and keep out of direct sunlight.

The system can use medical grade $CO_2$ gas as a coolant for a laser probe. Medical grade CO2 size "E" tanks, unless otherwise labeled, are MR Unsafe and should not be brought into the MR suite within the 5 Gauss line. The electronics rack can be designed to hold two "E" size tanks. For a particular implementation, pressure gauges for each tank should read >4500 kPa (>650 psi) for use. Exemplary pressures of the gas include 600-650, 650-700, 700-750, 750-800, 800-850 and 700-900 psi.

Procedure Workflow

A procedure includes, generally, identifying a tissue in a patient to be treated, planning one or more trajectories for treating the tissue, preparing the patient and components for the treatment, and performing the treatment. Aspects of the various parts of the treatment are described throughout this disclosure, and a particular sequence of treatment steps is described herein.

In pre-planning of a treatment of a patient, pre-treatment DICOM image data is loaded and co-registered via the workstation. An intended treatment region of interest(s) (ROI)(s) and initial trajectory(s) are created and established as desired.

A head coil and fixation system is attached to the patient, which includes positioning the head coil and stabilization system on the surgical table. The patient is immobilized using a head fixation ring. The patient head should be, secured with a head fixation device and remain fixed within magnet space for entire imaging portion of the outlined workflow. If the patient head position changes relative to the head fixation device at any point during the procedure, then new imaging should be acquired and co-registered as a master series or thermal energy may be delivered in an unintended area causing patient injury.

A probe entry location into the skull is identified, and a burr hole may be created prior to miniframe attachment or a twist-drill hole should be created following stereotactic miniframe trajectory alignment. The twist-drill hole can have a size of 1-5 mm, 2 mm, 3 mm, 4 mm or 4.5 mm. The stereotactic miniframe is attached to the patient's head, and the miniframe is aligned along the intended trajectory using image-guided navigation. The head coil and fixation system is then attached.

Depending on a site specific workflow, the interface platform may be attached prior to or after MRI trajectory confirmation. The order of these steps is typically determined with the MRI or surgical support team during on-site training. The interface platform is attached to the head end of the head coil and stabilization system, as shown in FIG. 6. Then, the IP power and motor plugs are connected, as shown in FIG. 10.

Trajectory confirmation and beam fiducial marker detection is then performed. The established trajectory of the miniframe should be evaluated using MRI prior to inserting a probe into the brain. Volumetric imaging is recommended to include the entire head and full extent of the miniframe. These images will also visualize a beam fiducial marker located in a portion of the miniframe. This marker is identified to orient the software to the physical direction of the probe. This image data can also be used for treatment planning if pre-treatment image data is not available.

The patient is positioned in the MRI, and MRI imaging is performed to confirm trajectory with an MRI trajectory wand inserted into the miniframe.

Using the workstation within a so-called "Plan Register" workflow step, acquired image data is loaded and co-registered with already loaded pre-planning image data (if any). Using the workstation within a so-called "Plan Volumes" workflow step of the workstation, treatment ROI(s) are defined, if not already defined. Using the workstation within a so-called "Plan Trajectories" workflow step, a rendered probe trajectory(s) along the imaged position of the MRI trajectory wand is established and/or adjusted. Using the workstation within a Treat Align and Auto-Detector step, the fiducial marker of the miniframe is identified/registered and set.

The follower is attached to the miniframe, and the rotary test tool is attached to the follower to provide position feedback for a probe drive self-test step, which confirms that inputs to the follower, via the commander, accurately drive the rotary test tool. Once successful, the rotary test tool is removed by depressing a release button on its side and pulling it back off of the follower. See FIG. 11b. Upon removal of test tool, the rotary position will no longer be valid and will be displayed on the interface platform as "Unset" until the probe is placed into position.

An appropriate probe size is selected, and a corresponding probe is removed from its sterile pouch and placed in the sterile field.

Figure 12:
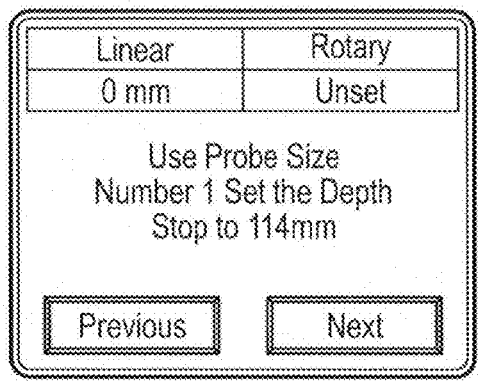
FIG. 12 is an exemplary screen shot of a display of an interface platform.

The following steps are taken to set and lock a probe depth stop. The workstation calculates the required length of the probe based on trajectory planning and the intended target. The interface platform displays the probe size for the user in two ways during a system self-test, as shown in FIG. 12, which includes an image of a display screen of the interface platform. FIG. 12 illustrates a required probe size and depth stop setting.

Figure 13:
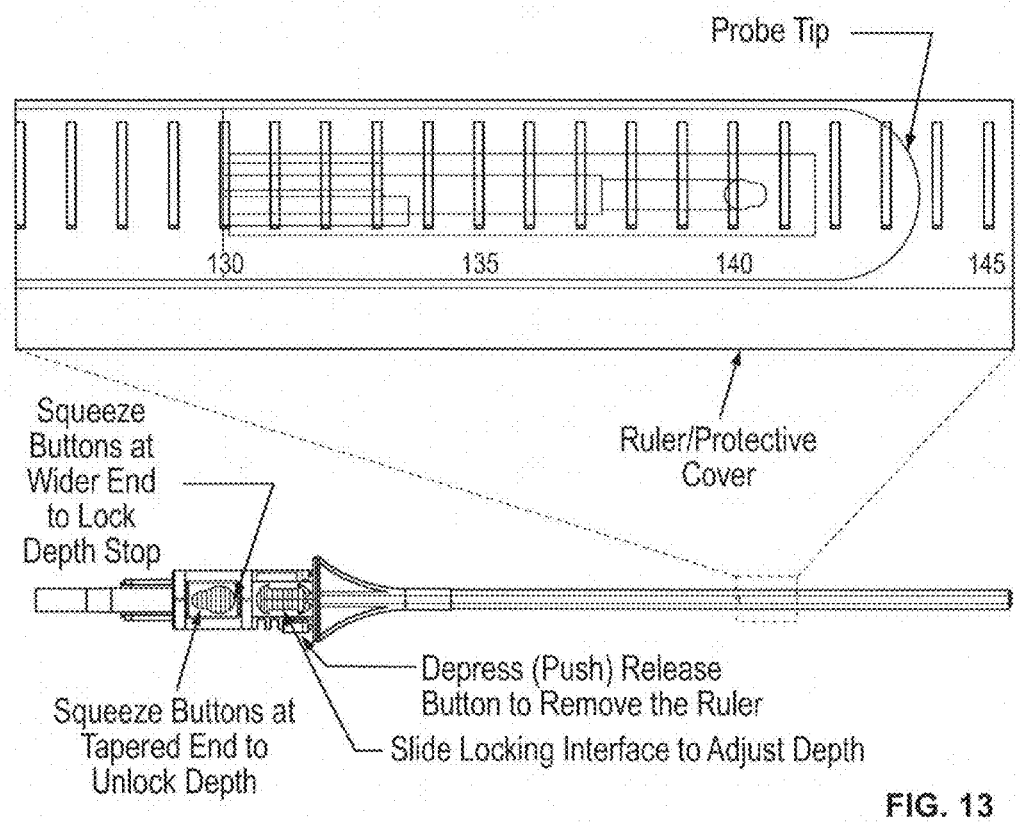
FIG. 13 illustrates a ruler and depth stop of an exemplary probe.

FIG. 13 illustrates adjustment and setting of a depth stop. A first step is to ensure a probe is fully inserted into the ruler/protective cover, as shown in FIG. 13. An audible click should be heard if reinserting the cover into the probe locking interface. The locking interface is then slid so that the probe tip aligns with the required distance measurement on the ruler. Locking buttons at the wider end are then squeezed to lock the depth stop, as shown in FIG. 13. An audible click should be heard when locked. A tapered part/end of both buttons can be squeezed to unlock the depth stop lock.

The proper depth of the probe can be rechecked by matching the probe tip to ruler graduations. Further, it should be rechecked that the depth stop is locked prior to inserting the probe into the brain. An improperly set depth stop can allow the probe tip to be delivered short of or deeper than intended/ planned, which may lead to patient injury. The ruler is then removed by depressing the release button shown in FIG. 13.

Figure 14:
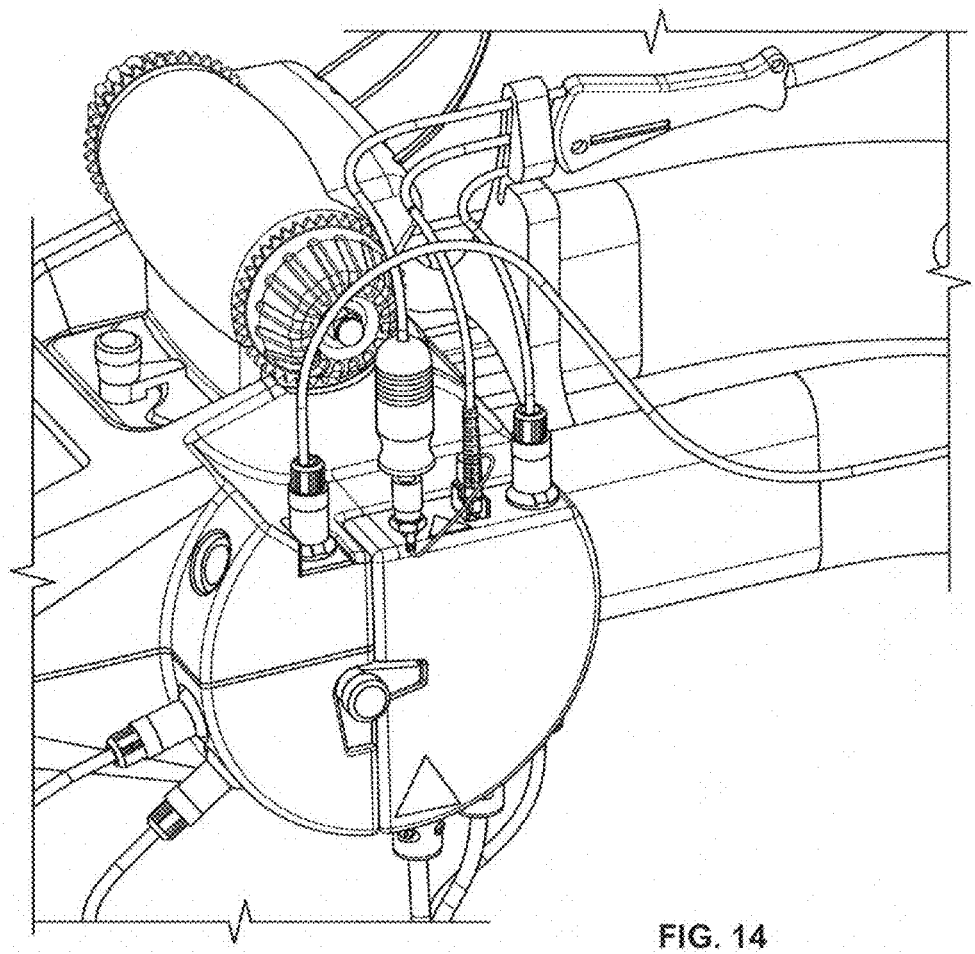
FIG. 14 is an illustration of a commander/interface platform engagement with a connector module.

FIG. 14 illustrates the location of probe connections on the interface platform. Preferably, the sterile person will hand off the probe connector plugs to a non-sterile person to insert the plugs to the associated receptacles on interface platform. The cooling plug is inserted into the mating receptacle (labeled CO2). It should click and lock when fully inserted. The arrow on the thermocouple plug should be aligned with the arrow on the receptacle marked THERMOCOUPLE. The plug should be inserted into the receptacle until it clicks and locks. The laser plug should be inserted into the mating receptacle (labeled LASER). Two clicks should be heard; one at half insertion and one at full insertion. With medium force, the connector should be pulled back to ensure it is fully seated and does not pull out. The three connector lines in the connector line bracket should be retained as shown in FIG. 14 to ensure that the lines remain fixed to the interface platform if the specific site that the workflow so requires.

The laser probe laser fiber connector should be completely engaged into the corresponding interface platform receptacle. Failure to do so can cause receptacle heating and reduce the energy delivered to the target tissue. This may result in fire or injury of the user or patient.

The three probe connector lines should be retained in the probe connector line bracket to ensure potential force during disconnection of the probe connectors is not transferred to the probe after insertion into the brain. Force applied to the probe after insertion into the brain can lead to patient injury or death.

Figure 15:
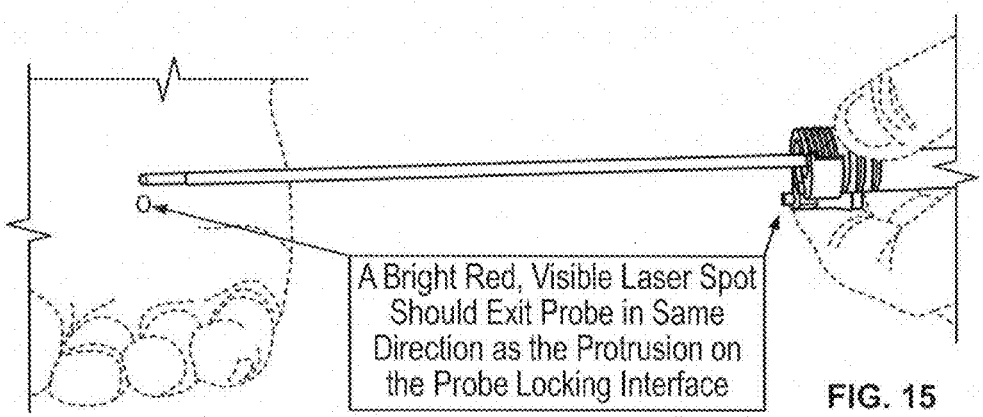
FIG. 15 is a photograph of testing an output of a probe.

The laser is physically interlocked by the workstation until the appropriate workflow step has been reached. The laser interlocks should remain disabled throughout the workflow until treatment monitoring begins. However, the visible pilot laser beam can be enabled. The visible pilot laser can be a class 2 laser product according to IEC 60825-1 having a maximum power of 1 mW. Other maximum powers include 0.5, 0.6, 0.7, 0.8, 0.9, 1.5 and 2-5 mW. The laser should not emit energy when a foot pedal is pressed during a self test. A bright, red laser light should be visible exiting the probe tip in the correct orientation from the probe. Aiming the beam at a surgical glove should produce a bright, red spot, as shown in FIG. 15. If the physician or a user does not see a strong, visible red aiming laser beam exiting the probe tip, then the full insertion of the probe laser plug should be ensured. Otherwise, the probe should be disconnected, and a second probe of the same size should be selected and registered as the first probe was.

When the beam test is successful, a next button can be depressed on the interface platform display to continue the workflow steps shown on the interface platform display. A gas cooling test can then begin. The Next button can be depressed when it has completed.

Figure 16:
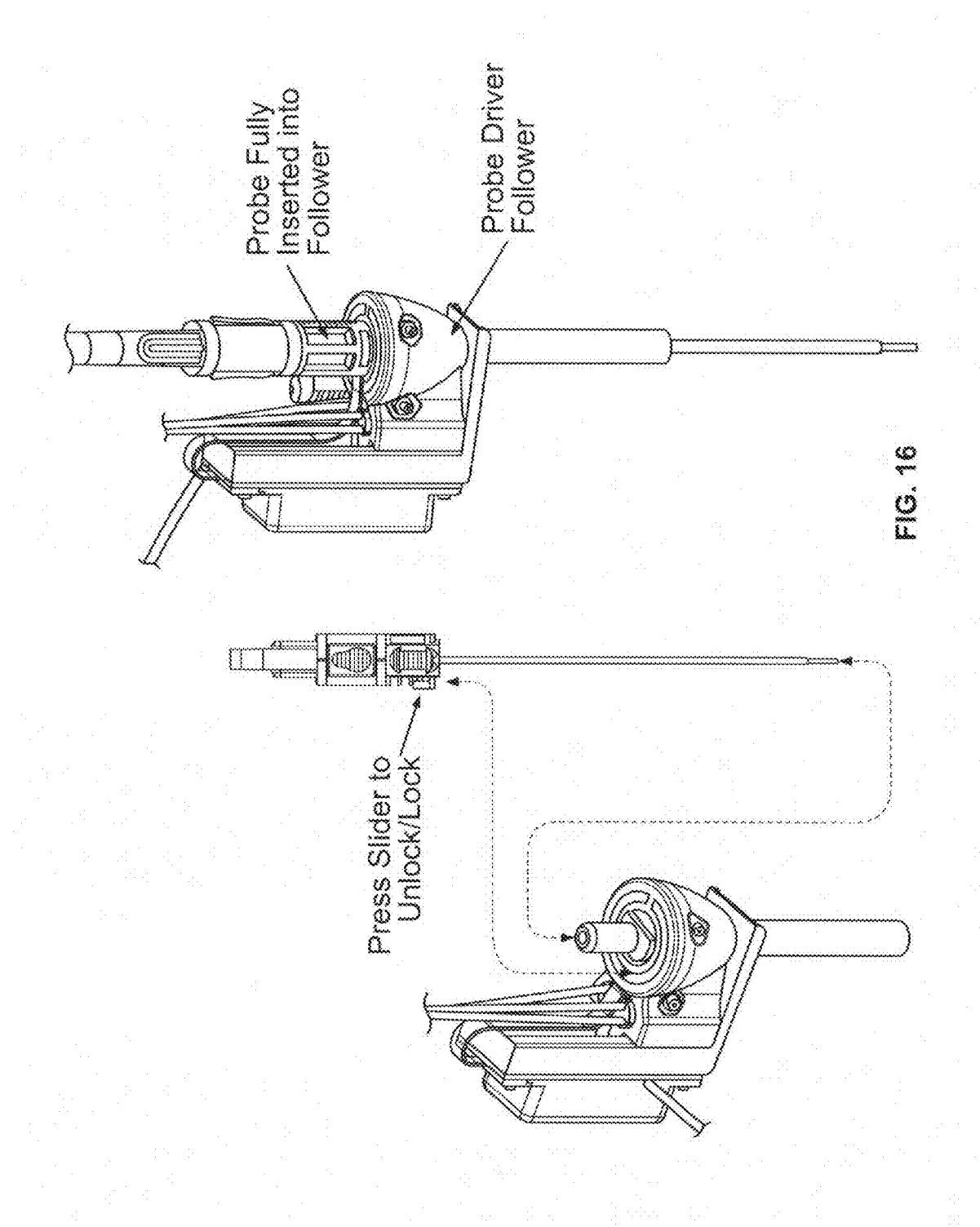
FIG. 16 illustrates sliding a probe into a probe follower.

The tip of the probe can then be inserted into the probe driver follower and into the brain until the probe locking interface comes in contact with a mating adapter on the follower. See FIG. 16. While gently pressing the probe toward the follower, the probe can be twisted until it fully locks onto the follower. An audible click should be heard when the probe is locked into position. This can be confirmed by gently pulling back on the probe to ensure it is properly locked in place, which is shown in FIG. 16.

MRI imaging is performed to confirm delivery of the probe along the intended trajectory. Acquired image data with already loaded pre-planning image data (if any) can be loaded using a Treat Insert workflow step of the workstation. The rendered probe in the workstation can then be adjusted as needed to match the probe artifact on the acquired image.

Once the software rendered probe matches the probe artifact on the screen, "Yes" or "Confirm" can be selected through the workstation to confirm trajectory.

In advance of each procedure, a data transfer interface should be enabled following patient registration on the MRI system. If the patient head position changes relative to the head fixation device at any point during the procedure the user should either register the patient in the MRI system as a new exam or use the MRI positioning lights to "re-landmark" the patient into magnet space center position. The entire head should be re-scanned to include the miniframe using a 3D volumetric scan. This scan should be co-registered with all other loaded planning sequences and be set as the master or thermal dose may be delivered in an unintended area causing patient injury.

Using the workstation, the rendered probe's trajectory can be adjusted to the desired linear position for thermal delivery. The rendered probe's rotary position can also be adjusted to the desired direction (angle) for thermal delivery. A scan plane can be selected under monitoring preferences of the workstation, and a thermal monitoring sequenced can be cued MRI system's sequence protocol list. The displayed scan plane parameters can be entered into the thermal monitoring sequences protocol's geometry parameters in the MRI.

An acquisition can then be started under a monitoring status bar of the workstation interface, and a thermal monitoring sequence on the MRI can be acquired. Under a noise masking heading of the workstation interface, 3 to 12, 4, 5, 6, 7, 9, 10, 11, 13 or 15-25 references points, such as 8 reference points, can be selected at the periphery of the overlaid, orange noise mask in each of the three displayed image monitoring view-panes surrounding the intended thermal delivery area.

Once "Ready" is displayed under a laser status heading, a foot peddle of the workstation can be depressed to deliver thermal energy to the intended area of the brain. Thermal energy can the be continuously delivered while monitoring created thermal dose contours overlaid onto the three thermal monitoring view-panes on the display screen of the work station. Thermal delivery can be stopped when desired by releasing the foot peddle.

The MRI is allowed to continue to acquire the thermal monitoring sequence until the tissue returns to baseline body temperature. Stop acquisition can then be selected through the workstation to stop acquiring the thermal monitoring sequence on the MRI. These steps can then be repeated until a desired thermal dose is received by the entire, intended volume of tissue.

Figure 17:
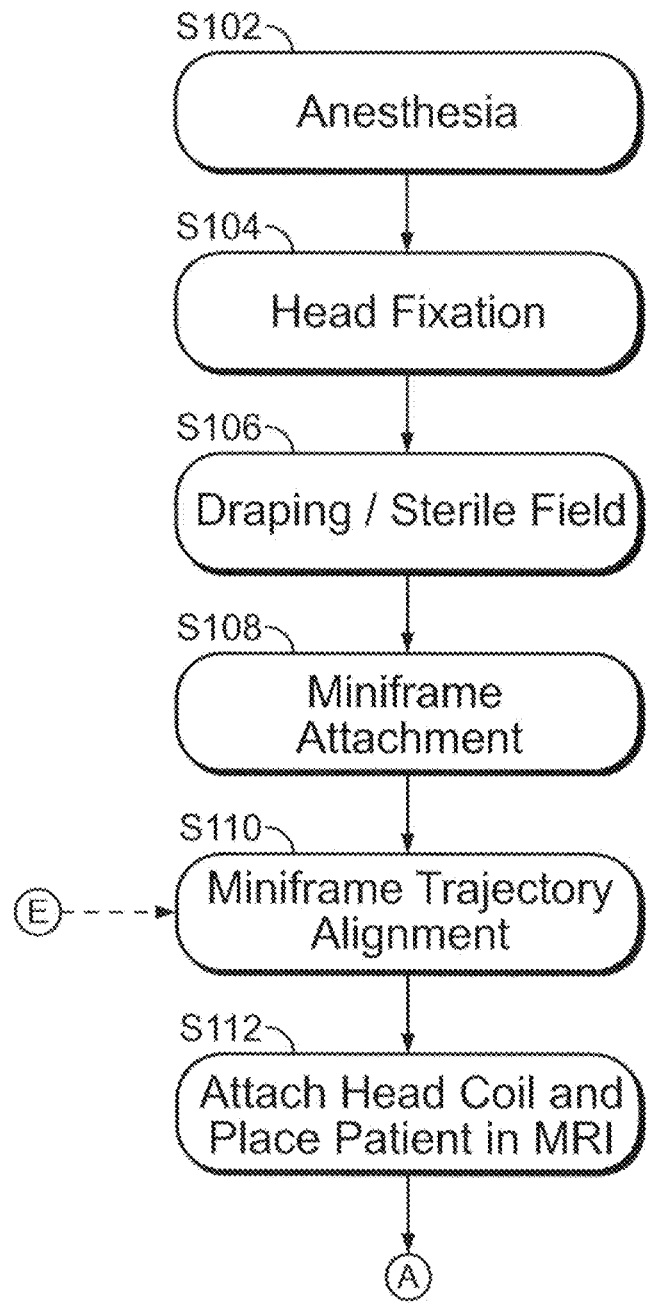
FIGS. 17-19 illustrate an exemplary procedure overview including an algorithmic process that outlines portions of a procedure for treating a patient.
Figure 18:
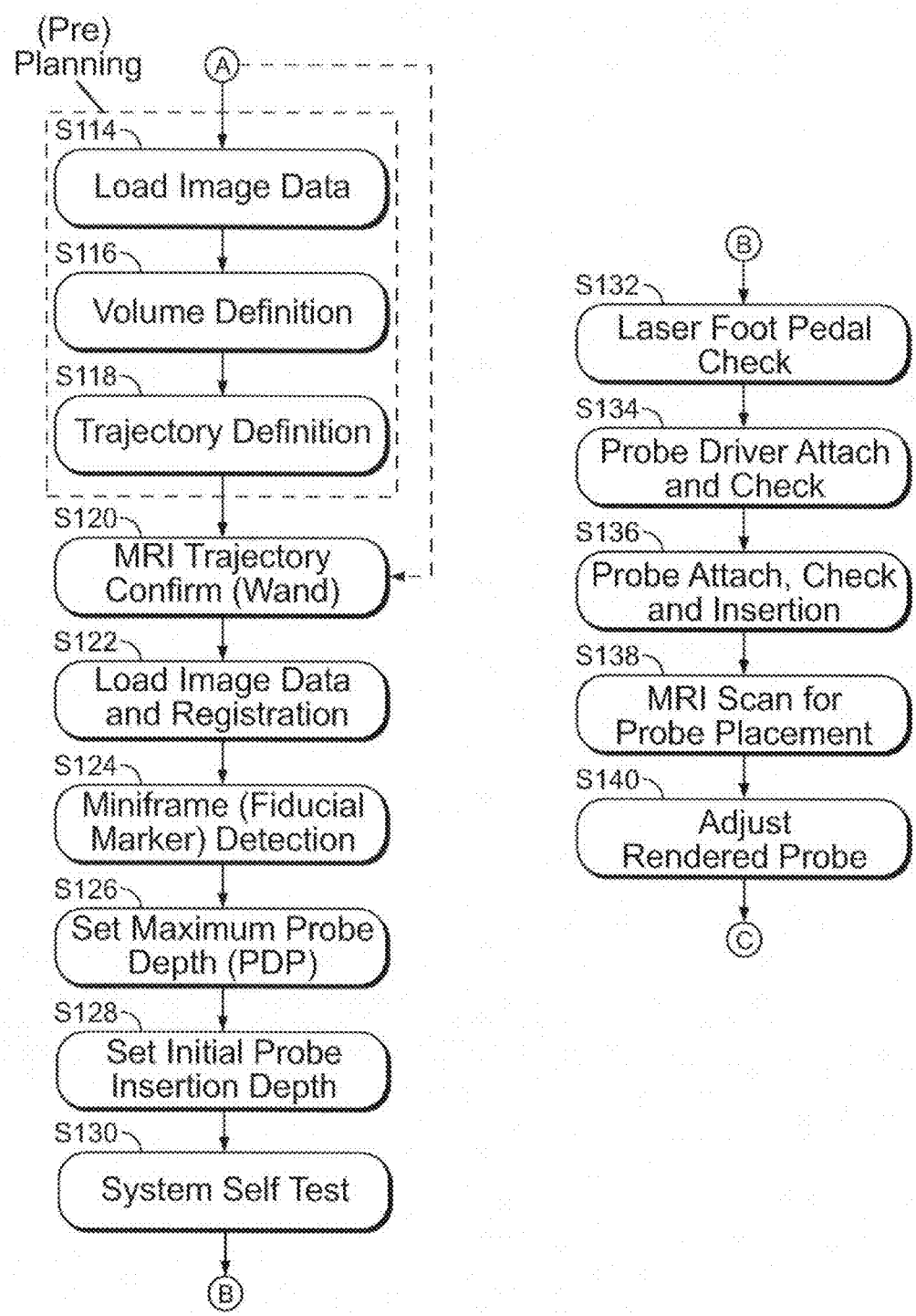
Figure 19:
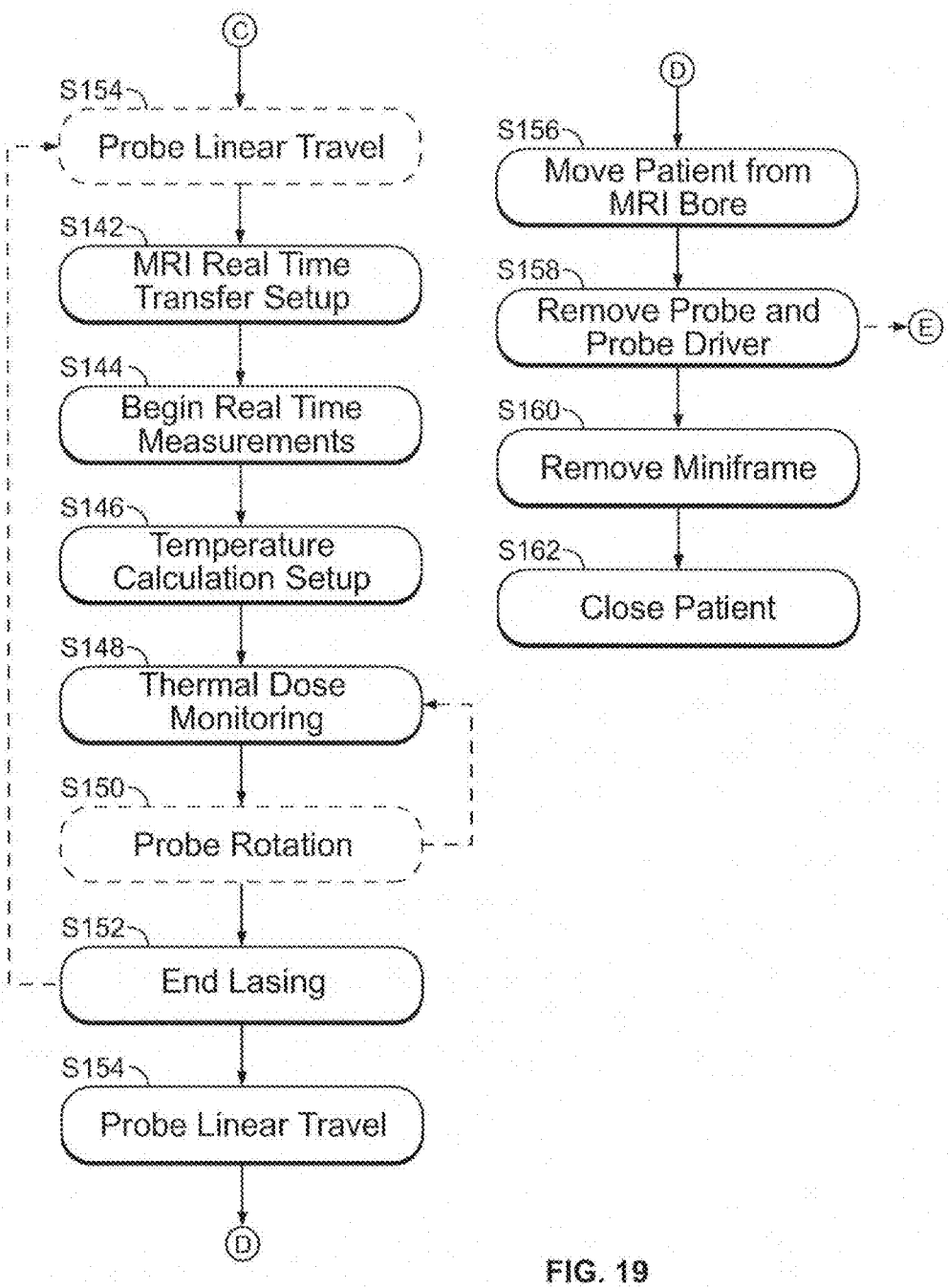

An exemplary procedure overview is shown in FIGS. 17-19, which includes algorithmic, computer-implemented processes and/or functions, together with operations performed by a user, technician, nurse and/or surgeon (or other physician or assistant). The steps shown herein generally include one or more sub steps consistent with the other portions or sections of this disclosure.

At S102, anesthesia is given to a patient. Anesthesia includes general and/or local anesthesia to sedate or put the patient under. The anesthesia may also merely numb or relieve pain, in some implementations. The patient's head is then fixated at S104. Before head fixation, a head coil and stabilization system can be utilized, as discussed in other portions of this disclosure. For example, a particular head coil and stabilization system is described in Section V.

The operation area of the patient's head is then draped to create a sterile field at S106. Such draping can include the placement of patches or sheets on and/or around the patient's head to minimize exposure and the chances for infection.

After the sterile field has been established, a miniframe is attached to the patient's head at S108. A particular miniframe in accordance with this disclosure is described in Section II. The miniframe is aligned at S110. A probe entry location into the skull is identified, and a burr hole may be created prior to miniframe attachment or a twist-drill hole can be created following stereotactic miniframe trajectory alignment. The twist-drill hole can have a size of 1-5 mm, 2 mm, 3 mm, 4 mm or 4.5 mm.

In this alignment, the trajectory and miniframe are adjusted so as to conform with a pre-planned trajectory for the insertion of a probe or other instrument into the patient's skull. Alignment at S110 can also include visual-based stereoscopic alignment with the assistance of three-dimensional renderings in an operating room. Such alignment can utilize instruments that include fiducial markers that specifically identify a three-dimensional position of the instruments relative to the patient's skull. Markers can include electronic (e.g., RFID—radio frequency identification) markers and/or visual markers.

At S112, the interface platform is attached to the head end of a head coil and stabilization system, as shown in FIG. 6, the patient is placed in an MRI, and a pre-planning procedure commences. The stabilization system can be attached to the patient on a patient table that moves with the patient between various rooms (including a surgical room, an operating room, and the MRI room). The patient can be immobilized using a head fixation ring. The patient's head should be secured with a head fixation device and remain fixed within the magnetic space for the entire imaging portion of the outlined workflow. In advance of each procedure, a data transfer interface should be enabled following patient registration on the MRI system. If the patient head position changes relative to the head fixation device at any point during the procedure the user should either register the patient in the MRI system as a new exam or use the MRI positioning lights to "re-landmark" the patient into magnet space center position. The entire head should be re-scanned to include the miniframe using a 3D volumetric scan. This scan should be co-registered with all other loaded planning sequences and be set as the master or thermal dose may be delivered in an unintended area causing patient injury. The head coil can be attached to the stabilization within the MRI room or in an operating room.

At S114, as part of a pre-planning procedure, image data is loaded from the MRI and a volume definition is generated and co-registered via the workstation at S116. Intended treatment region(s) of interest (ROI)(s) and initial trajectory(ies) is/are created and established as desired at S118. At the same time as the pre-planning procedure or after the trajectory definition is generated at S118, the MRI trajectory is confirmed at S120. This MRI trajectory can be confirmed via a wand that includes a material, such as a liquid, that is visible in the MRI image. The wand can be placed in the miniframe. Depending on a site specific workflow, the interface platform may be attached prior to or after the MRI trajectory confirmation at S120. The order of these steps is typically determined with the MRI or surgical support team during on-site training. Then, the IP power and motor plugs are connected, as shown in FIG. 10. Image data is then loaded and the trajectory is registered therewith at S122.

The miniframe includes fiducial markers that are detectable by the MRI such that image data includes the fiducial markers of the miniframe, and such that a position and orientation of the miniframe can be registered and detected by a workstation. At S124, the fiducial markers of the miniframe are detected by the MRI such that a position and orientation of the miniframe can be registered by a workstation. The established trajectory of the miniframe should be evaluated using MRI prior to inserting a probe into the brain. Volumetric imaging is recommended to include the entire head and full extent of the miniframe. This image data can also be used for treatment planning if pre-treatment image data is not available.

At S126, a maximum probe depth (PDP) is set. This maximum probe depth is set to reduce chances of inserting a probe or other instrument further into tissue of the patient than as previously planned, which can cause unintended damage to the tissue. An initial probe insertion depth is set at S128. Further aspects of the above pre-planning and setting and/or registration of probe depth and miniframe alignment are described in a particular implementation in Section VI.

A system self test commences at S130. This system self test can confirm operation and positioning of the various components discussed above. At S132, a foot pedal of the workstation is checked to confirm the foot pedal activates operation of, for example, a laser probe. At S134, a probe driver is attached to the miniframe, and alignment and positioning of the probe driver is checked with the workstation. Further, operation of the probe driver is verified. A particular implementation of a probe driver is described in Section III. A follower is attached to the miniframe, and a rotary test tool is attached to the follower to provide position feedback for a probe drive self-test step. Once the self-test step is determined as successful, the rotary test tool is removed by depressing a release button on its side and pulling it back off of the follower, as illustrated in FIG. 11b. Upon removal of the test tool, the rotary position will no longer be valid and will be displayed on the interface platform as "Unset" until a probe is placed into position.

A probe is attached and inserted into the probe driver and/or the patient's skull at S136. Particular implementations of the probe are described in Section IV. However, other types of probes or instruments can be utilized. Once an appropriate probe size is selected, a corresponding probe is removed from its sterile pouch and placed in the sterile field.

At S138, an MRI scan is conducted to ensure probe placement is correct and confirm delivery of the probe along the intended trajectory. Acquired image data with already loaded pre-planning image data (if any) can be loaded using a corresponding function (e.g., a graphical user interface) of the workstation. The rendered probe in the workstation can then be adjusted at S140 as needed to match the probe artifact on the acquired image to ensure that the alignment and arrangement of the probe as physically placed in the miniframe and inserted into the patient coincides with the rendered probe at the workstation. The rendered probe's trajectory can be adjusted to the desired linear position for thermal delivery. Further, the rendered probe's rotary position can also be adjusted to the desired direction (angle) for thermal delivery. Once the software rendered probe matches the probe artifact on the screen, "Yes" or "Confirm" can be selected through the workstation to confirm trajectory. A scan plane can be selected under monitoring preferences of the workstation, and a thermal monitoring sequence can be cued MRI system's sequence protocol list. The displayed scan plane parameters can also be entered into the thermal monitoring sequences protocol's geometry parameters in the MRI. Other aspects of this interface with the workstation is discussed in Section VI.

Treatment of a tissue can then commence, starting with setting up real-time transfer of MRI data, specifically imaging data, to the workstation at S142. At S144, real-time measurements can begin, and at S146, temperature calculation measurements can be set up and monitored. At this time, several images of a tissue to be treated are visible to a user at the workstation, and a probe is ready to be fired or activated to emit laser energy, for example, to the tissue to be treated. Under a noise masking heading of the workstation interface, eight reference points can be selected at the periphery of the overlaid, orange noise mask in each of the three displayed image monitoring view-panes surrounding the intended thermal delivery area. Once "Ready" is displayed under a laser status heading, a foot pedal of the workstation can be depressed to deliver thermal energy to the intended area of the brain. Thermal energy can the be continuously delivered while monitoring created thermal dose contours overlaid onto the three thermal monitoring view-panes on the display screen of the work station. Thermal delivery can be stopped when desired by releasing the foot pedal. At S148, the thermal dose of the laser is monitored, and effective treatment can be monitored. Further aspects are described in Section VI.

Once a thermal dose for a particular alignment and positioning of the probe is determined, the probe can be rotated at S150, and thermal dose monitoring at S148 can be repeated with various probe rotation alignments. Lasing (laser output) can then be terminated at S152, and the probe can be subjected to linear travel at S154 to various linear positions for creating an effective treatment region that is shaped to the to-be-treated tissue portion, by repeating steps S142-S154. Rotation and linear travel of the probe can be controlled by a probe driver, a particular implementation of which is described in Section III. The MRI is allowed to continue to acquire the thermal monitoring sequence until the tissue returns to baseline body temperature. "Stop acquisition" can then be selected through the workstation to stop acquiring the thermal monitoring sequence on the MRI. These steps can then be repeated until a desired thermal dose is received by the entire, intended volume of tissue.

Once treatment is completed the patient can be removed from the MRI bore at S156, and the probe and probe driver can be removed at S158. At this time, if another probe or probe driver is to be used, the procedure can be repeated by returning back to S110 to align the miniframe trajectory of the new probe and/or probe driver. Otherwise, the miniframe can be removed at S160, and the patient can be closed at S162.

In light of the descriptions provided herein:

An adjustable device, a miniframe, is provided that allows for a movable probe tilt point spaced apart from patient's head, while the miniframe is affixed to the patient's head. A probe attached to the miniframe can be advanced (laterally displace and/or rotated) under MRI guidance.

The head coil and stabilization system can fixate a patient and permit thermometry around substantially an entire crown line of the patient. In conjunction with the miniframe, steep and shallow probe insertion angles are available.

Multiple different probes can be utilized and swapped in the MRI room so as to provide different ablation patterns from different probes. For example, a symmetrical ablation probe can be used, followed by a side-fire (asymmetrical) ablation probe. A diffused tip probe can also be utilized.

A process of advancing probe, asymmetrically ablating, measuring, advancing probe and repeating is provided, such that the process does not require the interruption of a user-intervention in the MRI room to change probes or probe position.

Further, alterations to the procedures discussed herein can include the following:

The miniframe can be affixed in a preparation room, then placed in the MRI, and then the trajectory of the miniframe can be set in the preparation room. The hole can be drilled in the preparation room, and the patient can then be returned to the MRI for ablation procedure. This may proceed without an operation room (OR). The trajectory can also be optionally set based on images taken immediately prior to an ablation or treatment procedure. Further, a single burr hole and trajectory can be utilized by the use of family of probes. The procedure(s) can optionally be conducted without general anesthesia.

The miniframe provides a movable pivot or tilt point above a target, i.e., above the patient's head. The probe driver is attached to the interface platform, as shown in FIG. 10, allowing control of movement of a probe or other implement attached to a probe driver follower to be rotated or longitudinally moved. Thus, a movable pivot or tilt point above a target is provided for a probe or other implement, which can be advanced or rotated under MRI guidance, through control by an operator or a workstation that is located in a separate room.

A trajectory can be set, after the miniframe and head stabilization system are attached to a patient, by utilizing an MRI to visualize a trajectory of the miniframe and set/register/lock the miniframe and/or the head stabilization system to an appropriate alignment. Then, a burr hole can be drilled in a prep room using the registered miniframe. The patient is then returned to the MRI for treatment procedures.

In some aspects, one or more burr holes, the head fixation components, and the miniframe are attached without the use of an operating room.

The trajectory can be adjusted immediately prior to a treatment procedure (e.g., an ablation procedure), based on recent MRI imaging.

Consistent with Section IV, a plurality of trajectories and/or probes can be inserted into a single burr hole. Also, pursuant with Section IV, a plurality of probes can be utilized with a single trajectory and a single burr hole.

II. MINIFRAME

The miniframe in an implementation coincides with the frameless trajectory guide described in US 2010/0042111, which is incorporated herein by reference in its entirety. The miniframe can also be modified to conform with the examples shown and discussed herein.

Figure 20:
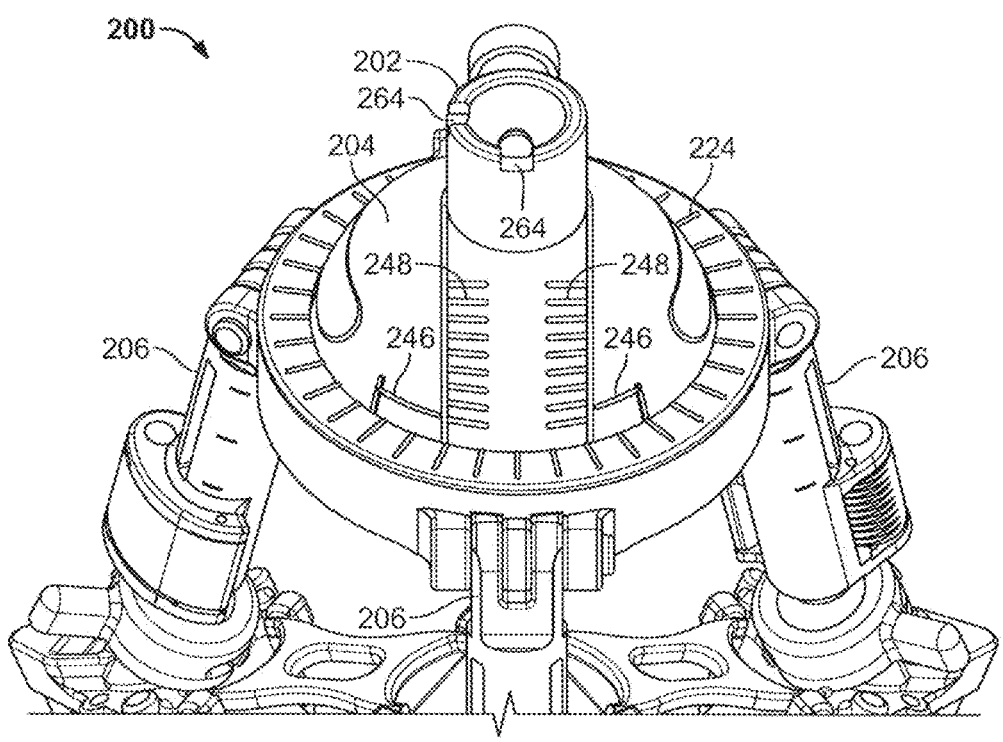
FIG. 20 is a perspective view of a portion of a miniframe.

FIG. 20 illustrates a miniframe 200, which can also be referred to as a frameless trajectory guide or simply as a trajectory guide. The miniframe 200 includes a tilt portion 202 and a rotation portion 204. The miniframe 200 also includes a plurality of legs 206.

Figure 21:
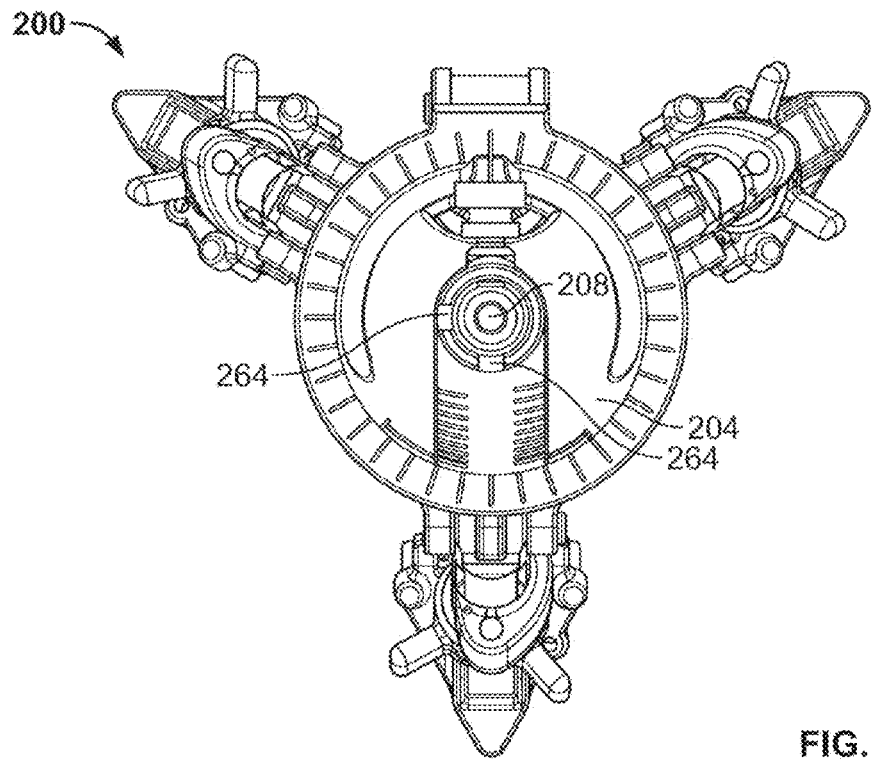
FIG. 21 is a top plan view of a miniframe according to a first rotational position.
Figure 22:
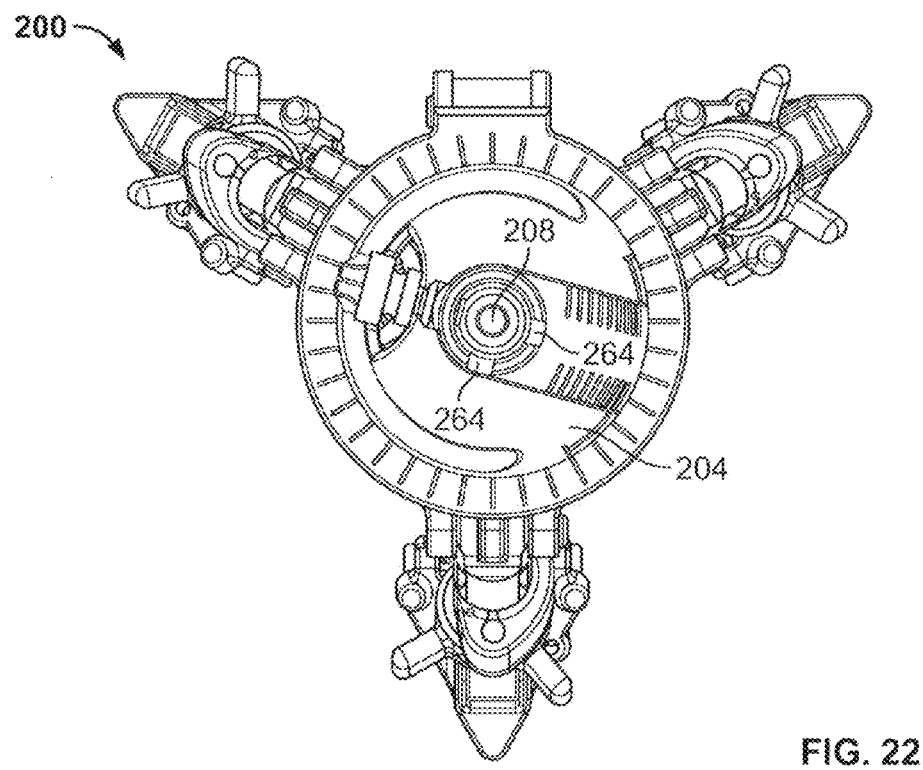
FIG. 22 is a top plan view of a miniframe according to a second rotational position.

FIGS. 21 and 22 illustrate two different rotational positions of the rotation portion 204. As shown in FIGS. 21 and 22, a rotation of the rotation portion 204 does not necessarily change the actual trajectory of the a through hole 208 of the tilt portion 202, through which an instrument, such as a probe, is insertable therein. The through hole 208 includes two alignment guides 264. These alignment guides 264 allow for proper pre-determined alignment between a probe and/or a probe follower and the miniframe 200.

Figure 23:
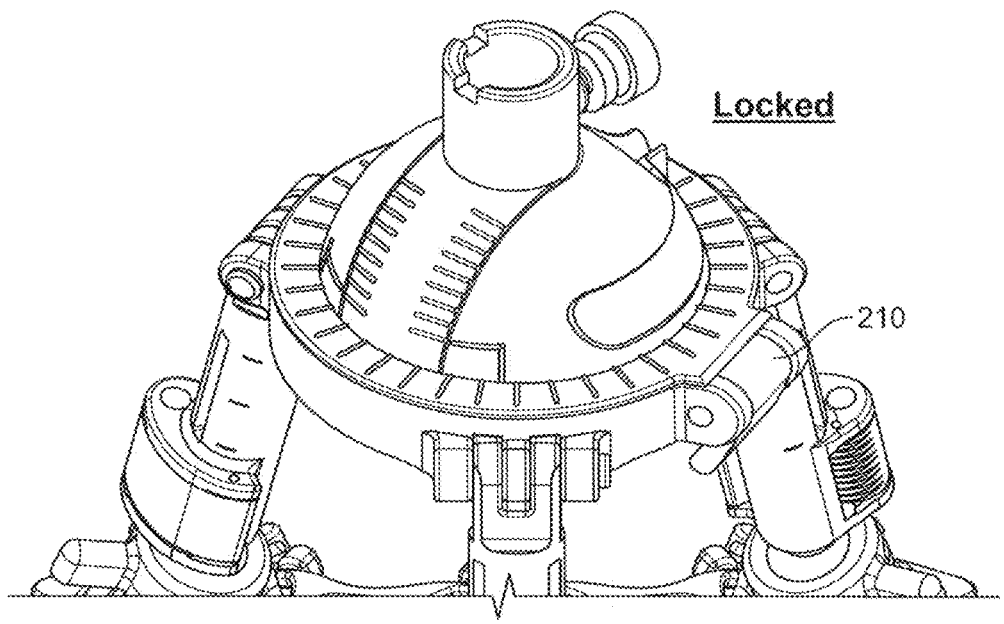
FIG. 23 is a perspective view of a rotation portion of a miniframe in a locked configuration.
Figure 24:
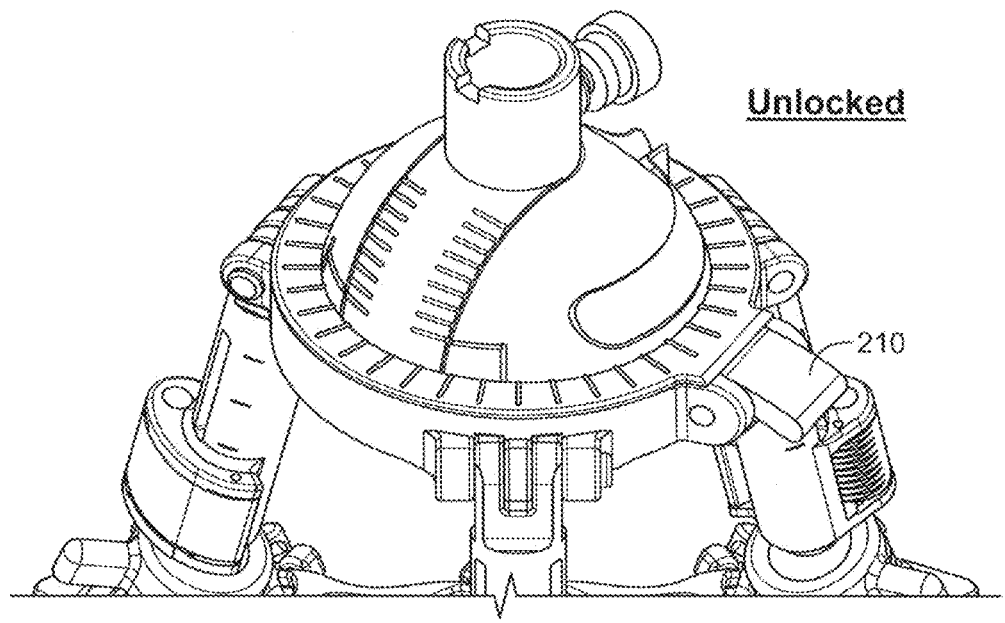
FIG. 24 is a perspective view of a rotation portion of a miniframe in an unlocked configuration.

Rotation of the rotation portion 204 can be locked via a cam 210. FIG. 23 illustrates a locked position of the cam 210, whereas FIG. 24 illustrates an unlocked position of the cam 210. In the unlocked position, the rotation portion 204 is free to rotate. On the other hand, in the locked position, the rotation portion 204 is inhibited or stopped from being rotated.

Figure 25:
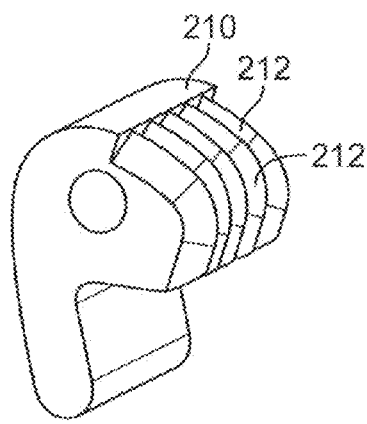
FIG. 25 is a perspective view of a cam of a miniframe.
Figure 26:
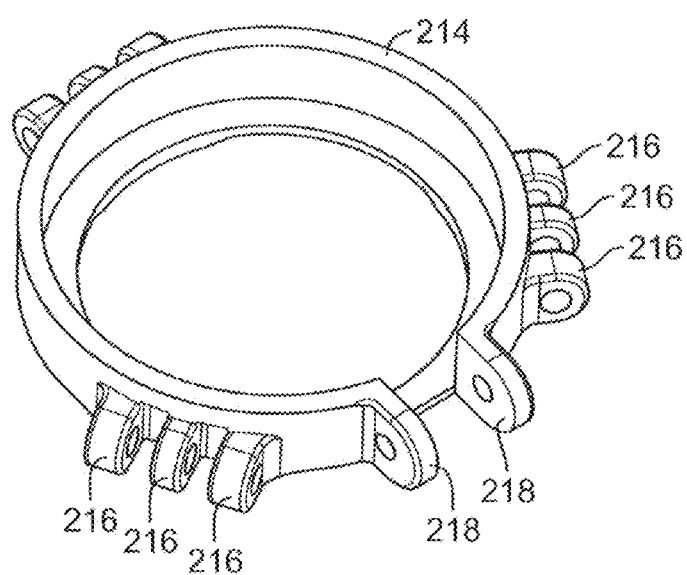
FIG. 26 is a perspective view of a frame of a miniframe.

FIG. 25 illustrates an exemplary cam in accordance with the shown implementation. The cam 210 includes a plurality of teeth 212. These teeth 212 are structured so as to engage corresponding teeth of the rotation portion 204, discussed below.

The rotation portion 204 includes a frame 214. The frame 214 includes a plurality of mounts 216 that are arranged so as to be coupled to the legs 206. Further, the frame 214 includes a cam mount 218 that is arranged to receive the cam 210.

Figure 27:
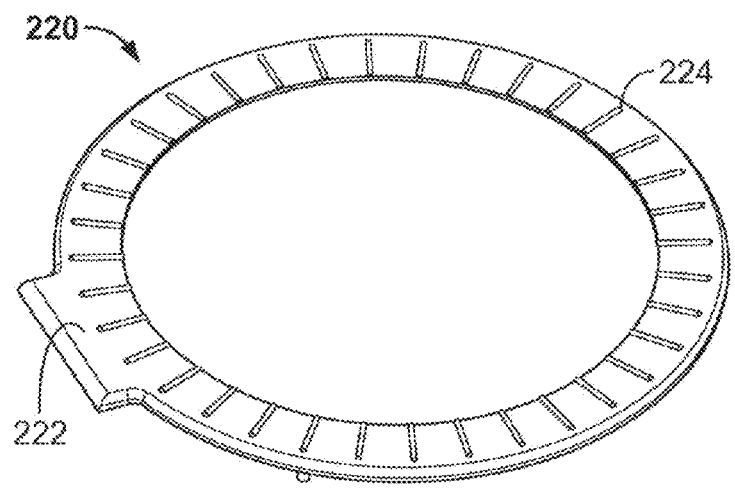
FIG. 27 is a perspective view of a retaining ring of a miniframe.

FIG. 27 illustrates a retaining ring 220, which includes a tab portion 222 and a plurality of alignment markings 224. The tab portion 222 is arranged so as to coincide with the cam mount 218 and the cam 210, as shown in FIGS. 23 and 24, for example. Further, the tab portion 222 provides a rotational stop to limit rotation of movement of the cam 210, as shown in FIG. 24, by example.

Figure 28:
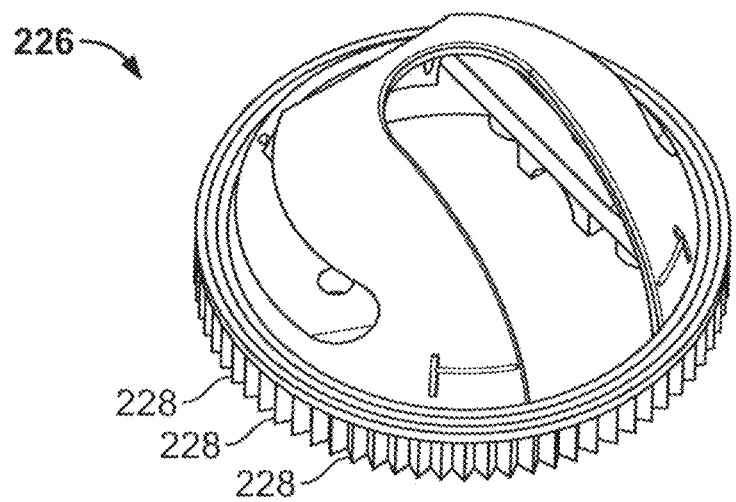
FIG. 28 is a top perspective view of a central housing of a miniframe.
Figure 29:
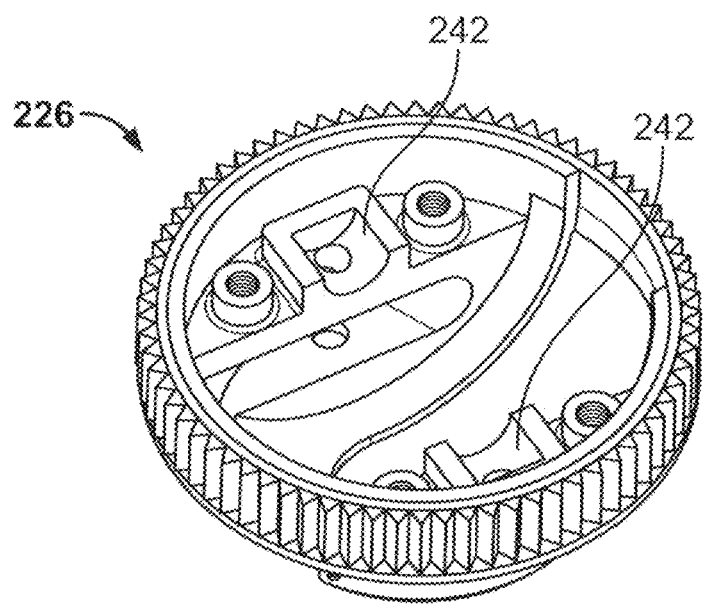
FIG. 29 is a bottom perspective view of a central housing of a miniframe.

FIGS. 28 and 29 illustrate top and bottom perspective views of a central housing 226 of the rotation portion 204. The central housing 226 includes a plurality of teeth 228 that are arranged to engage the corresponding teeth 212 of the cam 210.

Figure 30:
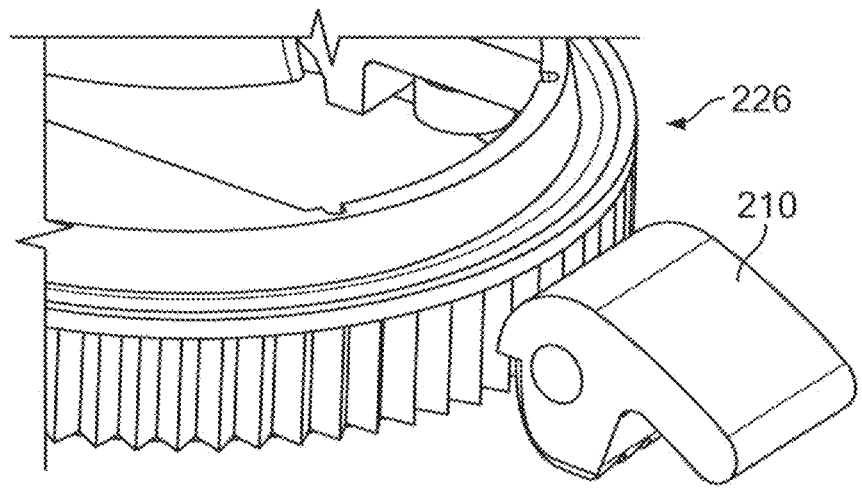
FIGS. 30-31 illustrate an unlocked engagement between a central housing and a cam.
Figure 31:
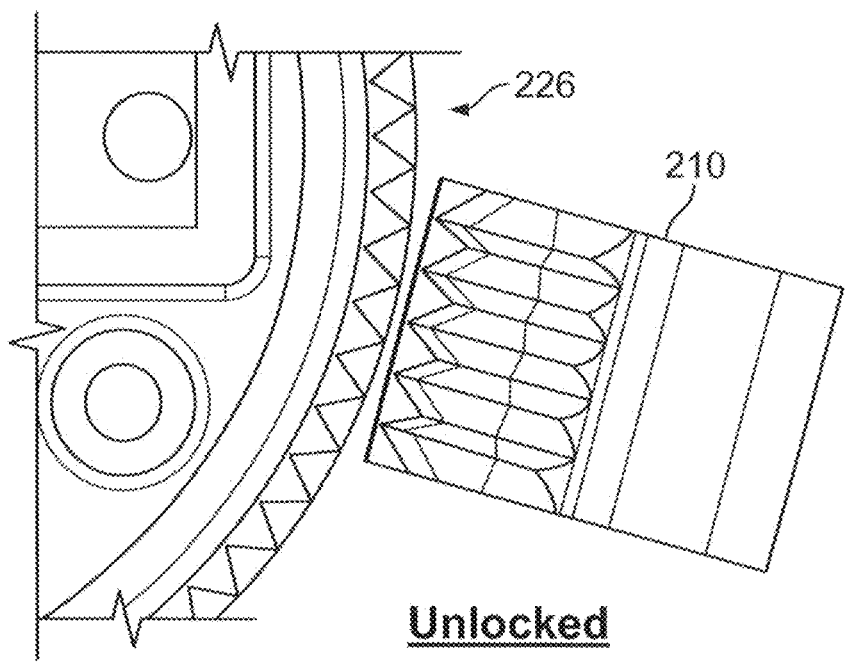
Figure 32:
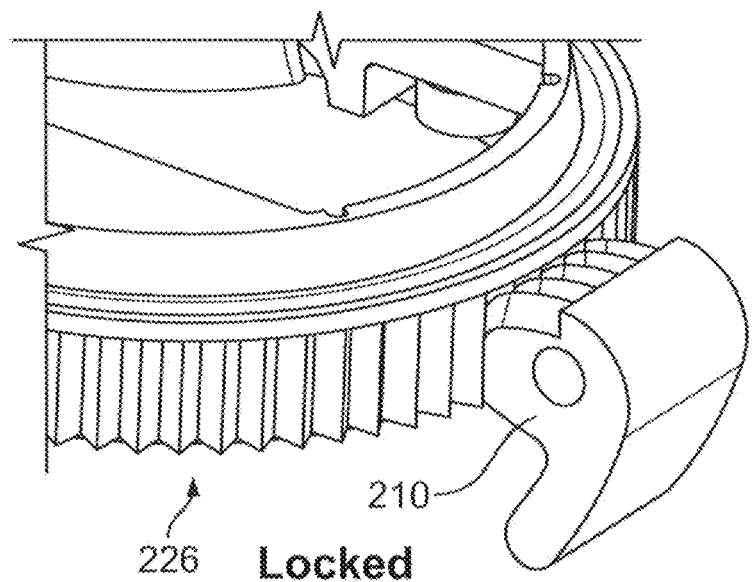
FIGS. 32-33 illustrate a locked engagement between a central housing and a cam.
Figure 33:
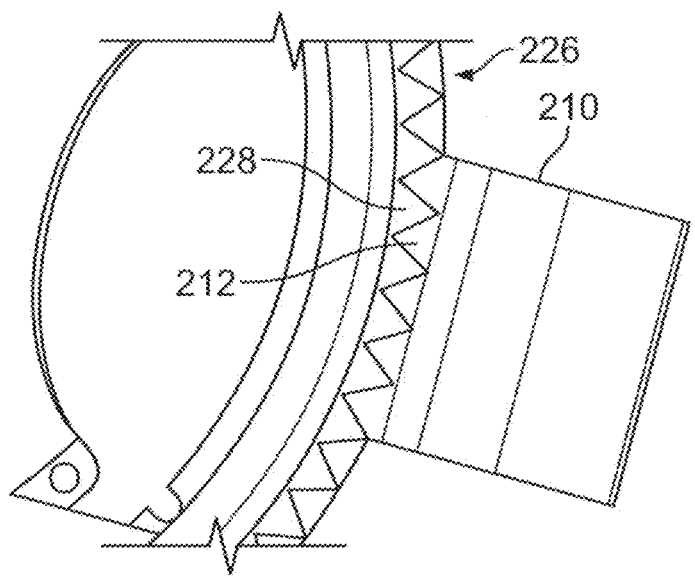

The engagement and non-engagement of the cam 210 to the central housing 226 is illustrated in FIGS. 30-33. FIGS. 30-31 illustrate an unlocked engagement, where the rotation portion 204 is free to rotate. FIGS. 32-33 illustrate a locked engagement in which the teeth 212 of the cam 210 create a locking engagement with the teeth 228 of the housing 226, as shown by the underside view of FIG. 33.

With the above locking mechanism provided by the cam 210 and the housing 226, relative rotation between the rotation portion 204 and the frame 214 is inhibited. The frame 214 is mounted via the legs 206, where the legs 206 provide an initial trajectory, which is defined by a placement of the legs 206, a length of the legs 206, and initial positions of the rotation portion 204 and the tilt portion 202. In one implementation, a tilt angle of the tilt portion 202, a rotation angle of the rotation portion 204, and lengths and placements of the legs 206 are set to a pre-planned trajectory, and the miniframe is 200 mounted to a patient's skull. For example, the rotation angle of the rotation portion 204 and the lengths and placements of the legs 206 can be set, and then the miniframe is attached to the patient. Thereafter, the tilt angle of the tilt portion 202 is set.

FIGS. 34 and 35 illustrate two different exemplary tilt angles of the tilt portion 202. Together, the tilt portion 202 and the rotation portion 204 can form a spherical shape, in which rotation and tilt are independently controlled and independently locked. The above description provided for the locking mechanism for rotation. The following describes a locking mechanism for tilting.

Figure 36:
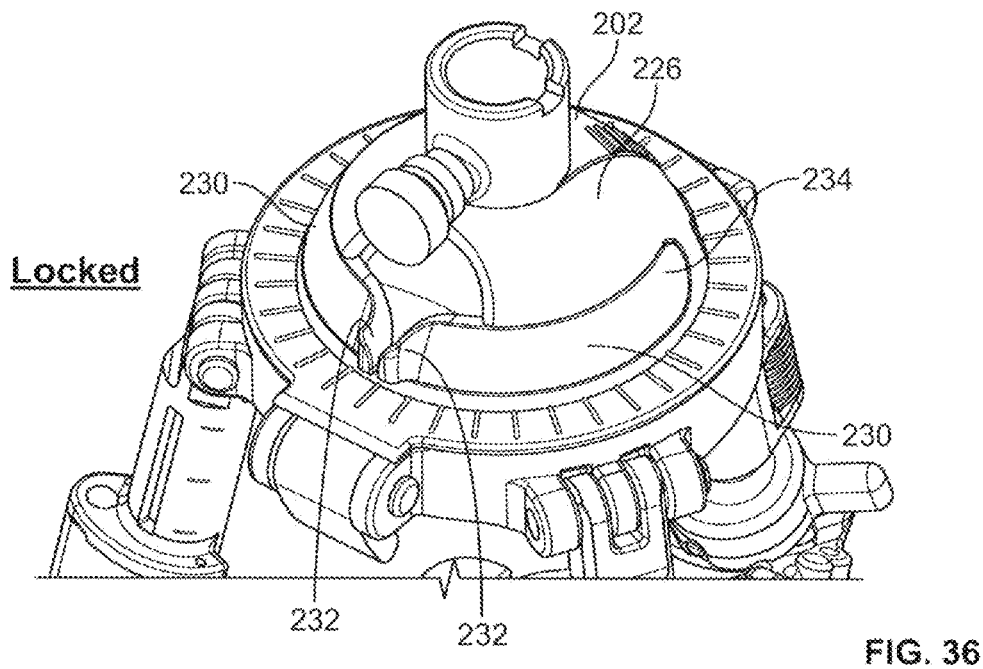
FIG. 36 is a perspective view of a tilt portion of a miniframe in a locked configuration.
Figure 37:
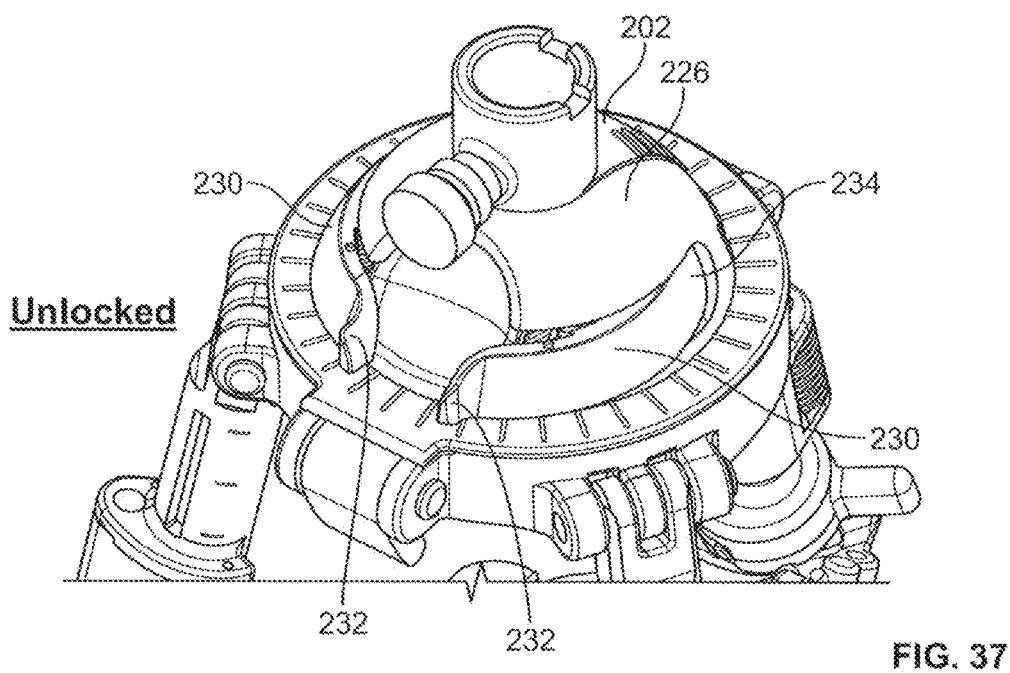
FIG. 37 is a perspective view of a tilt portion of a miniframe in an unlocked configuration.
Figure 38:
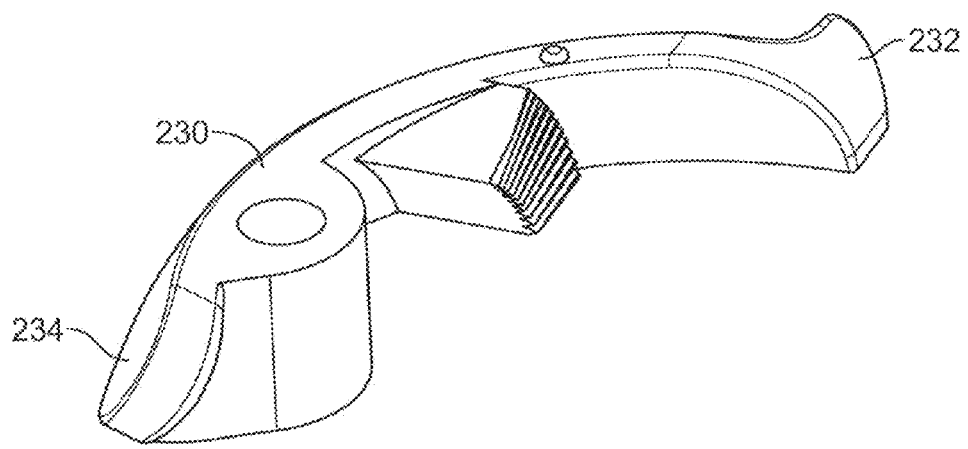
FIGS. 38-39 are front and rear top perspective views of a locking arm.
Figure 39:
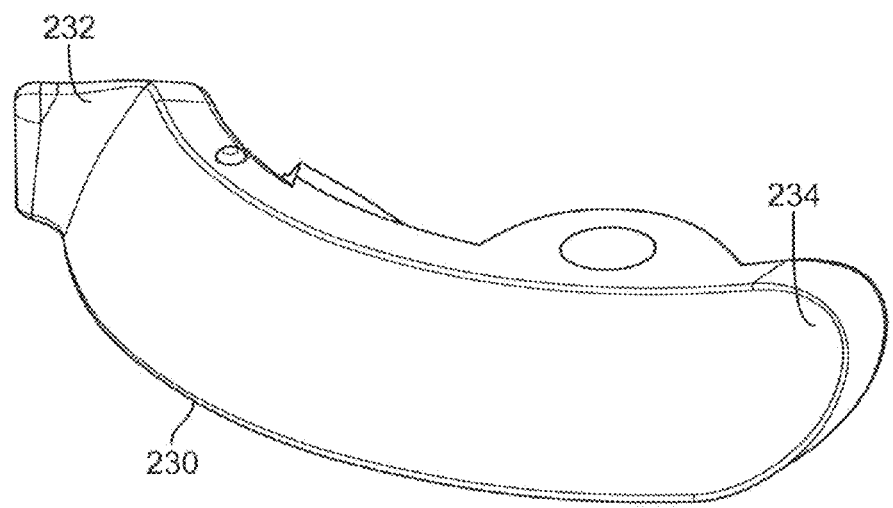

FIGS. 36 and 37 illustrate, respectively, locked and unlocked positions of locking arms 230 of the central housing 226 of the rotation portion 204. FIG. 36 illustrates a squeezed position in which locking arms 230 are squeezed together at tabs 232. As shown in FIG. 37, an unlocked position can be achieved by depressing the non-tabbed ends 234 of the locking arms 230. FIGS. 38-39 illustrate opposing prospective views of one of the locking arms 230. One of the locking arms 230 can be a mirror image of the other of the locking arms 230.

Figure 40:
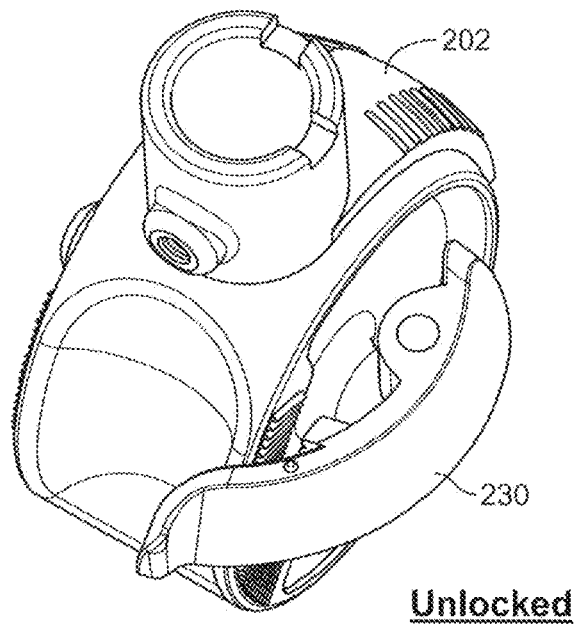
FIGS. 40-41 are top and bottom perspective views of a locking arm and a tilt portion in an unlocked position.

The locking arms 230 are provided on opposing sides of the tilt portion 202, as shown in FIG. 40, so as to pivot or rotate about a rotational engagement between the locking arms 230 and the tilt portion 202. Adverting back to FIGS. 36 and 37, it can be seen here that the central housing 226 of the rotation portion 204 covers the rotational engagement between the locking arms 230 and the tilt portion 202 when the central housing and the rotation portion 204 are assembled together.

Figure 41:
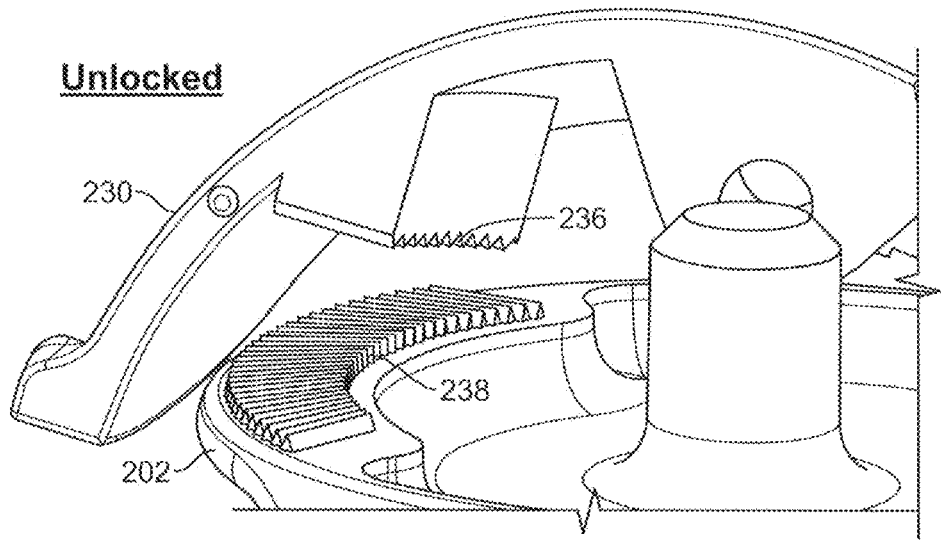
Figure 42:
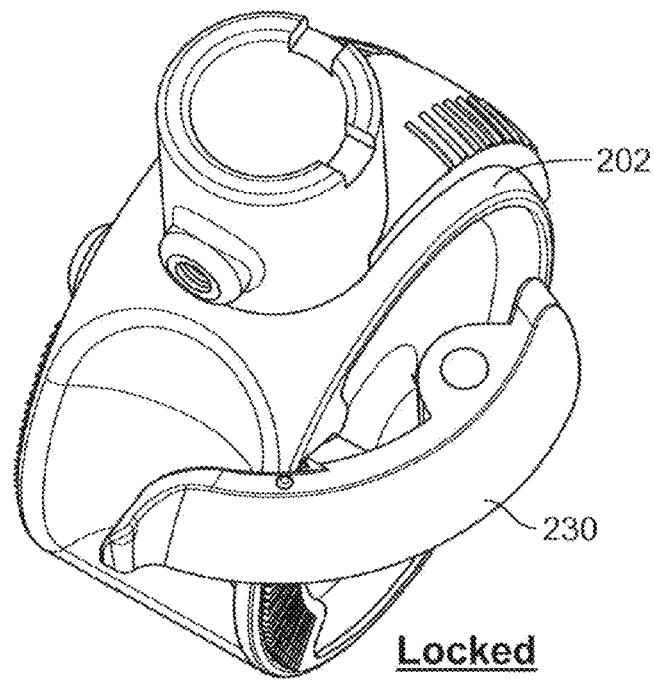
FIGS. 42-43 are top and bottom perspective views of a locking arm and a tilt portion in a locked position.
Figure 43:
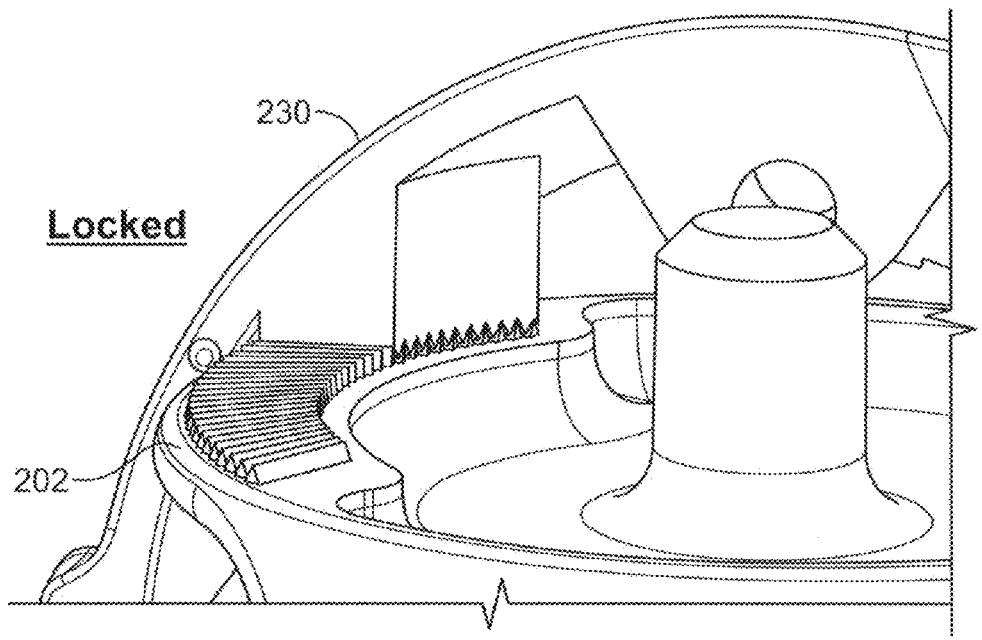

FIGS. 40-41 illustrate an unlocked position between a locking arm 230 and the tilt portion 202. Similar to the cam 210, the locking arm 230 includes a plurality of teeth 236. The tilt portion also includes a plurality of teeth 238 that are arranged to engage and create a locking engagement with the teeth 236 of the locking arm 230. FIGS. 42-43 illustrate a locked engagement.

Figure 44:
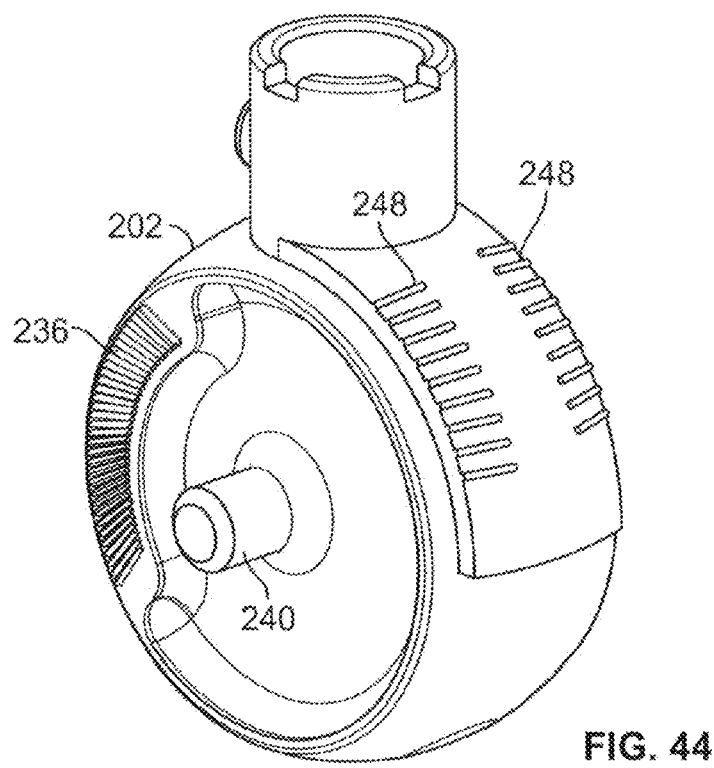
FIGS. 44-45 are top and bottom perspective views of a tilt portion.
Figure 45:
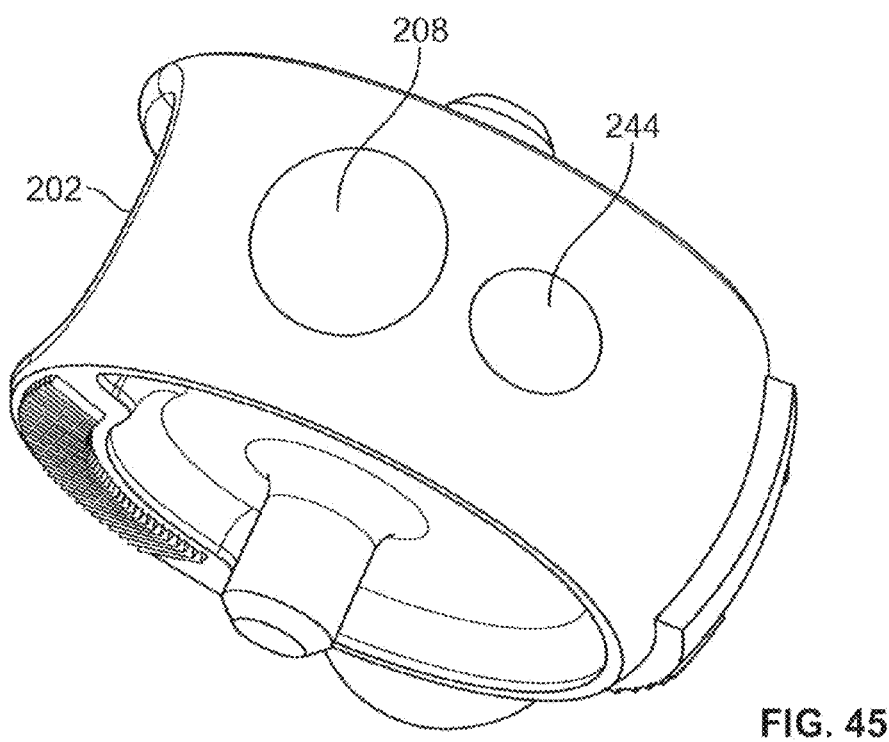

FIGS. 44 and 45 illustrate top and bottom perspective views of the tilt portion 202. The tilt portion includes a plurality of markings 238 for tilt alignment measurements, as well as a rotational axis 240 that is arranged to rest within a corresponding recess 242 provided in the central housing 226, as shown in FIG. 29.

FIG. 45 illustrates a fiducial marker 244 that is included in the tilt portion 202. This fiducial marker 244 can be arranged coaxially with the through hole 208. The fiducial marker 244 can be utilized via MRI imaging for trajectory verification. The fiducial marker 244 can include a fluid that is MRI visible. A diameter of the fiducial marker can be about 5.25 mm.

Adverting back to FIG. 20, the rotation portion 204 can include first and second alignment lines 246. The alignment markings 224 can be spaced every 10° and can be arranged so as to coincide with the first and second alignment lines 246 with respect to determining a rotational position of the rotation portion 204 and the tilt portion 202. The first and second alignment lines 246 can also coincide with tilt markings 248. These tilt markings 248 can be staggered and spaced several degrees apart, with respect to left and right sides, to limit the number of markings on the tilt portion 202. The tilt markings 248 can be spaced apart by 1°, 2°, 5°, 10°, 20°, 30° or 1-30°. Similarly, the first and second alignment lines 246 can be staggered by several degrees in the rotation and tilt directions to limit a number of alignment lines on the various components. The lines 246 can be spaced apart by 1°, 2°, 5°, 10°, 20°, 30° or 1-30°.

The legs 206 can resemble the legs described in US 2010/0042111. However, modifications can be made. FIGS. 46-47 illustrate a foot 250 of a leg 206. The foot 250 and the leg 206 can be coupled together by a ball-socket joint 252 that allows for both rotational and tilt motion therebetween. The joint 252 can include a spherical structure that extends from either one of the legs 206 or the foot 250. In the implementation shown, the spherical shape extends from the leg 206 and is coupled to the foot 250 by a foot cap 254. The foot cap 254 can be removed from the foot 250 using a twist bayonet-type locking mechanism. An unlocked position is shown in FIG. 46, whereas a locked position is shown in FIG. 47. In the locked position, relative movement between the leg 206 (the joint 252) and the foot 250 is impeded by a frictional engagement, whereas the frictional engagement is lessened and/or removed outright in the unlocked position of FIG. 46. The cutouts 268 have an angled edge which assists in keeping the foot cap 254 in the locked position via the protrusion 256. In the locked position, the protrusion 256 is held at a first position within the cutout 268. The foot cap 254 is moved to an unlocked position by twisting the foot cap 254 to cause the protrusion 256 to progress an inclined or angled edge 270 of the cutout 268 until the protrusion traversed the angled edge 270, and the foot cap 254 can decoupled from the protrusion 256.

Figure 48:
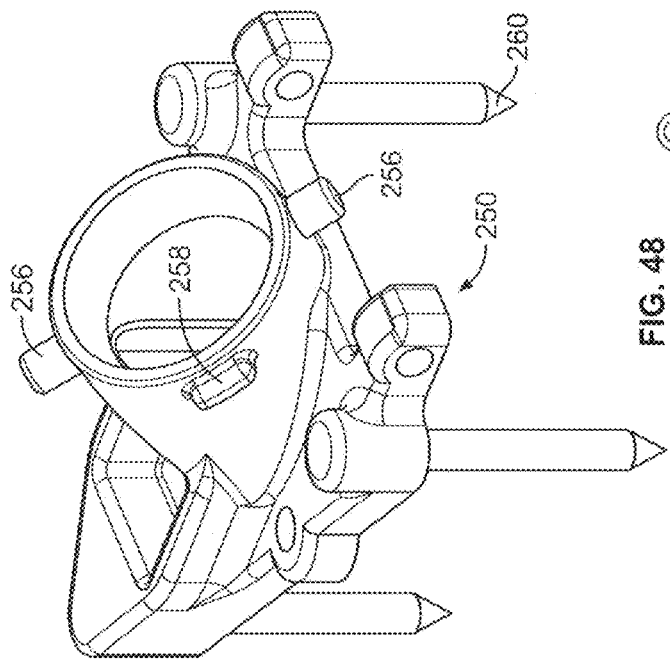
FIG. 48 is perspective view of a foot.

FIG. 48 illustrates the foot 250 as being completely disconnected from the leg 206 and the foot cap 254. As shown herein, the foot 250 includes protrusions 256 that are inserted into respective cutouts 268 of the foot cap 254, as well as a protrusion 258 that is arranged to maintain at least a loose coupling between the foot cap 254 and the foot 250, when the foot cap 254 is in an unlocked position. The foot 250 can also include a plurality of spikes 260 about 0.1-1.5 mm, such as 0.4, 0.5, 0.6, 0.8 or 1.0 mm in length, which may be made from a titanium material. The titanium material is strong and sharp and will not bend when being pressed into the skull.

Figure 49:
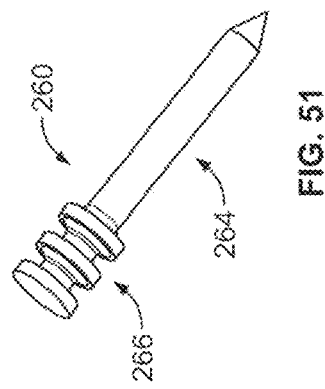
FIG. 49 is perspective view of a foot attached to a spike plate.
Figure 51:
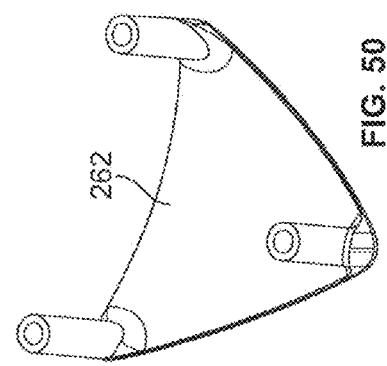
FIG. 51 is perspective view of a spike.
Figure 50:
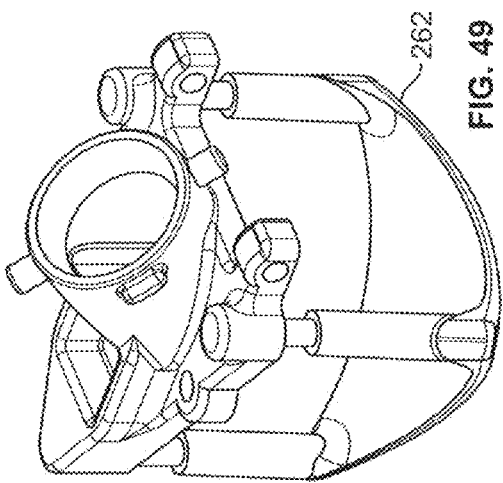
FIG. 50 is perspective view of to a spike plate.

Further, a straight profile of the spikes 260 reduces the resistance when being pressed into the scalp. The spikes 260 can be molded into the foot 250, which is also made of plastic or titanium. Prior to installation, as shown in FIG. 49, the spikes 260 can be covered by a spike plate 262. FIG. 50 illustrates the spike plate 262 by itself, and FIG. 51 illustrates a titanium spike 260 by itself. In FIG. 51, the titanium spike 260 is shown as including a nail portion 264 and a grooved portion 266. Several grooves are provided to create a rigid and reliable connection between the foot 250, which can be a molded plastic, and the titanium spike 260.

FIGS. 52-54 illustrate various views of the foot cap 254 having the cutouts 268. FIGS. 52 and 54 illustrate respective bottom and top perspective views of the foot cap 254, and FIG. 53 illustrates a side view of a foot cap 254. As shown in FIG. 53, the cutouts 268 include the angled edge 270 to promote a locked position with the protrusions 256.

Although not shown, the spike plate 262 can include holes and/or grooves so that a sterilization gas can contact the titanium spikes, which are intended to be inserted into a patient's skull. Such a sterilization gas can be, for example, ethylene oxide. Further, leg numbers can be added to the frame 214 and/or the retaining ring 220 such that identification of a particular leg of the miniframe can be easily identified from a look-down position. Further, the spikes 260 can be varied in length based on a particular placement, and the foot 250 can be increased in size to create a larger footprint to extend around areas where screws and/or spikes cannot be attached to a patient's skull.

Although a preferential order of alignment of the various components can include positioning and securing the legs 206, then rotating the rotation portion 204, and then adjusting the tilt portion 202, orientation of the miniframe 200 can be made following a different order of steps, without diverting from the steps of this disclosure. For instance, fiducial markers can be attached to the patient's skull to map a three-dimensional surface profile of the patient's skull, and the tilt and rotation and leg 206 lengths of the miniframe 200 can be calculated prior to mounting the miniframe 200 to the patient's skull. Once the calculations are verified, verification of the calculations being performed by modeling a rendered miniframe 200 or placing an actual miniframe 200 having the calculated settings applied thereto to the patient's skull either in the physical space or in the rendered space. Once verified, then the miniframe can be attached via spikes or screws to the patient's skull, and the trajectory can then be verified through MRI scanning or optical imaging.

In light of the above, it should be appreciated that the independently rotating and tilting portions of the miniframe can simplify adjustments, wherein a tilt-point (i.e., the tilt portion 202) is provided so as to be displaced from a patient's skull. The tilting and rotational portions can also be independently locked with non-friction (i.e., non-pressure based) locks. That is, teeth locks can be independently provided for each of the tilting and rotational portions. Pressure/friction-based locks/holders can be utilized to secure a probe and/or a probe driver or other instrument engaged with the miniframe via the tilting portion.

The miniframe can be a single-use, disposable component, in that a miniframe is used per patient. A single miniframe is usable with multiple probes, trajectories and procedures in succession for the patient.

The miniframe provides full rotational freedom of the rotating part and the tilt portion, and a wide range of tilt angles for the tilt portion. The locking mechanisms can be easily released and reset. Thus, a trajectory can be modified and re-locked in real-time based on real-time image data or to set a next trajectory in a treatment procedure.

In planning, setting, registering or modifying a trajectory, an MRI-visible portion of the miniframe (such as the fiducial marker 244) can be used, via MRI imaging, to verify a position of the miniframe, especially with respect to a target tissue or intended trajectory. Moreover, a further MRI-visible portion, such as a fluid filled tube, can be placed in the through hole 208 or in a device that is inserted into the through hole 208 to provide an MRI-visible indication of trajectory of the miniframe.

The miniframe provides a tilt/pivot point that is in a different radial position than an entry point, with respect to a spherical coordinate system.

III. PROBE DRIVER

An exemplary probe driver that can be utilized in accordance with the various aspects presented in this disclosure is described in U.S. Ser. No. 12/540,558, filed Aug. 13, 2009, published as US 2010/0042112, the entirety of which is incorporated herein by reference.

An exemplary probe driver is shown in FIG. 5. FIG. 5 illustrates the probe driver as including a commander, connected to a follower by umbilicals, and a position feedback plug connected to a potentiometer assembly of the follower. The position feedback plug is plugged into an interface platform and the umbilicals include sheathed wires that independently control rotational and longitudinal motion of a probe or other longitudinal member held by the follower. Independent control of the rotational and longitudinal motion is provided by rotating a respective one of the knobs or dials provided at either side of the commander. An exemplary structure for the corresponding mechanisms that provide the rotational and longitudinal motion is described and shown in US 2010/0042112, the entirety of which is incorporated herein by reference.

Figure 55:
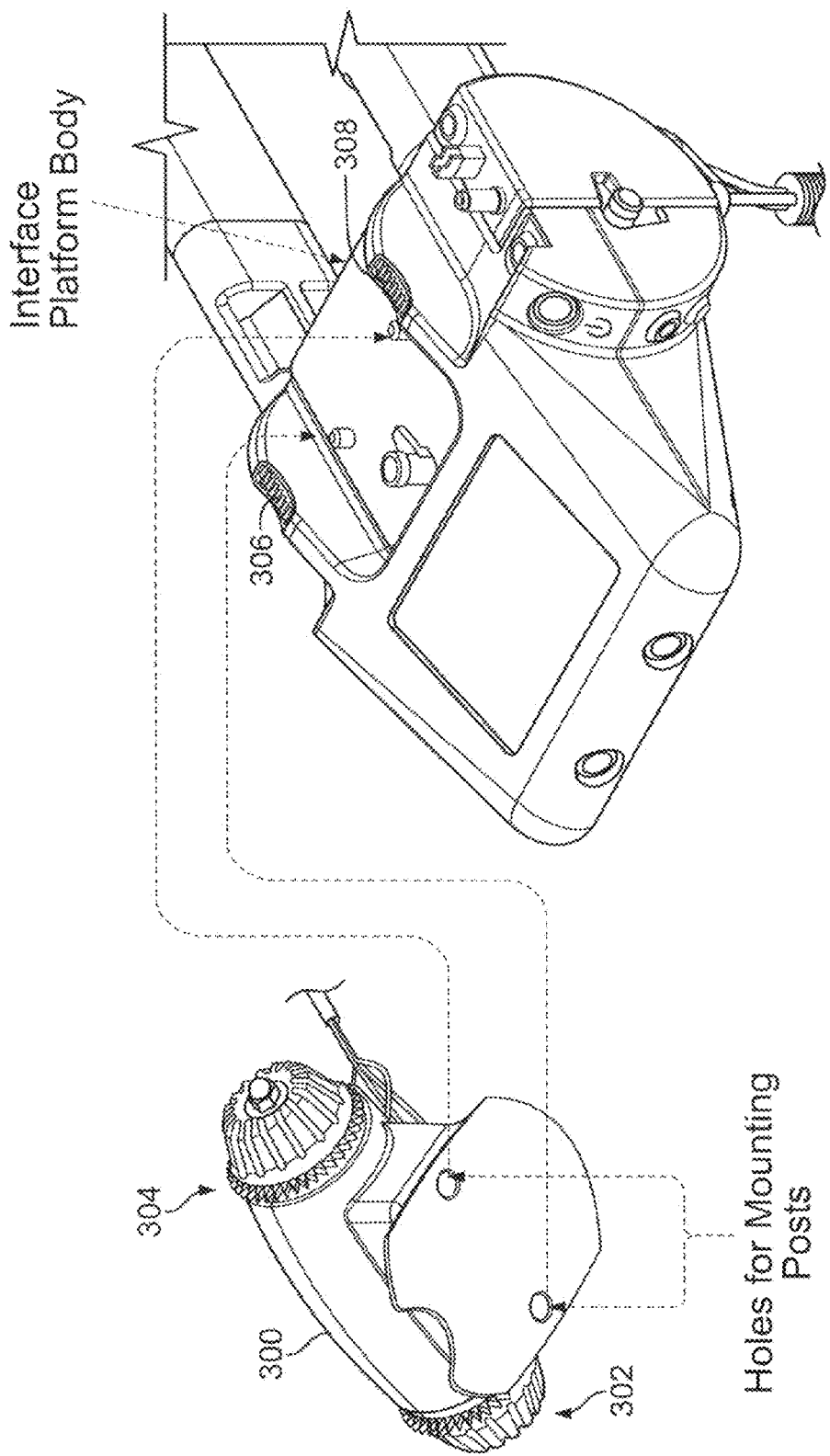
FIG. 55 is an illustration of a commander and an interface platform.

FIG. 55 illustrates a commander 300 of an exemplary probe driver. The commander 300 includes opposing knobs or dials 302 and 304 (herein knobs 302 and 304). These knobs 302 and 304 independently control longitudinal and rotational motion, e.g., in a manner that coincides with that described in the exemplary structure of US 2010/0042112. The commander 300 is arranged to be mounted to an interface platform body, as shown in FIG. 55, via corresponding holes and mounting posts.

The knobs 302 and 304 each include gear teeth that are structured to be engaged with corresponding gear teeth 306 and 308 of the interface platform. The interface platform includes motors to respectively rotate the gear teeth 306 and 308 in response to corresponding instructions (data) received from a workstation in an MRI control room (see FIG. 1). When the commander 300 is coupled to the interface platform, rotation of the gear teeth 306 and/or 308 is translated to the gear teeth of the knobs 302 and/or 304, which results in independent control of the rotational and longitudinal motion.

Figure 56:
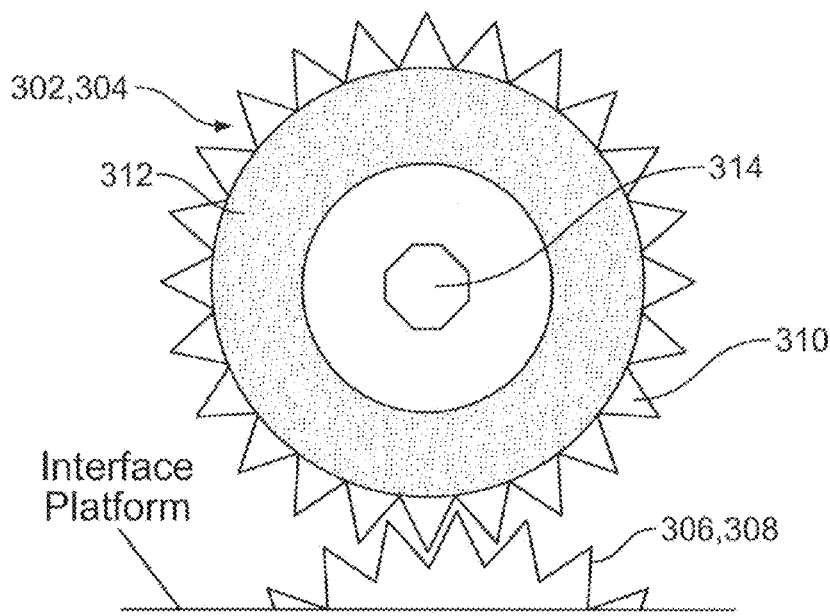
FIG. 56 is a schematic illustration of a knob of a commander coupled to a drive mechanism of an interface platform.

FIG. 56 schematically illustrates either of the knobs 302 and 304 engaged with the interface platform via an engagement between the teeth 310 of the knobs 302 and 304 and the teeth 306 and 308 of the interface platform. Either or both of the knobs 302 and 304 include a contoured surface 312 for manual manipulation thereof, as well as a bolt or fastener 314 that secures the knobs 302 and 304 to internal mechanisms of the commander 300.

Other engagements are also possible, including toothless friction rollers. With any type of engagement, a rotational motion originating from a workstation, that causes the gear teeth 306 and/or 308 (or other interface platform rotational driving mechanism) to rotate, causes the knobs 302 and/or 304 to rotate. Consequently, rotational and/or longitudinal movements via the follower are enacted. These movements are then tracked via a potentiometer assembly in the follower, and a feedback signal is provided to the interface platform. Consequently, a workstation receives electronic positional feedback and is able to verify that an instructed command resulted in an intended rotational and/or longitudinal alignment, and can responsively output further commands to the commander to achieve an intended alignment, should the initial command not result in a particular or intended position. The workstation monitors such unintended alignments to determine whether an amount of slippage in the various mechanisms is above a certain tolerance, and displays a warning error so that the mechanisms can be visually inspected to ensure proper setup and functioning.

In conjunction with electronic control provided via the workstation, a clinician at the workstation, which is coupled to the probe driver via the electronics rack and the interface platform, is provided with an automated drive means that is spaced apart from the MRI (that is, outside of the bore of the MRI), but is coupled to a flexible MRI-compatible umbilical, which is in turn coupled to a motorless drive system positioned within the bore of the MRI and/or a head coil positioned around the head of a patient. Actuation of the drive means can therefore be accomplished by a clinician who is not in the MRI room, but is rather in a control room, such as an MRI Control Room, and control of the motorless drive system can be provided while the MRI is operating and images are being collected. Further, continuous, uninterrupted control of neural laser ablation (or other treatment depending on the probe structure) is possible when the probe in use requires repositioning. That is, in a multi-step treatment, e.g., a multi-step ablation, operation of the MRI can be continuous while a probe position is changed in either or both of rotational and longitudinal directions.

In various implementations the probe driver provides full remote control to an operator that is located either: (1) in the proximity of the MRI and an interface platform that the probe driver is connected to, or (2) in a remote room, such as a control room, at a workstation, where the workstation sends positioning signals to the interface platform to actuate corresponding movements by the commander. Full remote control of the probe drive is thus provided, which reduces procedure time.

Further, the probe driver in this illustrated implementation can provide, at a minimum, a translation of 20-80 mm, 30-70 mm, 40-60 mm or 40 mm, with a maximum translation of 60 mm, 80 mm, 100 mm, 120 mm or 60-150 mm or more. The probe driver in this illustrated implementation can also provide, at a minimum, a rotation of 300°-340°, with a maximum rotation of 350°, 359°, 360°, 540°, 720° or more or of any angles therebetween.

IV. PROBE

A plurality of different probes can be utilized in accordance with the various aspects presented in this disclosure.

Exemplary probes are described in: U.S. Pat. No. 8,256,430, filed Dec. 17, 2007; U.S. Pat. No. 7,691,100, filed Aug. 25, 2006; U.S. Pat. No. 7,344,529, filed Nov. 5, 2003; U.S. Pat. No. 7,167,741, filed Dec. 14, 2001; PCT/CA01/00905, filed Jun. 15, 2001, published as WO 2001/095821; U.S. 61/728,068, filed Nov. 19, 2012; and U.S. 61/664,791, filed Jun. 27, 2012. These documents are incorporated herein in their entireties.

A. Side-Fire Probe

Figure 57:
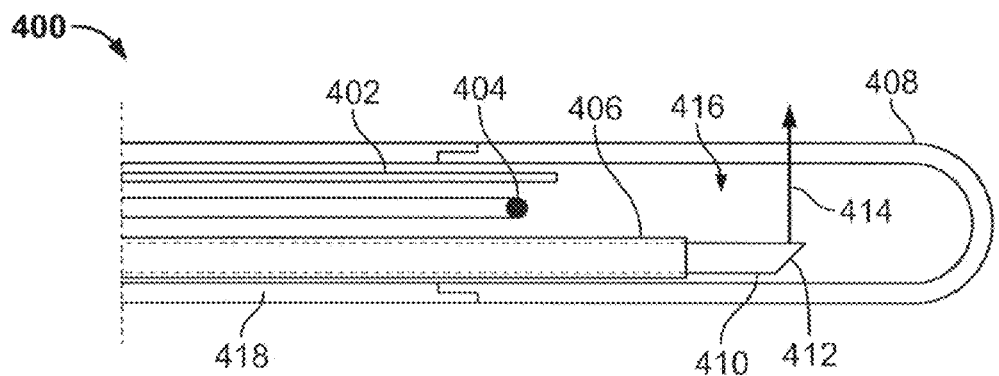
FIG. 57 is schematic cross section of a side-fire probe.

FIG. 57 illustrates an exemplary side-fire probe tip 400 (herein sometimes referred to as merely a probe 400). Probe 400 includes a cooling tube 402 and thermocouple 404. As shown in FIG. 3, these components are coupled to corresponding probe connectors that are secured to the interface platform, as further shown in FIGS. 10 and 14. The probe 400 also includes an optical fiber 406 as an active element. The cooling tube 402, the thermocouple 404 and the optical fiber 406 are enclosed in a capsule 408. In one implementation, the capsule 408 is a sapphire capsule. However, other materials can be used, including quartz. Further, when a non-laser probe or a non-light-based probe is utilized, a material suitable for ultrasound or radio frequency transmission can be used, and such a material can be the same as that used for the cannula. Otherwise, other crystal structures or glass-type structures can be utilized that effectively transmits light, without allowing for an effective amount of reflected light, when a laser probe or other light-based probe is utilized. Further, such materials can include coatings and films, such as optical films.

The optical fiber 406 includes a sheathed portion and an unsheathed portion 410. The unsheathed portion 410 includes a faceted end surface 412, which causes energy, such as laser energy, to be directed in the direction of arrow 414 to initiate therapy in a tissue. Therapy can include, for example, heating or light exposure. When heating a tissue, to control an amount of therapy or heat applied to the tissue, cooling is provided via the cooling tube 402, which outputs a cooling gas or fluid to the expansion chamber 416. The thermocouple 404 detects a temperature in the expansion chamber 416. A workstation can control an amount of cooling gas (either or both of a flow and pressure of the gas) or cooling fluid inputted into the expansion chamber 416 via the cooling tube 402 to control a temperature of the tissue via conduction through the capsule 408.

In one implementation the optical fiber 406 is rotatable with a rotation of the probe 400, for example, by rotating a follower of a probe driver. In another implementation, the optical fiber 406 is independently rotated by the follower, such that rotation of the optical fiber 406 does not necessitate rotation of the capsule 408. As a result of the side-firing capability of the laser energy, a plurality of rotationally different portions of the tissue can be treated with the laser energy by rotating the optical fiber 406 with or without rotating the capsule 408. Additionally, the capsule 408 can be longitudinally displaced by a follower of a probe driver to change a longitudinal position of the directionality of the laser energy within a tissue to be treated. This longitudinal movement of the capsule 408 results in movement of the cooling tube 402, the thermocouple 404, and the optical fiber 406 as one piece.

In another implementation, the optical fiber 406 can longitudinally move with respect to the capsule 408. Consequently, movement of the laser energy from the optical fiber 406 in the longitudinal direction can be achieved without moving the capsule 408 or other parts thereof.

The optical fiber 406 can be referred to as a core of an optical laser fiber. A tip of the core can be polished at an angle of 38 degrees to provide an exemplary side-fire probe.

B. Diffuse-Tip Probe

Figure 58:
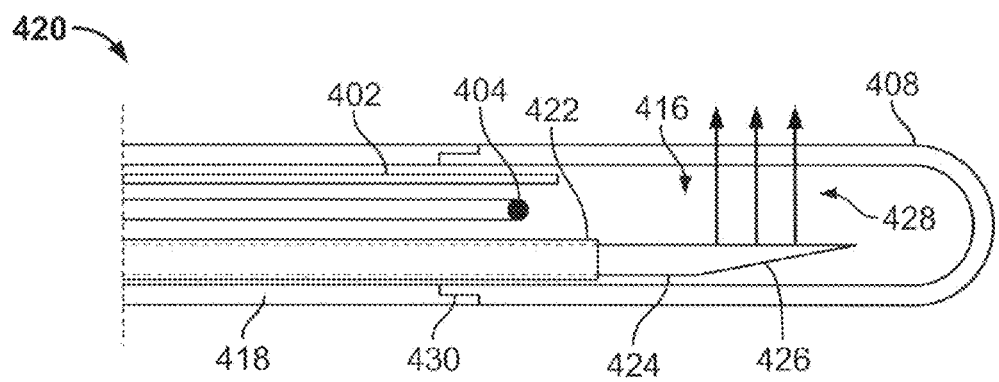
FIG. 58 is schematic cross section of a diffuse-tip probe.

FIG. 58 illustrates a diffuse-tip probe 420 (herein sometimes referred to as merely a probe 420). The probe 420 includes some components that are similar to that of probe 400. The probe 420 includes an optical fiber 422 that has a sheathed portion and an unsheathed portion 424. The sheath can be formed from a polymeric material such as nylon, ethylene-tetrafluoroethylene, polyamines, polyimides, and other plastics known for optical sheaths or jackets. The unsheathed portion 424 includes a faceted surface 426. The faceted surface 426 results in a diffused output of energy in a side-firing direction, such as in the direction of arrows 428.

The faceted surface 426 is an etched fuser tip, from which laser energy, for example, is delivered diffusely in an even or uneven distribution pattern into a tissue. A longitudinal length of the faceted surface 426, in a longitudinal direction, can be approximately 1, 1.4, 2, 3, 4-30 or 45-60 mm. A plurality of similarly structured diffused-tip probes can be provided with varying active lengths, where a particular active length can be selected based on a particular tumor size to be treated. An exemplary length is 6 mm or 4-7 mm.

With respect to the described examples, in general, the unsheathed portion of the optical fibers described herein includes a cladding, whereas the faceted surface(s) of the unsheathed portion do not include the cladding. Additionally, the faceted surface(s) can be etched by, for example, an acid treatment. In another implementation, one or more faceted surfaces are replaced by etched surfaces, in which the general structure of the optical fiber is maintained, but a clad is not present or removed, and the material of the optical fiber is etched to create one or more emission points. These emission points can be disposed along a longitudinal axis and/or circumferentially to form a symmetric or asymmetric energy emission pattern.

The capsule 408 can be fixed to a rigid cannula 418, and the capsule 408 can be made of quartz, sapphire or other such suitable materials. The rigid cannula 418 is formed of a suitable rigid MRI compatible material such as plastic so that it is stiff in resistance to bending and has sufficient strength to allow a surgeon to insert the cannula into a required location in the body of a patient. In another implementation, the rigid cannula 418 is only rigid in a torsional, rotational direction, and is flexible at one or more points so that it is bendable.

The cooling tube 402, the thermocouple 404 and the optical fiber can be attached by an adhesive to the cannula 418. The cooling tube is swaged at its end and projects into the capsule 408 to form a cross section of reduced inner diameter on the order of 0.002, 0.003, 0.004, 0.003 to 0.005 or 0.006 inches or values therebetween. The capsule 408 can include a step portion 430 that can be pressed fit and/or adhesively secured to the cannula 418. An outer diameter of the cannula 418 and the capsule 408 is the same, and an inner diameter of the capsule 408 and the cannula 418 is the same. However, the diameters can be varied. Additionally, a fiber optic thermometer, not shown, can be utilized instead of the thermocouple 404. The cooling tube 402 can supply pressurized carbon dioxide, for example, and the supplied fluid/gas can utilize Joule-Thomson cooling via Joule-Thomson expansion. However, cooling fluids which do not expand but rather circulate from the cooling tube 402 through a discharge duct can also be used.

A fluid supply for the cooling tube 402 originates from the electronics rack shown in FIG. 1. The electronics rack is coupled to the interface platform, which is in turn connected to the cooling tube 402 via the probe connectors shown in FIGS. 3 and 14. Similarly, the optical fiber and the thermocouple are connected to the electronics rack. Via the electronics rack, the workstation controls the flow rate of carbon dioxide, for example, in a cooling tube 402 to generate a predetermined pressure within the cooling tube 402, which can be varied so as to vary a flow rate of the fluid through a neck portion of the cooling tube 402. As a result, a Joule-Thomson effect is achieved, where gas exiting the reduced diameter neck portion expands into the expansion chamber 416 to cool the probe in contact with the tissue and cool the tip of the optical fiber that emits laser energy (such as the diffused tip portion provided by the faceted surface 426). The cooling fluid can be supplied at a normal or room temperature without cooling. The fluid is normally a gas at this pressure and temperature. Fluids that are liquid can also be provided such that they form a gas at the pressures from the expansion chamber 416, and therefore go through an adiabatic gas expansion process through the restricted orifice into the expansion chamber to provide the cooling effect. The restricted orifice or neck portion of the cooling tube 402 is therefore a venturi outlet and has a cross-sectional area that is smaller than a main-body of the cooling tube 402.

The interior of the probe serves as a return duct which discharges the cooling fluid/gas/liquid. An exhaust duct area of approximately 190 to 540 or 200 to 300 or 200 times larger than an orifice area of the cooling tube 402 can be achieved when considering a delivery orifice diameter of an exemplary 0.004 inches, or an exemplary 0.002, 0.003, 0.004, 0.003 to 0.005 or 0.006 inches or values therebetween. Cooling of at least −20° C. to +20° C. is achieved with at least a 200:1 (outlet:inlet) gas expansion ratio. This allows the gas, as it passes into the expansion chamber, to expand as a gas, thus cooling the capsule 408 and an interior thereof to a temperature in the range of at least −20° C. to +20° C. This range of temperatures has been found to be suitable in providing the required level of cooling to the surface of the capsule 408, so as to extract heat from the surrounding tissue at the required rate of cooling. Variations in the temperature range are achieved by varying the pressure of the cooling gas/fluid so that in one example the pressure of the gas is between 700 and 850 psi and has a flow rate of 1, 2, 3, 4, 5 or 6-15 liters per minute. Other achievable temperature ranges include −40° C. to +40° C., −35° C. to +35° C., −30° C. to +30° C., −25° C. to +25° C., −15° C. to +15° C., −10° C. to +10° C., and ranges therebetween. Other exemplary pressures of the gas include 600-650, 650-700, 700-750, 750-800, 800-850 and 700-900 psi.

To achieve a desired rate of cooling a probe is cooled to between 0° C. to 5° C., such as 1° C. to 3° C. or 2° C., by Joule-Thomson cooling. This temperature range is preferably maintained within an entirety of the probe before, throughout, and after a treatment or energy emission of the probe.

A discharge of the cooling gas through the cannula 418 is at a pressure of approximately 25-50, 75 or 50 psi in the example described herein. Thus, the gas may be discharged through the atmosphere if the gas is inert, discharged to an extraction system, or collected for cooling and returned if economically desirable. Cooling of the probe is necessary for optimum tissue penetration of the laser or heating energy. Cooling reduces tissue charring and sets localized cooling of the treated region. Probe cooling also protects the faceted surface or an otherwise active area of the optical fiber. The faceted surface 426, in the longitudinal direction, is shorter than an internal length of the capsule 408 so that the faceted surface 426, which defines the active length, can be approximately centered within the expansion chamber 416, and so that no or little to no energy is delivered to the sheath of the optical fiber. The faceted surface 426 is arranged such that it is surrounded by the cooling gas from the cooling tube 420 within the expansion chamber 416. As a result, in practice, no condensate forms on the faceted surface 426 that would otherwise interfere with reflective characteristics.

In operation, the temperature of the expansion chamber 416 is monitored by the thermocouple 404 so as to maintain the temperature at a predetermined level in relation to an amount of heat energy supplied through the optical fiber. Pressure of the cooling gas is varied to maintain the temperature at the predetermined set level during a hypothermic process.

FIGS. 59-66 illustrate alternative faceted surfaces or active areas for diffused-tip type probes. In these figures, the structures can be considered as being drawn to scale. The structures can also be considered as accentuated in size so that their shape is readily understood. Accordingly, in some aspects, the drawings can be considered as schematic in nature and as not being drawn to scale. Further, an effective/active area for laser-energy emission is shown by hash marks. In one implementation, the area of the optical fiber that is not sheathed and is not shown by hash marks includes cladding.

Figure 59:
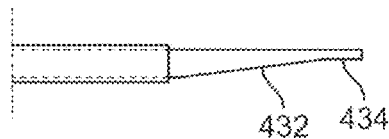
FIGS. 59-70 illustrate profiles of exemplary types of probe tips.
Figure 60:
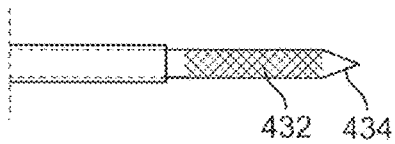

FIGS. 59 and 60 illustrate an implementation that includes a faceted surface/active area 432 that ends in a clad portion that comes to a tip 434. FIG. 59 is a side profile view of the faceted surface 432, where FIG. 60 is a view in which the faceted surface 432 is facing outwards. The faceted surface 432 includes one or more edges, in section, that can form a single inclined surface, a plurality of inclined surfaces, or a plurality of stepped portions.

Figure 61:
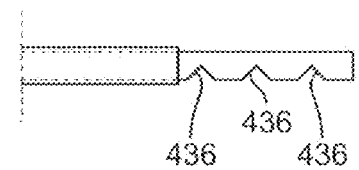
Figure 62:
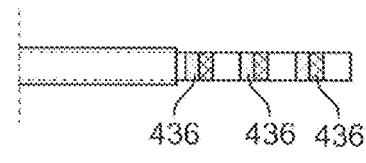

FIGS. 61 and 62 illustrate a plurality of side-firing points 436. FIG. 61 is a side profile view of the faceted surfaces providing these points 436, whereas FIG. 62 is a view in which the points 436 face outwards. The implementation shown in FIGS. 61 and 62 provide a plurality of longitudinally displaced side-firing points. The points 436 are formed by recess, which can have an angular (as shown) or a curved (not shown) section. The points 436 can also be formed by merely etching surfaces of the optical fiber.

Figure 63:
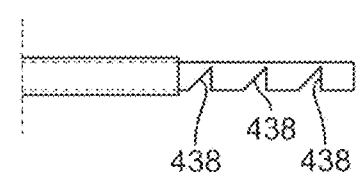
Figure 64:
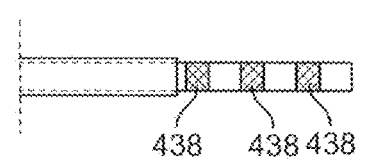

FIGS. 63 and 64 illustrate a structure that is similar to that shown in FIGS. 61 and 62. However, in FIGS. 63 and 64, the faceted surfaces are structured differently. In particular, the faceted surfaces of FIGS. 61 and 62 are a plurality of recesses 438 that form a saw tooth pattern. The difference in patterns between these two implementations varies a pattern of energy output. One may be preferable over the other for a particular tissue treatment shape or for a particular tissue shape/position.

Figure 65:
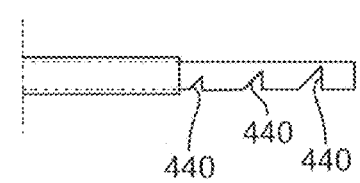
Figure 66:
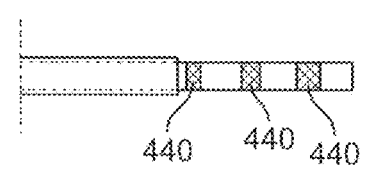

FIGS. 65 and 66 illustrate a further modification to the saw tooth pattern shown in FIGS. 63 and 64. In particular, FIGS. 65 and 66 illustrate a graduated saw tooth pattern where individual recesses 440 vary in size. The varying in size shown in these figures is shown as increasing as the optical fiber approaches its end. However, other variations are possible. In particular, a size of individual recesses included in an optical fiber can be varied to achieve a prescribed laser energy output profile. Further, if merely etching is utilized, a size of the etching can be varied among a plurality of longitudinally spaced active areas on the optical fiber, where a clad separates each of the active areas.

The particular implementations shown in FIG. 61-66 include three separate longitudinally displaced side-firing points. However, two or more side-firing points, such as any one of 2, 3, 4, 5, 6, 7, 8, 9 or 10 or more points can be provided.

Consequently, an energy emission member is provided which includes a plurality of longitudinally displaced points of energy emission, which can be tuned, by either surface treatment or recesses, to achieve a prescribed side-firing profile of energy emission.

Compared to a non-diffused-tip probe (a non-DTP), a DTP can output a side-firing profile of energy that has a much larger longitudinal length within the tissue. By increasing an amount of energy of the DTP, an amount of heat generated within a larger portion the tissue can be increased, relative to a non-DTP. Therefore, a temperature of the tissue can be increased at a greater rate with the DTP than with the non-DTP. Further, with effective cooling by the probe, an amount of heat generated by a portion of the DTP can be canceled out by the cooling. Consequently, a more steady-state temperate of portions of tissue surrounding a target area can be provided, and the portions of the tissue surrounding the target area can be prevented from cooling by an effective amount.

The structure of the DTP provides a combination of higher energy output and lower energy density, when compared to a non-DTP probe (such as a side-fire probe). A larger treatment area can be treated within a shorter time window, when compared to the non-DTP probe.

C. Symmetric Probe

Figure 67:
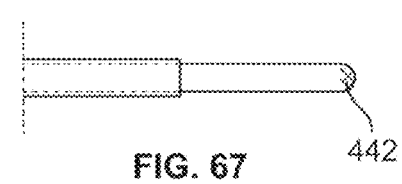
Figure 68:
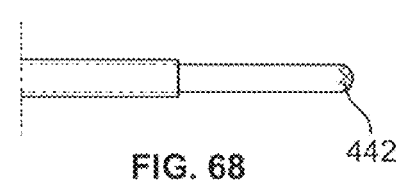
Figure 69:
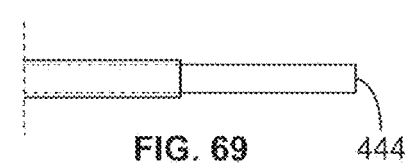
Figure 70:
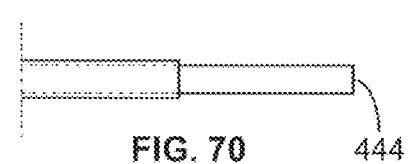

FIGS. 67 and 68 illustrate a symmetric probe with a symmetrical optical fiber having a curved or rounded faceted end 442. FIGS. 67 and 68 illustrate different sides of the optical fiber. FIGS. 69 and 70 illustrate another symmetrical optical fiber, showing different sides of the optical fiber, where the optical fiber has a flat faceted end 444. The ends of optical fibers shown in FIGS. 67-70 can include etching at ends 442 and 444.

The symmetric probes illustrated in FIGS. 67-70 provide symmetric ablation patterns, in which laser output is symmetric with respect to the longitudinal axis of the optical fiber.

The rounded end 442 shown in FIGS. 67 and 68 can provide a spherical or partial spherical laser light output, whereas the optical fibers shown in FIGS. 69 and 70, with the flat faceted end 444, can provide a point output.

Further, the other optical fibers described above can be modified to provide a symmetric output by providing a symmetric active area around a circumference of the optical fibers.

D. Guide Sheath

Figure 71A:
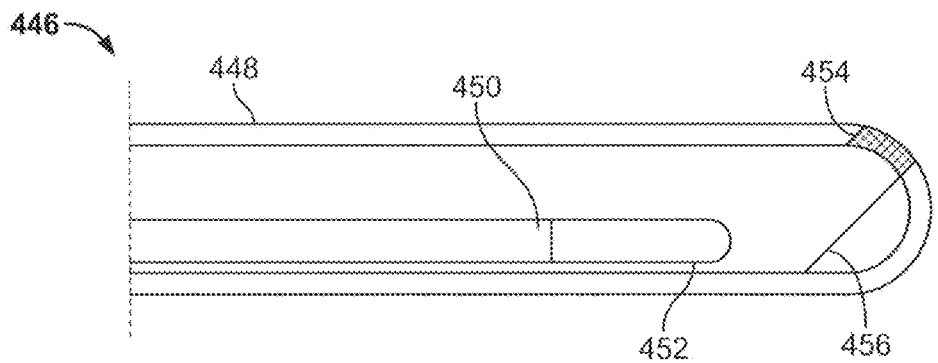
FIG. 71A illustrates a schematic cross section of a probe in a guide sheath having an off-axis hole.

FIG. 71A illustrates an exemplary guide sheath 446. The guide sheath can include a capsule 448 which is made out of a material that is the same as the capsule 408 or the cannula 418. The guide sheath 446 can include a plurality of probes 450, where each of the probes 450 includes a different probe tip 452. In the illustration of FIG. 71A, only one probe 450 is shown for simplicity. By rotation of the guide sheath 446 and/or the individual probes 450, treatment of a same or different tissue portion of a patient can be affected by one or more of the probes 450. Consequently, only one bore hole and guide sheath insertion is used/needed to allow for treatment of a tissue by the plurality of probes that are simultaneously inserted into the guide sheath 446. The guide sheath 446 shown in FIG. 71A is straight and rigid. However, the guide sheath can also be curved to accommodate a given trajectory. Additionally, the guide sheath 446 can include one or more off-axis delivery hole(s) 454. The off-axis delivery hole 454 allows for a probe to be extended therethrough via contact surface 456. Such a structure allows for flexibility in targeting particular tissues in the patient.

The contact surface 456 has a predefined angle, and the off-axis delivery hole 454 is predisposed. The angles shown in FIGS. 71A and 71B can be considered as drawn to scale in one implementation. However, the alignment of the contact surface 456 and the hole 454 can be varied by adjusting their respective axial angles. By adjusting these angles, a plurality of possible positions of a probe 450, for insertion into a tissue through the hole 454, are provided. Further, multiple holes and multiple contact surfaces can be provided, which are displaced from each other in a direction of the longitudinal axis of the guide sheath 446.

Figure 71B:
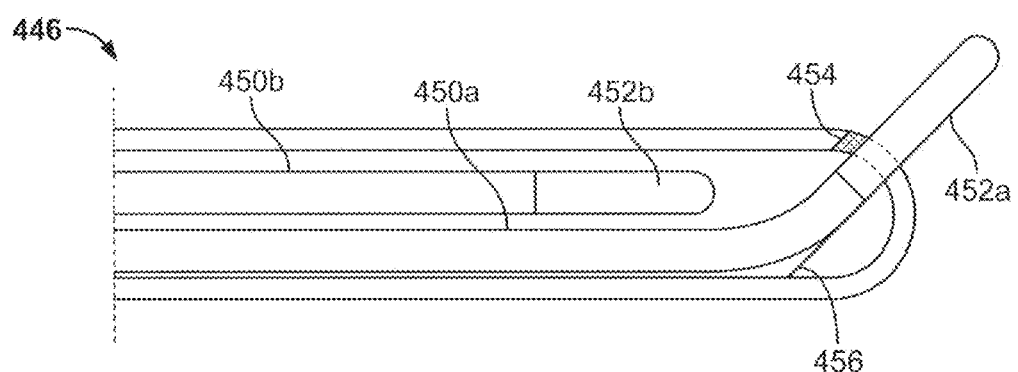
FIG. 71B illustrates a schematic cross section of a plurality of probes in a guide sheath having an off-axis hole.

FIG. 71B illustrates two probes 450a and 450b that are simultaneously inserted into the guide sheath 446 and can affect treatment of a tissue independently or at the same time.

The two probes can provide either or both asymmetrical (side-fire type probe) and symmetrical (point or spherical ablation type probe) treatment patterns. As shown in FIG. 71B, the contact surface 456 can direct a probe tip 452a of the probe 450a through the hole 454. The probe tips 452a and 452b can be commensurate with any of the probes, probe tips and optical fibers described herein.

The probes 450a and 450b can be independently or collectively controlled with respect to axial/longitudinal movement and/or rotational movement. Further, one of the probes 450a and 450b can be dedicated to cooling, whereas the other of the probes 450a and 450b can be dedicated to laser treatment. A cooling probe includes a cooling tube, temperature sensor and an expansion chamber in accordance with the descriptions provided herein.

The cannula of the probe 450a shown in FIG. 71B is flexible with respect to bending, such that the surface 456 causes the probe tip 452a to extend through the hole 454. A material for the cannula for the probe 450a can be selected such that the probe 450a has high torsional rigidity, and such that rotational movements of the probe 450a are effectively translated to the probe tip 452a. Additionally, a mesh joint or other type of joint can be utilized in at least a portion of the cannula for the probe 450a that allows for bending, but maintains torsional rigidity.

A side-fire probe can provide an asymmetrical treatment pattern, whereas a point or spherical ablation probe can provide a symmetrical treatment pattern. Multiple probes of either or both functions are inserted into a common sheath. With respect to the multiple probes illustrated in FIG. 71B, various exemplary sequences are available for an order of treatment. In particular, one probe can provide a symmetrical treatment pattern to affect a tissue, which can be followed by an asymmetrical treatment pattern. Further, a spherical ablation can then be followed by another probe, such as probe 450a, by treatment via an off-axis hole in a guide sheath. This other probe can be a symmetrical, asymmetrical or other type of probe.

With reference to FIG. 71B, this other probe can be the probe 452a, which can then be rotated. The probe tip 452a can also be retracted, the guide sheath 446 can be rotated, and then the probe tip 452a can be extended to continue another step of treatment. The probe tip 452a can be a symmetric or asymmetric probe tip.

The order of the above sequences can be altered.

The hole 454 can be provided at a tip/end of the guide sheath 446, and probes within the guide sheath 446 can be independently rotated with respect to the guide sheath 446. The probes can be rotated after being inserted through the hole 454 and/or before being inserted through the hole 454. The hole 454 can also be provided at various locations to alter a deflection angle, with respect to a longitudinal axis, of a probe inserted therethrough.

The guide sheath can be straight or designed to provide a fixed angle off-axis delivery. The guide sheath can also be curved. Trajectories can be planned that include multiple guide sheaths, including multiple burr holes, multiple trajectories and multiple guide sheath introductions.

E. Probe Modifications and Procedure Considerations

A family of probes can be defined as catheters which differ from one another with respect to one or more of the following variables:

i. A number of probes simultaneously positioned in a guide sheath, including one or more probes. With multiple probes, the probes can be provided with group or individual axial movement and/or rotation, one or more of the probes can be dedicated to cooling only, and probes can be individually extended and retracted from the guide sheath.

ii. Diffuse or point emission.

iii. Symmetrical or asymmetrical emission.

iv. Axial or off-axis probe delivery.

v. Steerable head, where the probe includes a structure that can change a course or trajectory of the probe with respect to a trajectory defined by a guide sheath or other axial guiding structure.

Examples described include those relating primarily to a laser-based probe tip, in which thermal energy is used to affect treatment to a tissue. However, other types of probes and probe tips can be utilized with aspects of the examples described herein. In particular, radio frequency emitting probe tips, high-intensity focused ultrasound probe tips, cryogenic probe tips, photodynamic therapy probe tips, and drug injection probe tips can be utilized independently or in conjunction with a light source emitting probe tip, such as the laser-based probes described herein.

A varied level of ablation control is available to a user. With multiple probes inserted into a common sheath, a workstation can independently control each probe within a sheath. Thus, each emission point of the probes can be independently controlled to obtain an arbitrary treatment shape of the tissue. Further, the probes can be independently rotated and longitudinally displaced. By combining the different probes within a common sheath, operation time can be reduced since various steps of the procedure shown in FIGS. 17-19 do not need to be repeated. In particular, various aspects of trajectory planning do not need to be repeated for a number of probes inserted into a common guide sheath.

In light of the descriptions provided herein, a neural ablative laser probe with Joule-Thomson cooling is provided. Further, a laser probe with longitudinally spaced apart emission points is provided, where the probe is rotatable about a longitudinal axis. Additionally, the illustrated longitudinal spaced emission points in the drawings in FIGS. 61-66 can be applied to other probe technologies, including radio frequency (RF) and high-intensity focused ultrasound (HiFu) technologies. HiFu technology, in particular, provides enhanced direction control and greater depth penetration. Further, constructive and destructive interference can be utilized by the plurality of different longitudinal spaced emission points to fine tune a position and depth of energy applied to a tissue.

Figure 72:
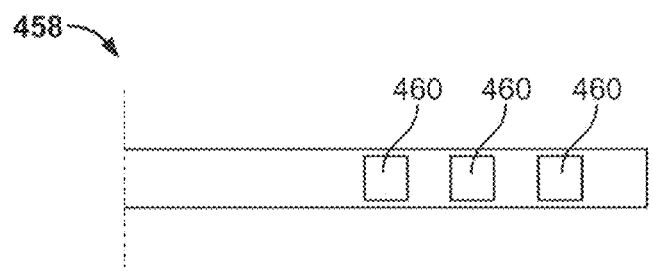
FIG. 72 is a schematic illustration of a probe tip having a plurality of longitudinally space apart energy emitters.

As shown in FIG. 72, a probe tip 458 can include electronic emitters 460. These electronic emitters 460 are longitudinally spaced apart, where the probe tip 458 is rotatable about its longitudinal axis. The longitudinally spaced apart emitters 460 are shown in a regular period. However, the spacing between the electronic emitters 460 can be varied and irregular. The electronic emitters are sonic energy emitters or radio frequency emitters. The probe tip 458 is combinable with the capsule described herein that includes a cooling tube and a thermocouple.

Rotation, intensity, duty cycle, longitudinal positioning, and cooling are controlled by the electronics rack and the workstation. A sequence, such as an algorithm or software encoding, can be executed to cause a probe tip or a plurality of probe tips to execute a particular ablation pattern to affect a predefined treatment scheme to a target tissue area. The ablation pattern can include rotational and/or longitudinal movements.

Figure 73:
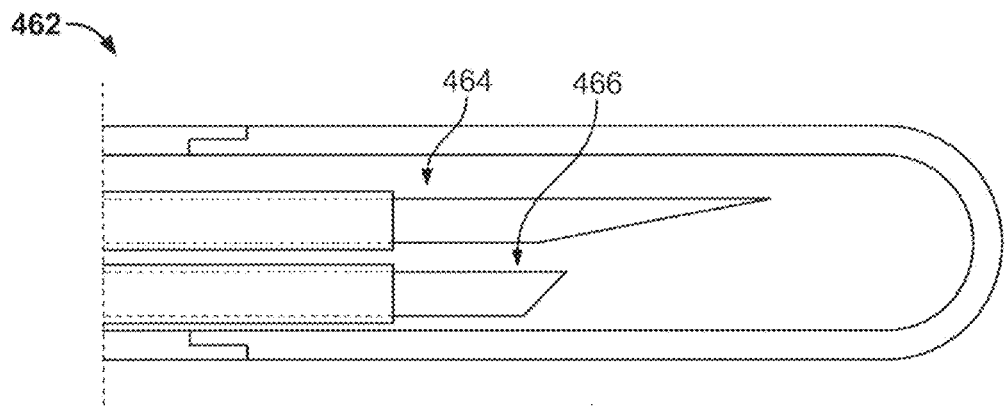
FIG. 73 is a schematic cross section of a side-fire probe and a diffuse tip probe together in a common capsule.

A probe tip 462, as shown in FIG. 73, can include two or more optical fibers 464 and 466. Optical fiber 464 is illustrated as a diffuse-tip optical fiber, whereas optical fiber 466 is illustrated as a side-fire point emission optical fiber. In this case, the probe tip 462 can provide two separate types of asymmetric ablation. The probe tip 462 also includes a cooling tube and thermocouple or other sensor, in a manner consistent with the other examples, but is not shown. Additionally, other combinations of faceted surfaces or active areas can be combined together, such that any of the laser emission examples described herein can be combined together in a singular probe tip to allow for ablation of a tissue with various types of emission patterns, without requiring a new probe to be inserted into a patient for each ablation pattern. Further, the probe tip 458 shown in FIG. 72 can be included with one or more of the optical fibers shown in FIG. 73.

Figure 74:
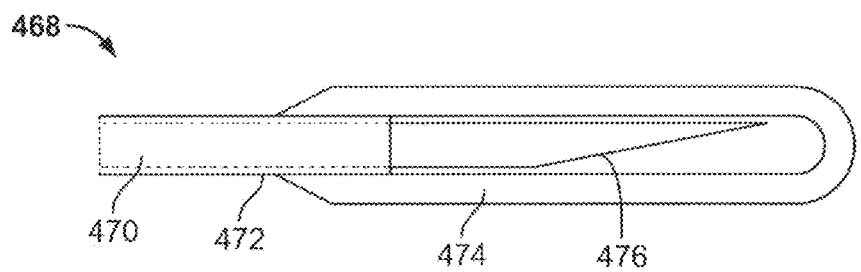
FIG. 74 is a schematic cross section of a capsule attached to a laser fiber.

As shown in FIG. 74, a probe 468 is illustrated. The probe 468 includes an optical fiber 470 that includes a sheath or clad 472. The sheath or clad 472 is fixed to a capsule 474. In this particular implementation, only the optical fiber 470 extends into the capsule 474. Within the capsule 474, the sheath or clad 472 (and in some implementations, both of a sheath and a clad) are removed from the optical fiber 470, and the optical fiber includes a faceted surface 476. Depending on a structure of the faceted surface 476, the probe 468 can be a diffused-tip probe, a side-fire probe, and/or have a structure that coincides with that illustrated in any of FIGS. 59-70 and 72. In the case of FIG. 72, the optical fiber is replaced with an electrical cable and suitable emitters 460.

In some implementations, the probe 468 can be utilized in the guide sheath 446, where the optical fiber 470 is flexible and allows the optical fiber 470 to bend by contacting a surface 456 and exit through a hole 454. The probe 468 can also be utilized individually, without cooling. A length of the capsule 474 can be approximately 3, 4, 5, 6, 7, 8, 9 or 10 mm, and a diameter of the capsule can be 0.3, 0.4, 0.5, 0.6, 0.7, 0.8, 0.9, 1.0 or 0.5 to 1.0 mm. A non-treatment end of the probe can be fixed to an adapter to connect to a follower to enable rotational and longitudinal control in accordance with the other portions of this disclosure. A diameter of the optical fiber 470 can be 150, 200-800, 300, 400, 500, 600, 700 or 800 micrometers.

A plurality of probe lengths are provided in any of the probe examples described herein based on a degree of longitudinal travel allowed by a follower and a depth of the tissue to be treated. An appropriate probe length can be determined by the interface platform and/or the workstation during a planning stage, or determined during a trajectory planning stage.

Exemplary probe lengths can be indicated on the probes with reference to a probe shaft color, in which white can indicate "extra short" having a ruler reading of 113 mm, yellow can indicate "short" having a ruler reading of 134 mm, green can indicate "medium" having a ruler reading of 155 mm, blue can indicate "long" having a ruler reading of 176 mm, and dark gray can indicate "extra long" having a ruler reading of 197 mm. Different model numberings can also be utilized on the probes to indicate different lengths.

Figure 75:
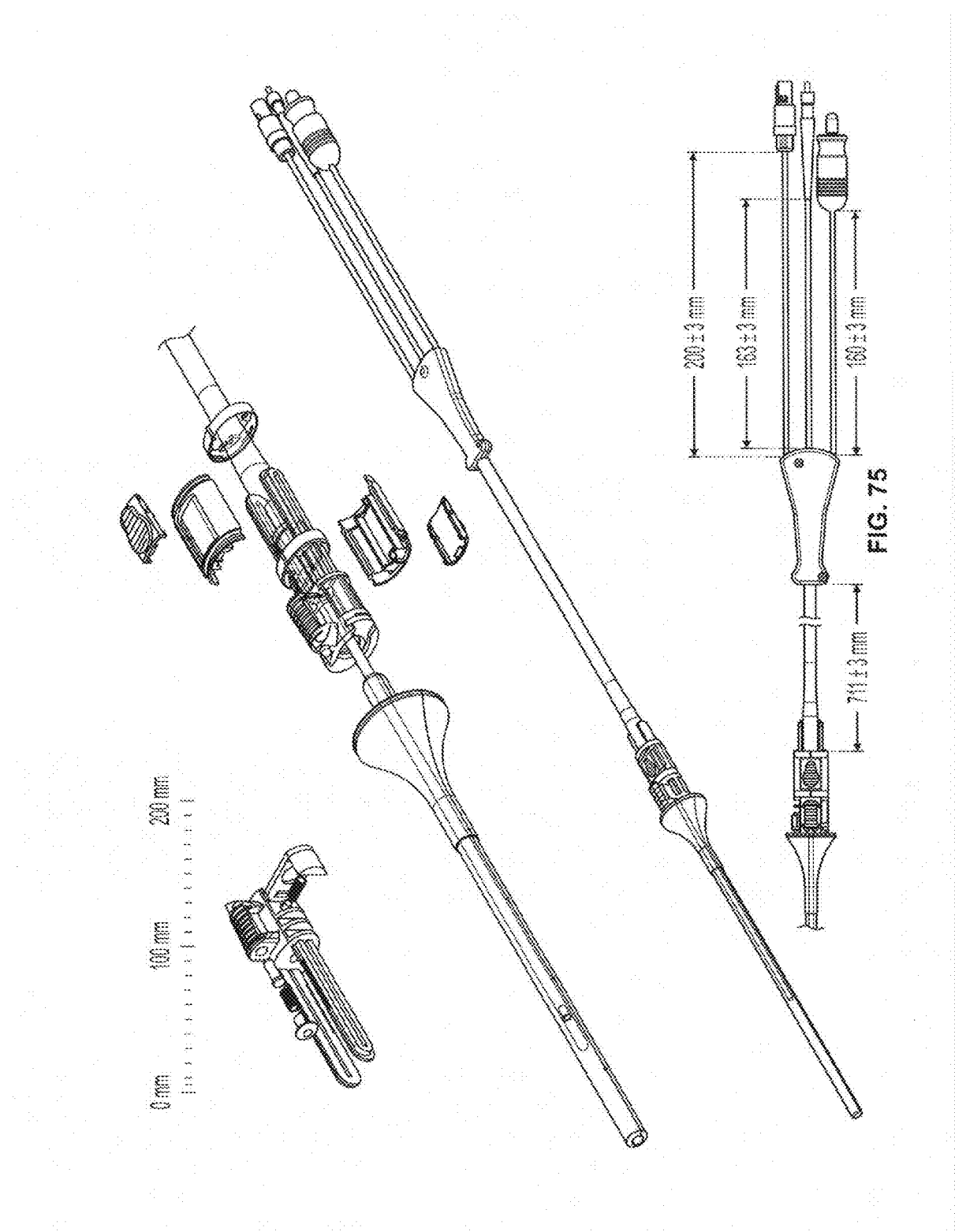
FIGS. 75-77 illustrate exemplary dimensions of components of an exemplary probe.
Figure 76:
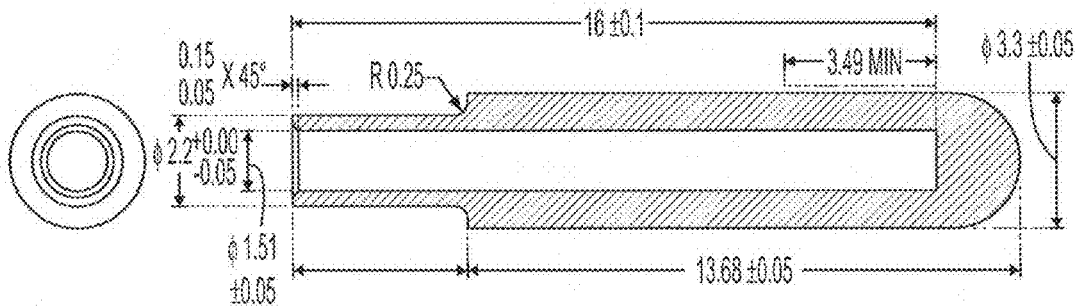
Figure 77:
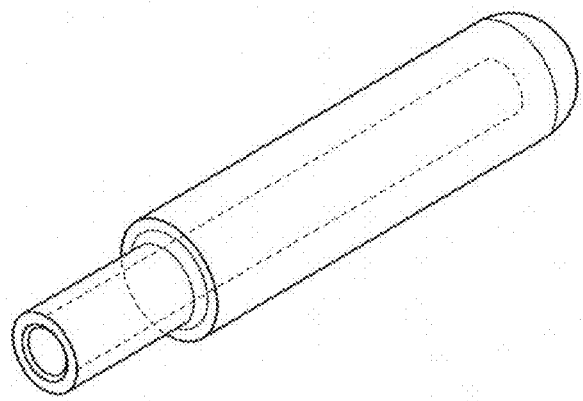

Exemplary lengths of the probe structures are shown in FIGS. 75-77. These figures are drawn to scale and measurements are given in millimeters, unless otherwise indicated. FIG. 75 illustrates the components of the probe shown in FIGS. 3-4. FIGS. 76-77 illustrate the dimensions of an exemplary capsule. An exemplary probe with an outer diameter of 3.3±0.05 mm is shown.

In exemplary implementations, the guide sheath is MRI compatible, and may be introduced through a burr-hole that is created surgically. A sheath with at least one distal opening to be placed in a target area corresponding to a region of interest can be utilized in one implementation. In another implementation, a sheath with at least one proximal opening can be provided for the delivery of other or a plurality of devices. In some aspects, the sheath may be air-tight for a neurosurgery operation. The sheath may also include a through lumen to allow other devices to be delivered therethrough. The sheath may include a walled structure to physically or mechanically support other devices inserted therein. A sheath may also be delivered with an introducer and a wire. A sheath in accordance with one or more of these aspects can allow for multiple accesses to a treatment site while avoiding undesired interruption of a meninges layer. A sheath in accordance with one or more of these aspects can allow for an expanded treatment space through multiple apparatuses with minimal invasive access.

V. HEAD COIL AND STABILIZATION SYSTEM

An exemplary head coil and stabilization system that can be utilized in accordance with the various aspects presented in this disclosure is described in WO 2012/137179, filed Apr. 5, 2012, the entirety of which is incorporated herein by reference.

FIG. 2 illustrates a patient inserted into a bore of an MRI. The patient's head is fixed to a head fixation ring by fixation pins. The ring is received in a ring mount of a platform. The platform extends, in a direction away from the bore, providing a head coil support. After a miniframe is installed onto the patient's head, and the patient's head is fixed to the head fixation ring, an MRI coil is coupled to the fixation ring and the coil support. Further, as shown in FIG. 2, the coil support includes receiving holes for attaching the interface platform thereto.

Figure 78:
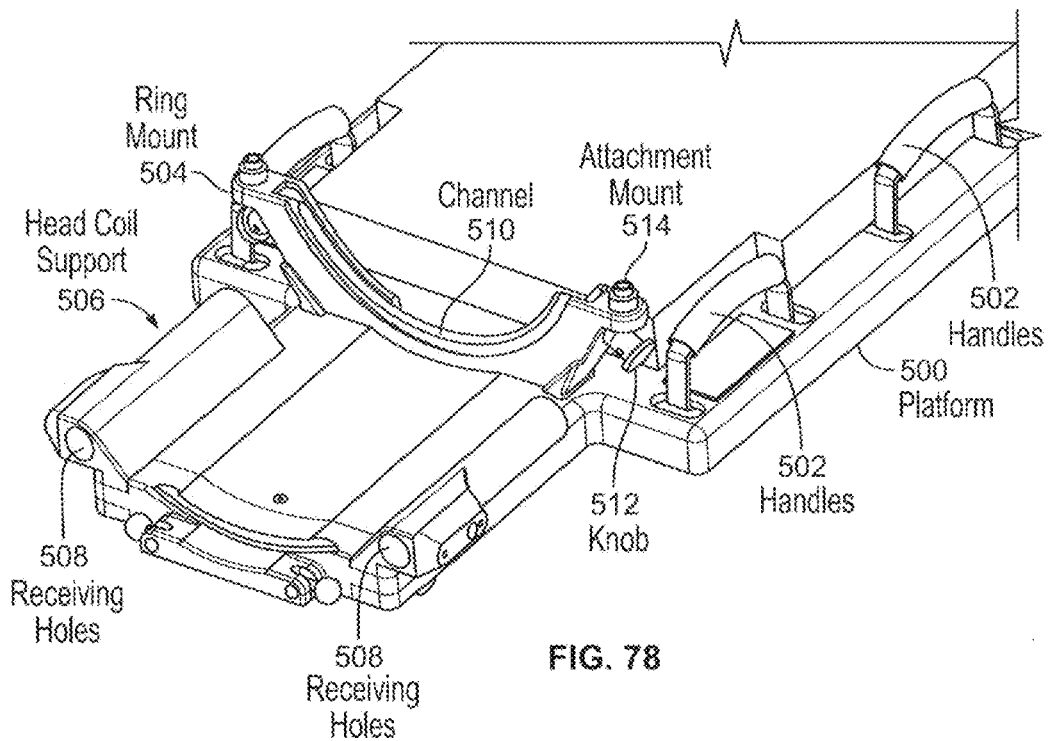
FIG. 78 is an illustration of a front perspective view of a patient platform incorporating portions of a head fixation and stabilization system.

FIG. 78 illustrates a platform 500 including a plurality of handles 502. After a patient is sedated, and the trajectory planning procedure is completed, a miniframe and/or fixation ring is attached to the patient's head. The fixation ring can be secured to the ring mount 504 in, e.g., an operating room in which the trajectory planning procedure is conducted. The patient can then be wheeled to an MRI room, where operators/assistants can utilize the handles to move the fixated patient from, e.g., a wheeled operating table to an MRI table. A head coil is fixed to the fixation ring and/or the head coil support 506 in the operating room on the operating table or in the MRI room on the MRI table. An interface platform is inserted into the receiving holes 508, which is illustrated in FIG. 6.

Figure 79:
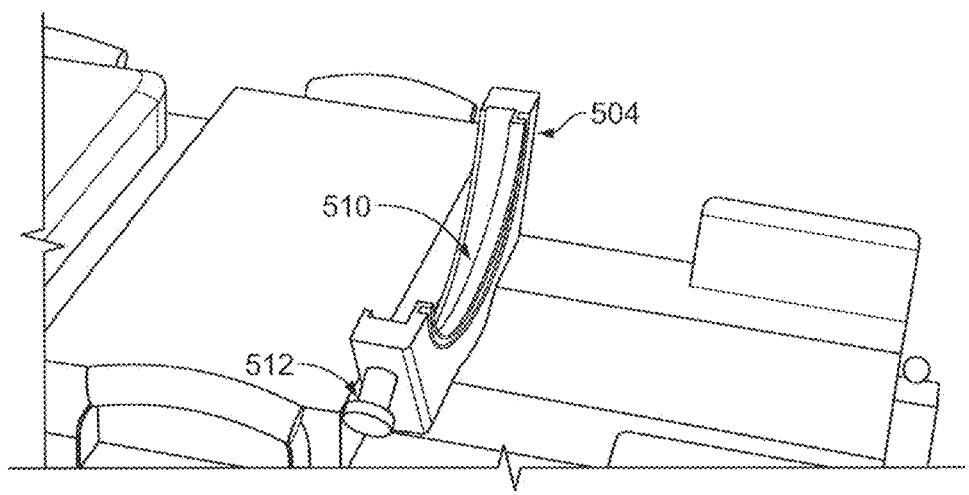
FIG. 79 is an illustration of a side perspective view of a patient platform incorporating portions of a head fixation and stabilization system.

As shown in FIGS. 78-79, the ring mount 504 includes a channel 510, in which a fixation ring rests. The fixation ring is locked into the ring mount 504 via knobs 512, which are provided at distal ends of the ring mount 504. FIGS. 78-79 illustrate alternate perspective views of the ring mount 504.

The ring mount 504 includes attachment mounts 514. The attachment mounts 514 can be utilized in a trajectory planning stage to mount a reference array, such as, e.g., a reference guide of an image-guided surgery system. In particular, a tracking instrument is attached to the attachment mounts 514 to locate the head fixation ring 516 (and therefore the other components of the stabilization system, including the head coil etc.) in rendered space. A convention reference array utilized in image-guided surgery can be utilized with the attachment mounts 514.

Figure 80:
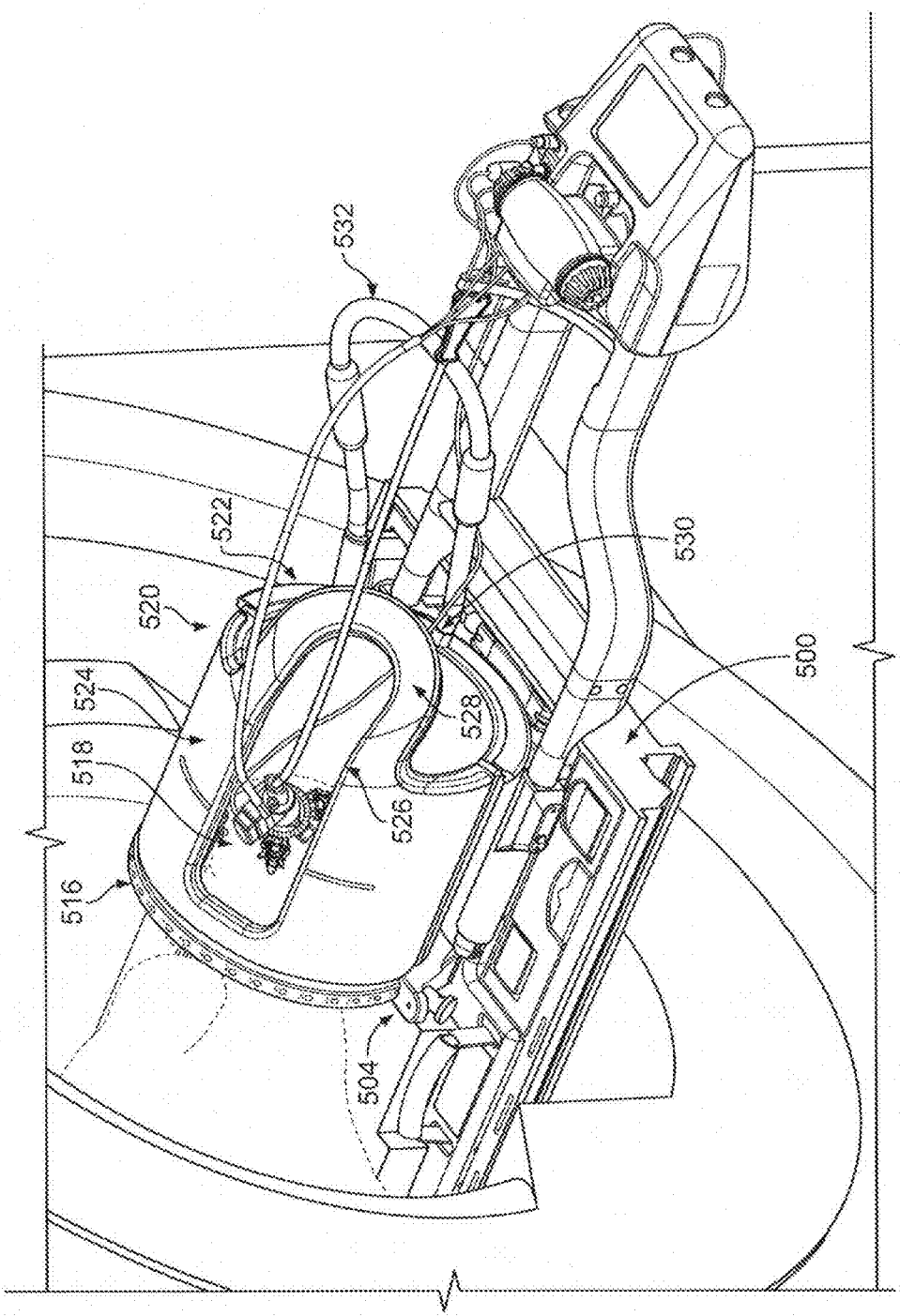
FIG. 80 is an illustration of a perspective view of a patient inserted into an MRI, with a head fixation and stabilization system installed.

FIG. 80 illustrates a head fixation ring 516 fixed to a patient's head 518. A miniframe, probe follower, and probe are attached to the patient's head, and an interface platform is coupled to the platform 500 and wired to the active components. A head coil 520 is fixed to the head fixation ring 516, and includes, generally, two halves. A first half 522 has a half-cylindrical shape and is substantially continuous. A second half 524 has a generally half-cylindrical shape, but includes a slot 526, which extends in a longitudinal direction of the patient. A bent portion 528 of the second half 524 of the head coil 520 bends towards a longitudinal axis of the patient in the direction towards the interface platform, in the direction away from the patient. As a result, a continuous coil can be provided, which allows for a trajectory to be aligned at or near a side to forehead region of the patient's head. In the event that a side trajectory (i.e., entry into a side of the patient's head) or a top-of-head trajectory is planned, a head coil that does not include a bent portion, but merely includes a slot that coincides with a cylindrical structure, can be utilized. These various head coils can be interchanged with the first half 522 of the head coil 520.

The first half 522 of the head coil 520 also includes a plug connector 530 that is coupled to a cable 532, which is in turn connected to the MRI system. This cable 532 energizes the head coil 520 and/or transmits data signals. The length of the cable 532 can be adjusted to accommodate a particular arrangement of head coils and other structures provided with the MRI.

Figure 81:
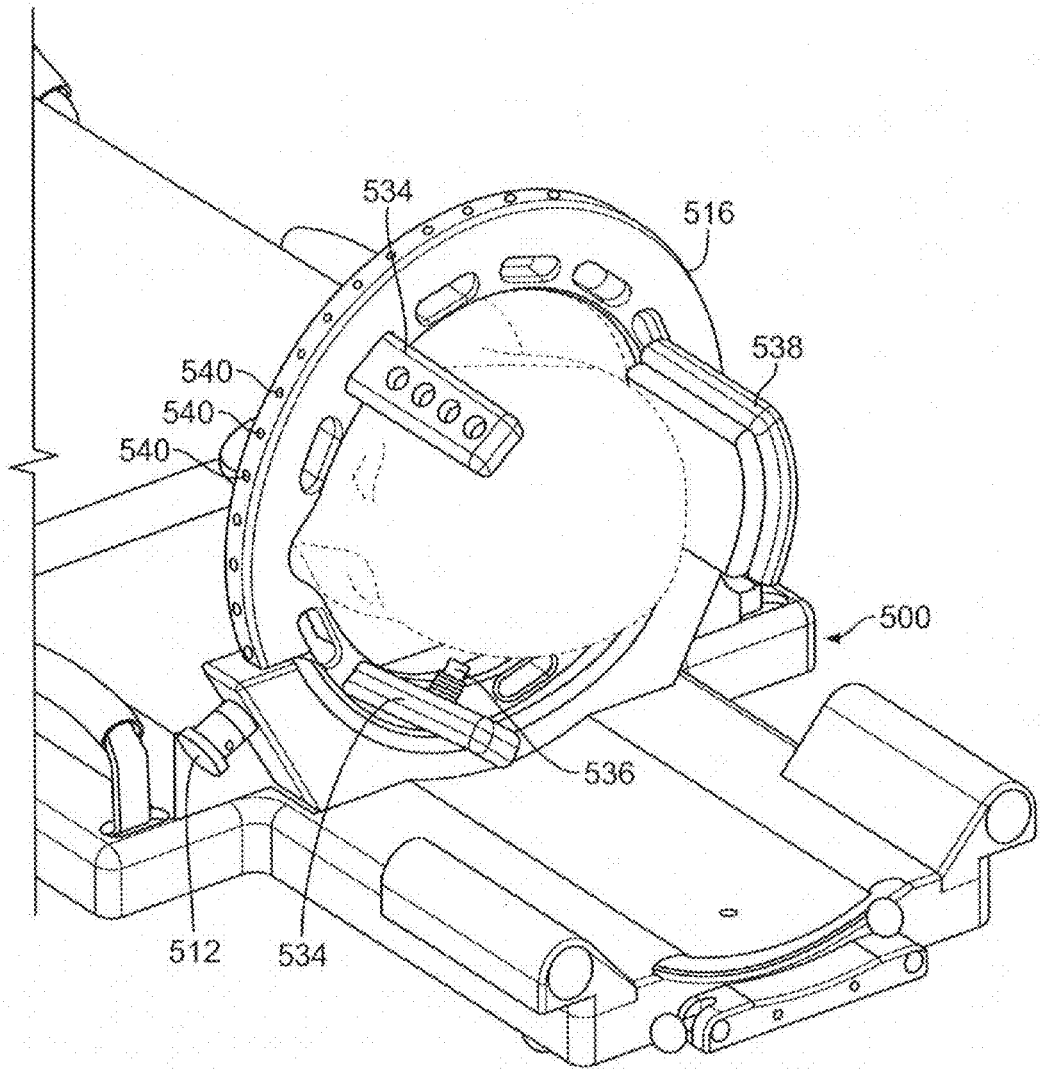
FIG. 81 is a schematic illustration of a head fixation ring attached to a patient's head.

FIG. 81 illustrates the head fixation ring 516 including a plurality, such as two, fixation posts 534. These posts 534 each include a series of holes, each of which can engage a fixation screw 536, which presses portions of the patient's skull above and in front of the patient's temples back against a backrest 538. The head fixation ring 516 includes a plurality of holes 540 that are provided to engage a locking pin (not shown) from the knobs 512. The head fixation ring 516 can rotate within the channel of the ring mount 504, but is rotationally locked by engaging the knobs 512 with one of the holes 540.

Figure 82:
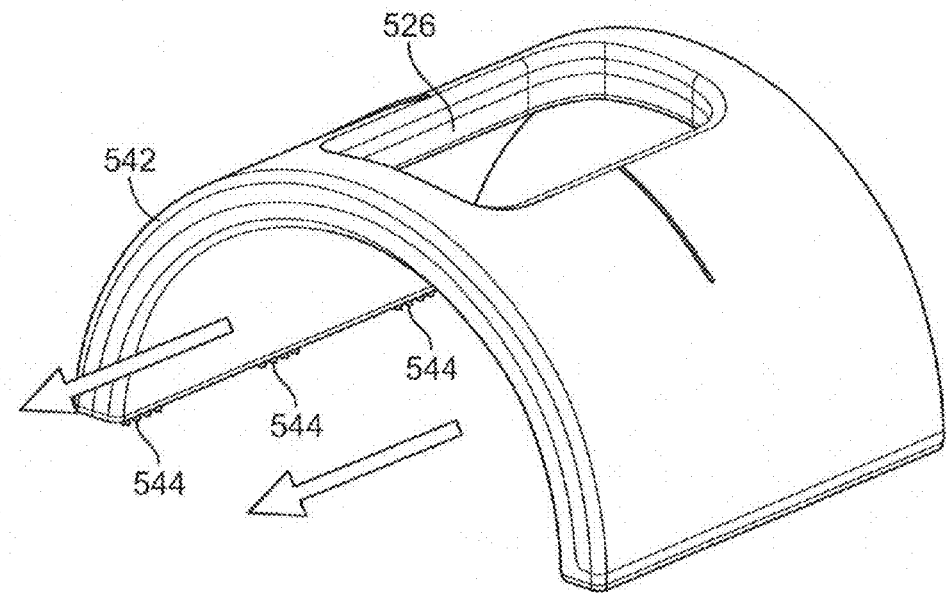
FIG. 82 is a schematic illustration of one second half of a head coil.
Figure 83:
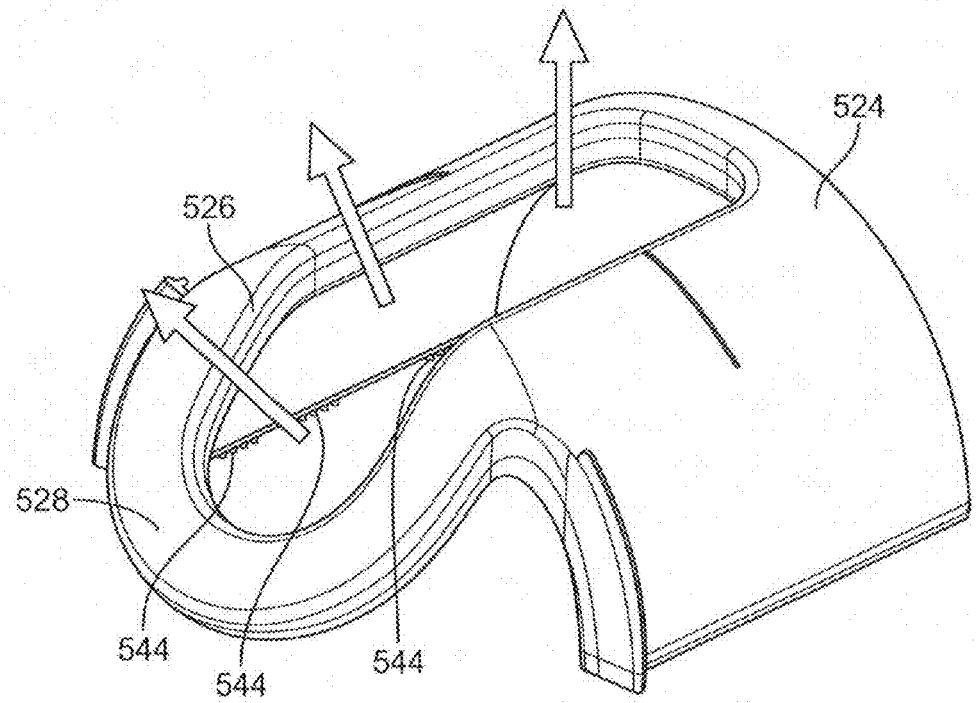
FIG. 83 is a schematic illustration of another second half of a head coil.

FIG. 82 illustrates an exemplary second half 542 of the head coil 520. The second half 542 includes a slot 526, and is suited for access in the direction of the bold arrows shown in FIG. 82. The second half 542 includes connectors 544 that provide alignment and electrical connections with corresponding connections on the first half 522 of the head coil 520. FIG. 83 illustrates another view of the second half 524 of the head coil 520, where access to a patient's head in the direction of the bold arrows is provided. As shown herein, the second half 524 also includes connectors 544.

In light of the descriptions provided herein, the head coil 520 and the head fixation ring 516 are rotated to suit a particular trajectory, and are locked into place. The interchangeability of the second halves of the head coil allows for flexibility in trajectory planning, and accommodates the physical presence of a miniframe, a follower, and a probe. Either of the second halves 524 and 542 allow for a rotatable portal, such as the slot 526. In particular, the slot 526 is rotatable about a longitudinal/patient axis, and can be fixed into place via the head fixation ring 516. The slot 526 allows for side or angled points of entry into a patient's skull. These points of entry can be referred to as radial points of entry, and the structures described herein allow for radial points of entry along an entire crown line of a patient, while fixating the patient's head. The bent portion 528 of the second half 524 provides a rotatable portal that allows midpoints between a side of a patient's head and a top of the patient's head to be accessed directly, while still maintaining continuity with respect to the electromagnetic properties of the coil.

Other coils can be attached to the head fixation ring 516 or to another type of ring that is fastened to the platform 500. The platform 500 can be adjusted to adapt and connect to various different MRI tables, such as different MRI tables provided with different MRI machines.

VI. VISUALIZATION AND CONTROL

FIG. 1 illustrates a control workstation provided in an MRI control room, as well as an electronics rack in an MRI equipment room. The electronics rack is coupled to an interface platform by various electronic, optical and cooling fluid cables. The electronics rack is also connected to the control workstation by, for example, network cabling or other data transfer cables. Although not shown, the electronics rack and the control workstation can be coupled together by a network, such as an Ethernet network. In another implementation, electronic data cables can be routed directly from the interface platform to the control workstation, without use of any intervening devices.

A. Planning i. Plan Register

Figure 84:
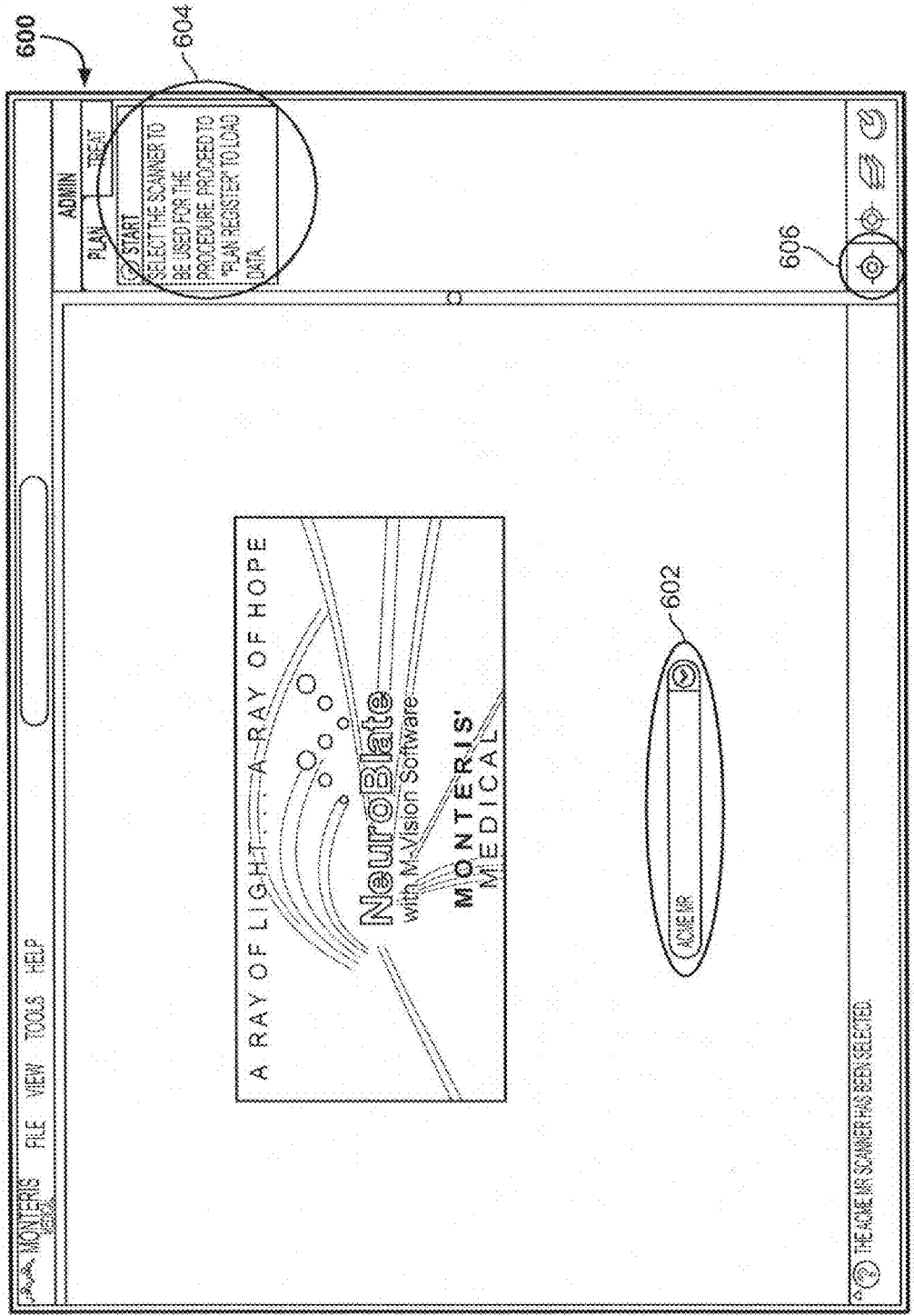
FIGS. 84-100 are exemplary screenshots of a graphical user interface of a workstation.

An operator can operate the workstation to initialize software executed on the workstation to provide a control terminal and graphic user interface for creating a plan, which defines an organization of appropriate information for the treatment of a particular tissue. To initiate and create a plan, the user operates the workstation to execute a graphic user interface, such as graphic user interface (GUI) 600, shown in FIG. 84. The GUI 600 includes a selectable area (herein referred to as an area, button or region) 602 for selecting a particular MRI system, such as a brand/model of an MRI. An area 604 is provided to include brief instructions and/or comments to an operator, and a start area 606 is provided to initiate the start of a plan.

Figure 85:
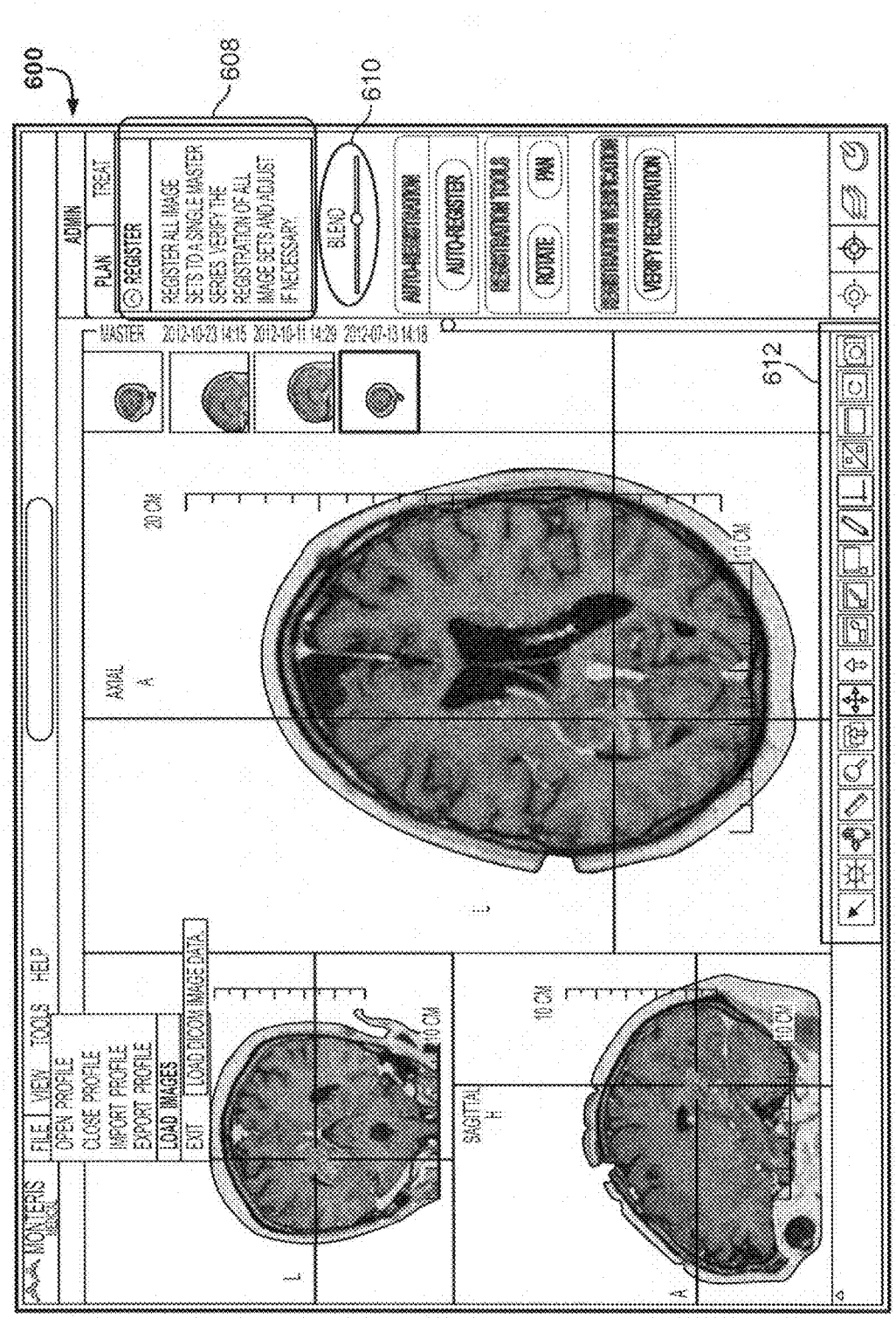

FIG. 85 illustrates a screenshot of a registration of the plan. In this screenshot, the GUI 600 includes an information area 608, which indicates that all image sets are registered to a single master series. Adjustments to images and images sets can be made via the GUI 600. For example, a blend area 610 is provided for adjusting a blending ratio. Further, an area 612 is provided for making other adjustments to the images, including magnification, panning, contrast, and others. Markers can also be included in the images to identify a particular tissue of interest. Further, in this screen, images can be loaded from the various data sources, including a network storage unit or a local portable storage unit, such as a USB drive. As shown in FIG. 85, multiple images can be arranged in a thumbnail view, which allows a particular thumbnail to be selected and shown in one of a plurality of larger views.

Figure 86:
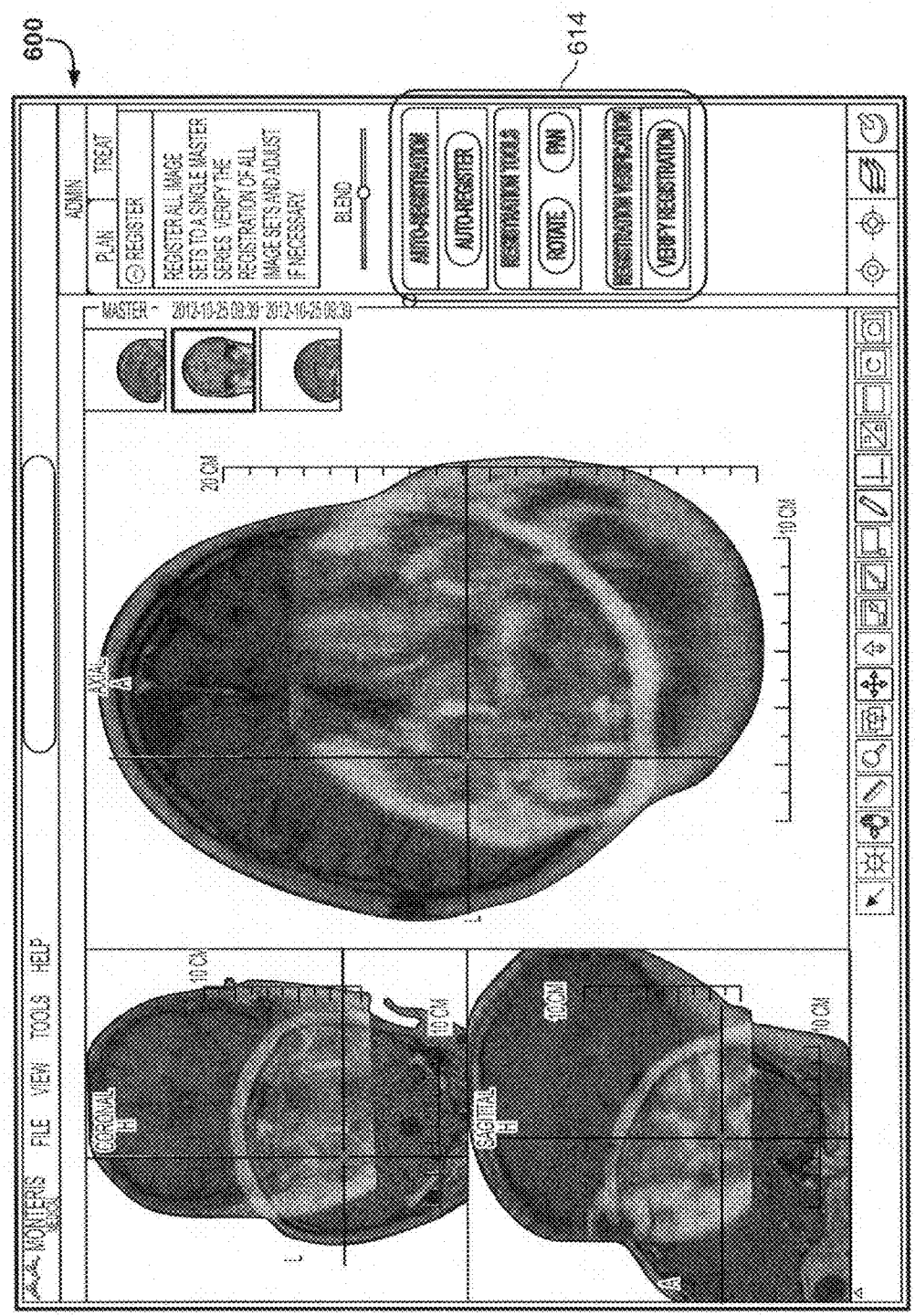

FIG. 86 illustrates registration amongst the plurality of images. In region 614, various selectable areas are included, including auto-registration, registration tools and registration verification. Auto-registration performs a best-fit analysis of two anatomical data sets (e.g., images) based on predetermined thresholds within an anatomy. If the auto-registration is deemed inaccurate by an operator, or if a manual registration is desired, the rotate and pan selectable areas of the registration tools can be operated to adjust the registration. The blend selectable area allows for an accuracy of the registration to be checked by a user, by blending a selected data set into or out of view with the master series. This tool is used to verify the registration accuracy of each image set registered to the master series. Once accurately registered and verified by the operator, the operator can indicate that the registration has been verified by selecting the verify registration area of the registration verification portion. After the images have been registered, a volume can be planned.

ii. Plan Volumes

Figure 87:
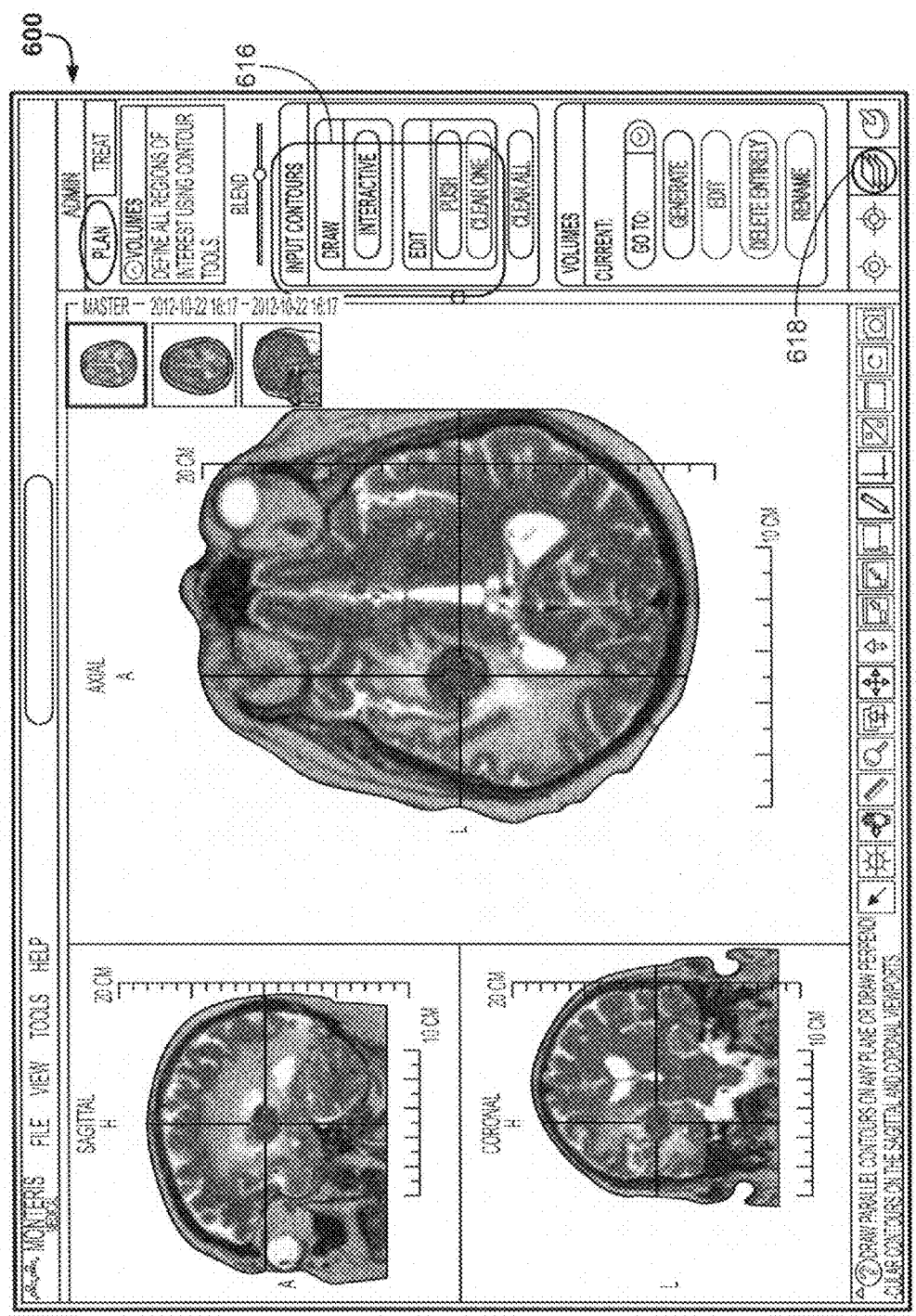

FIG. 87 illustrates a volume planning screen of the GUI 600. In this screen, contours can be inputted via the selectable areas including region 616. With this interface, an operator can define all regions of interest using contour tools. Parallel contours can be drawn on any plane. Perpendicular contours can be drawn on sagittal and coronal views. This interface allows an operator to generate volumes or intended treatment areas, also known as regions of interest (ROIs), within the data set in different pre-set colors. An ROI can be defined here using appropriate contour tools provided by the GUI 600. For treatment of a tissue, the operator creates at least one ROI over an intended treatment area. The planned volumes portion is accessible by selecting an appropriate selectable area, such as area 618 to select a volumes task.

Figure 88:
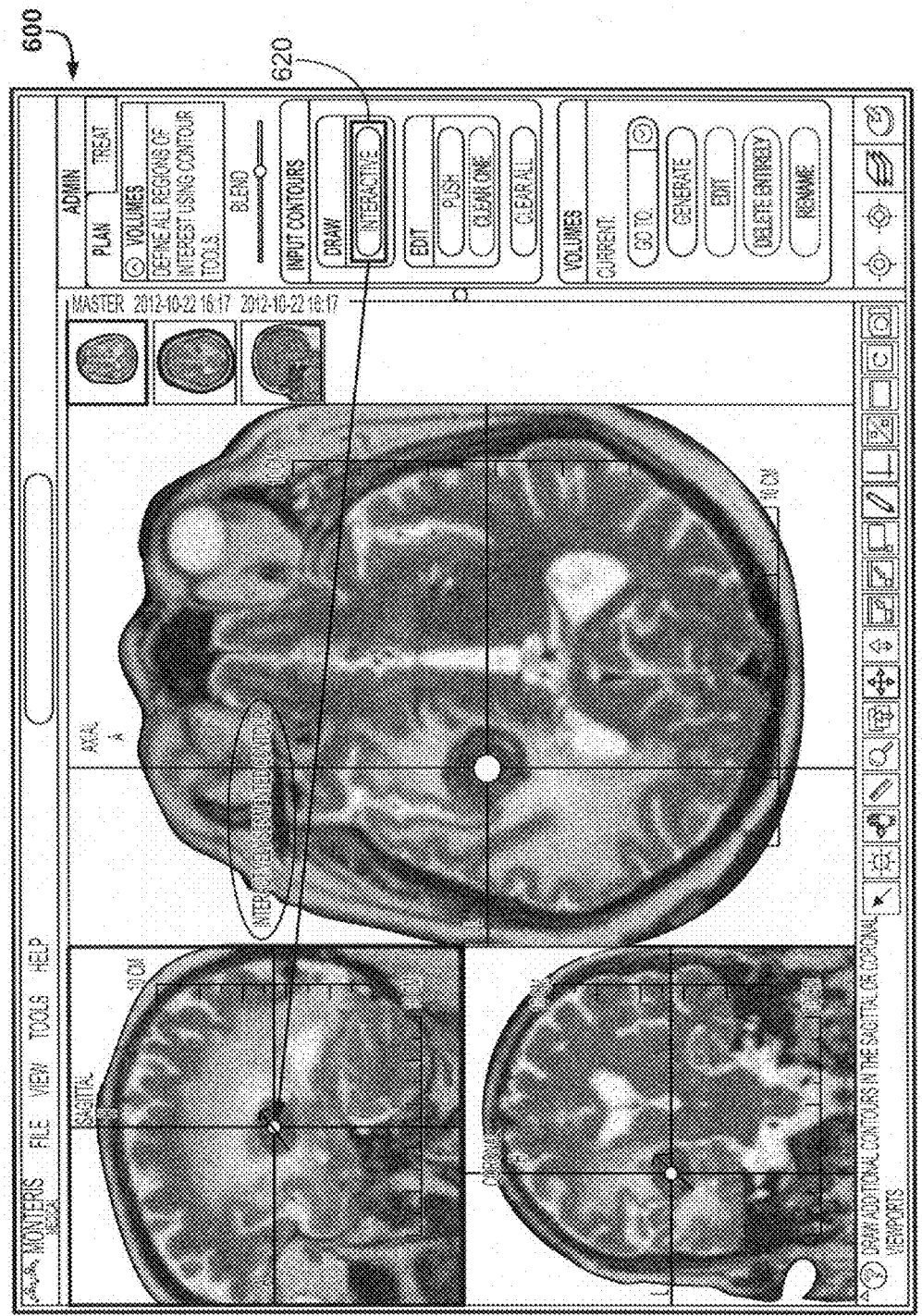

FIG. 88 illustrates an interactive method of generating a two-dimensional contour. An interactively segmented contour can be selected by selecting area 620 of the GUI 600. This outlines a desired region and then generates a volume from the contours. Different contours are drawn in the sagittal or coronal views, and these contours are computed, by the workstation, to generate a volume.

Figure 89:
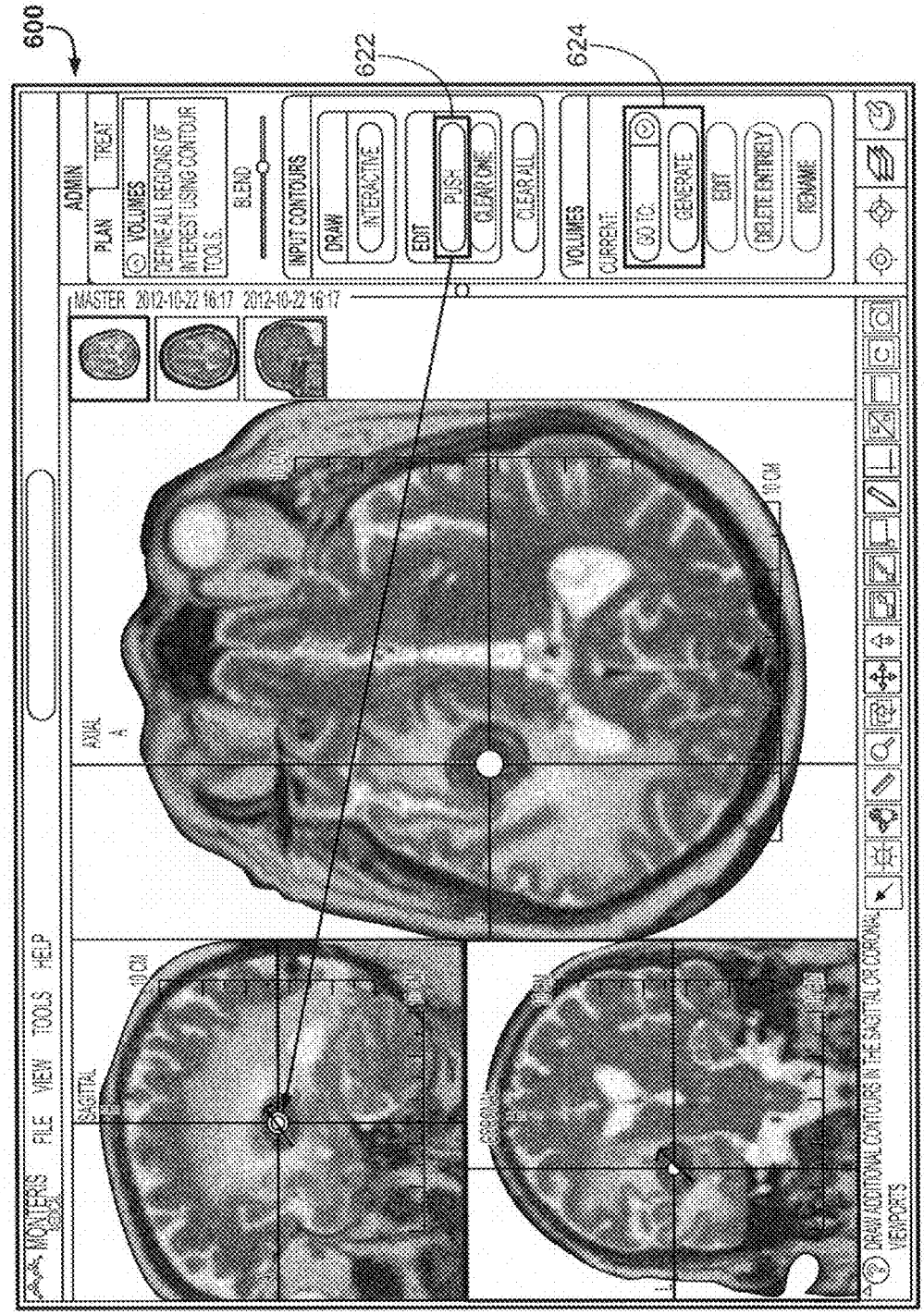

FIG. 89 illustrates how the contour can be adjusted by using an editing command, such as a push command, via selectable area 622. Since an intended area for treatment of a tissue is generally not symmetrical, the push command allows for a pushing action to be implemented on the contour shown in the various views of the GUI 600. In particular, a contour at an intended location can be created in each of various orthogonal views. This contour may initially resemble a geometric shape, such as a circle or an oval. Then, this or other contours can be edited as required by the operator with the push tool. By operating a mouse or other input instrument at the workstation, the operator can push the boundaries of a contour with, for example, the white circle shown in FIG. 89 to achieve a desired shape. The size of the white circle can be changed by toggling a button on the mouse to accommodate larger or smaller manipulations. For example, while activating a left or right click button of a mouse, the size of the push tool can be changed by operating a wheel of the mouse. Contour lines can also be deleted by checking a clear all button on the GUI 600, and a shape of the push tool can also be changed from a circle to, for example, an oval, a square or a triangle. Other geometric metric shapes can also be utilized.

After the contours have been defined in the orthogonal views, a volume can be generated by the workstation by selecting the area 624 shown in FIG. 89. This volume, as well as any other volumes created in accordance with the description provided herein, can be named, edited, deleted, renamed, and saved in a storage medium, such as a hard disk or portable drive, of the workstation.

iii. Plan Trajectory

Figure 90:
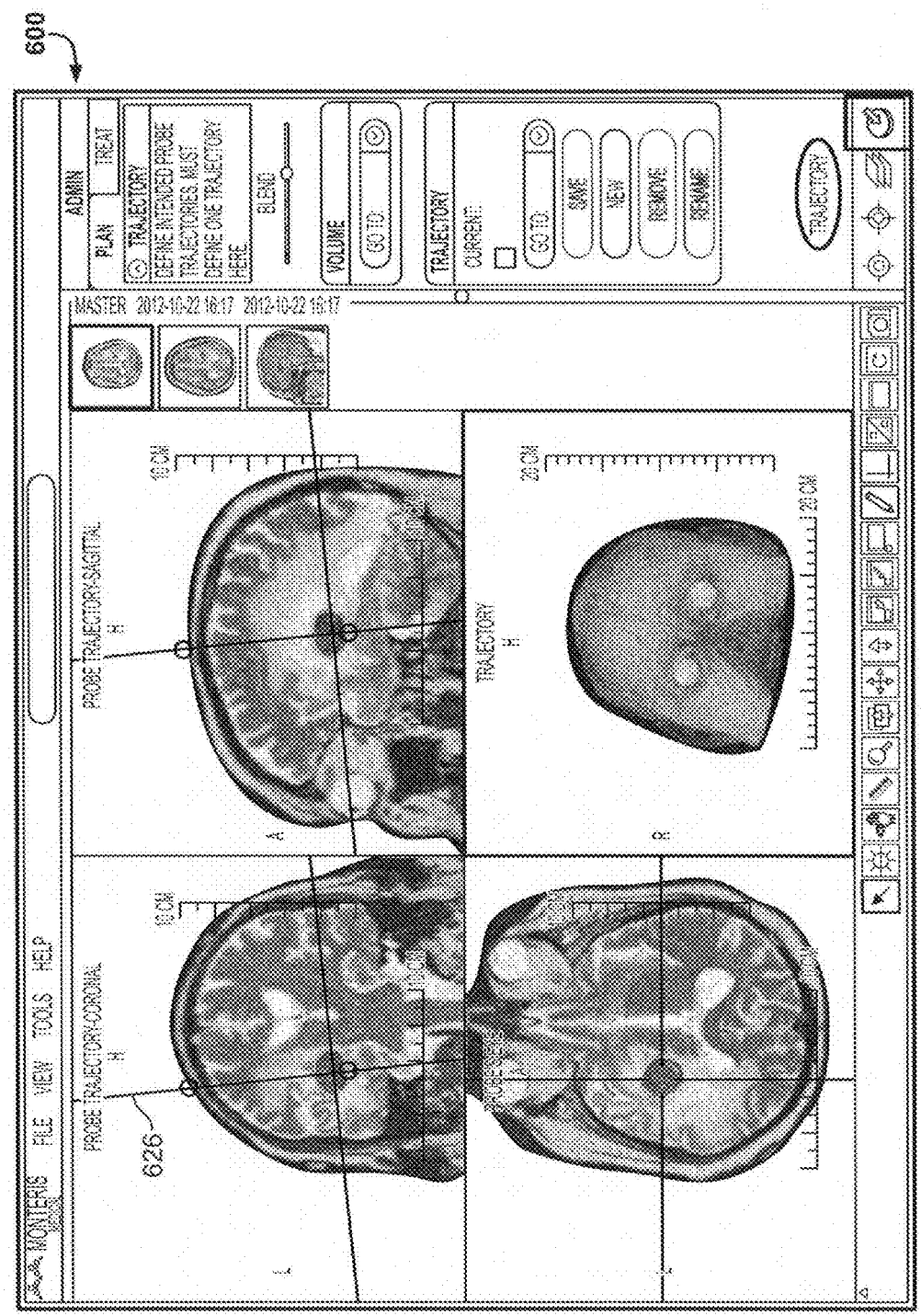

After a volume has been identified, or several volumes have been identified, a trajectory for affecting a treatment to the volume(s) can be planned. Trajectory planning is shown in FIG. 90. Here, the volume is encircled in several orthogonal views of the tissue, according to a saved or accessed volume plan. A probe trajectory-coronal view, a probe trajectory-sagittal view, and a probe's eye view are shown in FIG. 90. A trajectory 626 is planned for treating the encircled volume. White circles indicate insertion and maximum depth markings for the probe. This planning is intended to define an initial trajectory while in a planning phase. The final trajectory used for actual treatment can be modified later, if necessary. A new trajectory is defined by manipulating "grab-handles" (which are defined as the two white circles within the views). The point of deepest penetration (PDP) is defined by the workstation as a centroid of the deepest grab-handle to the deepest point in the brain allowable for probe insertion. This screen can also provide a 3D surface rendering, as shown in the lower right of the screen of FIG. 90.

Once a trajectory has been defined, a save command can be issued to save the trajectory. Once the trajectory is saved, a new trajectory can be generated for the same volume or for another volume. The trajectories can be saved so as to correspond with a particular volume. This correspondence can be saved by the workstation in an association file. For example, during the treatment stage, a particular volume can be identified, and the workstation can provide associated trajectories for that particular volume.

The various trajectories and volumes defined in accordance with the descriptions provided herein can be saved as a plan, as a file in the workstation. The file can be saved to a local or remote storage device. A saved plan can then be accessed later. For example, a plan can be accessed during a treatment planning stage, and the plan can be part of an executed sequence by the workstation to enable a continuous process of treating a plurality of volumes or a plurality of positions by the workstation without requiring further planning or setup input by an operator.

B. Pre-Treatment i. Preparation

After a plan has been generated, a patient is prepared and the appropriate components are collected for conducting a treatment. In particular, a miniframe and a delivery probe are acquired, in accordance with the disclosures provided herein Various drill bits are acquired for drilling a proper bore hole size into the patient's skull. Additionally, an image guided surgery alignment adapter is acquired. The particular image guided surgery alignment adapter is generally specific to the particular operating room and/or hospital and is mounted to, e.g., a stabilization system affixed to the patient.

At this time, operating systems of the electronics rack and the workstation can be verified. In particular, new medical grade carbon dioxide tanks can be installed into the electronics rack to be used for cooling, and power to the workstation can be verified. The patient is anesthetized according to anesthetic requirements for the procedure being performed. Further, the patient can be provided with earplugs in both ears in preparation for the MRI scanning, and a medically tested and MRI compatible temperature probe can be inserted into the nasopharynx of the patient for accurate temperature readings throughout the procedure.

ii. Head Fixation

Post-anesthesia, the patient's head is fixated within an MRI compatible head fixation device using MRI compatible fixation pins. An image guided navigation system is registered based off of a pre-operative scan. Once the image guided navigation system is accurately registered, an entry point is defined on the anatomy and the incision plan is made. An exemplary head fixation mechanism is described in Section V.

After the head fixation system has been successfully attached, proper sterile draping is applied. Further, since a miniframe and an interface platform need to operate in conjunction with the other components, care should be taken to ensure that the sterile draping does not interfere with any such components or other components utilized in the planned treatment. At this time, pilot holes can also be drilled into the patient, should the patient have a very dense/hard skull or if the patient has a cranial plating system.

iii. Miniframe

The miniframe is then mounted to the patient. An exemplary miniframe is described in Section II. At this time, the miniframe can be used as a drill guide. Otherwise, a different guide can be used as a drill guide.

Also, for each foot of the miniframe, the foot should be pressed firmly into the scalp at a respectively marked location until all spikes of the feet are fully seated on the skull surface.

Figure 91:
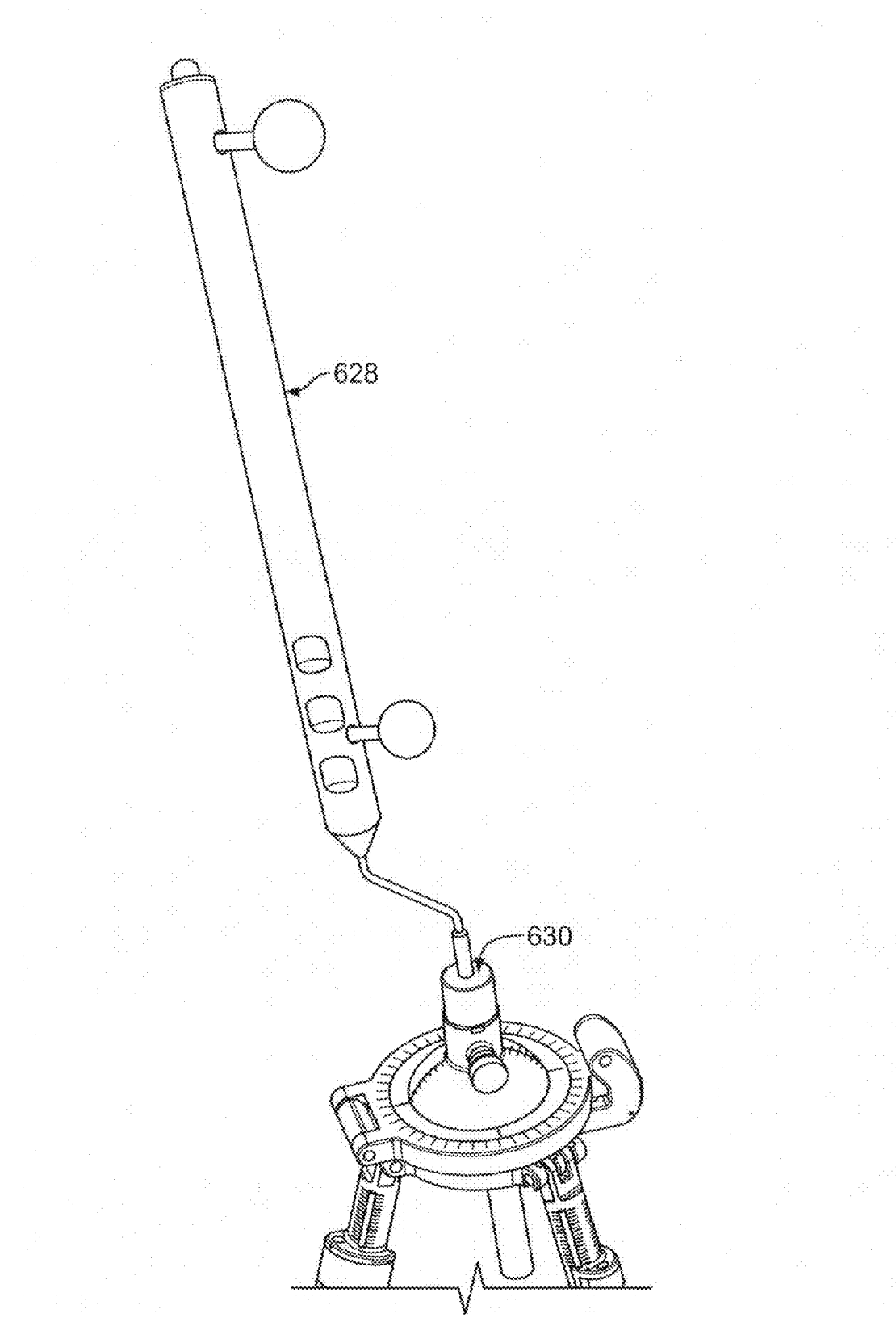

By holding a foot in place, the screws should be engaged with a sterile screwdriver. The screws should be alternately advanced until all screws are fully seated. The stability of the feet attachment should be verified before proceeding. A templace linkage, which maintains a predefined displacement between the feet of the miniframe, can then be removed. The miniframe can be aligned using the image guided navigation system. In particular, as shown in FIG. 91, an image guided navigation system pointer probe 628 is shown inserted into an alignment adapter 630 of the miniframe. As such, the image guided navigation system can visualize the trajectory into the anatomy on a pre-operative scan/screen. Once alignment is secured and the miniframe is locked into position, the pointer probe 628 can be removed and replaced with an appropriate drill. A depth to a predetermined target, i.e., the plan volume, can be determined via a biopsy needle or via the depth predefined in the image trajectory planning.

After the drilling has been completed, an MRI trajectory wand can be inserted into the miniframe. The patient can then be prepped and draped for insertion into the bore of the MRI.

C. Treatment i. Scan & Register

Figure 92:
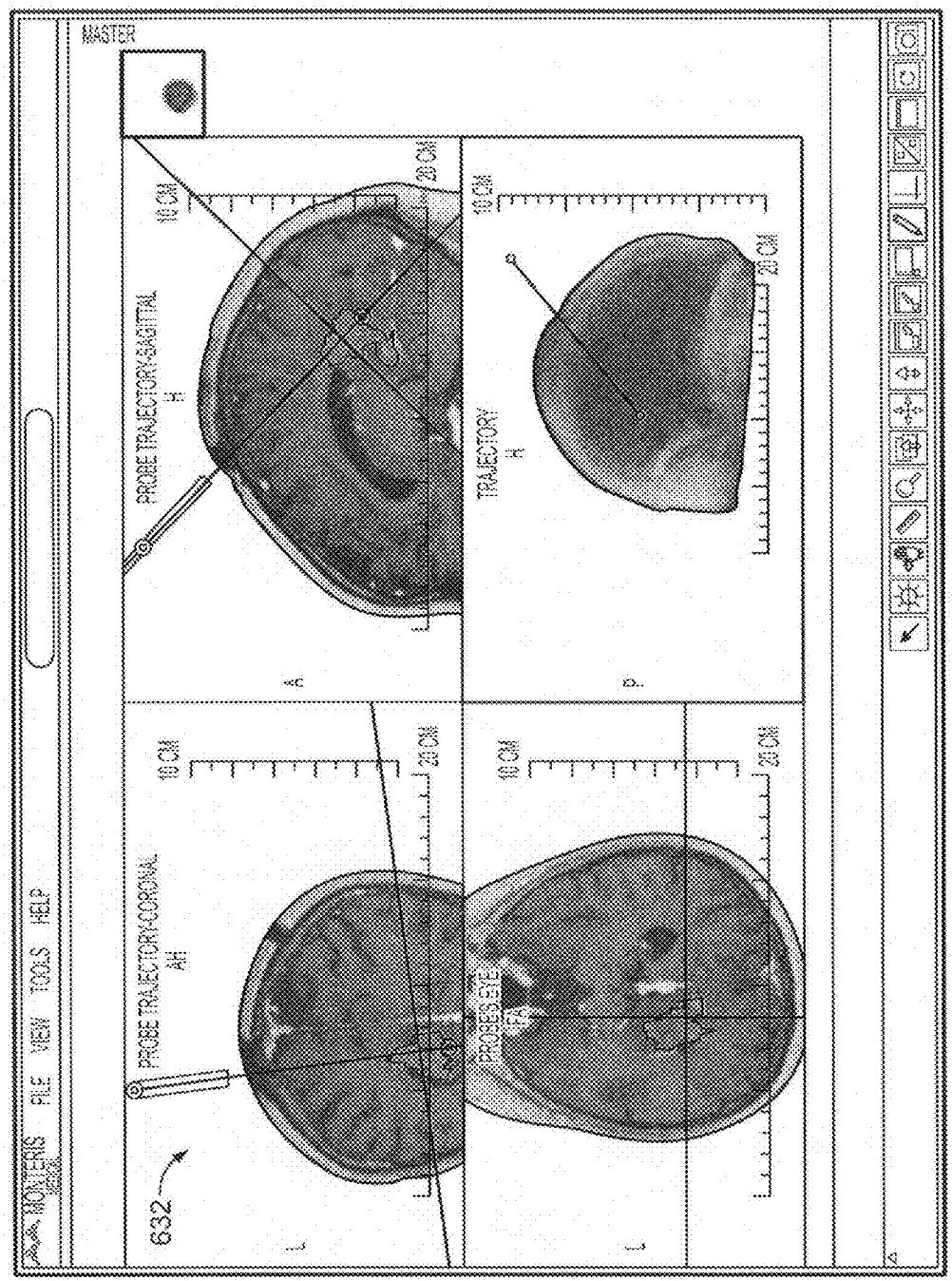

After the patient is loaded into the bore of the MRI, and the various corresponding components are attached and connected, in accordance with the other disclosures provided herein, the patient is scanned to detect the trajectory wand placed in the miniframe. An exemplary screenshot of an image including the trajectory wand is shown in FIG. 92 as item 632. Also shown in FIG. 92 are various orthogonal views of the patient's skull, together with a three-dimensional rendering. Based on these various views, an operator can verify an alignment of the trajectory wand 632 with the previously planned trajectory. Additionally, a new trajectory can be created if necessary.

Figure 93:
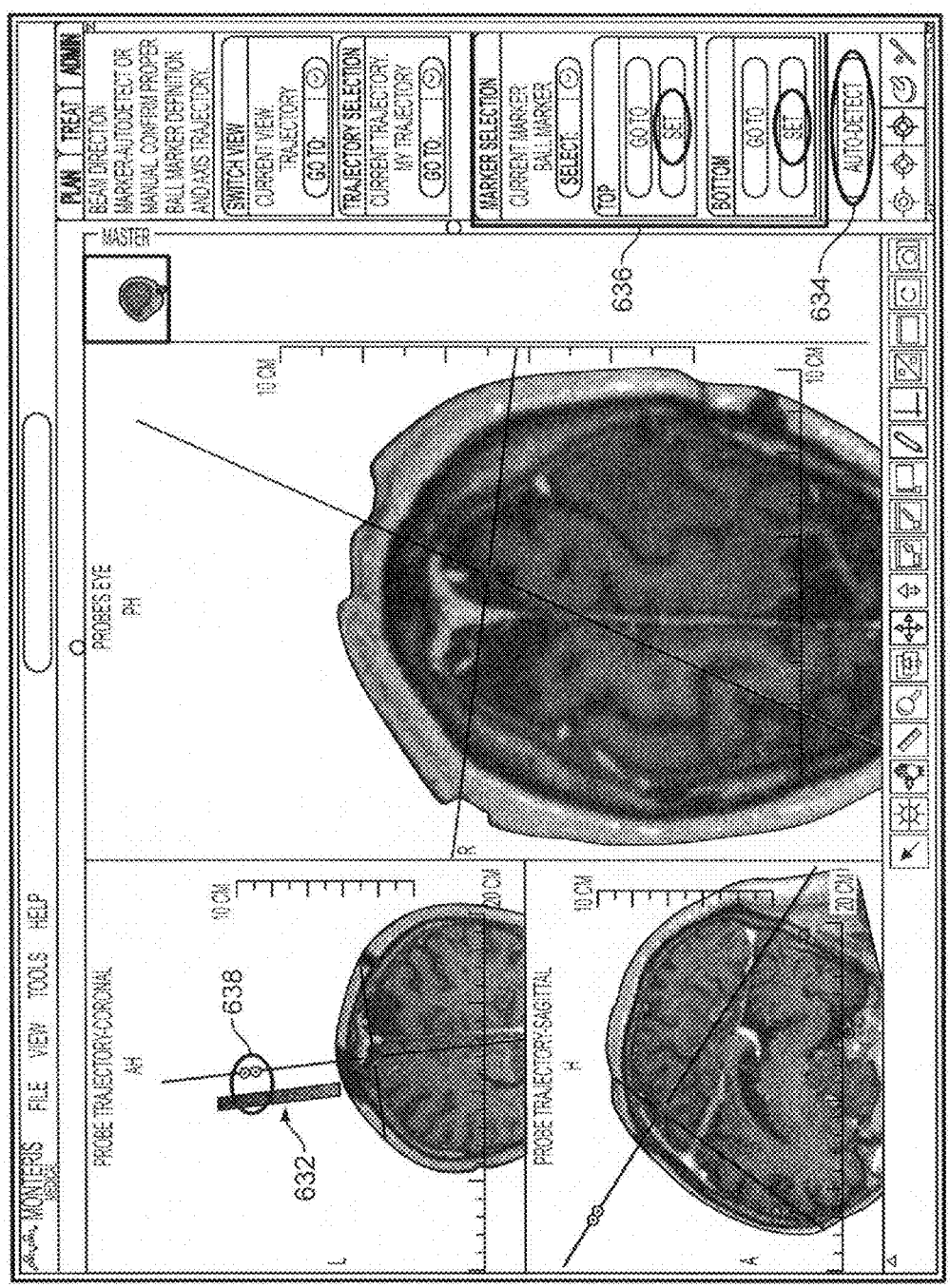

Once the trajectory has been aligned via the trajectory wand and saved within the planned trajectory section of the GUI, a detected fiducial marker within the miniframe is defined to provide a depth setting and a directionality for a probe within the GUI in accordance with the screen shown in FIG. 93. Fiducial markers can be auto-detected by selecting an auto-detect button 634 in the GUI. If the auto-detection does not result in detecting the fiducial markers for the miniframe, the fiducial marker can be manually set via the region of buttons 636 shown in FIG. 93. As a result, two circles or other markers 638 are indicated in the GUI as identifying the miniframe. Further, since the trajectory wand may still be inserted into the miniframe, the trajectory wand image 632 may still be visible within the image, and proper alignment amongst the various components can be verified within the GUI.

ii. Define ROI and Trajectories

A previously planned plan, i.e., ROIs and trajectories, is accessed via the workstation and loaded into the GUI. Consistent with the disclosures provided herein, a plan can be modified or ROIs and/or trajectories can be added to or deleted from a plan. Data management (i.e., saving/modification thereof) can be provided via a local storage unit of the workstation or via a portable storage unit (such as a USB drive that is particular to the patient).

iii. Probe Insertion

Figure 94:
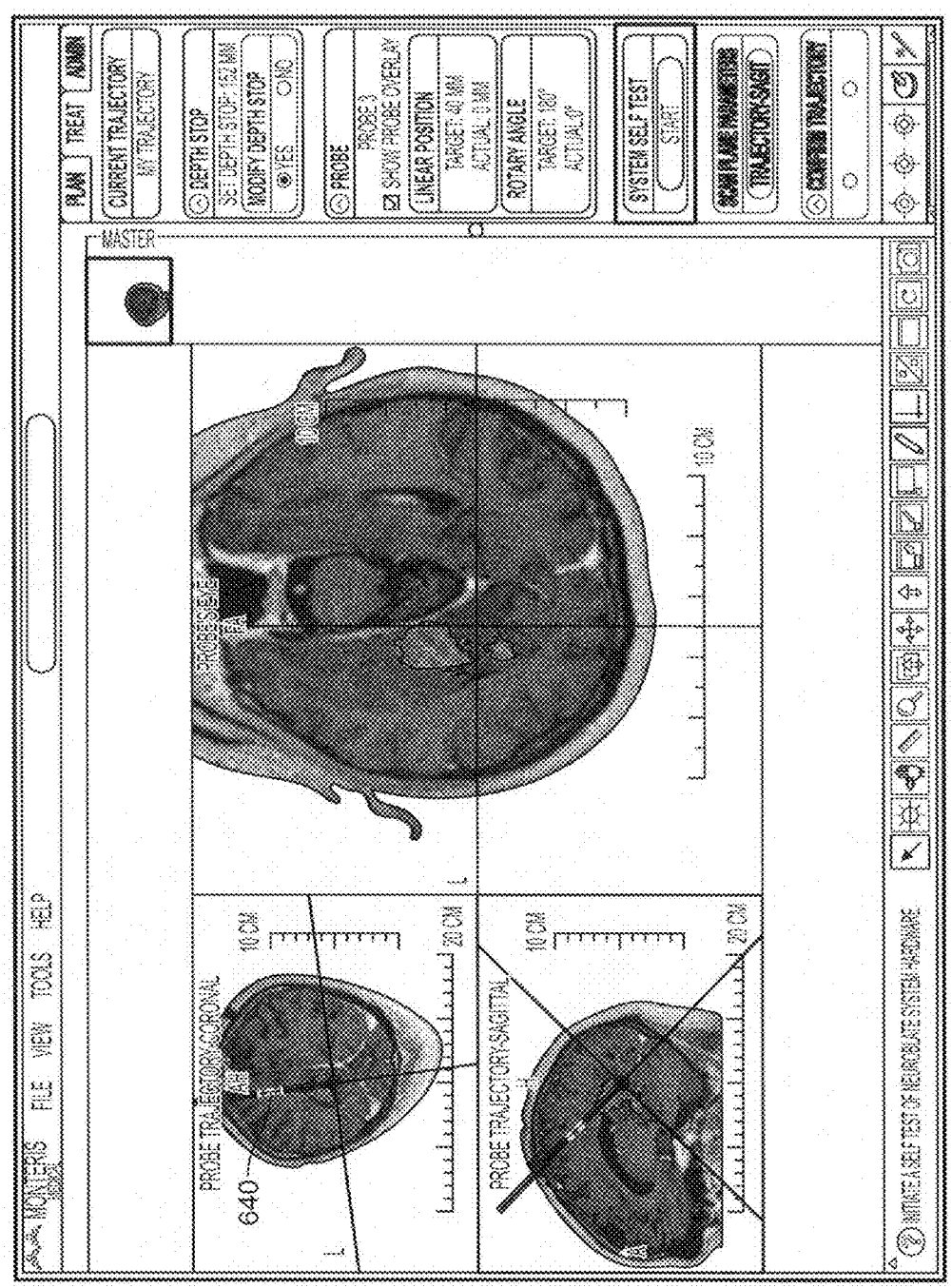

After a region of interest has been defined and image trajectories have been registered in the GUI and saved to the workstation, a pre-insertion point is then defined in the GUI for probe insertion. A manual self-test is then conducted to verify that the system is ready for treatment. The pre-insertion point is defined by moving a probe tip 640, as shown in FIG. 94, within the anatomy to the point that the operator wants to see the probe upon initial insertion into the desired area. Once this probe tip 640 is moved to the desired position, another manual self-test is performed. This test is started by clicking on a corresponding start button of the GUI. At this time, the probe tip 640 shown in FIG. 94 is a rendered probe tip, which does not correspond to a physical probe tip, at least yet. A last step in the self-test procedure is manually inserting in the probe. Once the probe is physically inserted into the patient, the GUI is operated to register or match the hardware of the probe with the probe tip rendered in the GUI.

iv. Software to Hardware Match

Figure 95:
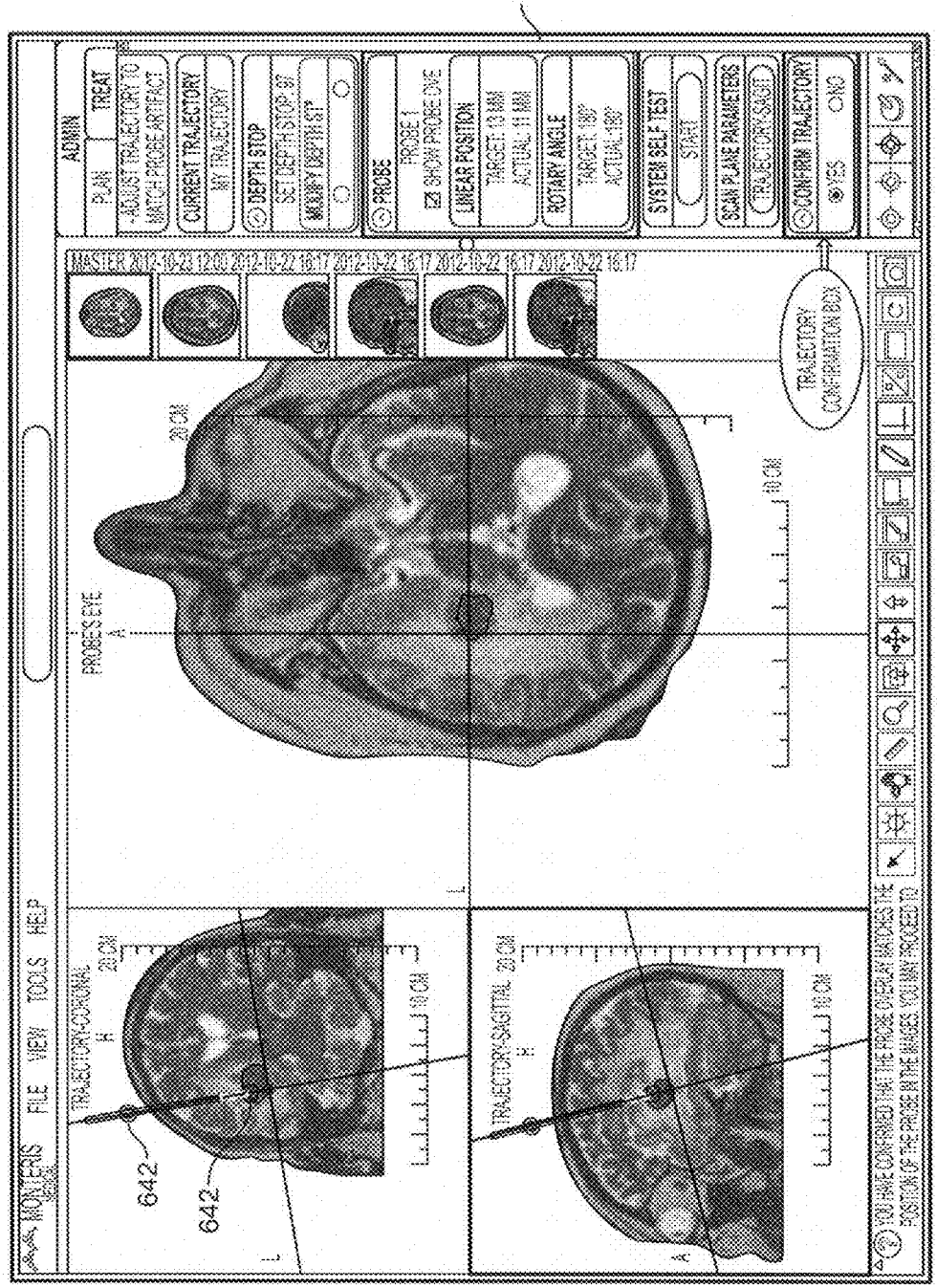

When scanned by the MRI, the physical probe inserted into the patient is viewed from the workstation as a probe artifact within the image. This probe artifact is registered and coincides with the probe tip 640 shown in FIG. 94. Scan plane parameters can be selected to coincide with the position of the probe inserted into the patient. Once a new image from these parameters is loaded into the GUI, an alignment of the probe artifact can be registered with the rendered probe by adjusting grab bars of the rendered probe to match perfectly with the alignment of the probe artifact, as shown by grab bars 642 of FIG. 95. Once the trajectory is perfectly aligned, a trajectory can be confirmed by selecting an appropriate box in the GUI. Additionally, as shown in FIG. 95, a depth stop, linear position and rotary angle of the probe can be tracked and/or set in area 644 of the GUI. The linear position and rotary angle of the probe is determined by the predefined relationships between the probe, the follower and the miniframe. These predefined relationships are spatial relationships that are utilized in image guided navigation systems and verified in MRI images.

v. Treatment

Once the trajectory is confirmed and the physical probe inserted into the patient has been registered with the GUI to coincide with the rendered probe image, a depth and direction of the probe is set to a first desired location to initiate treatment. Prior to treatment, and after registration of the patient has been completed, a real-time transfer from the MRI is established. This real-time transfer is established by issuing appropriate commands via the workstation to send images in real-time from the MRI to the workstation. At this time, the workstation receives real-time imagery from the MRI.

Figure 96:
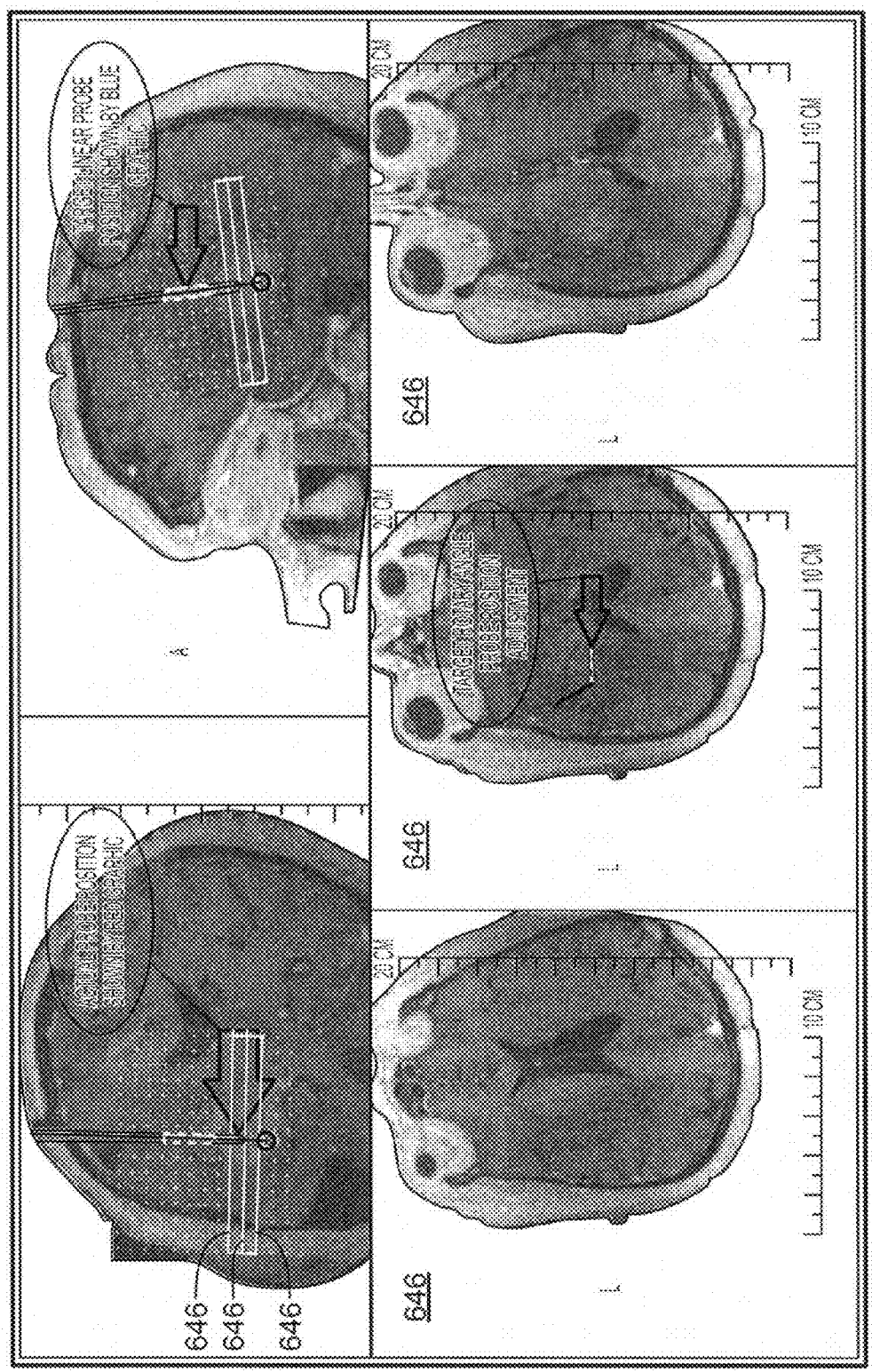

In receiving real-time images, since the actual probe position (i.e., the physical position of the probe inside the patient) is registered in the GUI and the workstation, the actual probe can be indicated by a color position. As shown in FIG. 96, this colored position is a red graphic. A target position of the probe can be rendered by a blue graphic, as further shown in FIG. 96. These colors and indications can coincide with the labeling and colors utilized in the probe information area 644 of FIG. 95. As shown in FIG. 96, target and actual longitudinal positions and rotary angle positions can be shown by corresponding red and blue graphics.

An adjustment of a linear or rotary position of the probe can be made by selecting the corresponding portion of region 644 of FIG. 95, and entering appropriate values through, for example, a keyboard. The target renderings of at least FIGS. 95-97 can also be selected by a cursor or mouse input by clicking thereon, and dragging the rendering into an intended position. In response, the workstation can transmit corresponding signals to the interface platform, which in turn can rotate corresponding knobs on a commander, and consequently affect movement of linear and rotary positions of the probe via the follower. This can all be done in real-time, where the workstation issues corresponding instructions and commands immediately in response to an operator's interface with the GUI. On the other hand, an execute or OK button can be provided with the GUI, to delay actuation of the probe to the intended position until the OK button is selected by the operator. Further, the GUI can include parameters indicating thresholds for linear and/or rotary travel, such that when an operator issues a command that is outside the threshold range, a warning is provided and the probe is not moved.

Moreover, the grabbing and repositioning of the probe can be stored as a sequence, which includes a plurality of positions and alignments of the probe, which correspond to a series of treatment positions for treating various portions of the ROI. This sequence can be executed in an automated or an assisted fashion via the workstation. In particular, in one implementation, an operator saves a sequence including a plurality of different probe positions, and the workstation transmits corresponding instructions to effect probe movement after predefined treatment levels are reached in each position. Treatment can then proceed to a next treatment, where the operator merely supervises progress or maintains activation via a foot pedal, the release of which would pause or stop probe activation/treatment. In this case, the workstation would effect proper probe and tissue cooling between each repositioning, and one or more ROIs can be treated continuously without interruption.

In another implementation, the workstation calculates a minimum number of positions or a minimum amount of time necessary to effect treatment of the ROI(s). Here, the workstation estimates an amount of time necessary to effect treatment of an ROI at a plurality of different positions, and compares the various positions with their respective amount of treatment times. Then, the workstation calculates a combination of positions and corresponding treatment times that result in a shortest operation period. The resulting combination of positions and treatment times can be displayed to the operator, either as a list of steps or in a preview. The preview can include a visual rendering of how the total procedure is expected to progress. This workstation-calculated sequence can be verified by the operator or particular portions of the sequence can be modified by the operator. The workstation-calculated sequence is performed based on an expected output of a particular probe, and can compare different types of probes and combinations of probes in a particular sequence. For instance, in one implementation, the workstation calculates steps in a sequence that starts with a symmetric treatment by a probe, and then calculates steps with an asymmetric treatment by another probe.

Treatment, in accordance with the workstation-calculated (and/or operator modified/confirmed) sequence, proceeds where the operator may merely supervise progress or maintains activation of one or more of the probes by, e.g., a foot pedal (the release of which would pause or stop probe activation/treatment). In this case, the workstation can effect proper probe and tissue cooling between each repositioning, and one or more ROIs can be treated continuously without interruption.

Figure 97:
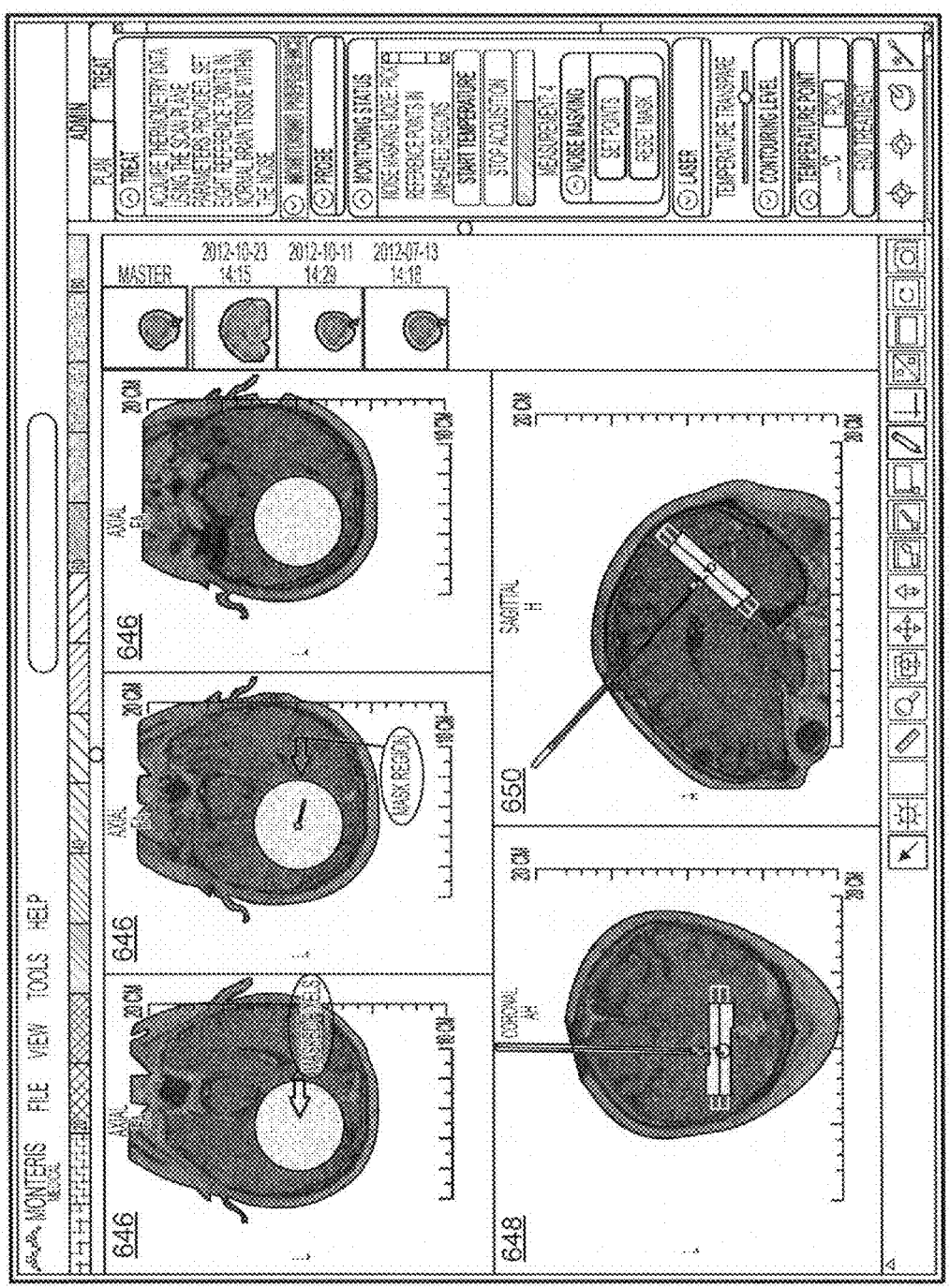

Linear and rotary travel (e.g., repositioning) of the probe is conducted while the MRI is in operation, and an operator is not present in the MRI scan room. Parameters are entered into the GUI or accessed by the workstation for a scan plane for a thermometry sequence prior to initiating a thermometry scan. At least FIGS. 96 and 97 illustrate exemplary scan planes 646, and an exemplary view of these scan planes 646. These scan planes are continuously scanned in sequence by the MRI and sent to the workstation in real-time. Lower images 648 and 650 of FIG. 97 are also imaged in sequence and sent to the workstation in real-time.

When the MRI images begin arriving from the MRI, an initialization phase of the workstation and GUI computes a noise mask and allows for reference point selection. The GUI receives data from the MRI and updates itself with a solid colored overlay indicating pixels that are a part of the mask, as shown in FIG. 97. The mask, in one implementation, is a circular region of six centimeters in diameter, which surrounds the probe and which represents a sub region of the MRI images being acquired. Any data, for thermometry purposes, outside of this region is ignored. The MRI data within the mask is analyzed for each measurement. Pixel locations which show excessive phase noise will not be used for temperature measurement and are cleared or rendered transparent in the mask overlay. These are referred to as masked pixels. An example is shown in FIG. 97.

As MRI acquisition continues, the operator selects a minimum of 8 reference points surrounding the treatment area within each view. Reference point selection is shown by example in FIG. 98. More or less reference points can be selected, such as 1, 2, 3, 4, 5, 6, 7, 9, 10 or more. However, 8 reference points is an exemplary suitable number. Further, the workstation can auto-select reference points, which are then confirmed by an operator. The workstation auto-selects reference points by selecting a plurality of points that are separated from each other, the ROI and/or masked pixels by predefined thresholds. The operator can also adjust reference points after the workstation auto-selects the reference points. The reference points indicate regions of the brain that are not intended to be heated, and are utilized in establishing a baseline temperature. In addition to the reference points, a minimum of eight measurements is acquired before an operator proceeds to temperature and thermal dosage or damage monitoring.

Figure 98:
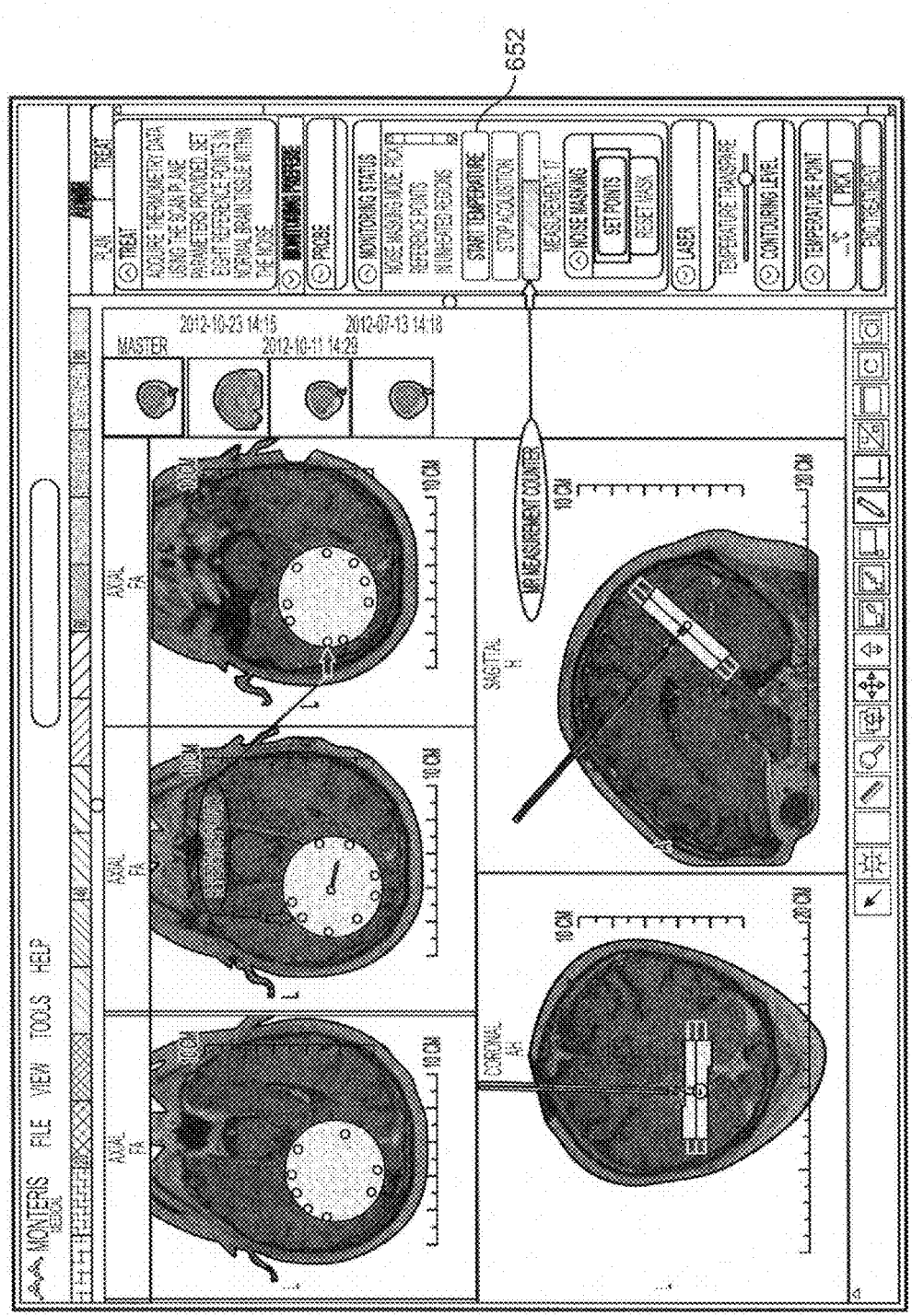

Once the reference points have been selected and a sufficient number of MRI measurements (e.g., eight) have been acquired, treatment monitoring can start by selecting a start temperature monitoring button 652 of the GUI, as shown in FIG. 98. Prior to proceeding with treatment, a current body temperature of the patient is entered into the workstation via the GUI, as well as a current probe temperature. The current probe temperature is retrievable via the workstation through a thermocouple connection within the capsule of the probe, which is coupled to the workstation via the interface platform, the electronics rack, and appropriate wiring connected to the workstation.

Figure 99:
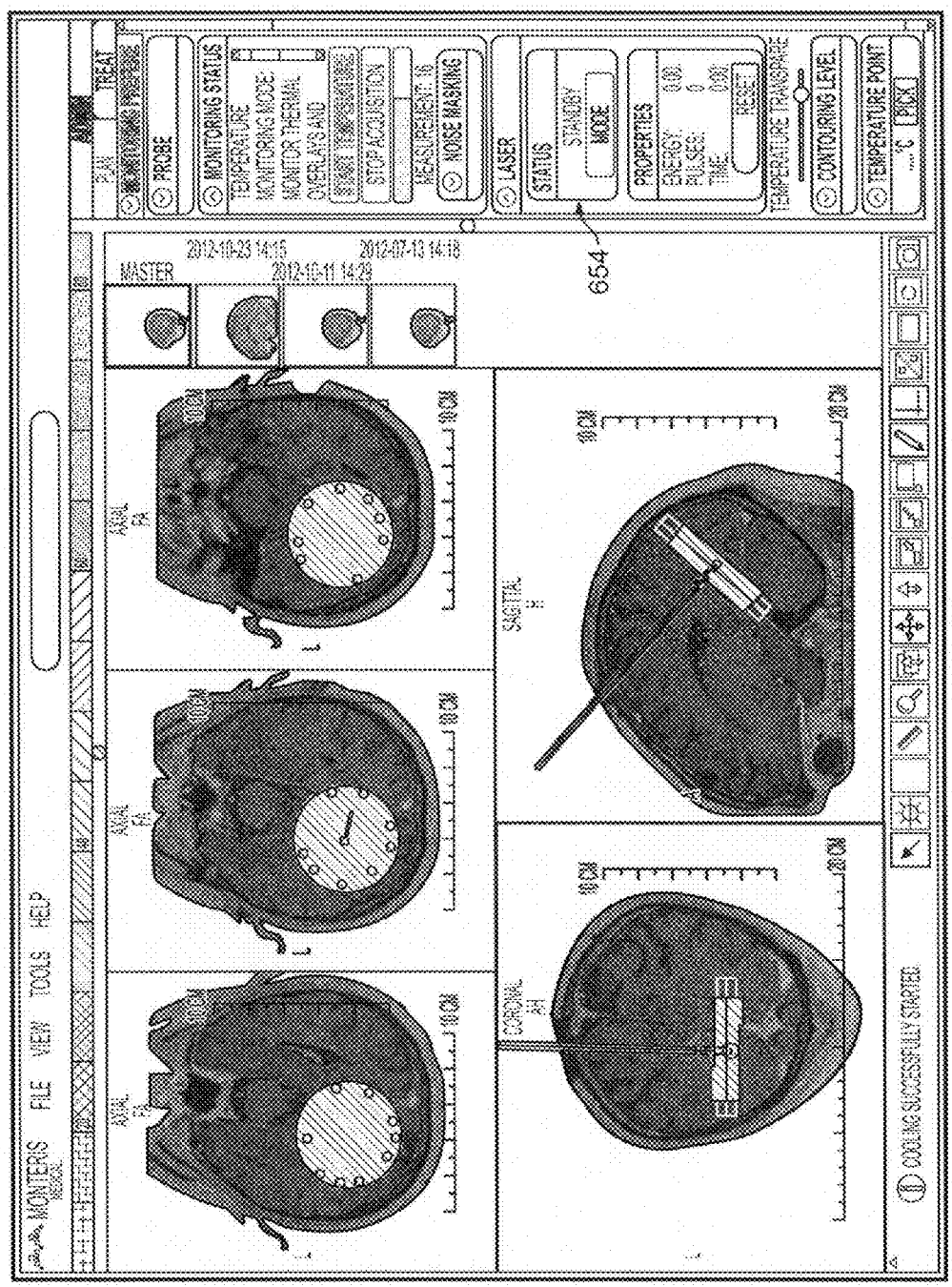

After inputting a baseline temperature, the color overlay of the masked region can be changed to a corresponding color on the color temperature map. FIG. 99 illustrates the mask region as a color which corresponds to a 37° C. baseline temperature. Other baseline temperatures within a range of 36-38° C. can also be utilized. This color can be green. At this time, probe cooling commences, which can cause the pixels in the vicinity of the probe to begin to shift from green into a blue region, indicating the tissue is being cooled. This verifies that the cooling in the probe is operating under normal conditions. An operator can stop the procedure to inspect and verify equipment if cooling does not appear to be operating as intended. Further, the workstation can detect an error and output a warning or discontinue treatment if a calculated amount of cooling does not result in an intended detected cooling within the ROI.

Figure 100:
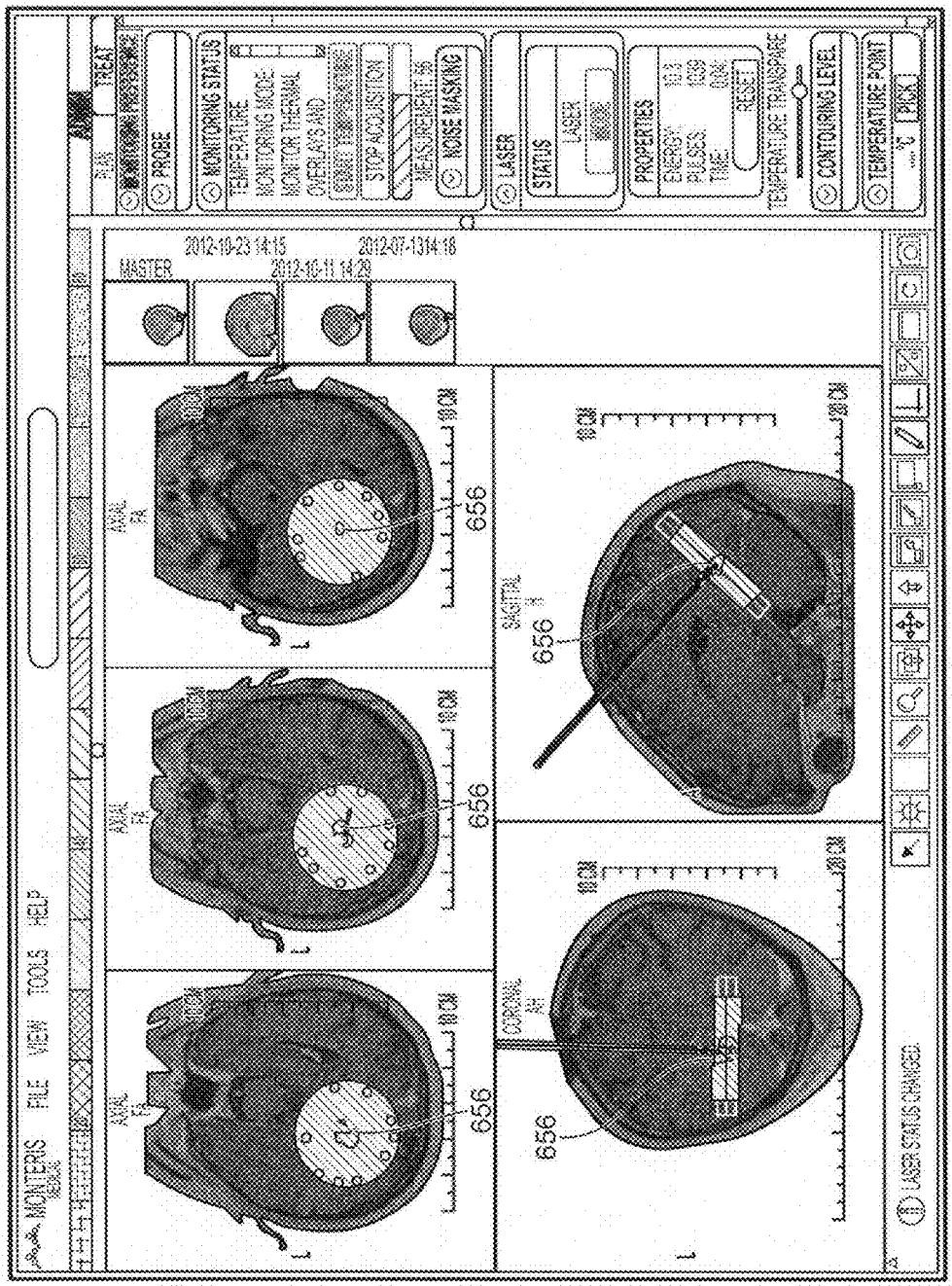

As illustrated in FIG. 99, an interface 654 within the GUI can be selected to change a mode of the probe from a standby mode to a ready mode, in which a foot pedal attached to the workstation is active to actuate a laser of the probe when the mode is switched to ready. If the standby mode is active, then the foot pedal does not control laser output or any probe activation. If probe cooling is not operating within set conditions or another problem is detected, then the GUI and the workstation inhibits an operator's selection of the ready mode for the probe. Lazing commences upon verification by the workstation and the GUI that settings are appropriate and conditions are within the predetermined thresholds. As illustrated in FIG. 100, treatment results in the GUI are shown by the GUI creating an isoline or contour line 656, which indicates a specified threshold of thermal dosage. The isoline or contour line 656 is illustrated contemporaneously, in real-time, in various views, including several (e.g., three) axial planar views, a coronal view and a sagittal view. The GUI and the workstation can halt treatment by the probe when the isoline or contour 656 coincides with a boundary of the region of interest that was planned in the trajectory and volume planning procedures, or when the isoline or the contour 656 satisfies a predetermined step within a sequence. Once the probe is stopped, the workstation and GUI can cool the ROI back down to the baseline temperature, initiate rotation and/or longitudinal repositioning of the probe and commence treatment at a different portion of the tissue. This procedure can be repeated until a plan volume has been detected as being treated to a sufficient level, by means of manual operation, a semi-automated operation or an automated operation.

During the entire procedure discussed above, the operator maintains activation of the foot pedal. Release of the foot pedal stops or pauses treatment. The treatment can be resumed upon reactivation of the pedal.

The various treatment trajectories for treating one or more volumes are stored in a workstation as individual sequences, which can be executed by the workstation automatically, without specifically requiring operator input to proceed from one sequence to a next sequence, or from one part of a sequence to a next sequence. A changeover between sequences or portions thereof can include at least one of rotational alignment change, longitudinal position change, laser fiber selection, probe tip selection, energy output, and duty cycle of energy output. In particular, when more than one probe is utilized contemporaneously, varying the probes in accordance with Section IV can be utilized in these sequences, and can be interchanged continuously without interruption of the operation of the MRI or the real time transfer of data from the MRI to the workstation.

vi. Noise Masking, Reference Points and Thermal Damage Monitoring

Further aspects of selecting reference points, masking noise and monitoring thermal damage are described herein.

Aspects of this disclosure encompass a system, method, devices, circuits and algorithms for monitoring the treatment of tissues, such as tumors, that include a process or algorithm for correcting incoming MRI data in order to compute accurate changes in temperature over time. MRI systems suffer from "phase drift," which may appear as a cyclical fluctuation of "phase data" that would otherwise remain constant if no other factors were present to influence the phase data. Factors that may influence phase data and cause such fluctuation may include, for example, tissue heating or motion. The selection of "reference points" may be used to compensate for phase drift in order to provide accurate temperature and thermal damage values to a user.

Magnetic resonance data includes complex numbers where both a magnitude and phase component exists. The magnitude data may be used to illustrate the "magnitude image," the most common data form used to visualize MR data. The magnitude image may provide, for example, a typical grayscale image of the brain showing contrast between different structures. The second set of data that is acquired is known as "phase data," which is representative of a phase of the image being displayed. Most MRI applications do not have a use for phase data, and merely discard this type of data. However, certain applications, such as phase contrast angiography, MR elastography and the temperature monitoring application described herein, may utilize the phase data. One reason for its value is that temperature is sensitive to the water proton chemical shift which is determined by the proton resonant frequency. This can be quantified from the phase component of the MR complex data.

Each pixel in a phase image has a value, particularly, an angle expressed in radians. Generally speaking, as long as the temperature of the tissue being monitored remains substantially constant, the phase values associated with the tissue should also remain substantially constant. For example, if an image of the brain is viewed every few seconds, such as 3, 4, 5, 6, 7, 9, 10 or more seconds (such as 8) for 2, 3, 4, 5, 6, 7, 8, 9, 10 or more minutes (such as 5), and then a specific pixel in the image is selected and plotted over time, ideally the phase number value for the selected pixel should be the same throughout the entire duration so long as the temperature remained substantially constant. Furthermore, if the temperature of the brain was raised or lowered, the phase number value should also be adjusted accordingly in response to the temperature change. Temperature is inversely proportional to phase change. For example, if the temperature of the brain was lowered, then there would be a corresponding increase in the phase number value, and vice versa.

One problem addressed herein results from the fact that MRI systems are not perfect. Such systems actually force a natural fluctuation of phase over time due to fluctuations in the magnetic field. Therefore, even when no heating is being applied to the tissue, the phase value of a selected point on an image may fluctuate over a period of time. For instance, the graph of phase values over time may appear sinusoidal. This type of fluctuation is problematic for temperature mapping because if the system does not correct for the fluctuation, the user may incorrectly think that the temperature is increasing or decreasing when in actuality it is substantially constant.

For example, until heat is applied to a brain during a treatment procedure, the brain tissue should remain at a baseline temperature of. Therefore, when phase values are plotted over time, the fact that the phase value fluctuates may mean that there is, for example, a drift in the magnet in the MRI. Workstations are useful for tracking this drift. As will be explained in further detail to follow, reference points may be selected in tissue areas that a user knows will remain at the baseline temperature prior to any heat treatment. Thus, by looking at the pattern of the drift in the reference points, the workstation or an MRI control workstation extrapolates the drift pattern to all of the areas in the image in order to compensate subsequently received images. As a result, the phase drift can be accounted for (as a constant) and removed so that any fluctuation that an operator observes is actually related to temperature, and not extraneous factors.

In one example, eight reference points may be selected within each of a plurality of predefined treatment slices of brain tissue and used to compensate for phase drift during the treatment. These reference points preferably reside within native brain tissue but are far enough away from the position of a treatment probe such that the tissue surrounding the points will not experience any substantial heating. Preferably, treatment should not be allowed to commence until the reference points are selected and confirmed by the operator. In one exemplary process, five of the eight reference points may be the "primary" points that are initially used in a masking phase, while the remaining three reference points may be used as "buffers" in case some of the primary points are dropped due to poor signal quality as the MR acquisition continues.

In one example, the user may select the reference points in a generally circular pattern surrounding the targeted treatment area. Selecting reference points surrounding the treatment area may provide a substantially uniform correction around the treatment area.

A two stage noise masking phase can be used to assist an operator in selecting reference points. In particular, when MRI thermometry data (both phase and magnitude) is validated and accepted by the workstation, a mask may be computed to hide those pixels which are considered to be "noisy." Until the operator selects to proceed in the workflow to view temperature data, the MRI raw data may be shown as a binary image of pixels that pass the noise masking stage and those that do not pass the noise masking stage. For example, the pixels that pass the noise masking stage may be made opaque, while the pixels that do not pass the noise masking stage may be made transparent. Other methods of distinguishing the pixels that pass the noise masking stage from those that do not pass the noise masking stage are also possible.

Figure 101:
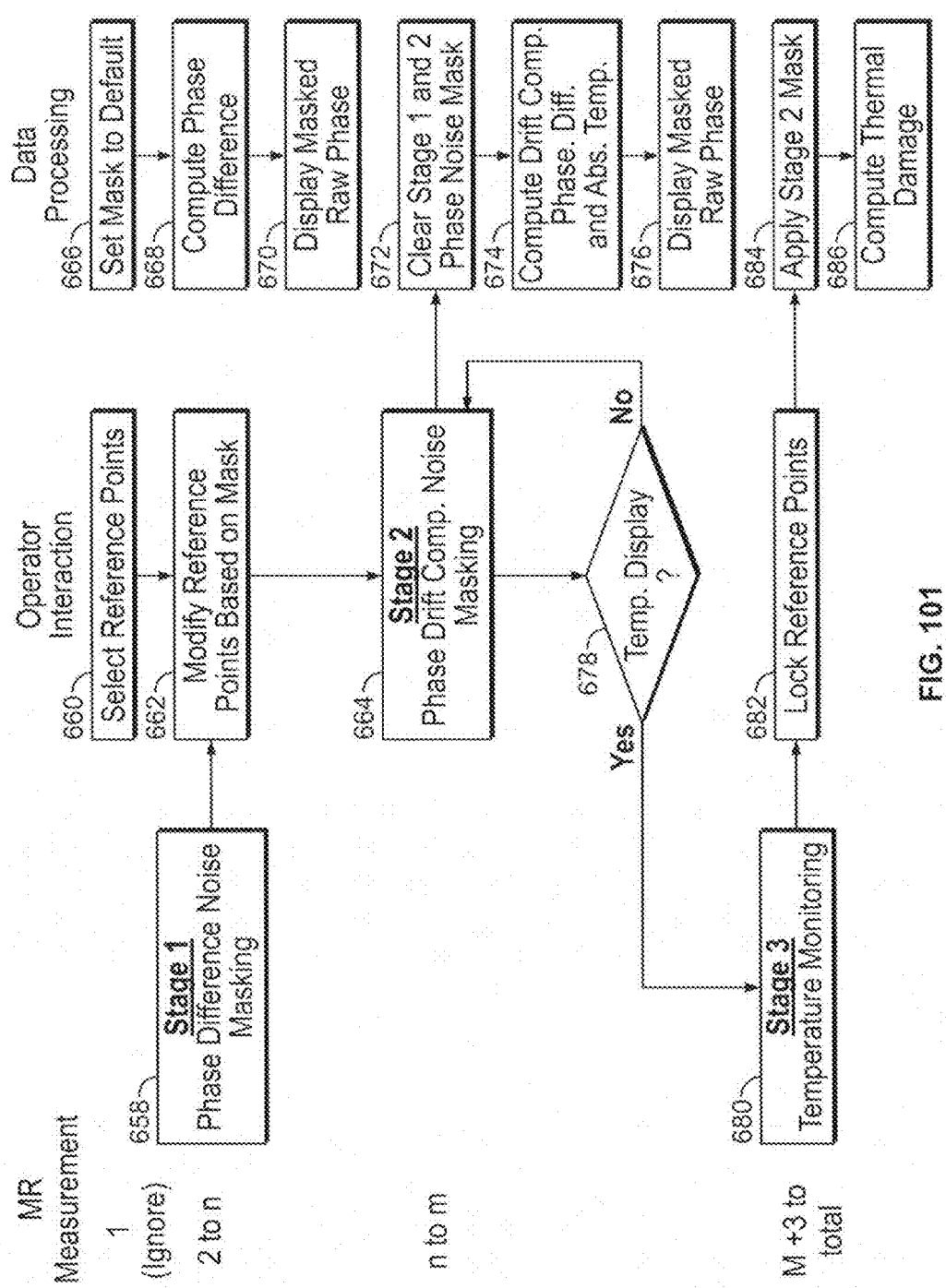
FIG. 101 is an illustration of an algorithmic sequence for reference point selection, noise masking, and thermal shaping.

FIG. 101 illustrates a sequence of processes performed via operator interaction and by data processing by, e.g., a workstation. The sequence is set forth in three stages in a time-wise sequence based on an MR measurement number. This sequence is exemplary and includes various computations performed by the workstation.

With reference to FIG. 101, the first stage of noise masking (Stage 1) may simply analyze the quality of the incoming phase data, applying a threshold to formulate a masked image. During this process, the operator may select reference points in each of a plurality of views. Points that do not fall within the noise mask may be deleted. Once the minimum number of reference points has been selected, the process may then continue to a Stage 2 noise mask to compute a phase drift compensated temperature difference. Stage 1 may be immediately skipped if the reference points already exist prior to MRI data arriving.

In Stage 2, the reference points selected in Stage 1 may be "validated." The reference points are used to compute a temperature difference at every location within the Stage 1 masked region. A temperature threshold can then be applied. Pixels whose temperature difference exceeds the threshold can be removed or masked, indicating to the operator the stability of the temperature mapping in the treatment area prior to treatment. The operator can continue to select additional reference points or delete existing reference points in order to produce a stable temperature map.

More particularly, two parallel actions are occurring as soon as the MRI system begins to take measurements. First, the operator may begin selecting reference points in the Stage 1 noise masking process in order to begin the reference point correction sequence. However, parallel to the Stage 1 noise masking process an optional "filtering" sequence of steps that filters out noisy points may be performed. In particular, the filtering sequence may begin by generating a default mask wherein all of the overlay pixels are opaque. The system may be designed such that the masked raw phase data may be displayed, for example, so that opaque pixels represent stable phase locations. Thus, at the most basic level the filtering sequence may involve comparing a first image to a second image and masking the pixels when unreliable data exceeds some threshold.

Within Stage 1, the operator begins selecting reference points based on the masked phase data resulting from the filtering sequence previously described. As briefly mentioned above, reference points are points on an MRI image that may be selected by the operator, such as by pointing and "clicking" a mouse cursor at a desired image location. For example, when an MRI system is running it typically may send data about every eight seconds updating the image. In overlaying the MRI image there may be another image that may ultimately become the temperature mask. The temperature mask may be made transparent or opaque through the use of a transparency control. Within the overlay, the operator selects points that are sufficiently far from the area that will be heated during treatment. These points are the reference points, and they all should fall within the brain.

The reference points are indicators of image or phase drift in the MRI. Because a certain amount of image or phase drift occurs naturally, once this natural image or phase drift in the MRI is determined, all of the subsequent phase data for the image may be compensated. The reference points may be selected either subjectively by the operator or automatically by reference point selection software. Whether the selection is performed manually or automatically, it will involve numerous factors including determining the location of the brain, segmenting the brain from the skull and other anatomical parts, and the like. If the minimum number of reference points has been selected, then the operator is free to move on to Stage 2.

Any number of reference points may be used in accordance with the descriptions provided herein. A single reference point may provide only a single point correction and a substantially planar fit providing a single correction value to all pixels within the image. Two or three reference points can provide a planar fit which may not describe the variable phase drift in the image correctly. Thus, when a planar fit is used, there is no "averaging" component. However, with more reference points, the points can be extrapolated to the entire image, providing for a polynomial surface fit in 3-D space. Thus, using a polynomial fit through the selected points is preferable because it allows for suitable correction throughout the entire image. In some implementations, the polynomial fit is superior to a planar fit generated by 1, 2 or 3 reference points. Fitting a polynomial surface to the selected points can create a correction throughout the entire treatment area without actually having to pick points at every location.

Further, although as few as one reference point may be sufficient for a basic planar fit, a larger number may be preferable because the operator may unintentionally pick one or more "unusable" points. This can occur when the signal intensity at the reference point location drops too low indicating poor signal and thus an unreliable phase value. Although eight reference points are described, any number of reference points having any number of extra "buffers" may be used without departing from the intended scope of the descriptions provided herein.

Once the minimum number of reference points is selected in Stage 1, the process continues to Stage 2 where the reference points may be used to correct for the phase drift. Until the operator transitions to the Stage 3 temperature monitoring stage, the operator remains in the masking stage and temperature is not yet being shown. In particular, during this masking stage the system assumes that the brain tissue is at a stable baseline temperature. As a result, all of the pixels displayed in the treatment area on the screen should be at approximately the same, constant temperature. The temperature of each pixel is computed and compared against a threshold to filter those regions where excessive temperature changes are occurring based on the currently selected reference points. Thus, the operator should be careful so as to select the reference points in a substantially homogenous brain tissue because too many pixels can be masked out due to reference point locations to correct for drift.

The result of the Stage 2 computations may be a phase map comprising a polynomial surface. More particularly, when computing the polynomial surface in accordance with the descriptions provided herein, the algorithm should include each of the reference points selected by the operator. The algorithm then functions to create a "surface" that represents the "best fit" through all of the selected points, or alternatively close to all of the selected points. As will be appreciated by those skilled in the art, when four or more reference points are selected, a polynomial surface fit should be used because it may be mathematically impossible to fit a planar surface through four reference points. Utilizing a polynomial surface fit is preferable when MRI phase drift is not linear. In one example, there may be slightly more phase drift at the top of the brain and slightly less phase drift at the bottom of the brain. Thus, the correction across the entire image preferably utilizes a polynomial fit rather than a planar fit.

After the corrected phase has been computed, the method proceeds to compute a drift compensated phase difference based upon the current corrected phase and a baseline phase that is stored in memory, such as an electronic memory of the workstation. Next, the drift compensated phase difference is then multiplied by a constant (a PRF factor), which gives us a temperature change in degrees Celsius. The baseline temperature is added to the temperature change to arrive at a current absolute temperature value. The baseline temperature may generally be about 37° C., which is the "normal" temperature of brain tissue prior to any heating or cooling. Other temperatures can be set, including 35° C., 36° C., 38° C., 39° C. or any fractional temperatures therebetween.

In Stage 2, temperature is not yet being displayed, but rather is rendered just as a mask. Therefore, what is being displayed in Stage 2 are pixels representing computed temperatures that fall within a predefined tolerance. If the computed temperatures fall within the tolerance, then the corresponding pixels are not masked out. However, if a computed temperature change is outside of the tolerance, then the corresponding pixel is masked out. This step in the process may be performed to illustrate how stable the data is so that prior to actually transitioning to the treatment mode (Stage 3), the operator may visualize the overlay mask on the image. If the operator observes that too many pixels have dropped out, then this serves as an indication that there may be a problem with the phase MRI. For instance, the MRI may not be functioning properly or there may be something wrong with the acquisition of the data that is creating too much variation in the phase data, thereby indicating that the temperature changes are really not representative of what is actually occurring.

As long as large numbers of pixels are not dropping out, everything appears stable to the operator and/or the workstation through monitoring of the data, and the predefined minimum number of reference points remain available, the operator may provide instructions to proceed to the Stage 3 temperature display and treatment mode. However, if too many pixels have dropped out and/or the predefined minimum number of reference points is not available, then additional reference points should be selected prior to proceeding to Stage 3. The workstation can inhibit the operator from proceeding until further reference points are selected. Moreover, the workstation can select reference points or identify reference points for the operator, which the operator can confirm.

Once Stage 3 is entered, the operator may initially be required to enter the appropriate baseline temperature, such as 37° C., for the brain tissue in the illustrated example. Since all of the required reference points have been collected prior to proceeding to Stage 3, there is no need to select additional reference points. The selection can be locked by the workstation.

In Stage 3, the actual tissue temperature is now displayed instead of merely the mask. Thus, in the illustrated example, Stage 3 includes the computation of thermal damage. That is, a real temperature is actually being computed and retained in Stage 3, and is not used as a mask. In one exemplary implementation, the thermal damage or "dose" may be computed using an Arrhenius-type relationship between time and tissue temperature. This allows the operator to view temperature maps of the brain tissue illustrating predictive damage that the software has calculated based on the sequencing of MRI data while providing the required treatment.

Also in Stage 3, a corrected phase is calculated as per Stage 2. A drift compensated phase difference is calculated by subtracting a baseline phase from the corrected phase. A current absolute temperature is calculated by adding a baseline temperature to a multiplication of the PRF factor and the drift compensated phase difference.

Thermal damage can be computed by a piecewise integration method. One method is to calculate an equivalent amount of time "t" (in minutes, hours or seconds) a tissue has been held at a specified temperature "T", which can be expressed as $t_{T,i}$. This specified temperature can represent a temperature above the baseline temperature, and/or a temperature at which thermal damage can be caused. Exemplary temperatures include 41° C., 42° C., 43° C., 44° C., 45° C., 46° C., 47° C., 48° C., 49° C., 50° C., 51° C.-60° C., 42° C.-46° C., or any fractional temperatures or ranges therebetween. "i" can refer to a time point or measurement number. A constant (R) is integrated according to the time point/measurement number and a difference between the specific temperature t and an actual temperature to compute thermal damage.

The constant R can be defined as a constant having values that are dependent on a current temperature, and thus, in some aspects can be a constant that varies according to a step function based on a current temperature. Tissue damage can be a complex function of time-temperature history, and the calculation of thermal damage can compare a time required for thermal injury to a reference temperature, based on findings that, for most soft tissue, a temperature above the specified temperature, such as 42° C., 43° C., 44° C., 45° C. or 46° C., causes thermal injury to the tissue.

A calculation of $t_{T,i}$ can be equated to one of various threshold times that can be indicated by one or more colored lines to indicate a tissue or portion of a tissue has been held at an equivalent temperature of the specified temperature for that threshold time. Adverting back to FIG. 100, the isoline or contour line 656 is displayed so as to coincide with a tissue or portions of a tissue that reach a first threshold.

Multiple isolines or contour lines can be simultaneously displayed in the GUI, where each of the lines corresponds to a different threshold. Exemplary thresholds can be set at 1, 2, 3, 4, 5, 10, 15, 20, 30, 45 and 60 minutes for specified temperatures of 42° C., 43° C., 44° C., 45° C. or 46° C. With such lines, such as two or three, being displayed simultaneously or contemporaneously, a progression of treatment can be monitored by an operator. Preferably one or more of the thresholds corresponds to a 100% or near 100% "kill rate" in that all or generally all biological functions of a tissue is destroyed at that amount of exposure to energy. However, other thresholds can be set to monitor treatment.

For cooling probes, an opposing relationship is viewable via the GUI for monitoring an equivalent temperature below the baseline temperature that indicates treatment or necrotizing of a tissue.

Through noise masking, real-time shaping is enabled to monitor treatment through a graphical user interface or other display. Color maps can be utilized in conjunction with isolines and/or contour lines that indicate a treatment shape. By tracking a probe position within tissue through feedback, multiple data slices provided around the probe position can be processed to monitor treatment and view thermal data. Thus, noise masking in combination with real-time probe feedback enables the calculation and display of real-time shaping of a treatment region. Further, real-time shaping utilizes multiple slices of image data and noise masking.

vii. Forecasting

Forecasting errors and issues with the MRI systems and various components is preferable to avoid procedure interruption. Forecasting can include continuous data filtration in connection with real-time shaping data rendering.

The workstation, either alone or in combination with a workstation or processing system dedicated to the MRI, monitors the reception of real time data from the MRI system. Based on statistics and averages of time delays (e.g., a latency) in receiving data (i.e., images) from the MRI system, a warning signal can be issued or displayed to an operator when a delay in receiving an expected image exceeds a threshold value. Based on a magnitude of the delay or repeating delays, the workstation can deactivate an energy output of a probe, and place the GUI of the workstation in a standby mode.

Similarly, the workstation can monitor temperature fluctuations in one or more of the reference points, within the patient, the MRI control room, the MRI system room or any other room. Excessive temperature fluctuations of tissue within the patient or within any of the rooms can indicate issues with the various components or accessory devices. Accordingly, based on a magnitude of the fluctuations of temperature in the reference points or any monitored area or portion of the patient, the workstation can deactivate an energy output of a probe, and place the GUI of the workstation in a standby mode.

A signal strength from the MRI is also monitored by the workstation. If a signal strength is too low, temperature data is unreliable and the operator is warned of the issue. Based on a magnitude of the signal strength, the workstation can deactivate an energy output of a probe, and place the GUI of the workstation in a standby mode.

An image quality of the images received by the workstation can be monitored and measured for quality. Quality measuring identifies potentially harmful issues such as patient motion, RF noise, and other artifacts due to external causes. For example, a non-MRI compatible device or equipment near the patient can cause such artifacts. Quality measuring can include scanning received images to detect artifacts or unexpected pixel information. Based on image quality, the workstation can deactivate an energy output of a probe, and place the GUI of the workstation in a standby mode.

Once in standby mode, the workstation can automatically recover to resume treatment by selecting a new reference point and/or adjusting a noise mask, and then the operator can recommence treatment after confirming any data errors have been addressed and treatment of the patient is not impaired.

The workstation, either alone or in combination with a workstation or processing system dedicated to the MRI, can also perform signal filtration of MR raw data. The filtration can help identify issues that impact temperature sensitivity, accuracy and the ultimate prediction of thermal dose. Features or parts of a signal that are filtered include: range, outliers, sequence, and notification packets. These features or parts are processed by an algorithm of the workstation to collect, filter, sort and weight data. A corresponding display is displayed to an operator to inform the operator of potential issues, and allow the operator to continue with a treatment, pause a treatment or halt a treatment. The workstation can also provide recommendations for taking action based on predefined criteria and a history of analyzed data.

VII. CONCLUSION

The procedures and routines described herein can be embodied as a system, method or computer program product, and can be executed via one or more dedicated circuits or programmed processors. Accordingly, the descriptions provided herein may take the form of exclusively hardware, exclusively software executed on hardware (including firmware, resident software, micro-code, etc.), or through a combination of dedicated hardware components and general processors that are configured by specific algorithms and process codes. Hardware components are referred to as a "circuit," "module," "unit," "device," or "system." Executable code that is executed by hardware is embodied on a tangible memory device, such as a computer program product. Examples include CDs, DVDs, flash drives, hard disk units, ROMs, RAMs and other memory devices.

Reference has been made to flowchart illustrations and block diagrams of methods, systems and computer program products according to implementations of this disclosure. Aspects thereof are implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer-readable medium that can direct a computer or other programmable data processing apparatus to function in a particular manner, such that the instructions stored in the computer-readable medium produce an article of manufacture including instruction means which implement the function/act specified in the flowchart and/or block diagram block or blocks.

The computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide processes for implementing the functions/acts specified in the flowchart and/or block diagram block or blocks.

A number of implementations have been described. Nevertheless, it will be understood that various modifications may be made without departing from the spirit and scope of this disclosure. For example, preferable results may be achieved if the steps of the disclosed techniques were performed in a different sequence, if components in the disclosed systems were combined in a different manner, or if the components were replaced or supplemented by other components. The functions, processes and algorithms described herein may be performed in hardware or software executed by hardware, including computer processors and/or programmable circuits configured to execute program code and/or computer instructions to execute the functions, processes and algorithms described herein. Additionally, some implementations may be performed on modules or hardware not identical to those described. Accordingly, other implementations are within the scope that may be claimed.

A system for effecting treatment to a tissue can include: an automated drive mechanism including a holder to hold a treatment device, wherein the drive mechanism is coupled to one or more wires such that a translation of the one or more wires effects one or more of a longitudinal displacement of the holder and a rotation of the holder; and a controller including an input interface to process position control signals for setting a position of the treatment device, and an output interface to translate the one or more wires based on the position control signals.

The system can further include: a guide mechanism that is attachable to a surface of a patient, wherein the guide mechanism includes a base structure that is configured to remain stationary relative to the patient when the guide mechanism is attached to the surface of the patient in a locked state, the guide mechanism includes a tilt portion that is coupled to the base structure, the tilt portion is structured so as to hold the drive mechanism at a position that is separated from the surface of the patient, and the tilt portion provides an adjustable tilt between a trajectory of the drive mechanism and the base structure. The guide mechanism can further include a rotation portion that provides an adjustable rotation of the tilt portion relative to the base structure.

The drive mechanism can be motorless and consists of thermal imaging compatible components.

The controller can be configured to process a sequence of the position control signals to: move the holder to a first position for effecting the treatment to the tissue at a first portion of the tissue that coincides with the first position; and move the holder to a second position for effecting the treatment to the tissue at a second portion of the tissue that coincides with the second position. The system can further include a workstation to transmit the position control signals to the controller and to display thermometry images of the tissue. The workstation can continuously display the thermometry images of the tissue during the treatment to the tissue at the first and second portions of the tissue, and while the holder moves between the first and second positions.

The system can further include an energy emission probe as the treatment device, wherein the probe generates a plurality of different output patterns. The probe can include a first laser fiber for outputting a symmetrical output pattern with respect to a longitudinal axis of the first laser fiber, and the probe can include a second laser fiber for outputting an asymmetrical output pattern with respect to a longitudinal axis of the second laser fiber.

The system can further include: an energy source to generate energy for the probe; and a workstation to transmit the position control signals to the controller, and to transmit energy control signals to the energy source, wherein the workstation is configured to process a sequence of the energy control signals to: effect a symmetrical treatment to the tissue with the probe; and effect an asymmetrical treatment to the tissue with the probe after the symmetrical treatment.

The system can also include: a laser source to generate laser energy for the laser probe; and a workstation to transmit the position control signals to the controller, and to transmit laser control signals to the laser source, wherein the workstation is configured to process a sequence of the position and laser control signals to: move the holder to a first position for effecting the treatment to the tissue at a first portion of the tissue that coincides with the first position; effect a symmetrical treatment to the first portion of the tissue with the first laser fiber; move the holder to a second position for effecting the treatment to the tissue at a second portion of the tissue that coincides with the second position; and effect an asymmetrical treatment to the second portion of the tissue with the second laser fiber. The workstation can be configured to display thermometry images of the tissue continuously throughout processing of the sequence of the position and laser control signals and throughout moving the holder and effecting the symmetrical and asymmetrical treatments.

The system can include an imaging system to output images of the tissue and the treatment device, including thermometry images of the tissue, in real time, continuously throughout one or more steps of effecting the treatment to the tissue; and a workstation to transmit the position control signals to the controller based on one or more of the images, as the images are received by the workstation in real time, and to display, in real time, one or more of the images throughout the one or more steps of effecting the treatment to the tissue.

The workstation can be configured to display, in real time, the thermometry images of the tissue with the images of the tissue and the treatment device continuously throughout a processing of the position control signals and throughout moving the holder and effecting the treatment to the tissue.

The workstation can be configured to process, in real time, the images of the tissue and the treatment device and the thermometry images of the tissue to forecast errors or interruptions in the treatment to the tissue and display a corresponding warning.

The system can further include an energy emission probe as the treatment device, the energy emission probe including one or more emitters selected from: a laser fiber, a radiofrequency emitter, a high-intensity focused ultrasound emitter, a microwave emitter, a cryogenic cooling device, and a photodynamic therapy light emitter. The energy emission probe can include a plurality of the emitters. The plurality of the emitters can be longitudinally spaced with respect to a longitudinal axis of the energy emission probe.

The system can further include a guide sheath including a plurality of probes of different modalities as the treatment device, wherein the modalities include one or more of: laser, radiofrequency, high-intensity focused ultrasound, microwave, cryogenic, photodynamic therapy, chemical release and drug release. The guide sheath can include one or more off-axis holes for positioning an emitting point of one or more of the plurality of probes at an off-axis angle.

The invention claimed is:

1. A system for effecting treatment to a tissue, comprising:
a motorless drive mechanism that is compatible with and can operate within an operational field of a medical imaging system to image the tissue without substantially disrupting imaging performed by the medical imaging system, the motorless drive mechanism including a holder to hold a treatment device to treat the tissue, and a first wire translation mechanism that couples one or more wires to the holder, such that a translation of the one or more wires effects one or more of a longitudinal displacement of the holder and a rotation of the holder;
a base unit that is coupled to the motorless drive mechanism by the one or more wires, the base unit including a second wire translation mechanism to translate the one or more wires;
an electronic controller including an input interface to receive position control signals for setting a position of the treatment device, and an output interface that is coupled to the second wire translation mechanism of the base unit, such that the output interface effects movements of the second wire translation mechanism to translate the one or more wires based on the position control signals received by the input interface to effect movements of the first wire translation mechanism, such that one or more of the longitudinal displacement of the holder and the rotation of the holder are effected based on the position control signals received by the input interface;

an energy emission probe as the treatment device, wherein the probe generates a plurality of different output patterns, including, with respect to a longitudinal axis of the probe, a symmetrical output pattern and an asymmetrical output pattern;

an energy source to generate energy for the probe; and a workstation adapted to transmit the position control signals to the electronic controller, and to transmit energy control signals to the energy source, wherein the workstation is adapted to process a sequence of the position and energy control signals to:

move the holder to a first position and effect a symmetrical treatment to a first portion of the tissue that coincides with the first position with the probe, and move the holder to a second position and effect an asymmetrical treatment to a second portion of the tissue that coincides with the second position with the probe after the symmetrical treatment.

2. The system according to claim 1, further comprising a guide assembly that is attachable to a surface of a patient, the guide assembly including:

a base structure that remains stationary relative to the patient when the guide assembly is attached to the surface of the patient in a locked state; and a tilt portion that is coupled to the base structure, the tilt portion that holds the motorless drive mechanism at a position that is separated from the surface of the patient, and the tilt portion providing an adjustable tilt between a trajectory of the motorless drive mechanism and the base structure when the base structure remains stationary relative to the patient.

3. The system according to claim 2, wherein the guide assembly further includes a rotation portion that provides an adjustable rotation of the tilt portion relative to the base structure.

4. The system according to claim 1, wherein:

the medical imaging system is a magnetic resonance imaging (MRI) system that includes a thermal imaging function, and the motorless drive mechanism consists of MRI and thermal imaging compatible materials and structures.

5. The system according to claim 1, wherein:

the electronic controller is adapted to cause the holder to move from the first position to the second position while the medical imaging system continuously images the tissue.

6. The system according to claim 5, wherein the workstation is adapted to transmit the position control signals to the electronic controller and to display thermometry images of the tissue.

7. The system according to claim 6, wherein the workstation is adapted to continuously display the thermometry images of the tissue during the treatment to the tissue at the first and second portions of the tissue, while the medical imaging system continuously images the tissue, and while the holder moves between the first and second positions.

8. The system according to claim 1, wherein the probe includes:

a first laser fiber to output the symmetrical output pattern, and a second laser fiber to output the asymmetrical output pattern.

9. The system according to claim 8, wherein:

the energy source is a laser source to generate laser energy for the laser probe; and the workstation is adapted to transmit the position control signals to the electronic controller, and to transmit the energy control signals to the laser source, wherein the workstation is adapted to process the sequence of the position and energy control signals to:

effect the symmetrical treatment to the first portion of the tissue with the first laser fiber, and effect the asymmetrical treatment to the second portion of the tissue with the second laser fiber.

10. The system according to claim 9, wherein the workstation is to display thermometry images of the tissue continuously throughout processing of the sequence of the position and laser control signals and throughout moving the holder and effecting the symmetrical and asymmetrical treatments.

11. The system according to claim 1, further comprising:

the medical imaging system to output images of the tissue and the treatment device, including thermometry images of the tissue, in real time, continuously throughout one or more steps of effecting the treatment to the tissue, wherein the workstation is adapted to transmit the position control signals to the electronic controller based on one or more of the images, as the images are received by the workstation in real time, and to display, in real time, one or more of the images throughout the one or more steps of effecting the treatment to the tissue.

12. The system according to claim 11, wherein the workstation is adapted to display, in real time, the thermometry images of the tissue with the images of the tissue and the treatment device continuously throughout a processing of the position control signals and throughout moving the holder and effecting the treatment to the tissue.

13. The system according to claim 11, wherein the workstation is adapted to process, in real time, the images of the tissue and the treatment device and the thermometry images of the tissue to forecast errors or interruptions in the treatment to the tissue and display a corresponding warning.

14. The system according to claim 1, wherein the energy emission probe includes one or more emitters selected from: a laser fiber, a radiofrequency emitter, a high-intensity focused ultrasound emitter, a microwave emitter, a cryogenic cooling device, and a photodynamic therapy light emitter.

15. The system according to claim 14, wherein the energy emission probe includes a plurality of the emitters.

16. The system according to claim 15, wherein the plurality of the emitters are longitudinally spaced with respect to a longitudinal axis of the energy emission probe.

17. The system according to claim 1, further comprising:

a guide sheath including the energy emission probe and one or more other probes, wherein the energy emission probe and the one or more other probes are of different modalities, and the modalities include one or more of: laser, radiofrequency, high-intensity focused ultrasound, microwave, cryogenic, photodynamic therapy, chemical release and drug release.

18. The system according to claim 17, wherein the guide sheath includes one or more off-axis holes for positioning an emitting point of one or more of the plurality of probes at an off-axis angle.

* * * * *